US008034770B2

(12) United States Patent
Belouski et al.

(10) Patent No.: US 8,034,770 B2
(45) Date of Patent: Oct. 11, 2011

(54) FGF21 POLYPEPTIDES COMPRISING TWO OR MORE MUTATIONS

(75) Inventors: Edward John Belouski, Camarillo, CA (US); Murielle Marie Ellison, Thousand Oaks, CA (US); Agnes Eva Hamburger, Newbury Park, CA (US); Randy Ira Hecht, Thousand Oaks, CA (US); Yue-Sheng Li, Thousand Oaks, CA (US); Mark Leo Michaels, Encino, CA (US); Jeonghoon Sun, Thousand Oaks, CA (US); Jing Xu, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 207 days.

(21) Appl. No.: 12/455,610

(22) Filed: Jun. 3, 2009

(65) Prior Publication Data

US 2009/0305986 A1    Dec. 10, 2009

Related U.S. Application Data

(60) Provisional application No. 61/058,861, filed on Jun. 4, 2008, provisional application No. 61/058,919, filed on Jun. 4, 2008, provisional application No. 61/164,364, filed on Mar. 27, 2009, provisional application No. 61/175,736, filed on May 5, 2009.

(51) Int. Cl.
*A61K 38/18* (2006.01)
*C07K 14/50* (2006.01)

(52) U.S. Cl. ............ 514/9.1; 530/350; 530/399

(58) Field of Classification Search .......... None
See application file for complete search history.

(56) References Cited

U.S. PATENT DOCUMENTS

| | | | |
|---|---|---|---|
| 3,773,919 A | 11/1973 | Boswell et al. |
| 4,179,337 A | 12/1979 | Davis et al. |
| 4,301,144 A | 11/1981 | Iwashita et al. |
| 4,376,110 A | 3/1983 | David et al. |
| 4,496,689 A | 1/1985 | Mitra |
| 4,640,835 A | 2/1987 | Shimizu et al. |
| 4,670,417 A | 6/1987 | Iwasaki et al. |
| 4,791,192 A | 12/1988 | Nakagawa et al. |
| 4,816,567 A | 3/1989 | Cabilly et al. |
| 4,892,538 A | 1/1990 | Aebischer et al. |
| 4,945,050 A | 7/1990 | Sanford et al. |
| 4,970,154 A | 11/1990 | Chang |
| 5,011,472 A | 4/1991 | Aebischer et al. |
| 5,106,627 A | 4/1992 | Aebischer et al. |
| 5,217,889 A | 6/1993 | Roninson et al. |
| 5,229,501 A * | 7/1993 | Keifer et al. |
| 5,234,784 A | 8/1993 | Aslam et al. |
| 5,252,714 A | 10/1993 | Harris et al. |
| 5,272,071 A | 12/1993 | Chappel |
| 5,288,855 A * | 2/1994 | Bergonzoni et al. |
| 5,364,791 A | 11/1994 | Vegeto et al. |
| 5,489,743 A | 2/1996 | Robinson et al. |
| 5,545,807 A | 8/1996 | Surani et al. |
| 5,557,032 A | 9/1996 | Mak |
| 5,585,089 A | 12/1996 | Queen et al. |
| 5,589,362 A | 12/1996 | Bujard et al. |
| 5,593,875 A | 1/1997 | Wurm et al. |
| 5,635,399 A | 6/1997 | Kriegler et al. |
| 5,650,298 A | 7/1997 | Bujard et al. |
| 5,654,168 A | 8/1997 | Bujard et al. |
| 5,670,323 A * | 9/1997 | Nova et al. |
| 5,672,510 A | 9/1997 | Eglitis et al. |
| 5,676,954 A | 10/1997 | Brigham |
| 5,679,559 A | 10/1997 | Kim et al. |
| 5,693,762 A | 12/1997 | Queen et al. |
| 5,707,632 A * | 1/1998 | Williams et al. |
| 5,811,234 A | 9/1998 | Roninson et al. |
| 6,133,426 A | 10/2000 | Gonzalez et al. |
| 6,150,098 A | 11/2000 | Zhang |
| 6,214,795 B1 * | 4/2001 | Benjamin et al. |
| 6,255,454 B1 * | 7/2001 | Kiefer et al. |
| 6,350,593 B1 * | 2/2002 | Williams et al. |
| 6,355,440 B1 * | 3/2002 | Williams et al. |
| 6,384,191 B1 | 5/2002 | Williams et al. |
| 6,548,634 B1 | 4/2003 | Ballinger et al. |
| 6,579,850 B1 | 6/2003 | Nabeshima et al. |
| 6,639,063 B1 | 10/2003 | Edwards |
| 6,716,626 B1 | 4/2004 | Itoh |
| 6,844,168 B1 | 1/2005 | Keifer et al. |
| 7,259,248 B2 | 8/2007 | Itoh |
| 7,288,406 B2 | 10/2007 | Bogin et al. |
| 7,408,047 B1 | 8/2008 | Thomason |
| 7,491,697 B2 | 2/2009 | Beals |
| 7,531,304 B2 | 5/2009 | Bange et al. |
| 7,563,769 B2 | 7/2009 | Bogin et al. |
| 7,645,857 B2 | 1/2010 | Zhou et al. |
| 7,667,005 B2 | 2/2010 | Nabeshima et al. |
| 7,678,890 B2 | 3/2010 | Bosch et al. |
| 7,695,938 B2 | 4/2010 | Thomason et al. |
| 7,696,172 B2 | 4/2010 | Thomason et al. |
| 7,700,558 B2 | 4/2010 | Thomason et al. |
| 7,704,952 B2 | 4/2010 | Thomason et al. |
| 7,727,742 B2 | 6/2010 | Thomason et al. |
| 7,879,323 B2 | 2/2011 | Thomason et al. |

(Continued)

FOREIGN PATENT DOCUMENTS

EP     0036676 A1    9/1981

(Continued)

OTHER PUBLICATIONS

Nishimura et al. (2000), "Identification of a novel FGF, FGF-21, preferentially expressed in the liver(I)." Biochim Biophys Acta 21: 203-6.

(Continued)

*Primary Examiner* — Christine J Saoud
(74) *Attorney, Agent, or Firm* — John A. Lamerdin

(57) ABSTRACT

The invention provides nucleic acid molecules encoding FGF21 mutant polypeptides, FGF21 mutant polypeptides, pharmaceutical compositions comprising FGF21 mutant polypeptides, and methods for treating metabolic disorders using such nucleic acids, polypeptides, or pharmaceutical compositions.

15 Claims, 89 Drawing Sheets

U.S. PATENT DOCUMENTS

| | | | |
|---|---|---|---|
| 7,887,799 | B2 | 2/2011 | Thomason et al. |
| 2001/0012628 | A1 | 8/2001 | Agarwal et al. |
| 2002/0081663 | A1 | 6/2002 | Conklin |
| 2002/0164713 | A1 | 11/2002 | Itoh |
| 2003/0220246 | A1 | 11/2003 | Conklin |
| 2004/0018499 | A1 | 1/2004 | Lal |
| 2004/0185494 | A1 | 9/2004 | Itoh |
| 2004/0259780 | A1 | 12/2004 | Glasebrook |
| 2005/0037457 | A1 | 2/2005 | Itoh |
| 2005/0176631 | A1 | 8/2005 | Heuer |
| 2005/0187150 | A1 | 8/2005 | Mohammadi et al. |
| 2006/0223114 | A1 | 10/2006 | Stemmer |
| 2007/0036806 | A1 | 2/2007 | Glaesner |
| 2007/0128619 | A1 | 6/2007 | Itoh |
| 2007/0142278 | A1 | 6/2007 | Beals |
| 2007/0237768 | A1 | 10/2007 | Glaesner |
| 2007/0238657 | A1 | 10/2007 | Itoh |
| 2007/0265200 | A1 | 11/2007 | Glaesner |
| 2007/0293430 | A1 | 12/2007 | Frye |
| 2007/0299007 | A1 | 12/2007 | Frye |
| 2008/0071065 | A1 | 3/2008 | Thomason |
| 2008/0071066 | A1 | 3/2008 | Thomason |
| 2008/0103096 | A1 | 5/2008 | Frye |
| 2008/0242607 | A1 | 10/2008 | DeFrees |
| 2008/0248959 | A1 | 10/2008 | DeFrees |
| 2008/0253992 | A1 | 10/2008 | DeFrees et al. |
| 2008/0255040 | A1 | 10/2008 | DeFrees |
| 2008/0255045 | A1 | 10/2008 | Cujec |
| 2008/0261236 | A1 | 10/2008 | Kuro-o |
| 2008/0261875 | A1 | 10/2008 | Etgen |
| 2008/0274958 | A1 | 11/2008 | DeFrees |
| 2009/0074776 | A1 | 3/2009 | Itoh |
| 2009/0118190 | A1 | 5/2009 | Beals et al. |
| 2009/0123462 | A1 | 5/2009 | Bange et al. |
| 2009/0192087 | A1 | 7/2009 | Glass et al. |
| 2009/0305986 | A1 | 12/2009 | Belouski et al. |
| 2010/0158911 | A1 | 6/2010 | Williams et al. |
| 2010/0158914 | A1 | 6/2010 | Desnoyers |
| 2010/0184665 | A1 | 7/2010 | Suzuki et al. |
| 2010/0226921 | A1 | 9/2010 | Thomason et al. |
| 2010/0233169 | A1 | 9/2010 | Thomason et al. |
| 2010/0285131 | A1 | 11/2010 | Belouski et al. |
| 2010/0310566 | A1 | 12/2010 | Thomason et al. |
| 2011/0003302 | A1 | 1/2011 | Thomason et al. |

FOREIGN PATENT DOCUMENTS

| | | | |
|---|---|---|---|
| EP | 0058481 | A1 | 8/1982 |
| EP | 0088046 | A2 | 9/1983 |
| EP | 0133988 | A2 | 3/1985 |
| EP | 0143949 | A1 | 6/1985 |
| EP | 0154316 | A2 | 9/1985 |
| EP | 0401384 | A1 | 12/1990 |
| EP | 0545343 | A1 | 6/1993 |
| EP | 0315456 | B1 | 6/1994 |
| EP | 0546073 | B1 | 9/1997 |
| EP | 2060270 | A2 | 5/2009 |
| EP | 2163626 | A1 | 3/2010 |
| WO | 90/04036 | A1 | 4/1990 |
| WO | 91/09955 | A1 | 7/1991 |
| WO | 91/10425 | A1 | 7/1991 |
| WO | 91/10470 | A1 | 7/1991 |
| WO | 91/10741 | A1 | 7/1991 |
| WO | 93/15722 | A1 | 8/1993 |
| WO | 94/02602 | A1 | 2/1994 |
| WO | 94/20069 | A1 | 9/1994 |
| WO | 94/28122 | A1 | 12/1994 |
| WO | 95/05452 | A2 | 2/1995 |
| WO | 95/34670 | A2 | 12/1995 |
| WO | 96/11953 | A1 | 4/1996 |
| WO | 96/32478 | A1 | 10/1996 |
| WO | 96/33735 | A1 | 10/1996 |
| WO | 96/37609 | A1 | 11/1996 |
| WO | 96/40958 | A1 | 12/1996 |
| WO | 96/41865 | A1 | 12/1996 |
| WO | 97/31899 | A1 | 9/1997 |
| WO | 97/34631 | A1 | 9/1997 |
| WO | 99/10494 | A2 | 3/1999 |
| WO | 00/18921 | A2 | 4/2000 |
| WO | 00/24782 | A2 | 5/2000 |
| WO | 00/54813 | A2 | 9/2000 |
| WO | 01/18172 | A2 | 3/2001 |
| WO | 01/18209 | A1 | 3/2001 |
| WO | 01/32678 | A1 | 5/2001 |
| WO | 01/36640 | A2 | 5/2001 |
| WO | 01/38357 | A2 | 5/2001 |
| WO | 01/49849 | A1 | 7/2001 |
| WO | 01/72957 | A2 | 10/2001 |
| WO | 03/011213 | A2 | 2/2003 |
| WO | 03/059270 | A2 | 7/2003 |
| WO | 2004/044011 | A2 | 5/2004 |
| WO | 2004/110472 | A2 | 12/2004 |
| WO | 2005/037235 | A2 | 4/2005 |
| WO | 2005/061712 | A1 | 7/2005 |
| WO | 2005/072769 | A1 | 8/2005 |
| WO | 2005/091944 | A2 | 10/2005 |
| WO | 2005/113606 | A2 | 12/2005 |
| WO | 2006/028595 | A2 | 3/2006 |
| WO | 2006/028714 | A1 | 3/2006 |
| WO | 2006/050247 | A2 | 5/2006 |
| WO | 2006/065582 | A2 | 6/2006 |
| WO | 2006/078463 | A2 | 7/2006 |
| WO | 2007/055789 | A2 | 5/2007 |
| WO | 2007/100695 | A2 | 9/2007 |
| WO | 2008/011633 | A2 | 1/2008 |
| WO | 2008/121563 | A2 | 10/2008 |
| WO | 2008/151258 | A2 | 12/2008 |
| WO | 2008/153705 | A2 | 12/2008 |
| WO | 2009/020802 | A2 | 2/2009 |
| WO | 2009149171 | A2 | 12/2009 |
| WO | 2010006214 | A1 | 1/2010 |
| WO | 2010129503 | A2 | 11/2010 |

OTHER PUBLICATIONS

Parthiban et al., 2006, "MSH2 is essential for the preservation of genome integrity and prevents homeologous recombination in the moss *Physcomitrella patens*" Nucleic Acids of Res. 34: 232-42.

Plotnikov et al. (1999), "Structural Basis for FGF Receptor Dimerization and Activation" Cell 98: 641-650.

Riechmann et al., 1998, "Reshaping human antibodies for therapy" Nature 332: 323-27.

Sidman et al., 1983, "Controlled release of macromolecules and pharmaceuticals from synthetic polypeptides based on glutamic acid" Biopolymers 22: 547-56.

Trouiller, et al. (2006), "MSH2 is essential for the preservation of genome integrity and prevents homeologous recombination in the moss *Physcomitrella patens*" Nucleic Acids Research vol. 34, (1): 232-242.

Verhoeyen et al., 1988, "Reshaping human antibodies: grafting an antilysozyme activity" Science 239: 1534-36.

Wente et al. (2006), "Fibroblast Growth Factor-21 Improves Pancreatic B-Cell Function and Survival by Activation of Extracellular Signal-Regulated Kinase ½ and Akt Signaling Pathways" Diabetes 55: 2470-2478.

Wischke & Schwendeman, 2008, "Principles of encapsulating hydrophobic drugs in PLA/PLGA microparticles" Int. J. Pharm. 364: 298-327.

Xu et al., (2009) "Fibroblast Growth Factor 21 Reverses Hepatic Steatosis, increases Energy Expenditure, and Improves Insulin Sensitivity in Diet-Induced Obese Mice" Diabetes 58(1):250-9.

Yie et al., 2009, "FGF21 N- and C-termini play different roles in receptor interaction and activation" FEBS Lett. 583:19-24.

Faham, S. et al., (1998) "Diversity does make a difference: fibroblast growth factor-heparin interactions," Curr. Opin. Struct. Biol. 8(5): 578-586.

GenBank Acc. No. AB006136, Aug. 27, 1997.

GenBank Acc. No. AQ175436, Sep. 21, 1998, accessed Nov. 18, 2005.

GenBank Acc. No. AV050323, Jun. 16, 1999, accessed Nov. 18, 2005.

GenBank Acc. No. BAA99415, Aug. 3, 2000.

GenBank Acc. No. BAA99416, Jul. 11, 2000.

GenBank Acc. No. NP_061986, Apr. 6, 2003.

GenBank Acc. No. Q9NSA1, Oct. 1, 2000.
Ghielli et al. (1998), "Regeneration processes in the kidney after acute injury: role of infiltrating cells," Exp. Nephrol. 6: 502-507.
Hoppenreijs et al. (1996), "Corneal endothelium and growth factors." Surv. Ophthalmol. 41: 155-64.
Hu et al., (1998), "FGF-18, a novel member of the fibroblast growth factor family, stimulates hepatic and intestinal proliferation," Mol. Cell. Biol. 18(10): 6063-6074.
Itoh and Ornitz (2004), "Evolution of the FGF and FGFR gene families." Trends in Genetics 20(11): 563-569.
Kaufman et al. (1999), "Transgenic analysis of a 100-kb human beta-globin cluster-containing DNA fragment propagated as a bacterial artificial chromosome." Blood 94: 3178-3184.
Kennell (1971), "Principles and practices of nucleic acid hybridization," Progr. Nucl. Acid Res. Mol. Biol. 11: 259-301.
Kornmann et al. (1998), "Role of fibroblast growth factors and their receptors in pancreatic cancer and chronic pancreatitis." Pancreas 17: 169-75.
Parthiban et al. (2007), "Computational modeling of protein mutant stability: analysis and optimization of statistical potentials and structural features reveal insights into prediction model development," BMC Struct. Biol. 7:54.
Ledley (1996), "Pharmaceutical Approach to Somatic Gene Therapy." Pharm. Res. 13(11): 1595-161.
Lewis et al. (1997), "Angiogenesis by gene therapy: a new horizon for myocardial revascularization?" Cardiovasc. Res. 135: 490-497.
Liu et al. (2007), "FGF18 is required for early chondrocyte proliferation, hypertrophy and vascular invasion of the growth plate." Dev. Biol. 302: 80-91.
Mahairas et al. (1999), "Sequence-tagged connectors: a sequence approach to mapping and scanning the human genome." PNAS 96(17): 9739-9744.
Mikkelsen (1993), "Interpreting sequence motifs: a cautionary note," Trends Genet. 9(5): 15.
Nakamura et al. (1995), "The murine lymphotoxin-beta receptor cDNA: isolation by the signal sequence trap and chromosomal mapping," Genomics 30(2): 312-19.
Ngo et al. (1994), "Computational complexity, protein structure prediction, and the Levinthal paradox," in The Protein Folding Problem and Tertiary Structure Prediction, Merz & Le Grand ed., Birkhauser: Boston, pp. 491-495.
Niyogi (1969), "The influence of chain length and base composition on the specific association of oligoribonucleotides with denatured deoxyribonucleic acid," J. Biol. Chem. 244(6): 1576-81.
Peus and Pittelkow (1996), "Growth factors in hair organ development and the hair growth cycle." Dermatol. Clin. 14:559-72.
Phillips (2001), "The challenge of gene therapy and DNA delivery." J. Pharm. Pharmacology 53: 1169-1174.
Francis at al. (1992), "Protein modification and fusion proteins," Focus on Growth Factors 3:4-10.
Podolsky (1997), "Healing the epithelium: solving the problem from two sides." J. Gastroenterol. 32: 122-6.
Polejaeva at al. (2000), "New advances in somatic cell nuclear transfer: application in transgenesis," Theriogenology 53(1): 117-26.
Plotnikov et al. (2000), "Crystal Structures of Two FGF-FGFR Complexes Reveal the Determinants of Ligand-Receptor Specificity," Cell 101: 413-24.
Ratajczak (1997), "Fibroblast growth factors and early hemopoietic cell development." Leuk. Lymphoma 27: 221-9.
Rulicke et al. (2000), "Germ line transformation of mammals by pronuclear microinjection," Exp. Physiol. 85(6): 589-601.
Skolnick et al. (2000), "From genes to protein structure and function: novel applications of computational approaches in the genomic era," Trends Biotechnol. 18(1): 34-39.
Smallwood et al. (1996), "Fibroblast Growth Factor (FGF) homologous factors: new members of the FGF family implicated in nervous system development", PNAS 93: 9850-9857.
Smith et al. (1997), "The challenges of genome sequence annotation or 'The devil is in the details,'" Nat. Biotechnol. 15(12):1222-23.
Verma et al. (1997), "Gene therapy—promises,problems and prospects." Nature 389: 239-242.

Wang et al. (1999), "Rapid analysis of gene expression (RAGE) facilitates universal expression profiling." Nuc. Acids Res. 27: 4609-4618.
Webster (1997), "Growth factors and myelin regeneration in multiple sclerosis." Mult. Scler. 3:113-20.
Yamaoka and Itakura (1999), "Development of pancreatic islets (review)." Int. J. Mol. Med. 3: 247-61.
Remington's Pharmaceutical Sciences (18th Ed., A.R. Gennaro, ed., Mack Publishing Company 1990).
Rudolph et al., 1997, "Folding proteins," Protein Function: A Practical Approach (Creighton, ed., New York, IRL Press) 57-99.
Sambrook, et al. Molecular Cloning: A Laboratory Manual (Cold Spring Harbor Laboratory Press, 1989).
Zola, Monoclonal Antibodies: A Manual of Techniques 147-158 (CRC Press, Inc.,1987).
The ADHR consortium (2000), "Autosomal dominant hypophosphataemic rickets is associated with mutations in FGF23." Nature Genetics 26: 345-348.
Arner et al. (2008) "FGF21 attenuates lipolysis in human adipocytes—A possible link to improved insulin sensitivity" FEBS Letters 582: 1725-1730.
Artuc et al. (1999), "Mast cells and their mediators in cutaneous wound healing—active participants or innocent bystanders?" Exp. Dermatol. 8: 1-16.
Bayer et al., 1990, "Protein biotinylation" Meth. Enz. 184: 138-63.
Beck and Podolsky (1999), "Growth factors in inflammatory bowel disease." Inflamm. Bowel Dis. 5: 44-60.
Bishop (1996), "Chromosomal insertion of foreign DNA," Reprod. Nutr. Dev. 36(6): 607-18.
Bork et al. (1996), "Go hunting in sequence databases but watch out for the traps," Trends Genet. 12(10): 425-27.
Bork et al. (1998), "Predicting functions from protein sequences—where are the bottlenecks?" Nature Genetics 18(4): 313-18.
Bork (2000), "Powers and pitfalls in sequence analysis: the 70% hurdle," Genome Res. 10(4): 398-400.
Branch (1998), "A good antisense molecule is hard fo find." Trends Biochem Sci. 23(2): 45-50.
Brenner (1999), "Errors in genome annotation," Trends Genet. 15(4): 132-33.
Brodeur et al., Monoclonal Antibody Production Techniques and Applications 51-63 (Marcel Dekker, Inc., 1987).
Bruggermann et al., (1993), "Designer mice: the production of human antibody repertoires in transgenic animals" Year in Immuno. 7: 33.
Capon et al., (1989), "Designing CD4 immunoadhesins for AIDS therapy" Nature 337: 525-31.
Debernardez Clark E., (1998), "Refolding of recombinant proteins" Curr. Opin. Biotechnol. 9: 157-63.
Cunha et al. (1996), "Keratinocyte growth factor as mediator of mesenchymal-epithelial interactions in the development of androgen target organs," Semin Cell Dev Biol 7: 203-210.
Dailey, et al. (2005), "Mechanisms underlying differential responses to FGF signaling," Cytokine & Growth Factor Reviews 16:233-247.
Doerks et al. (1998), "Protein annotation: detective work for function prediction," Trends Genet. 14(6): 248-50.
Ebadi et al. (1997), "Neurotrophins and their receptors in nerve injury and repair." Neurochem. Int. 30: 347-74.
Econs and McEnery (1997) "Autosomal dominant hypophosphatemic rickets/osteomalacia: clinical characterization of a novel renal phosphate-wasting disorder," J Clin Endocrinol Metab 82:674-681.
Ellison et al., (1982), "The nucleotide sequence of a human immunoglobulin Cγ1 gene" Nucleic Acids Res. 10: 4071-9).
Eppstein, et al.,(1985) "Biological activity of liposome-encapsulated murine interferon γ is mediated by cell membrane receptor" Proc. Natl. Acad. Sci. U.S.A. 82:3688-92.
Freiberg & Zhu, (2004) "Polymer microspheres for controlled drug release" Int. J. Pharm. 282:1-18.
Galzie Z, et al, (1997), "Fibroblast Growth Factors and their Receptors", Biochemistry and Cell Biology 75(6): 669-685.
Goldfarb (1996), "Functions of fibroblast growth factors in vertebrate development," Cytokine Growth Factor Rev. 7 (4): 311-325.

Hoogenboom et al., 1991, "By-passing immunisation. Human antibodies from synthetic repertoires of germline VH gene segments rearranged in vitro"J. Mol. Biol. 227:381.

Hsu et al. (1999), "Heparin Is Essential for a Single Keratinoctye Growth Factor Molecule to Bind and Form a Complex with Two Molecules of the Extracellular Domain of Its Receptor," Biochemistry 38: 2523-34.

Hull et al (1997), "Healing with basic fibroblast growth factor is associated with reduced indomethacin induced relapse in a human model of gastric ulceration," Gut 40: 204-10.

Eswarakumar, et al. (2005) "Cellular signaling by fibroblast growth factor receptors" Cytokine & Growth Factor Reviews 16: 139-149.

Ishibashi et al., 2005, "Is arginine a protein-denaturant?" Protein Expr. Purif. 42: 1-6.

Jakobovits et al., 1993, "Analysis of homozygous mutant chimeric mice: deletion of the immunoglobulin heavy-chain joining region blocks B-cell development and antibody production" Proc. Natl. Acad. Sci. U.S.A. 90: 2551-55.

Jakobovits et al., 1993, "Germ-line transmission and expression of human-derived yeast artificial chromosome"Nature 362: 255-58.

Jones et al., 1986, "Replacing the complementarity-determining regions in a human antibody with those from a mouse" Nature 321: 522-25.

Kurosu et al. (2007), "Tissue-specific Expression of Klotho and Fibroblast Growth Factor (FGF) Receptor Isoforms Determines Metabolic Activity of FGF19 and FGF21. " J. Biol. Chem. 282(37): 26687-26695.

Kharitonenkov et al. (2008), "Fibroblast Growth Factor-21 as a Therapeutic Agent for Metabolic Diseases" Biodrugs 22 1: 37-44.

Kharitonenkov et al. (2006), "The metabolic state of diabetic monkeys is regulated by FGF-21" Endocrinology. DOI:10.1210/en.2006-1168.

Kharitonenkov et al. (2005), "FGF-21 as a novel metabolic regulator." J. Clin. Invest. 115: 1627-1635.

Kohler et al., 1975, "Continuous cultures of fused cells secreting antibody of predefined specificity"Nature 256: 495-97.

Kozbor, 1984, "A human hybrid myeloma for production of human monoclonal antibodies" J. Immunol. 133: 3001.

Laemmli, 1970, "Cleavage of structural proteins during the assembly of the head of bacteriophage T4" Nature 227: 680-85.

Langer et al., 1981, "Biocompatibility of polymeric delivery systems for macromolecules" J. Biomed. Mater. Res. 15: 267-277.

Langer et al., 1982, "Controlled release of macromolecules" Chem. Tech. 12: 98-105.

Mannall et al., 2007, "Factors affecting protein refolding yields in fed-batch and batch-refolding system" Biotechnol. Bioeng. 97: 1523-34.

Marks et al., 1991, "By-passing immunization. Human antibodies from V-gene libraries displayed on phage" J. Mol. Biol. 222: 581-597.

Mohammadi, et al. (2005), "Structural basis for fibroblast growth factor receptor activation" Cytokine & Growth Factor Reviews 16: 107-137.

Morrison et al., 1985, "Chimeric human antibody molecules: mouse antigen-binding domains with human constant region domains" Proc. Natl. Acad. Sci. U.S.A. 81: 6851-55.

Moyers et al. (2007), "Molecular Determinants of FGF-21 Activity-Synergy and Cross-Talk with PPARγ Signaling" J. Cell. Phys. 210: 1-6.

Beenken, Andrew and Mohammadi, Moosa (2009), "The FGF family: biology, pathophysiology and therapy," Nature Reviews 8:235-253.

R&D Systems, Catalog No. MAB3738, Lot No. XRU02 (2007). "Monoclonal anti-human/mouse Klotho Beta antibody," XP-002624719.

Suzuki, Masashi et al. (2008) "Beta-klotho is required for fibroblast growth factor (FGF) 21 signaling through FGF receptor (FGFR) 1c and FGFR3c," Mol. Endocr. 22(4):1006-1014.

Li, Xiaofan, et al. (2009) "Inhibition of lipolysis may contribute to the acute regulation of plasma FFA and glucose by FGF21 in ob/ob mice," FEBS Letters 583: 323-03234.

Wu, Xinle et al. (2008) "C-terminal tail of FGF19 determines its specificity toward klotho co-receptors," J. Biol. Chem. 283 (48): 33304-33309.

Wu, Xinle et al. (2007) "Co-receptor requirements for fibroblast growth factor-19 signaling," J. Biol. Chem. 282 (40): 29069-29072.

Wu, Xinle et al. (2009) "Selective activation of FGFR4 by an FGF19 variant does not improve glucose metabolism in ob/ob mice." PNAS 106 (34): 14379-14384.

Wu, Xinle et al. (2010) "Separating mitogenic and metabolic activities of fibroblast growth factor 19 (FGF19)," PNAS 107 (32): 14158-14163.

Xu, Jing et al. (2009) "Acute glucose-lowering and insulin-sensitizing action of FGF21 in insulin-resistant mouse models-association with liver and adipose tissue effects," Am. J. Physiol. Endocrinol. Metab. 297: E1105-E1114.

Fukumoto, Seiji, (2008) "Actions and mode of FGF19 subfamily members," Endocr. J. 55:23-31.

Goetz et al., "BBA—Molecular and Cell Biology of Lipids," Mol. Cell. Biol. 27:3417-28 (2007).

Kharitonenkov et al. (2007), "The metabolic state of diabetic monkeys is regulated by FGF-21" Endocrinology 148:774-781.

Ogawa. Y., et al. (2005) "Klotho is required for metabolic activity of fibroblast growth factor 21," Proc. Natl. Acad. Sci. USA 104:7432-7437.

Schlessinger, J. et al., "Crystal Structure of a Ternary FGF-FGFR-Heparin Complex Reveals a Dual Role for Heparin in FGFR Binding and Dimerization," Mol. Cell 6:743-50 (2000).

Ogawa et al. (2007), "Beta-Klotho is required for metabolic activity of fibroblast growth factor 21." PNAS 104(18) 7432-7437.

Wu, X. et al. (2010) "FGF19 induced hepatocyte proliferation is mediated through FGFR4 activation." J. Biol. Chem. 285:5165.

* cited by examiner

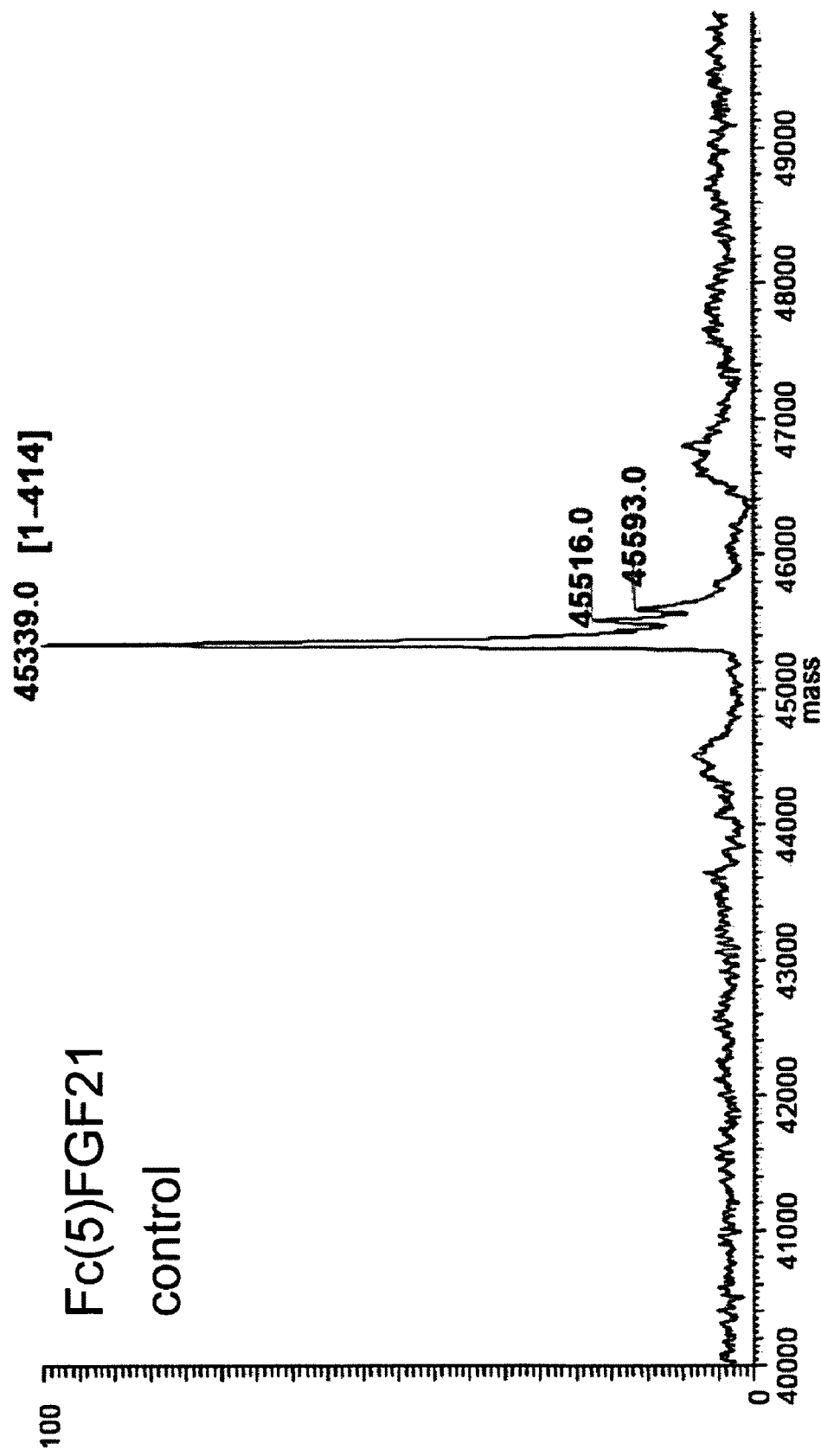

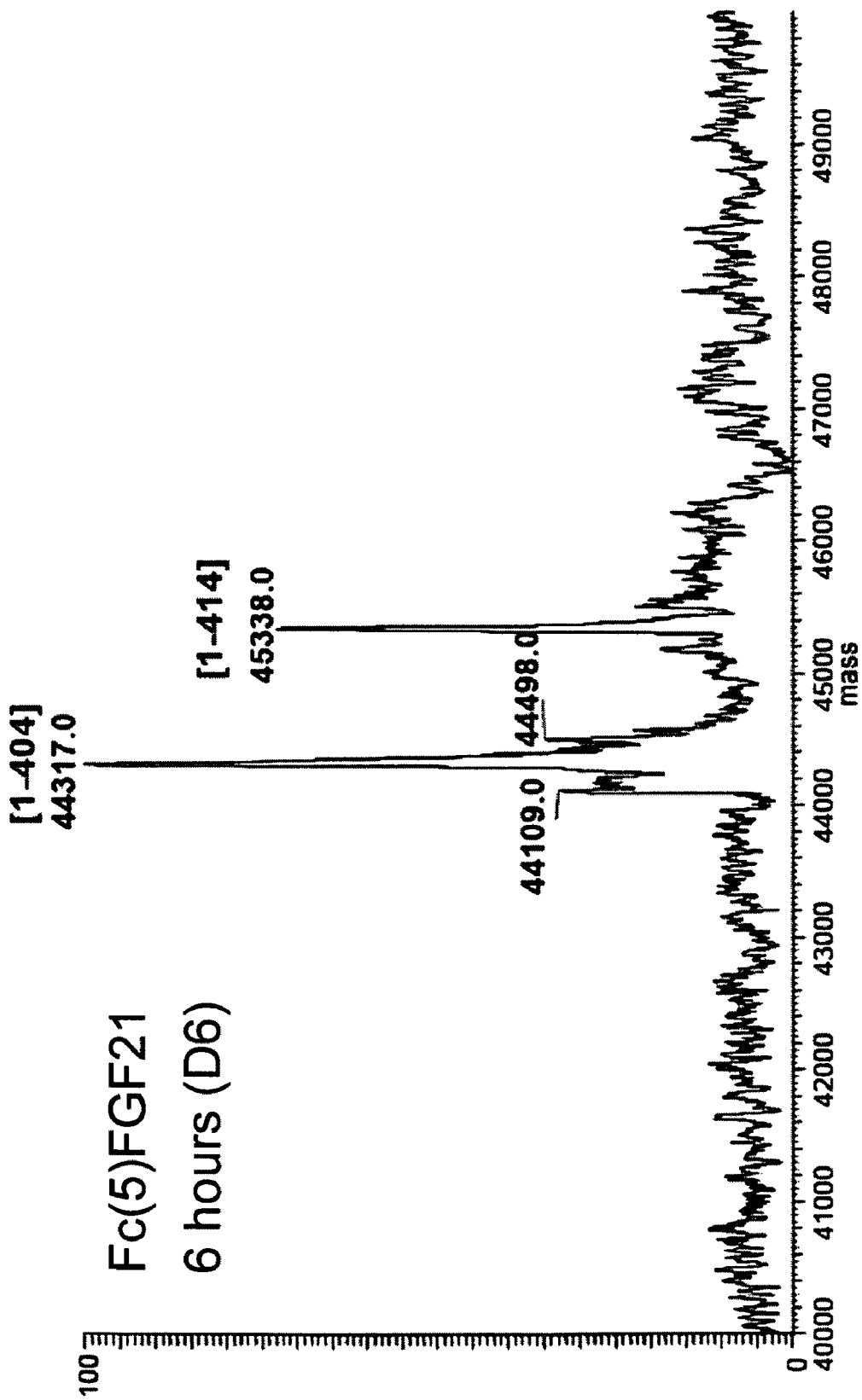

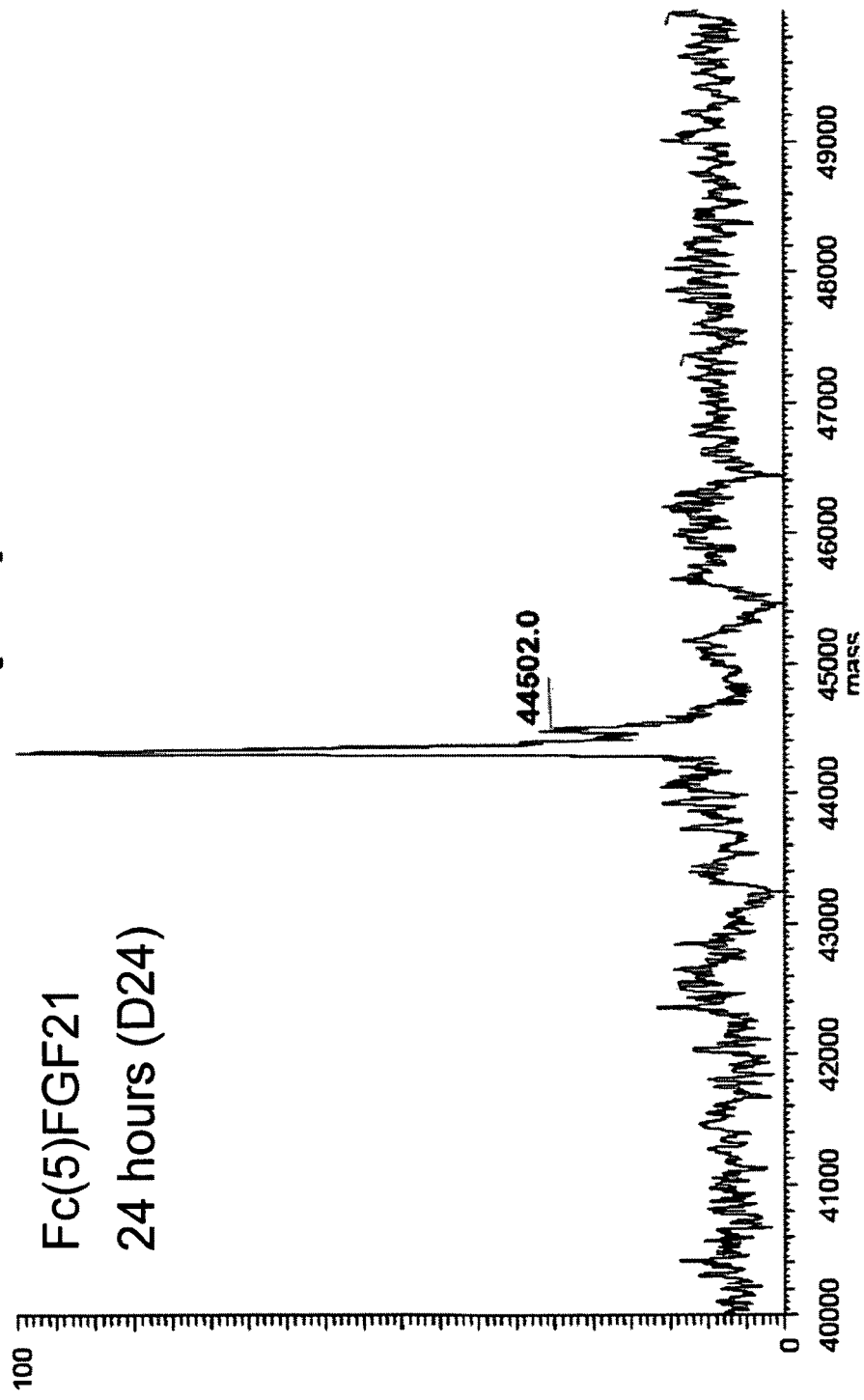

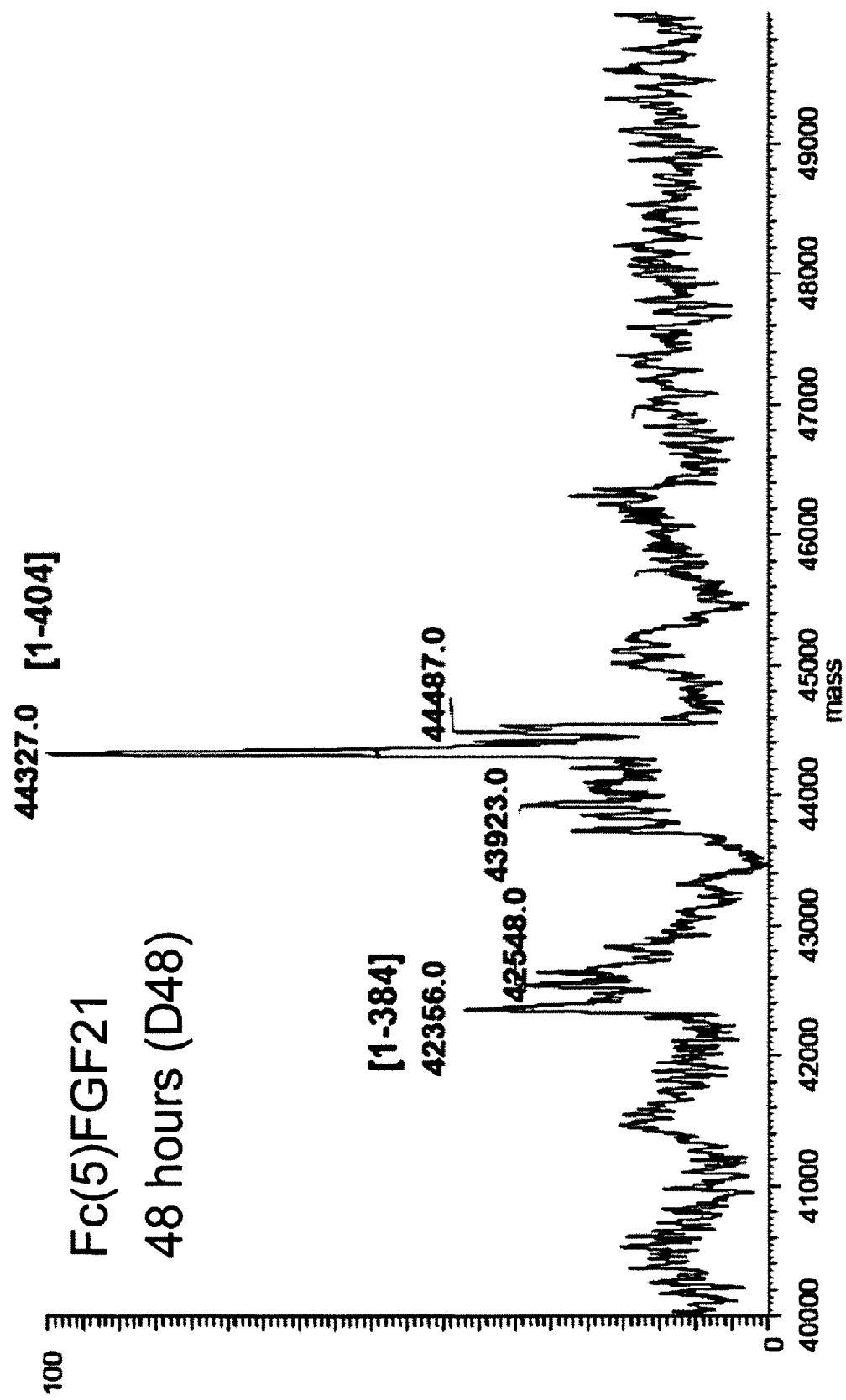

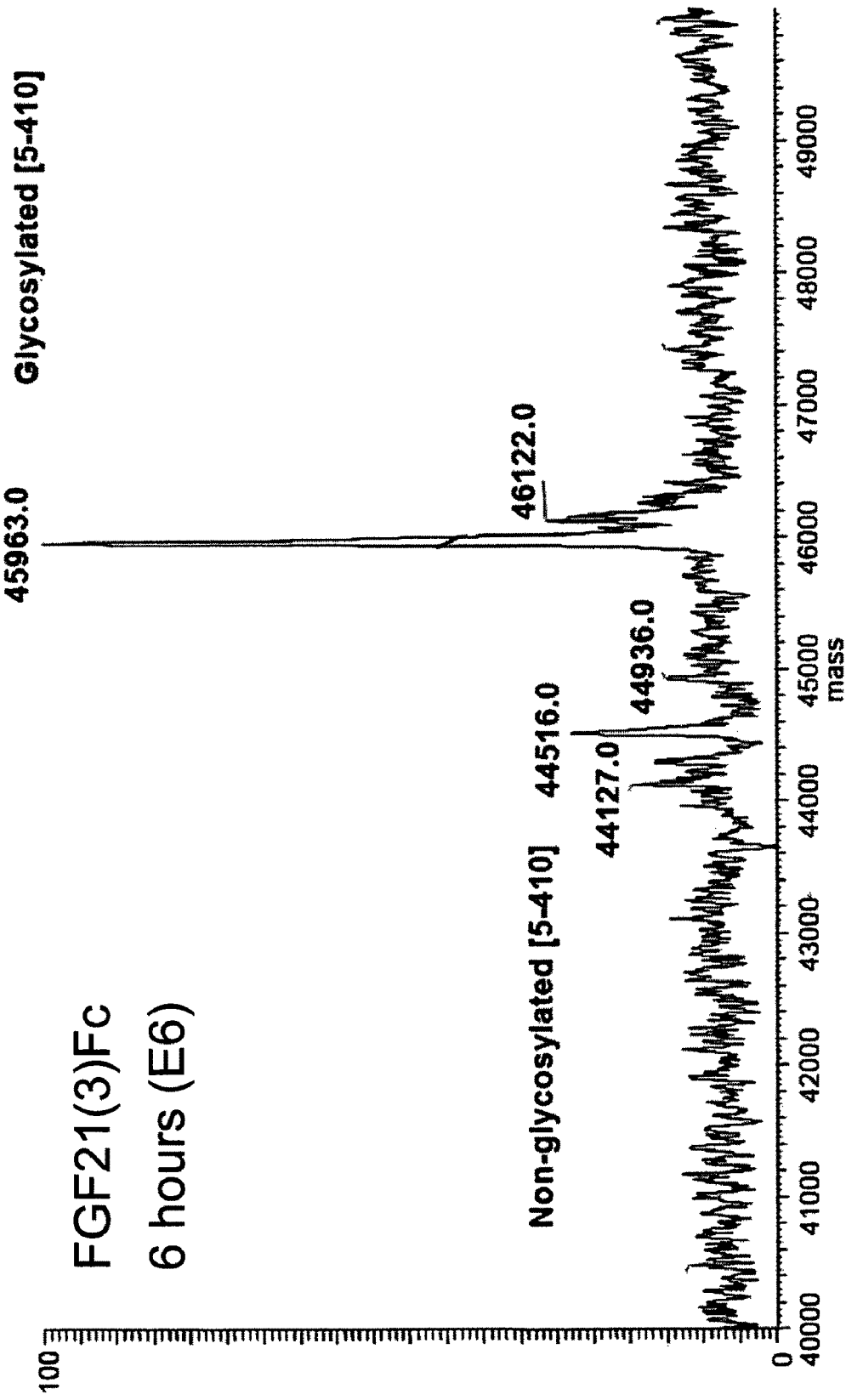

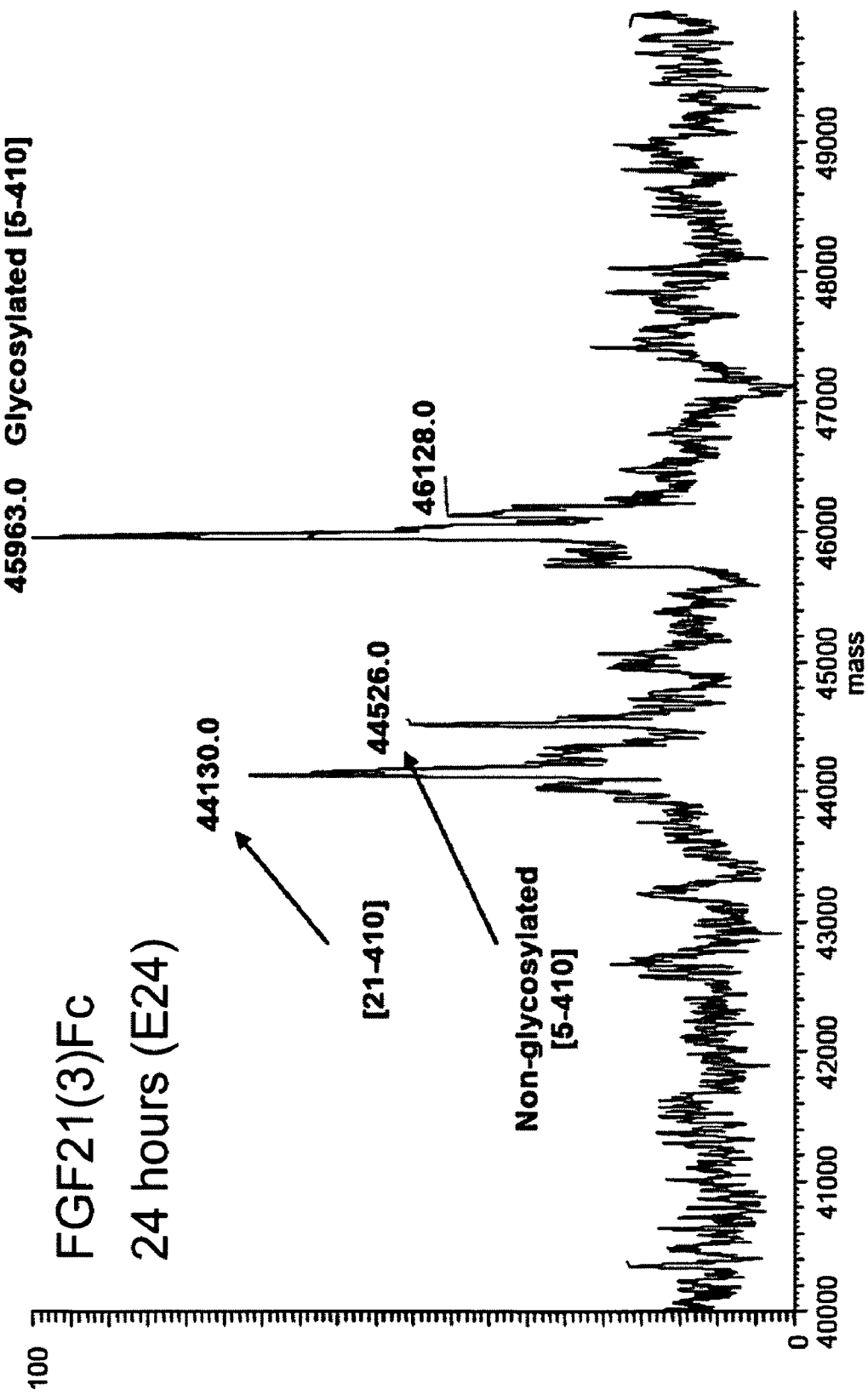

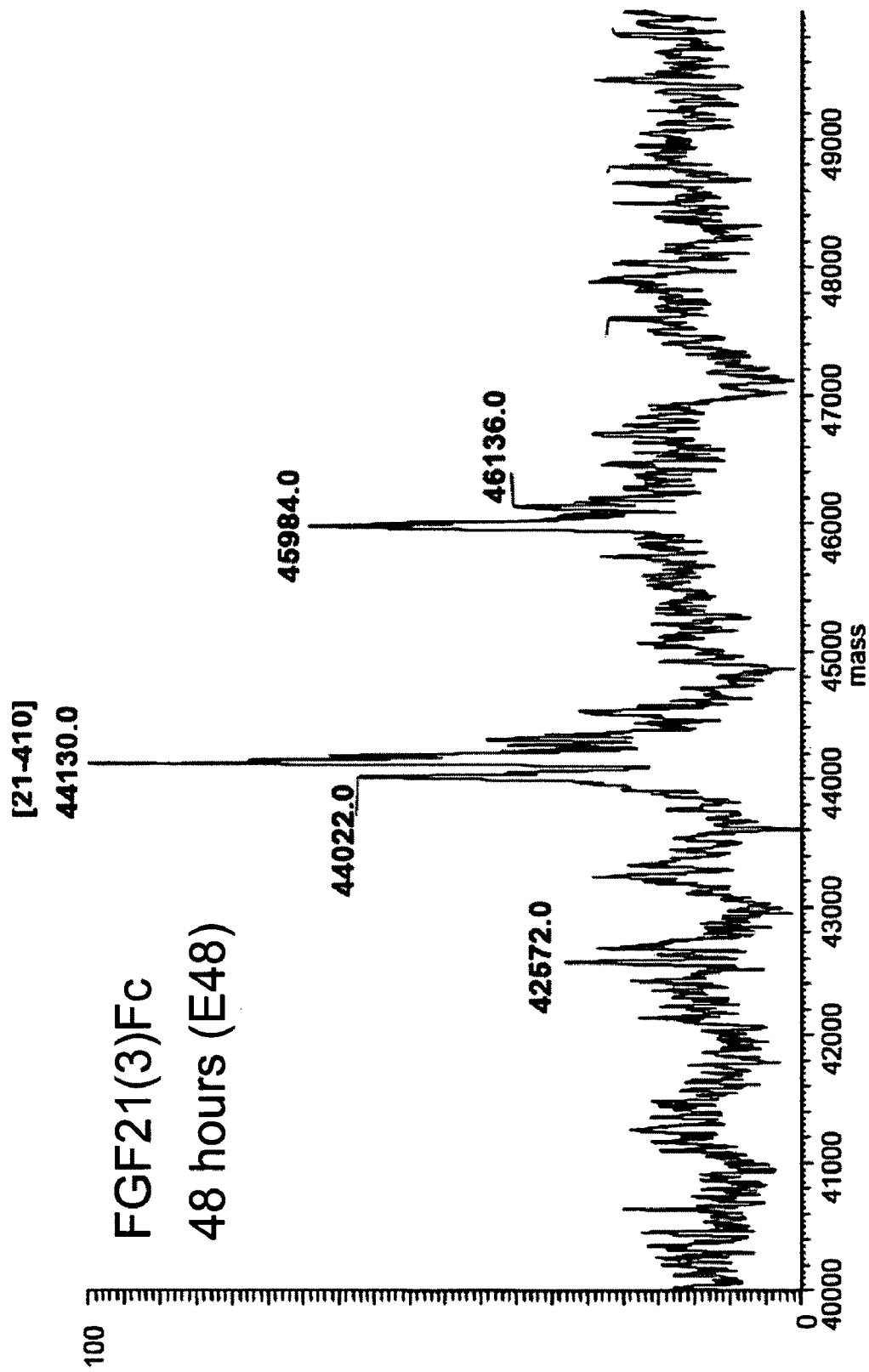

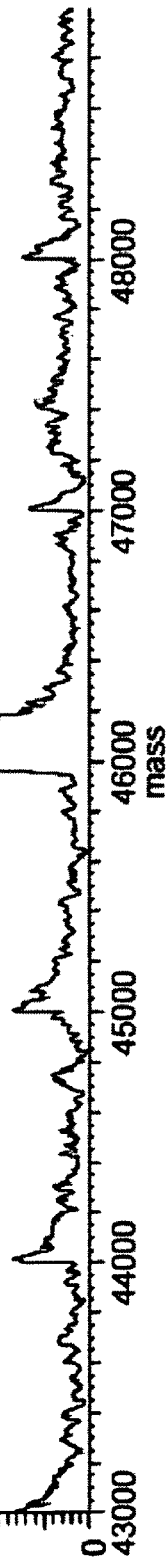

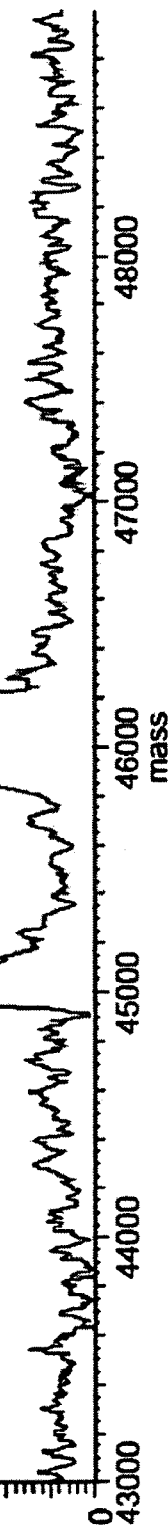

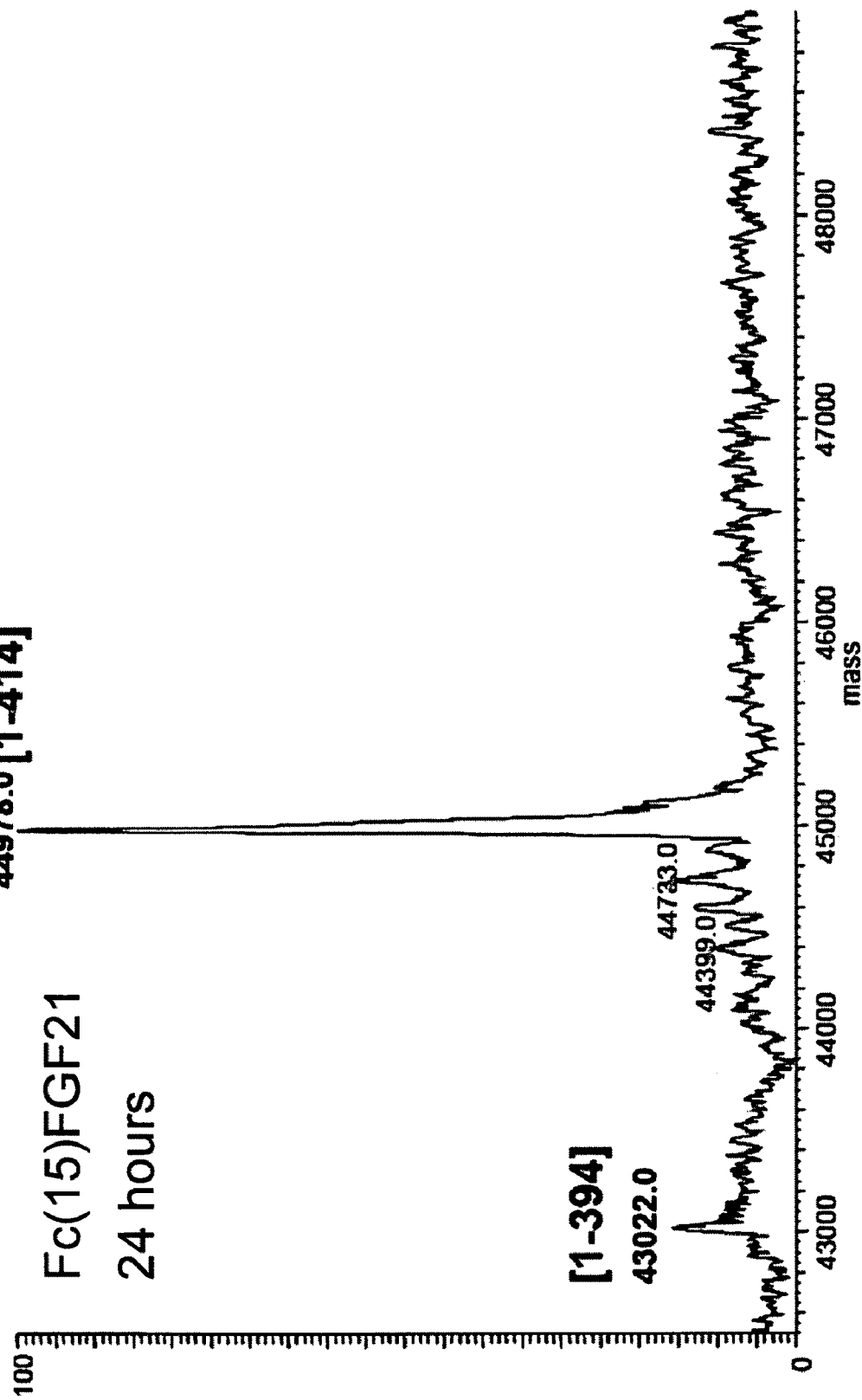

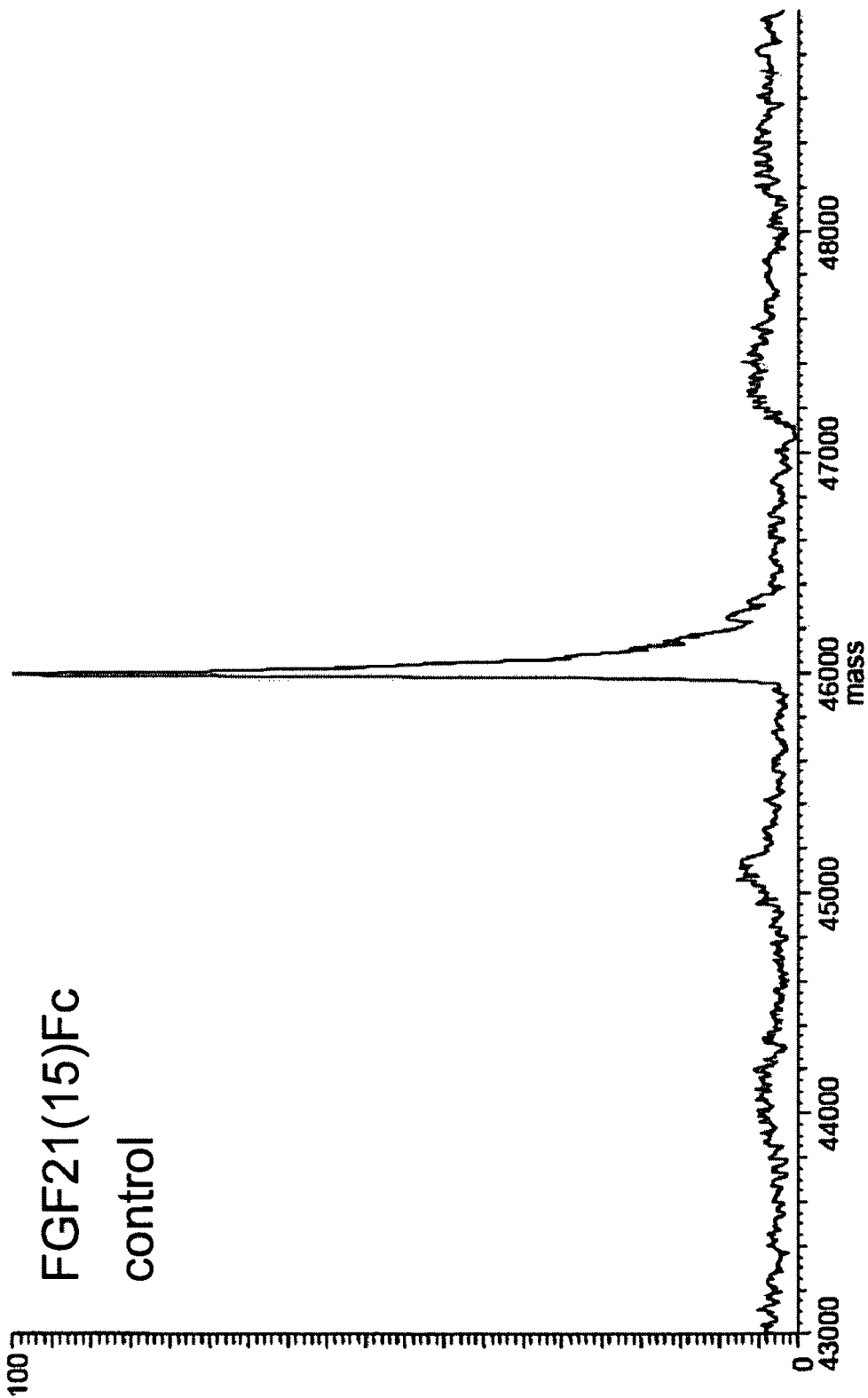

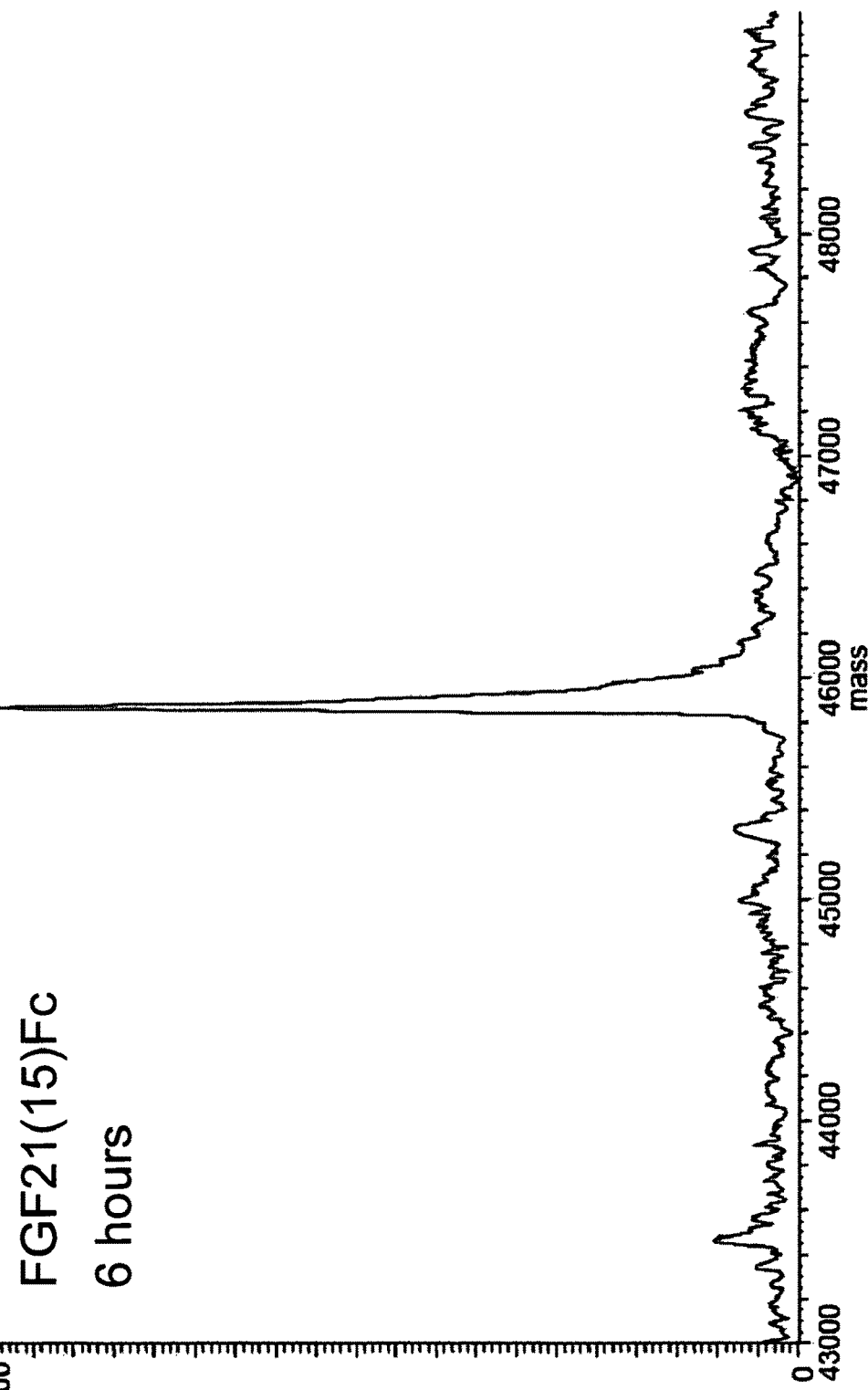

FIG. 10A

Fc(15)FGF21

MDKTHTCPPCPAPELLGGPSVFLFPPKPKDTLMISRTPEVTCVVVDV
SHEDPEVKFNWYVDGVEVHNAKTKPREEQYNSTYRVVSVLTVLHQD
WLNGKEYKCKVSNKALPAPIEKTISKAKGQPREPQVYTLPPSRDELT
KNQVSLTCLVKGFYPSDIAVEWESNGQPENNYKTTPPVLDSDGSFFL
YSKLTVDKSRWQQGNVFSCSVMHEALHNHYTQKSLSLSPGKGGGG
GSGGGGSGGGGSHPIPDSSPLLQFGGQVRQRYLYTDDAQQTEAHLEI
REDGTVGGAADQSPESLLQLKALKPGVIQILGVKTSRFLCQRPDGAL
YGSLHFDPEACSFRELLLEDGYNVVQSEAHGLPLHLPGNKSPHRDP
APRGPARFLPLPGLPPAPPEPPGILAPQPPDVGSSDPLSMVGPSQG
RSPSYAS

← 24 hrs (15%) [1-394]
48 hrs (40%)

← 6 hrs (35%) [1-414]
24 hrs (85%)
48 hrs (60%)

FIG. 10B

24 hrs (35%) [6-423]
48 hrs (20%)

24 hrs (25%) [22-423]
48 hrs (65%)

MHPIPDSSPLLQFGGQVRQRYLYTDDAQQTEAHLEIREDGTVGGAA
DQSPESLLQLKALKPGVIQILGVKTSRFLCQRPDGALYGSLHFDPEA
CSFRELLEDGYNVYQSEAHGLPLHLPGNKSPHRDPAPRGPARFLP
LPGLPPAPPEPPGILAPQPPDVGSSDPLSMVGPSQGRSPSYASGGG
GGSGGGGSGGGGSDKTHTCPPCPAPELLGGPSVFLFPPKPKDTLMIS
RTPEVTCVVVDVSHEDPEVKFNWYVDGVEVHNAKTKPREEQYNSTY
RVVSVLTVLHQDWLNGKEYKCKVSNKALPAPIEKTISKAKGQPREP
QVYTLPPSRDELTKNQVSLTCLVKGFYPSDIAVEWESNGQPENNYK
TTPPVLDSDGSFFLYSKLTVDKSRWQQGNVFSCSVMHEALHNHYTQ
KSLSLSPGK

6 hrs (100%) [1-423]

FGF21(15)Fc

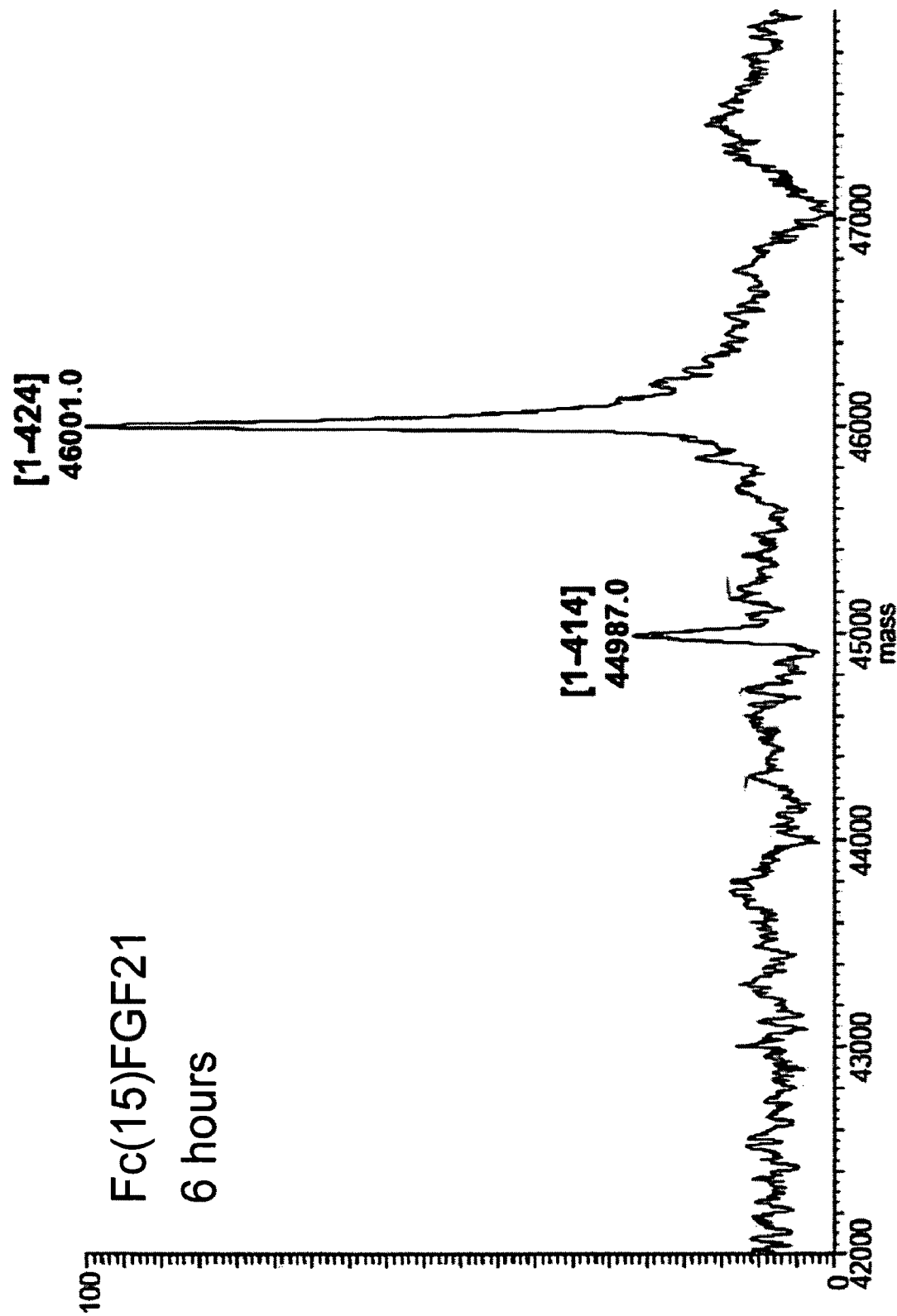

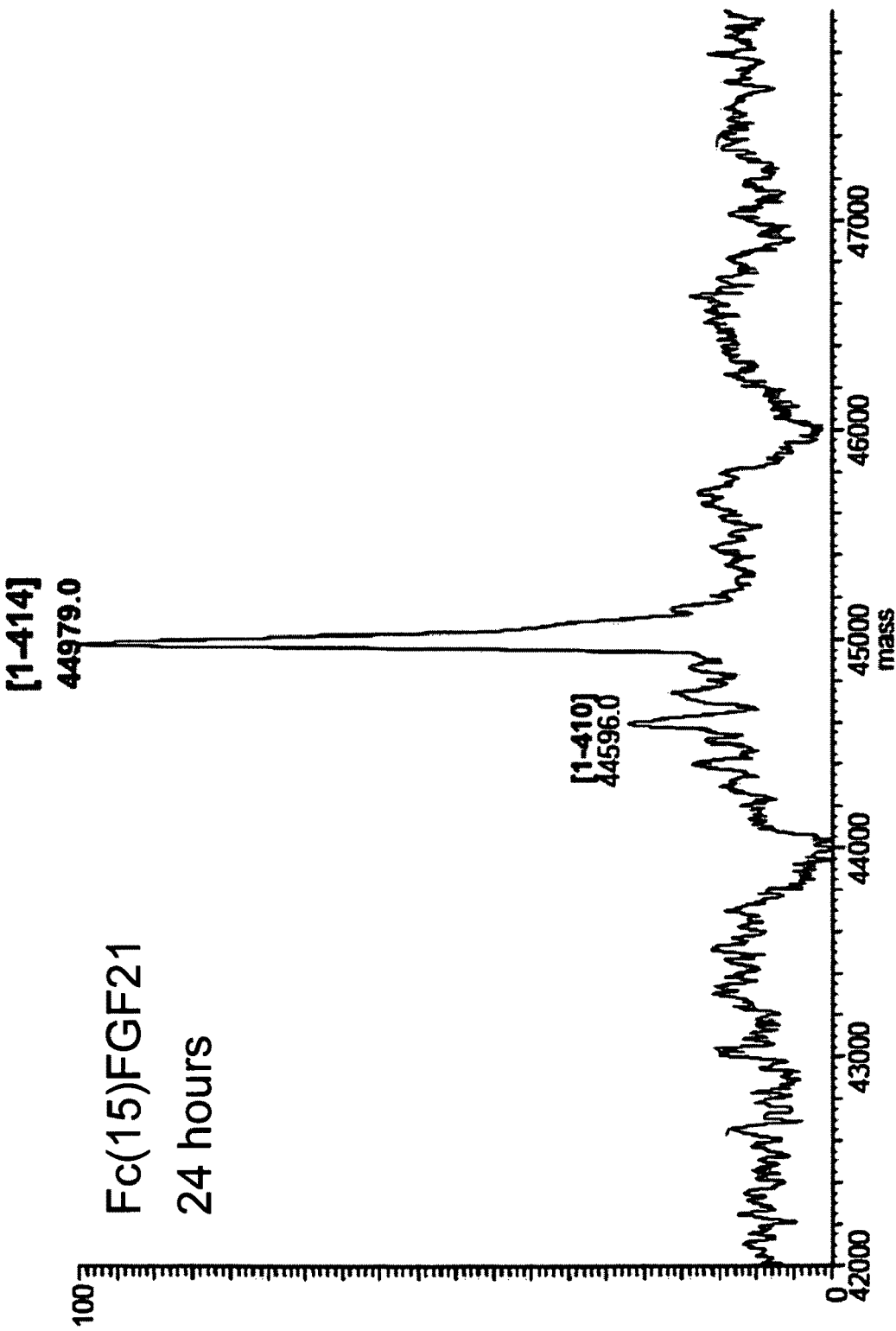

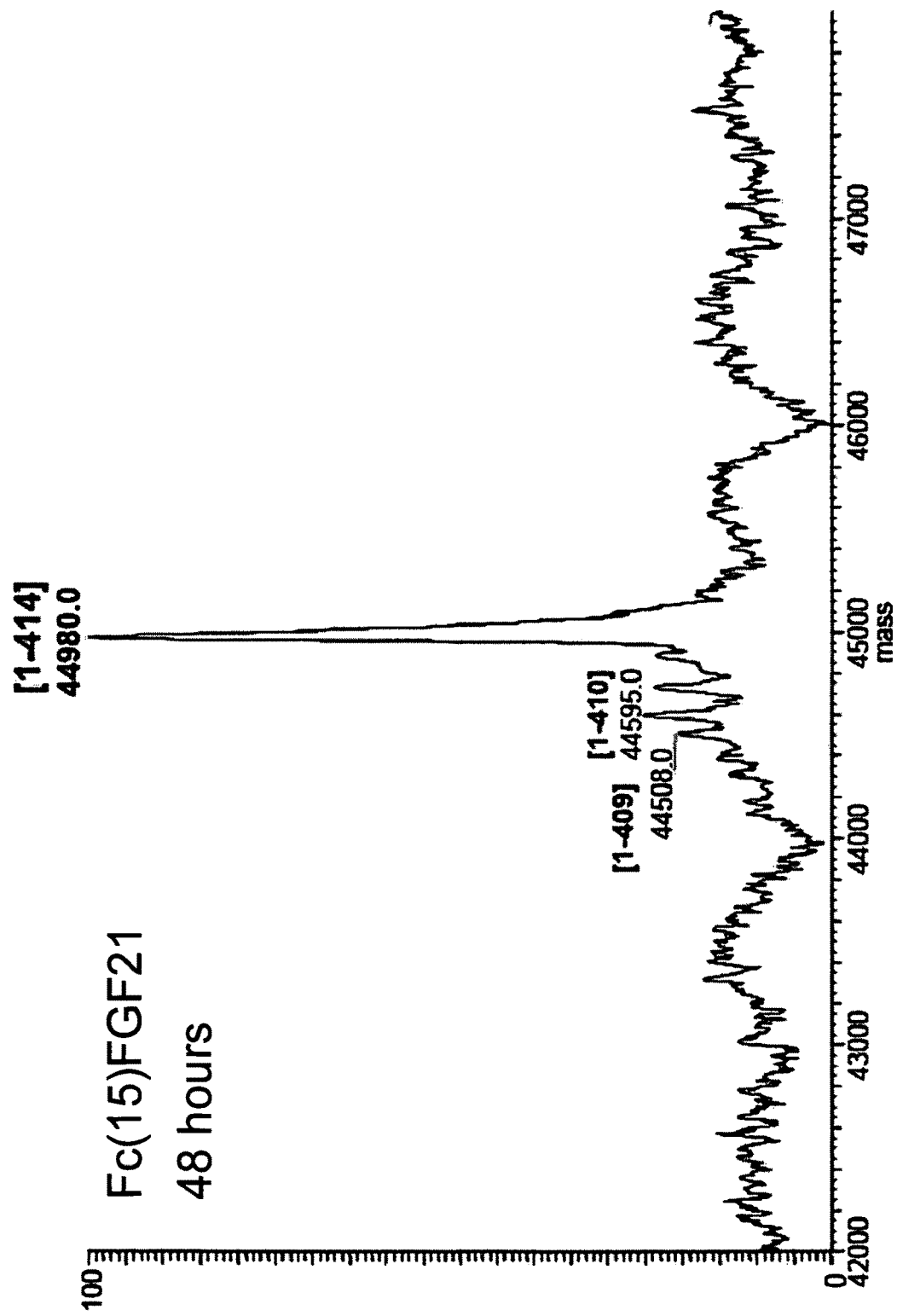

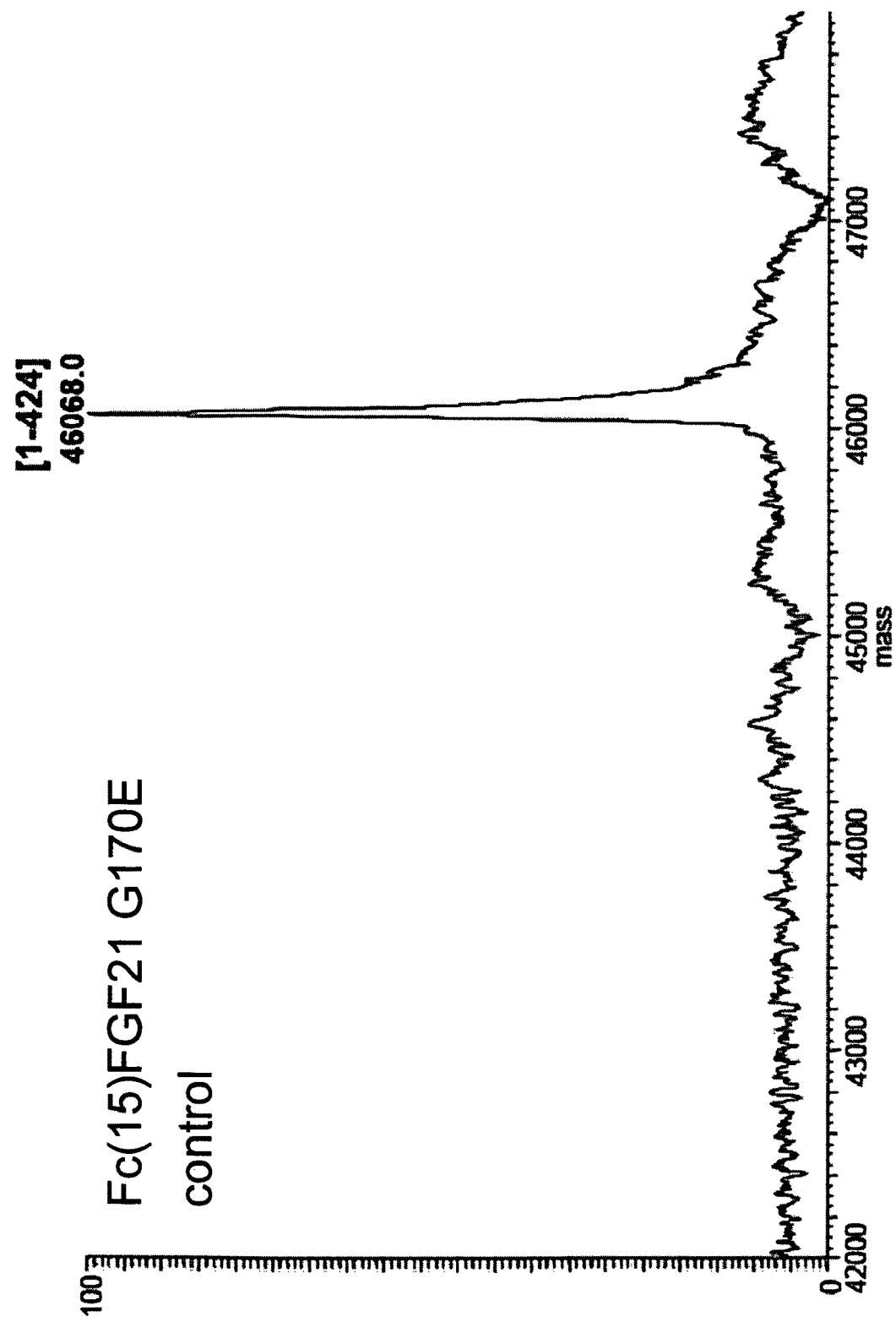

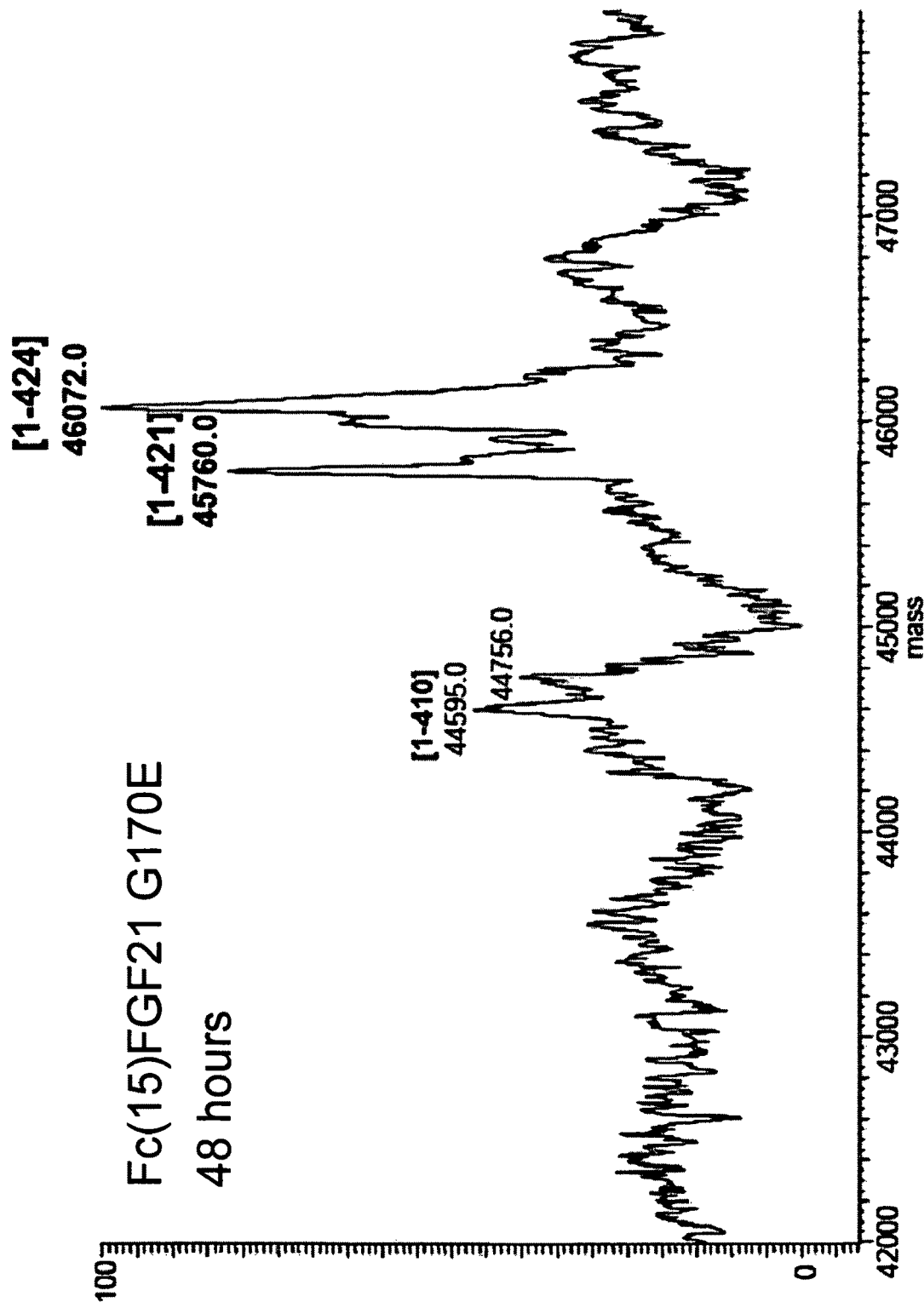

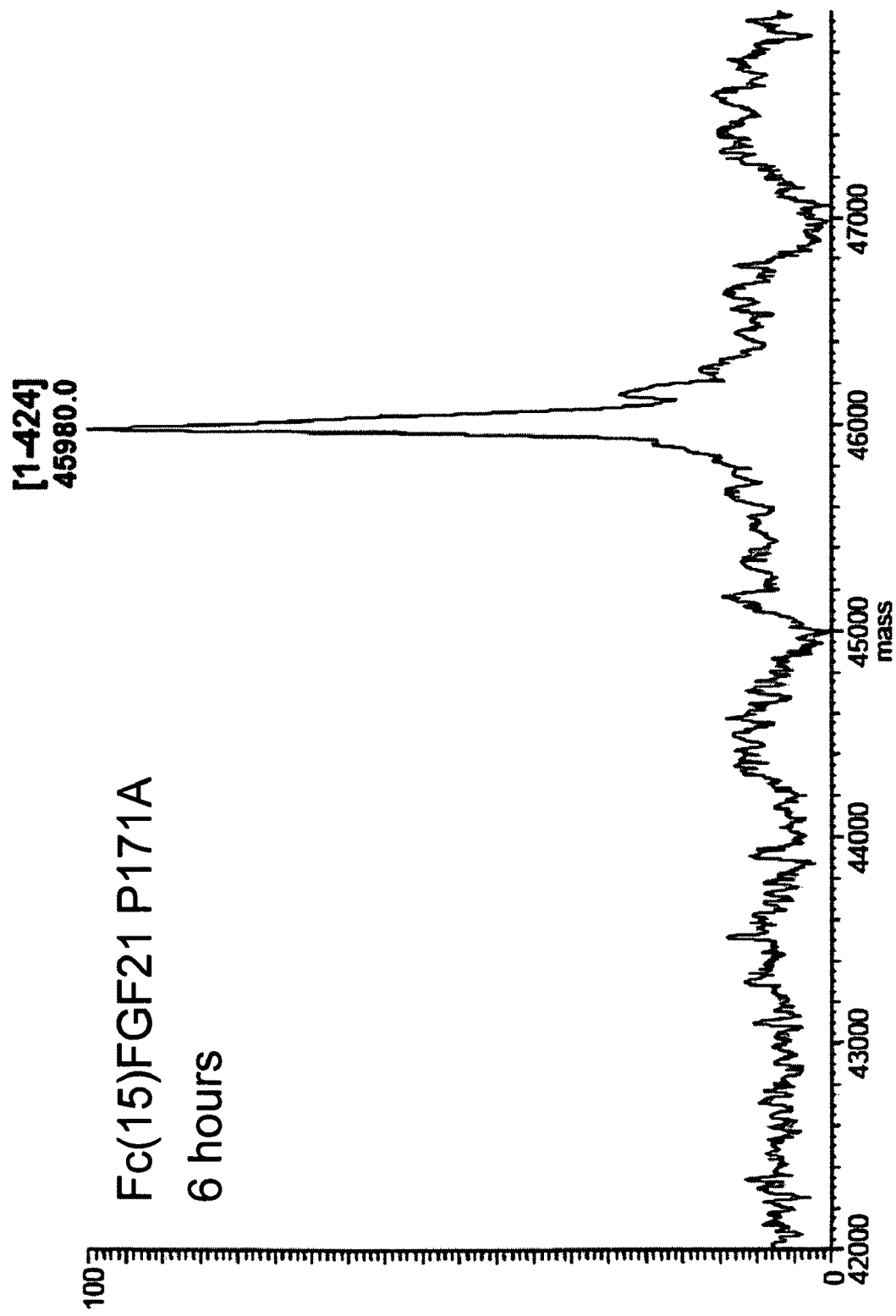

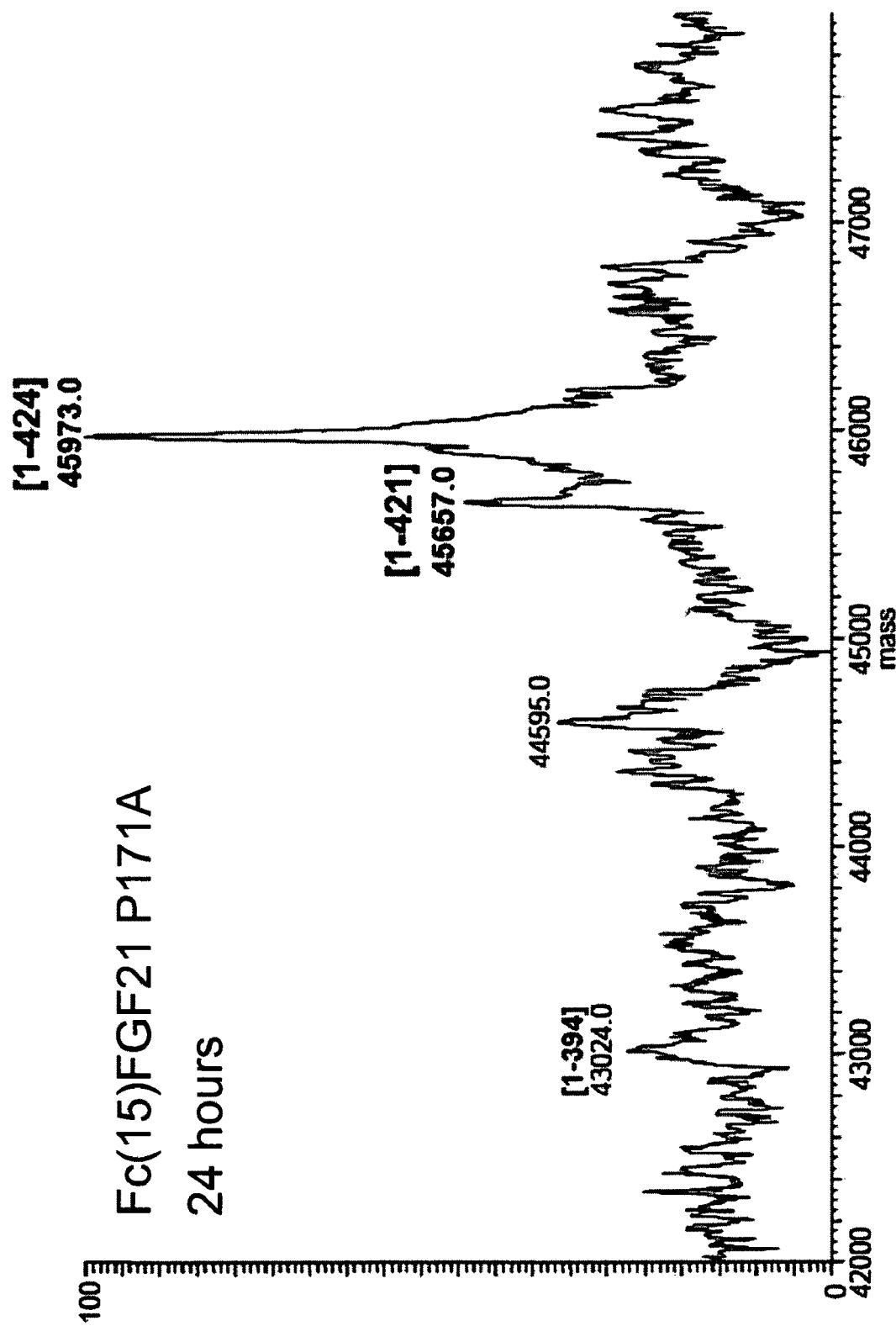

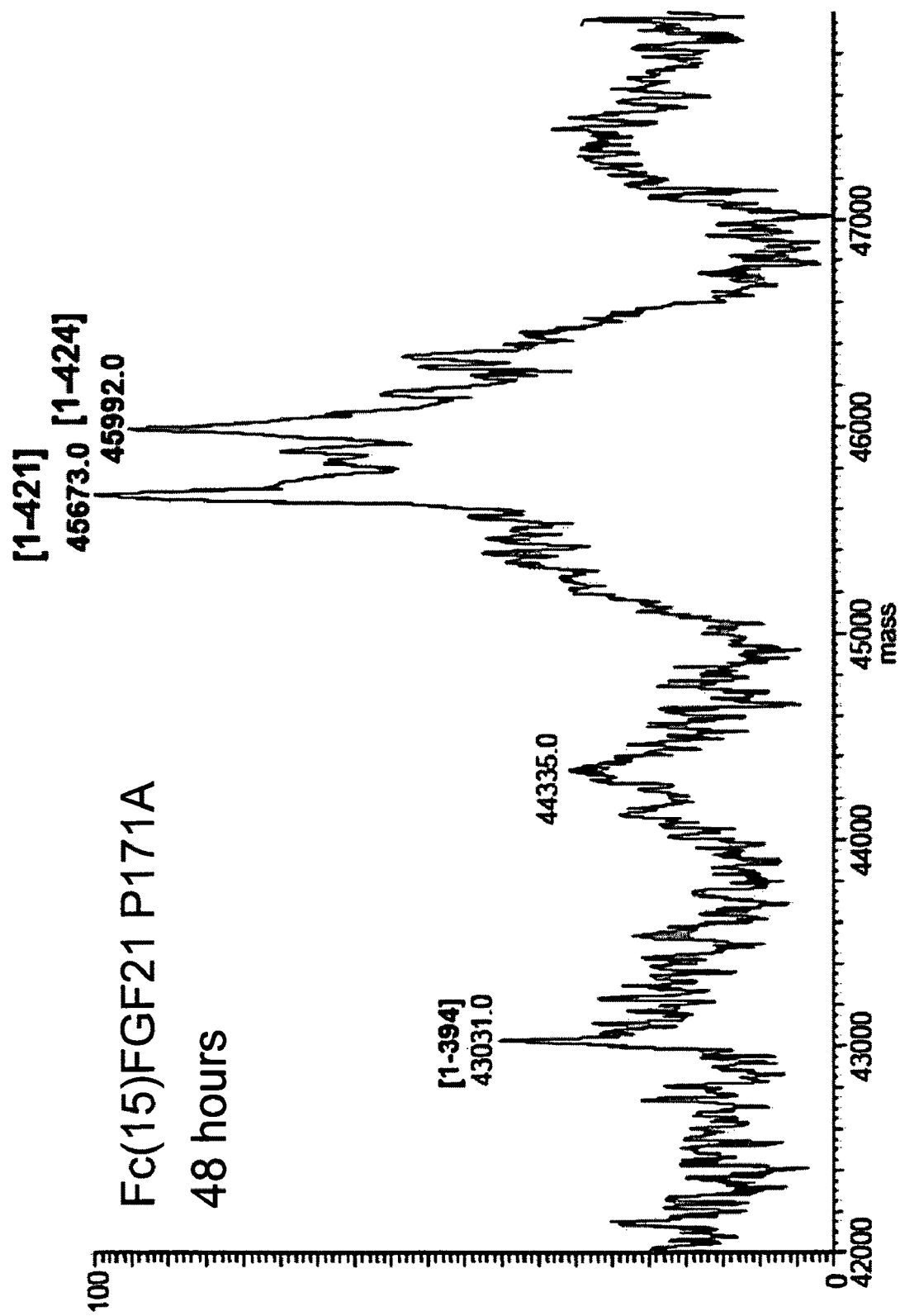

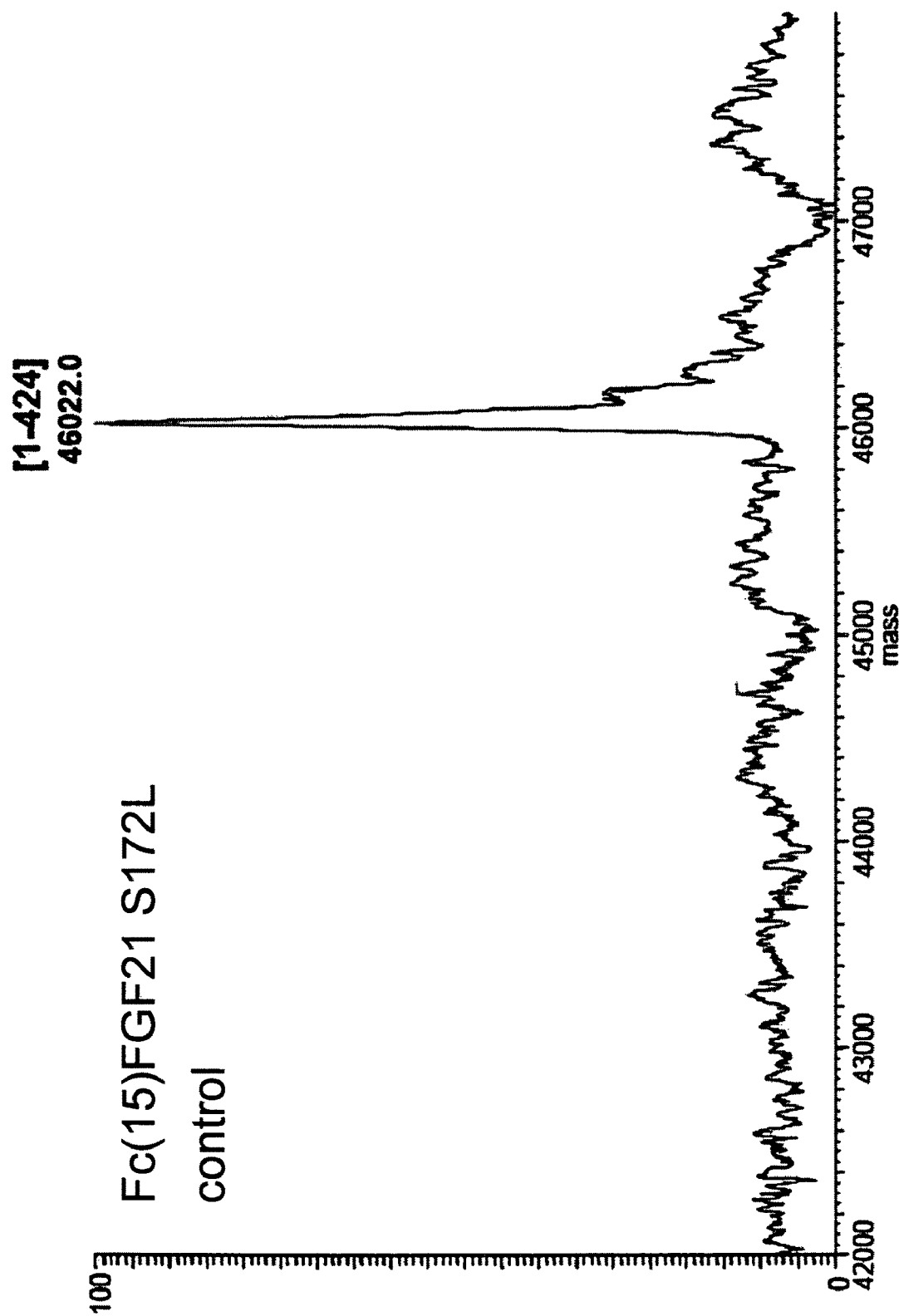

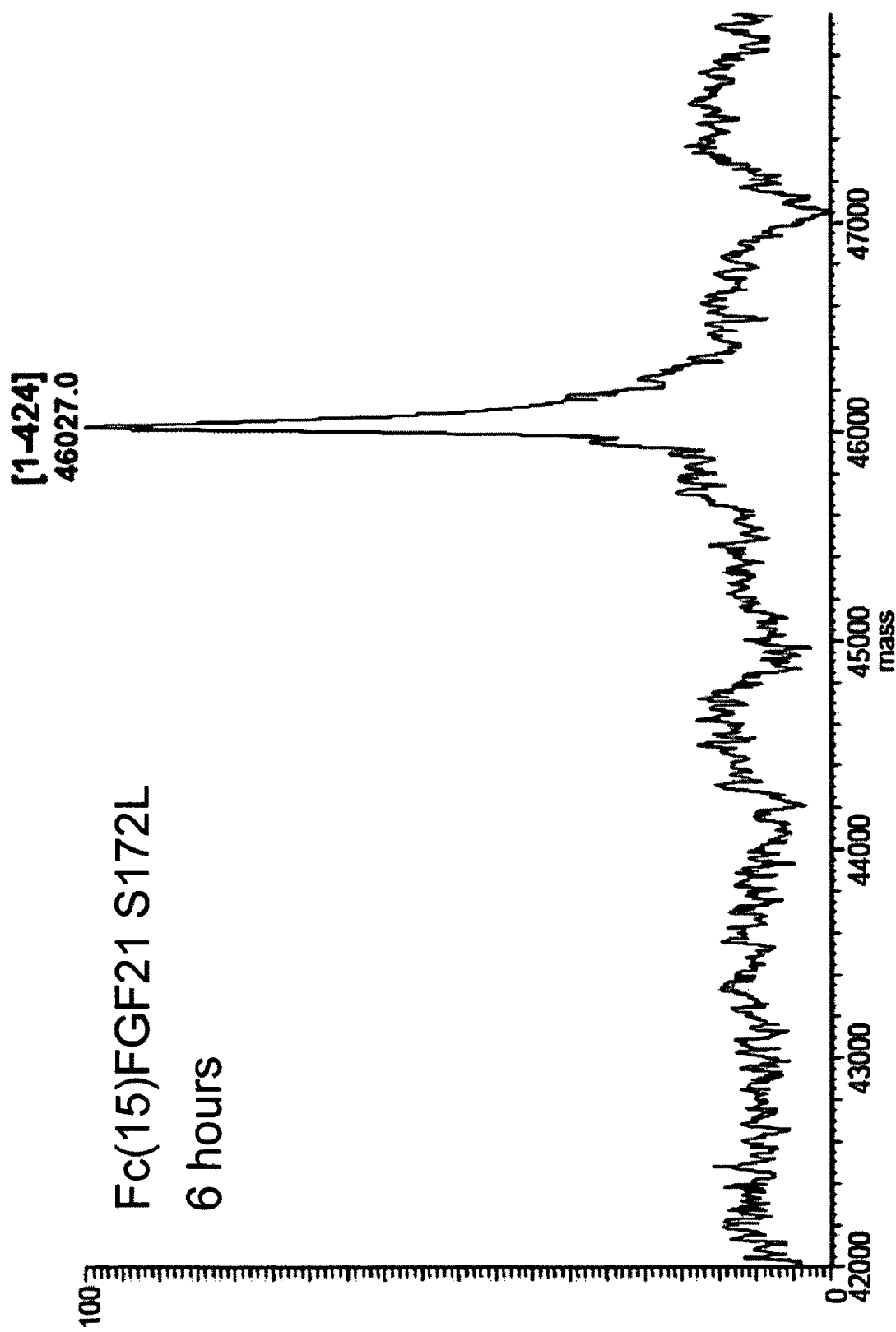

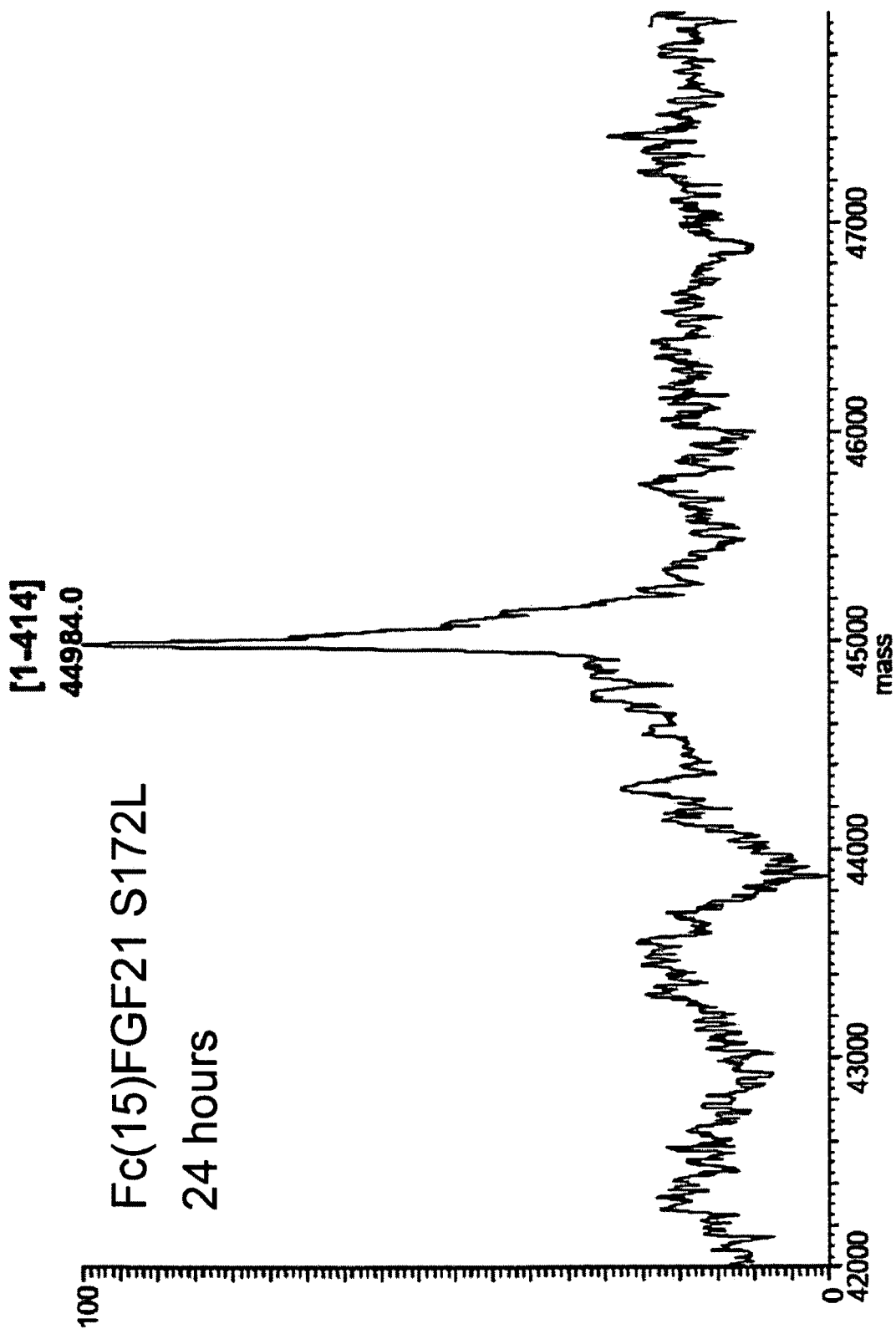

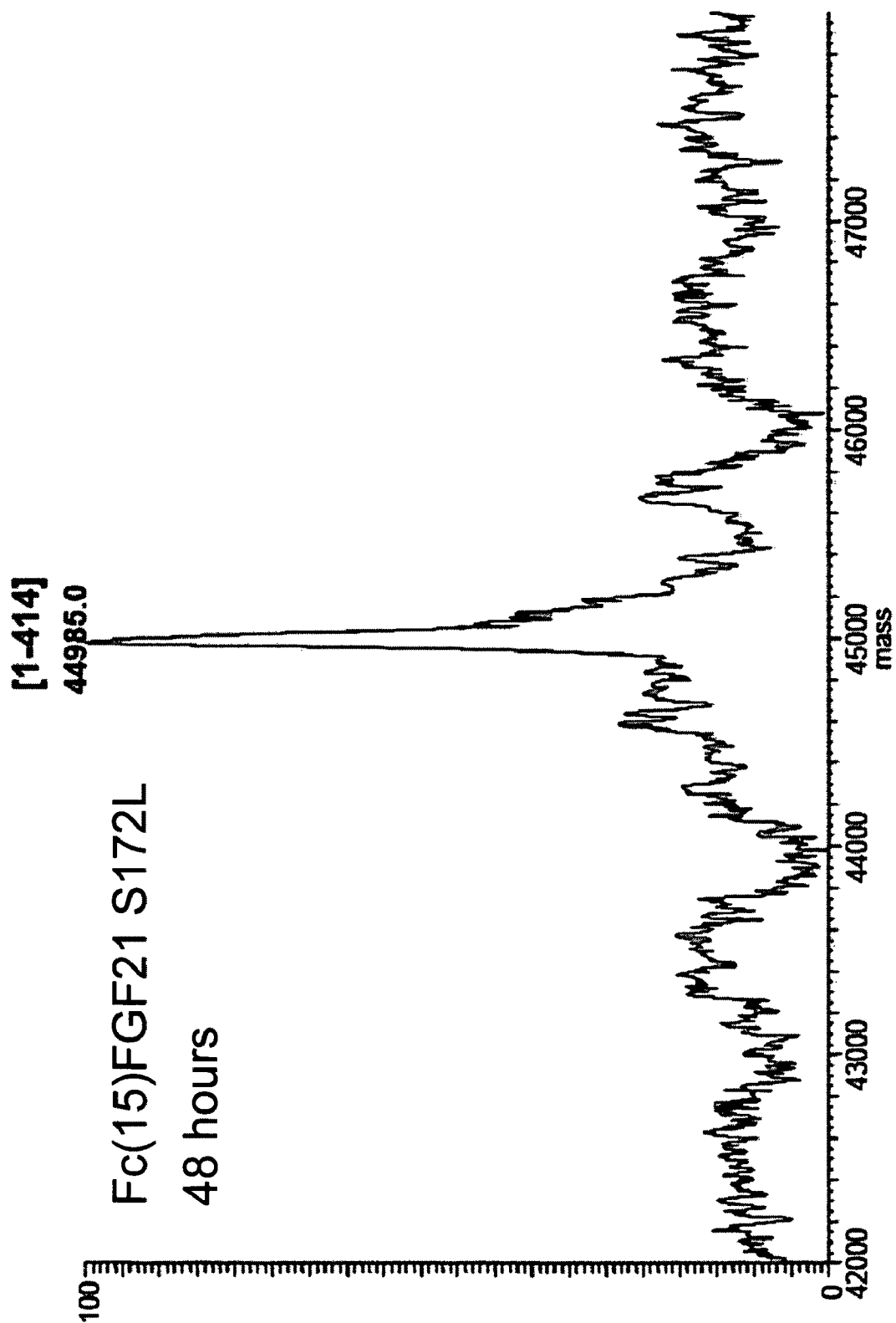

FIG. 23A

Fc(15)FGF21

MDKTHTCPPCPAPELLGGPSVFLFPPKPKDTLMISRTPEVTCVVVDV
SHEDPEVKFNWYVDGVEVHNAKTKPREEQYNSTYRVVSVLTVLHQD
WLNGKEYKCKVSNKALPAPIEKTISKAKGQPREPQVYTLPPSRDELT
KNQVSLTCLVKGFYPSDIAVEWESNGQPENNYKTTPPVLDSDGSFFL
YSKLTVDKSRWQQGNVFSCSVMHEALHNHYTQKSLSLSPGKGGGG
GSGGGGSGGGGSHPIPDSSPLLQFGGGVRQRYLYTDDAQQTEAHLEI
REDGTVGGAADQSPESLLQLKALKPGVIQILGVKTSRFLCQRPDGAL
YGSLHFDPEACSFRELLLEDGYNVVQSEAHGLPLHLPGNKSPHRDP
APRGPARFLPLPGLPPAPPEPPGILAPQPPDVGSSDPLSMVGPSQG ← 6 hrs (20%)
RSPSYAS        24 hrs (100%) [1-414]
              48 hrs (~100%)

FIG. 23B

Fc(15)FGF21 G170E

MDKTHTCPPCPAPELLGGPSVFLFPPKPKDTLMISRTPEVTCVVVDV
SHEDPEVKFNWYVDGVEVHNAKTKPREEQYNSTYRVVSVLTVLHQD
WLNGKEYKCKVSNKALPAPIEKTISKAKGQPREPQVYTLPPSRDELT
KNQVSLTCLVKGFYPSDIAVEWESNGQPENNYKTTPPVLDSDGSFFL
YSKLTVDKSRWQQGNVFSCSVMHEALHNHYTQKSLSLSPGKGGGG
GSGGGSGGGGSHPIPDSSPLLQFGGQVRQRYLYTDDAQQTEAHLEI
REDGTVGGAADQSPESLLQLKALKPGVIQILGVKTSRFLCQRPDGAL
YGSLHFDPEACSFRELLLEDGYNVYQSEAHGLPLHLPGNKSPHRDP
APRGPARFLPLPGLPPAPPEPPGILAPQPPDVGSSDPLSMVEPSQG
RSPSYAS 6 hrs (0%)
                24 hrs (20%)  [1-421]
                48 hrs (~40%)

FIG. 23C

Fc(15)FGF21 P171A

MDKTHTCPPCPAPELLGGPSVFLFPPKPKDTLMISRTPEVTCVVVDV
SHEDPEVKFNWYVDGVEVHNAKTKPREEQYNSTYRVVSVLTVLHQD
WLNGKEYKCKVSNKALPAPIEKTISKAKGQPREPQVYTLPPSRDELT
KNQVSLTCLVKGFYPSDIAVEWESNGQPENNYKTTPPVLDSDGSFFL
YSKLTVDKSRWQQGNVFSCSVMHEALHNHYTQKSLSLSPGKGGGG
GSGGGGSGGGGSHPIPDSSPLLQFGGQVRQRYLYTDDAQQTEAHLEI
REDGTVGGAADQSPESLLQLKALKPGVIQILGVKTSRFLCQRPDGAL
YGSLHFDPEACSFRELLLEDGYNVYQSEAHGLPLHLPGNKSPHRDP
APRGPARFLPLPGLPPAPPEPPGILAPQPPDVGSSDPLSMVGASQG
RSPSYAS ↑

6 hrs (0%)
24 hrs (~30%)   [1-421]
48 hrs (~50%)

FIG. 23D

Fc(15)FGF21 S172L

MDKTHTCPPCPAPELLGGPSVFLFPPKPKDTLMISRTPEVTCVVVDV
SHEDPEVKFNWYVDGVEVHNAKTKPREEQYNSTYRVVSVLTVLHQD
WLNGKEYKCKVSNKALPAPIEKTISKAKGQPREPQVYTLPPSRDELT
KNQVSLTCLVKGFYPSDIAVEWESNGQPENNYKTTPPVLDSDGSFFL
YSKLTVDKSRWQQGNVFSCSVMHEALHNHYTQKSLSLSPGKGGGG
GSGGGGSGGGGSHPIPDSSPLLQFGGQVRQRYLYTDDAQQTEAHLEI
REDGTVGGAADQSPESLLQLKALKPGVIQILGVKTSRFLCQRPDGAL
YGSLHFDPEACSFRELLLEDGYNVVQSEAHGLPLHLPGNKSPHRDP
APRGPARFLPLPGLPPAPPEPPGILAPQPPDVGSSDPLSMVGPLQG
RSPSYAS

[1-414]  6 hrs (0%)
24 hrs (100%)
48 hrs (100%)

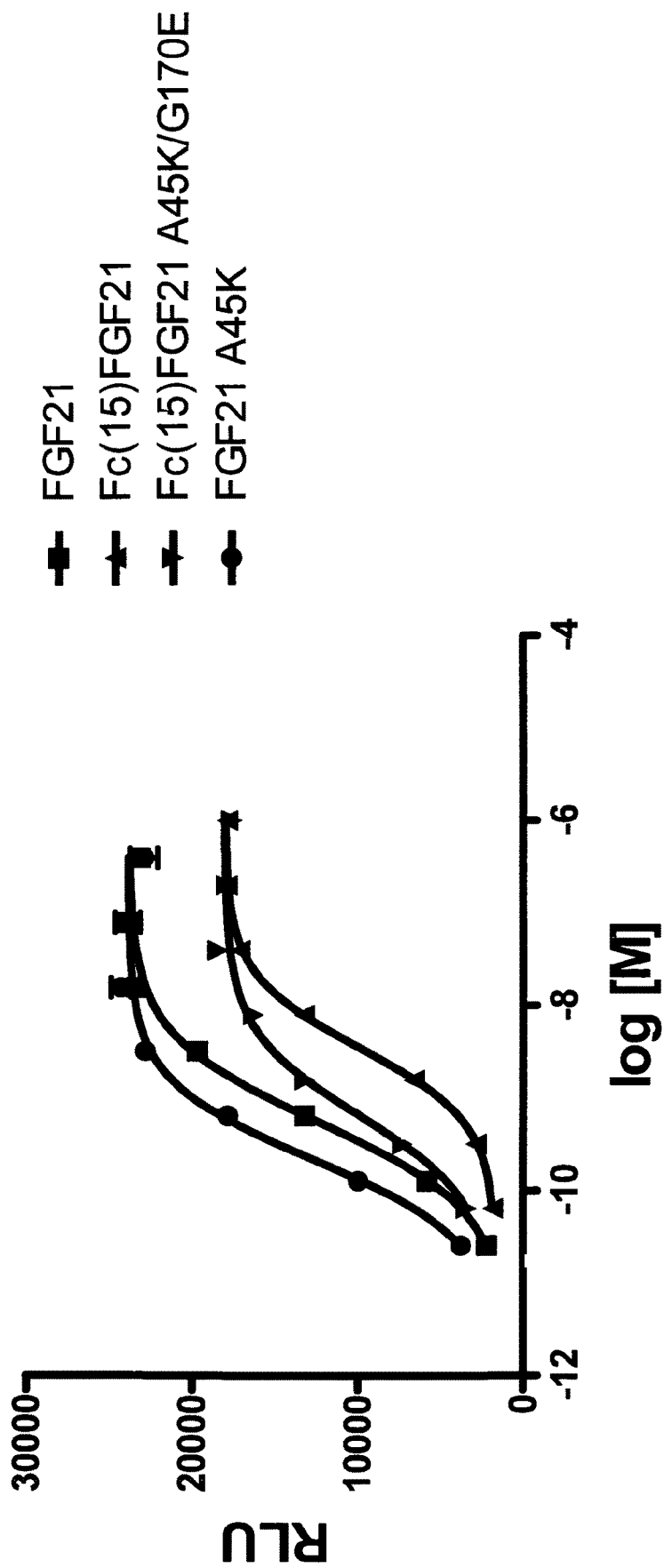

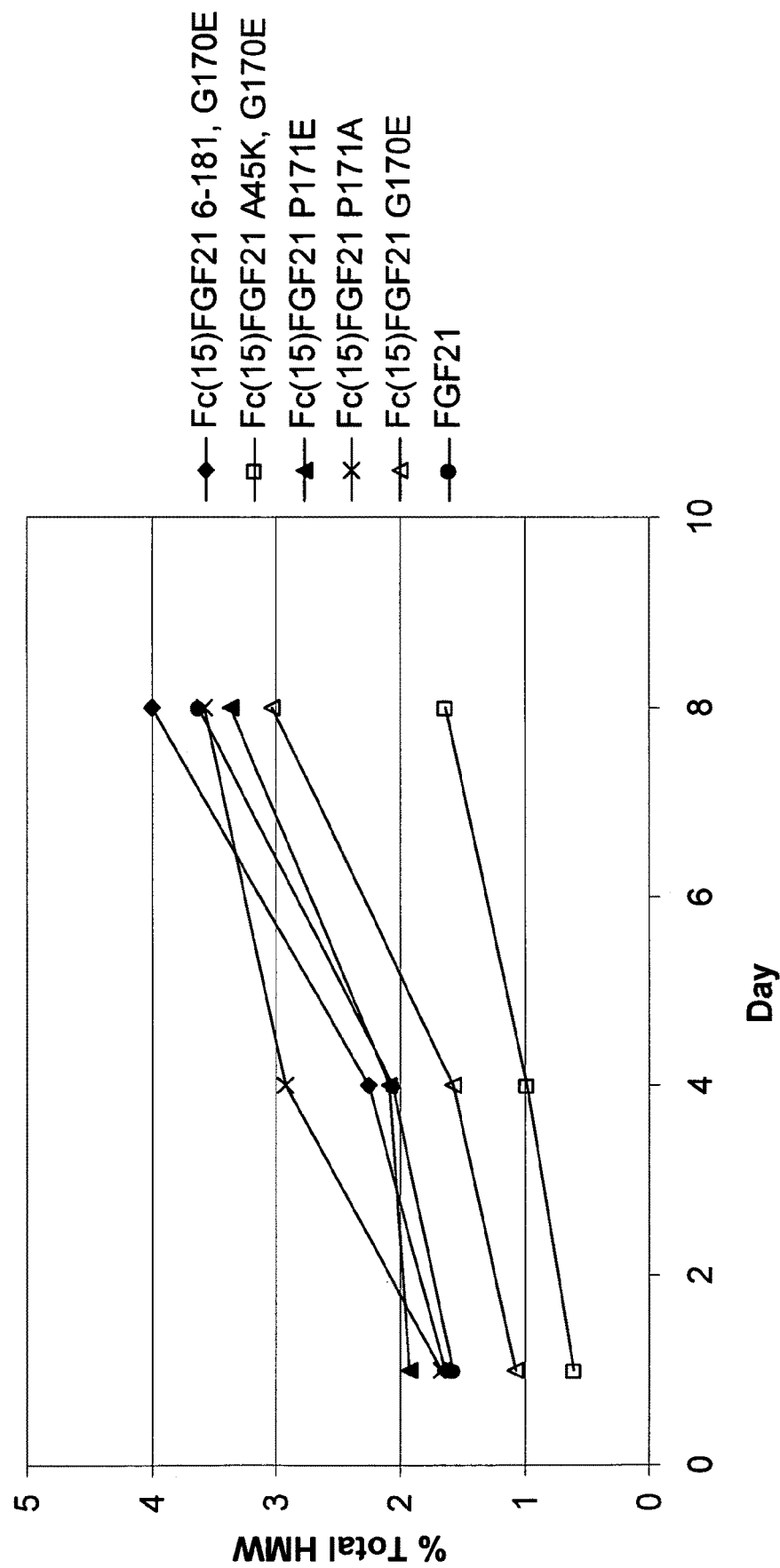

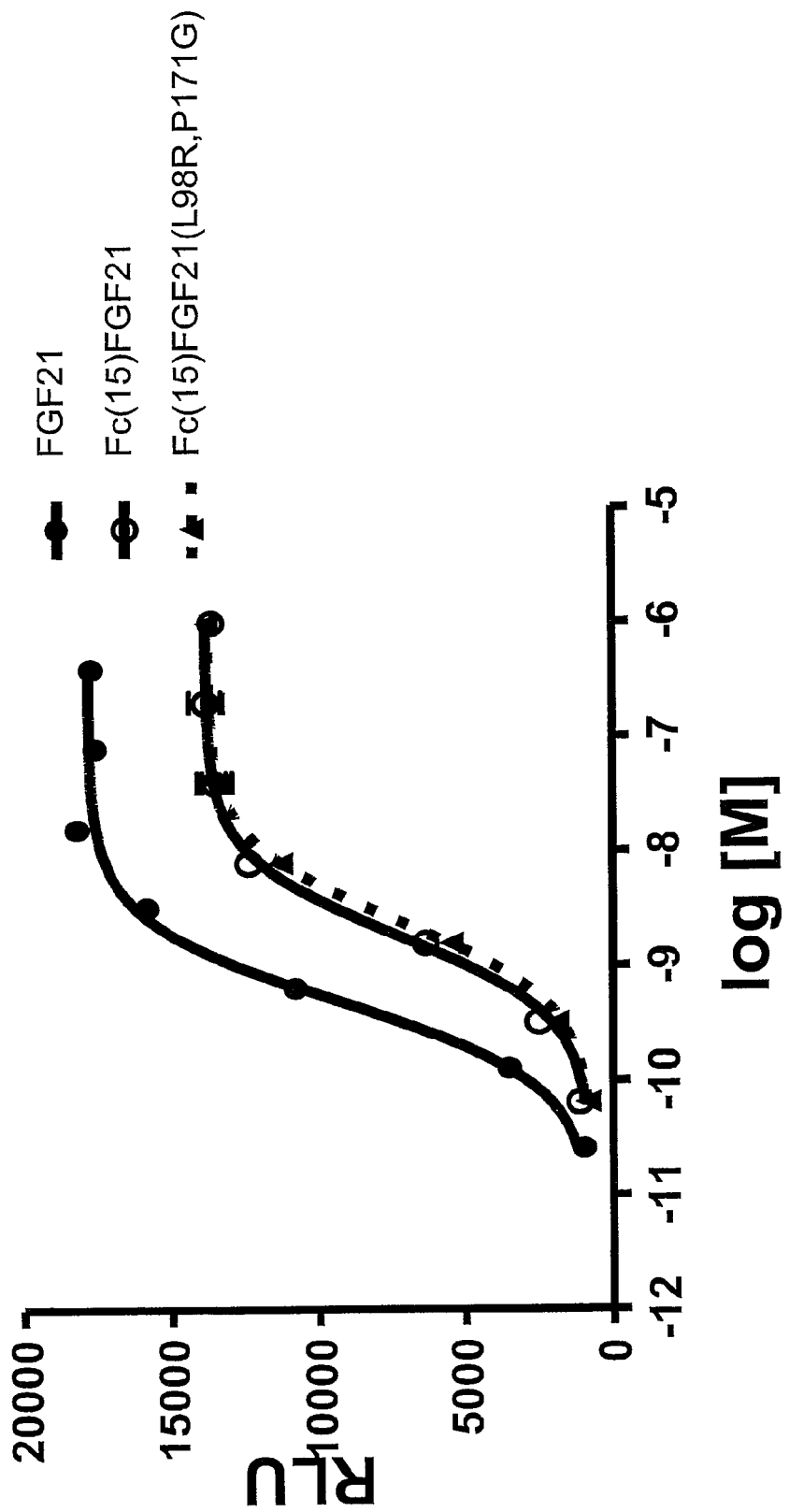

FGF21 POLYPEPTIDES COMPRISING TWO OR MORE MUTATIONS

This application claims priority benefit of U.S. Provisional Patent Application No. 61/058,861 filed Jun. 4, 2008, U.S. Provisional Patent Application No. 61/058,919 filed Jun. 4, 2008, U.S. Provisional Patent Application No. 61/164,364 filed Mar. 27, 2009, and U.S. Provisional Patent Application No. 61/175,736 filed May 5, 2009, each of which is incorporated herein in its entirety.

BACKGROUND OF THE INVENTION

1. Field of the Invention

The invention relates to nucleic acid molecules encoding FGF21 mutant polypeptides, FGF21 mutant polypeptides, pharmaceutical compositions comprising FGF21 mutant polypeptides, and methods for treating metabolic disorders using such nucleic acids, polypeptides, or pharmaceutical compositions.

2. Background of the Invention

FGF21 is a secreted polypeptide that belongs to a subfamily of fibroblast growth factors (FGFs) that includes FGF19, FGF21, and FGF23 (Itoh et al., 2004, *Trend Genet.* 20: 563-69). FGF21 is an atypical FGF in that it is heparin independent and functions as a hormone in the regulation of glucose, lipid, and energy metabolism.

FGF21 was isolated from a liver cDNA library as a hepatic secreted factor. It is highly expressed in liver and pancreas and is the only member of the FGF family to be primarily expressed in liver. Transgenic mice overexpressing FGF21 exhibit metabolic phenotypes of slow growth rate, low plasma glucose and triglyceride levels, and an absence of age-associated type 2 diabetes, islet hyperplasia, and obesity. Pharmacological administration of recombinant FGF21 protein in rodent and primate models results in normalized levels of plasma glucose, reduced triglyceride and cholesterol levels, and improved glucose tolerance and insulin sensitivity. In addition, FGF21 reduces body weight and body fat by increasing energy expenditure, physical activity, and metabolic rate. Experimental research provides support for the pharmacological administration of FGF21 for the treatment of type 2 diabetes, obesity, dyslipidemia, and other metabolic conditions or disorders in humans.

Human FGF21 has a short half-life in vivo. In mice, the half-life of human FGF21 is 1 to 2 hours, and in cynomolgus monkeys, the half-life is 2.5 to 3 hours. In developing an FGF21 protein for use as a therapeutic in the treatment of type 2 diabetes, an increase in half-life would be desirable. FGF21 proteins having an enhanced half-life would allow for less frequent dosing of patients being administered the protein. Such proteins are described herein.

SUMMARY OF THE INVENTION

The present disclosure provides an isolated polypeptide comprising an amino acid sequence of SEQ ID NO:4, further comprising the substitution of any amino acid for: the alanine residue at position 45, the leucine residue at position 86, the leucine residue at position 98, the alanine residue at position 111, the alanine residue at position 129, the glycine residue at position 170, the proline residue at position 171 or the serine residue at position 172, and combinations thereof In one embodiment the isolated polypeptide comprises the substitution of any amino acid for: the leucine residue at position 98, the proline residue at 171 or both the leucine residue at position 98 and the proline residue at position 171. In another embodiment the isolated polypeptide comprises the substitution of any amino acid for both the leucine residue at position 98 and the proline residue at position 171.

The present disclosure also provides an isolated polypeptide comprising an amino acid sequence of SEQ ID NO: 4 having: (a) at least one amino acid substitution that is: (i) a glutamine, isoleucine, or lysine residue at position 19; (ii) a histidine, leucine, or phenylalanine residue at position 20; (iii) an isoleucine, phenylalanine, tyrosine, or valine residue at position 21; (iv) an isoleucine, phenylalanine, or valine residue at position 22; (v) an alanine or arginine residue at position 150; (vi) an alanine or valine residue at position 151; (vii) a histidine, leucine, phenylalanine, or valine residue at position 152; (viii) an alanine, asparagine, aspartic acid, cysteine, glutamic acid, glutamine, proline, or serine residue at position 170; (ix) an alanine, arginine, asparagine, aspartic acid, cysteine, glutamic acid, glutamine, glycine, histidine, lysine, serine, threonine, tryptophan, or tyrosine residue at position 171; (x) a leucine or threonine residue at position 172; or (xi) an arginine or glutamic acid residue at position 173; and (b) at least one amino acid substitution that is: (i) an arginine, glutamic acid, or lysine residue at position 26; (ii) an arginine, glutamic acid, glutamine, lysine, or threonine residue at position 45; (iii) a threonine residue at position 52; (iv) a cysteine, glutamic acid, glycine, or serine residue at position 58; (v) an alanine, arginine, glutamic acid, or lysine residue at position 60; (vi) an alanine, arginine, cysteine, or histidine residue at position 78; (vii) a cysteine or threonine residue at position 86; (viii) an alanine, arginine, glutamic acid, lysine, or serine residue at position 88; (ix) an arginine, cysteine, glutamic acid, glutamine, lysine, or threonine residue at position 98; (x) an arginine, aspartic acid, cysteine, or glutamic acid residue at position 99; (xi) a lysine or threonine residue at position 111; (xii) an arginine, asparagine, aspartic acid, glutamic acid, glutamine, histidine, or lysine residue at position 129; or (xiii) an arginine, glutamic acid, histidine, lysine, or tyrosine residue at position 134; and combinations thereof. In one embodiment the residue at position 98 is arginine and the residue at position 171 is proline, and in another embodiment the polypeptide can comprise an amino acid sequence that is at least 85 percent identical to the amino acid sequence of SEQ ID NO: 4, but wherein the at least one amino acid substitution of (a)(i)-(xi) and (b)(i)-(xiii) is not further modified.

The present disclosure additionally provides an isolated polypeptide comprising an amino acid sequence of SEQ ID NO: 4 having at least one amino acid substitution that is: (a) a glutamine, lysine or isoleucine residue at position 19; (b) a histidine, leucine, or phenylalanine residue at position 20; (c) an isoleucine, phenylalanine, tyrosine, or valine residue at position 21; (d) an isoleucine, phenylalanine, or valine residue at position 22; (e) an alanine or arginine residue at position 150; (f) an alanine or valine residue at position 151; (g) a histidine, leucine, phenylalanine, or valine residue at position 152; (h) an alanine, aspartic acid, cysteine, or proline residue at position 170; (i) an alanine, arginine, asparagine, aspartic acid, cysteine, glutamic acid, glutamine, glycine, histidine, lysine, serine, threonine, tryptophan, or tyrosine residue at position 171; (j) a leucine residue at position 172; or (k) an arginine or glutamic acid residue at position 173; and combinations thereof. In one embodiment the residue at position 171 is proline, and in another embodiment the polypeptide can comprise an amino acid sequence that is at least 85 percent identical to the amino acid sequence of SEQ ID NO: 4, but wherein the at least one amino acid substitution of (a)-(k) is not further modified.

The present disclosure further provides an isolated polypeptide comprising an amino acid sequence of SEQ ID NO: 4 having at least one amino acid substitution that is: (a) an arginine, glutamic acid, or lysine residue at position 26; (b) an arginine, glutamic acid, glutamine, lysine, or threonine residue at position 45; (c) a threonine residue at position 52; (d) a glutamic acid, glycine, or serine residue at position 58; (e) an alanine, arginine, glutamic acid, or lysine residue at position 60; (f) an alanine, arginine, or histidine residue at position 78; (g) an alanine residue at position 88; (h) an arginine, glutamic acid, glutamine, lysine, or threonine residue at position 98; (i) an arginine, aspartic acid, cysteine, or glutamic acid residue at position 99; (j) a lysine or threonine residue at position 111; (k) an arginine, asparagine, aspartic acid, glutamic acid, glutamine, histidine, or lysine residue at position 129; or (l) an arginine, glutamic acid, histidine, lysine, or tyrosine residue at position 134; and combinations thereof. In one embodiment, the residue at position 98 is arginine and in another embodiment the polypeptide can comprise an amino acid sequence that is at least 85 percent identical to the amino acid sequence of SEQ ID NO: 4, but wherein the at least one amino acid substitution of (a)-(l) is not further modified.

In various embodiments, the polypeptides disclosed herein can further comprise at least one amino acid substitution that is: (a) a phenylalanine, proline, alanine, serine or glycine at position 179; (b) a glutamic acid, glycine, proline, or serine at position 180; or (c) a lysine, glycine, threonine, alanine, leucine, or proline at position 181 and can further comprise 1 to 10 amino acid residues fused to the C-terminus of the polypeptide, and can be any amino acid, for example, one or more residues selected from the group consisting of glycine, proline and combinations thereof.

In various embodiments, the polypeptides disclosed herein can comprise (a) an amino-terminal truncation of no more than 8 amino acid residues, wherein the polypeptide is capable of lowering blood glucose in a mammal; (b) a carboxyl-terminal truncation of no more than 12 amino acid residues, wherein the polypeptide is capable of lowering blood glucose in a mammal; or (c) an amino-terminal truncation of no more than 8 amino acid residues and a carboxyl-terminal truncation of no more than 12 amino acid residues, wherein the polypeptide is capable of lowering blood glucose in a mammal.

In some embodiments, the polypeptides disclosed herein can be covalently linked to one or more polymers, such as PEG. In other embodiments, the polypeptides of the present invention can be fused to a heterologous amino acid sequence, optionally via a linker, such as GGGGGSGGGSGGGGS (SEQ ID NO: 23). The heterologous amino acid sequence can be an IgG constant domain or fragment thereof, such as the amino acid sequence of SEQ ID NO:13. Such fusion polypeptides disclosed herein can also form multimers.

The present disclosure also provides pharmaceutical compositions comprising the polypeptides disclosed herein and a pharmaceutically acceptable formulation agent. Such pharmaceutical compositions can be used in a method for treating a metabolic disorder, and the method comprises administering to a human patient in need thereof a pharmaceutical composition of the present invention. Metabolic disorders that can be treated include diabetes and obesity.

Also provided are isolated nucleic acid molecules encoding the polypeptides of disclosed herein, as well as vectors comprising such nucleic acid molecules and host cells comprising such nucleic acid molecules.

Truncated forms of the polypeptide of SEQ ID NO:4 are also disclosed. In various embodiments the polypeptide can comprise: (a) an amino-terminal truncation of no more than 8 amino acid residues, wherein the polypeptide is capable of lowering blood glucose in a mammal; (b) a carboxyl-terminal truncation of no more than 12 amino acid residues, wherein the polypeptide is capable of lowering blood glucose in a mammal; or (c) an amino-terminal truncation of no more than 8 amino acid residues and a carboxyl-terminal truncation of no more than 12 amino acid residues, wherein the polypeptide is capable of lowering blood glucose in a mammal.

The present disclosure additionally provides an isolated fusion protein that can comprise: (a) an IgG constant domain; (b) a linker sequence fused to the IgG constant domain; and (c) an FGF21 mutant fused to the linker sequence and comprising the amino acid sequence of SEQ ID NO: 4 wherein the an arginine residue has been substituted for the leucine residue at position 98 and a glycine residue has been substituted for the proline residue at position 171. In one embodiment, the linker sequence can comprise GGGGGSGGGSGGGGS (SEQ ID NO:23) and in another the IgG constant domain can comprise SEQ ID NO: 13. In another embodiment, the linker sequence comprises GGGGGSGGGSGGGGS (SEQ ID NO:23) and the IgG constant domain comprises the amino acid sequence of SEQ ID NO: 13. In still another embodiment the N terminus of the linker is fused to the C terminus of the IgG constant domain and the N terminus of the FGF21 mutant is fused to the C terminus of the linker. The disclosed fusion proteins can form multimers.

In various embodiments of the fusion protein, the FGF21 mutant component can comprise at least one amino acid substitution that is: (a) a phenylalanine, proline, alanine, serine or glycine at position 179; (b) a glutamic acid, glycine, proline, or serine at position 180; or (c) a lysine, glycine, threonine, alanine, leucine, or proline at position 181 and can further comprise 1 to 10 amino acid residues fused to the C-terminus of the FGF21 mutant, and the 1 to 10 amino acid residues, and can be any amino acid, for example, one or more residues selected from the group consisting of glycine, proline and combinations thereof.

In still other embodiments of the fusion protein, the FGF21 mutant component can comprise: (a) an amino-terminal truncation of no more than 8 amino acid residues, wherein the polypeptide is capable of lowering blood glucose in a mammal; (b) a carboxyl-terminal truncation of no more than 12 amino acid residues, wherein the polypeptide is capable of lowering blood glucose in a mammal; or (c) an amino-terminal truncation of no more than 8 amino acid residues and a carboxyl-terminal truncation of no more than 12 amino acid residues, wherein the polypeptide is capable of lowering blood glucose in a mammal. In another embodiment, the FGF21 mutant component of a fusion protein can comprise an amino acid sequence that is at least 85 percent identical to the amino acid sequence of SEQ ID NO: 4, but wherein the arginine and glycine residues are not further modified.

The present disclosure also provides pharmaceutical compositions comprising the fusion protein disclosed herein and a pharmaceutically acceptable formulation agent. Such pharmaceutical compositions can be used in a method for treating a metabolic disorder, the method comprising administering to a human patient in need thereof a pharmaceutical composition of the present invention. Metabolic disorders that can be treated include diabetes and obesity.

Also provided are isolated nucleic acid molecules encoding the fusion protein disclosed herein, as well as vectors comprising such nucleic acid molecules and host cells comprising such nucleic acid molecules.

Specific embodiments of the present invention will become evident from the following more detailed description of certain embodiments and the claims.

BRIEF DESCRIPTION OF THE DRAWINGS

FIGS. 6A-6D show the results of liquid chromatography-mass spectrometry (LC-MS) analysis of a human Fc(5) FGF21 control sample (FIG. 6A) and samples of Fc(5)FGF21 drawn from mice at 6 hours (Sample D6; FIG. 6B), 24 hours (Sample D24; FIG. 6C), and 48 hours (Sample D48; FIG. 6D) after injection.

FIGS. 7A-7D show the results if LC-MS analysis of a mammalian-derived human FGF21(3)Fc control sample (FIG. 7A) and samples of FGF21(3)Fc drawn from mice at 6 hours (Sample E6; FIG. 7B), 24 hours (Sample E24; FIG. 7C), and 48 hours (Sample E48; FIG. 7D) after injection.

FIGS. 8A-8D show the results of LC-MS analysis of an Fc(15)FGF21 control sample (FIG. 8A) and samples of Fc(15)FGF21 drawn from mice at 6 hours (FIG. 8B), 24 hours (FIG. 8C), and 48 hours (FIG. 8D) after injection.

FIGS. 9A-9D show the results of LC-MS analysis of an FGF21(15)Fc control sample (FIG. 9A) and samples of FGF21(15)Fc drawn from mice at 6 hours (FIG. 9B), 24 hours (FIG. 9C), and 48 hours (FIG. 9D) after injection.

FIGS. 10A-10B show the cleavage sites identified by LC-MS analysis of Fc(15)FGF21 (FIG. 10A, SEQ ID NO: 39) and FGF21(15)Fc (FIG. 10B, SEQ ID NO:25) fusion proteins injected into mice.

FIGS. 19A-19D show the results of LC-MS analysis of an Fc(15)FGF21 control sample (FIG. 19A) and samples drawn from mice at time 6 hours (FIG. 19B), 24 hours (FIG. 19C), and 48 hours (FIG. 19D) after injection.

FIGS. 20A-20D show the results of LC-MS analysis of an Fc(15)FGF21 G170E control sample (FIG. 20A) and samples of Fc(15)FGF21 G170E drawn from mice at 6 hours (FIG. 20B), 24 hours (FIG. 20C), and 48 hours (FIG. 20D) after injection.

FIGS. 21A-21D show the results of LC-MS analysis of an Fc(15)FGF21 P171A control sample (FIG. 21A) and samples of Fc(15)FGF21 P171A drawn from mice at 6 hours (FIG. 21B), 24 (FIG. 21C), and 48 hours (FIG. 21D) after injection.

FIGS. 22A-22D show the results of LC-MS analysis of an Fc(15)FGF21 S172L control sample (FIG. 22A) and samples of Fc(15)FGF21 S172L drawn from mice at 6 hours (FIG. 22B), 24 hours (FIG. 22C), and 48 hours (FIG. 22D) after injection.

FIGS. 23A-23D show the cleavage sites identified by LC-MS analysis of Fc(15)FGF21 (FIG. 23A, SEQ ID NO: 39), Fc(15)FGF21 G170E (FIG. 23B, SEQ ID NO: 40), Fc(15)

FGF21 P171A (FIG. 23C, SEQ ID NO: 41), and Fc(15) FGF21 S172L (FIG. 23D, SEQ ID NO: 42) fusion proteins injected in mice.

Figure 24A:
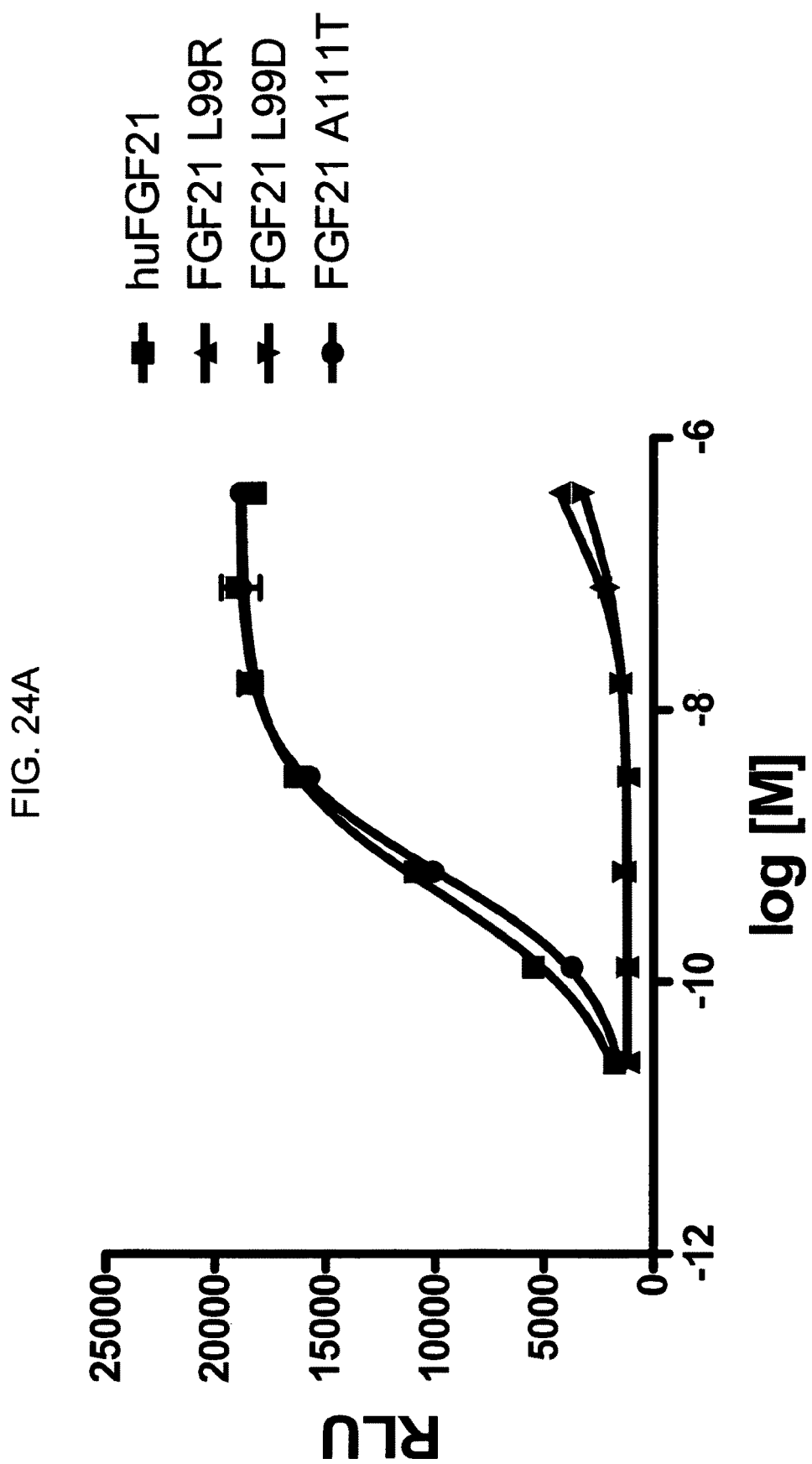
Figure 24B:
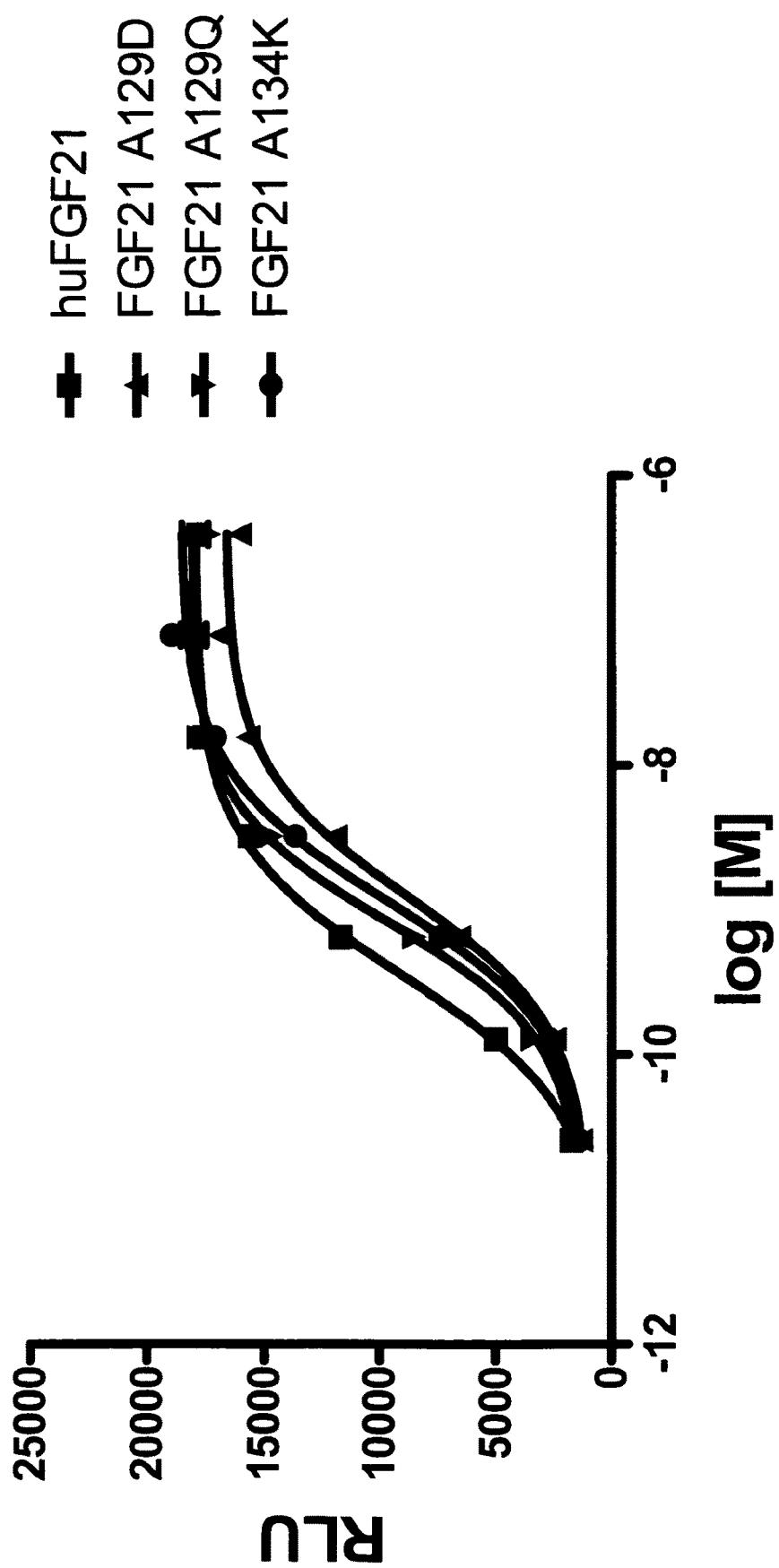
Figure 24C:
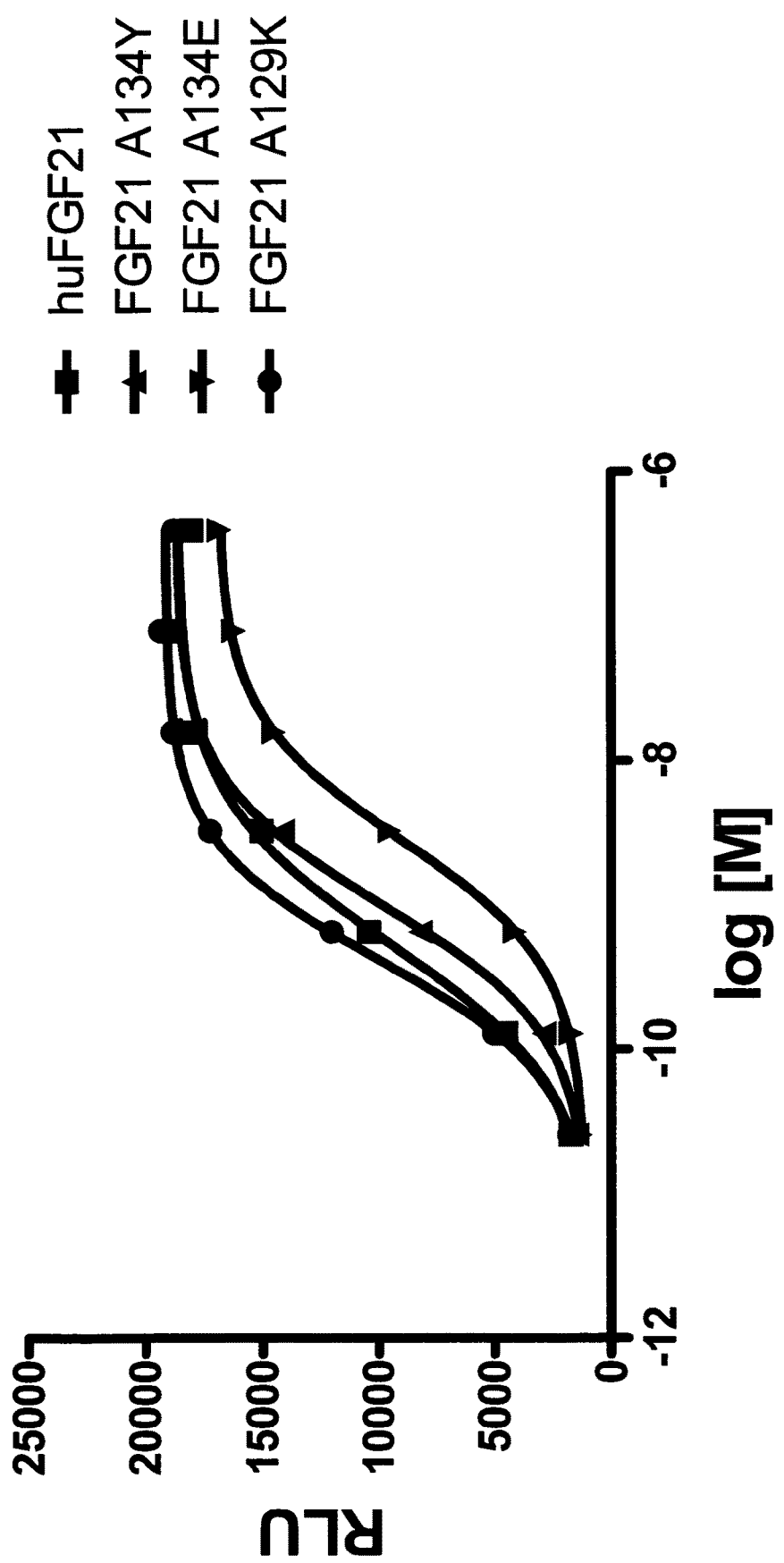

FIGS. 24A-24C show the results of an ELK-luciferase activity assay performed on the FGF21 mutants FGF21 L99R, FGF21 L99D, and FGF21 A111T (FIG. 24A); the FGF21 mutants FGF21 A129D, FGF21 A129Q, and FGF21 A134K (FIG. 24B); and the FGF21 mutants FGF21 A134Y, FGF21 A134E, and FGF21 A129K (FIG. 24C); each panel shows the results obtained for a human FGF21 control.

Figure 25A:
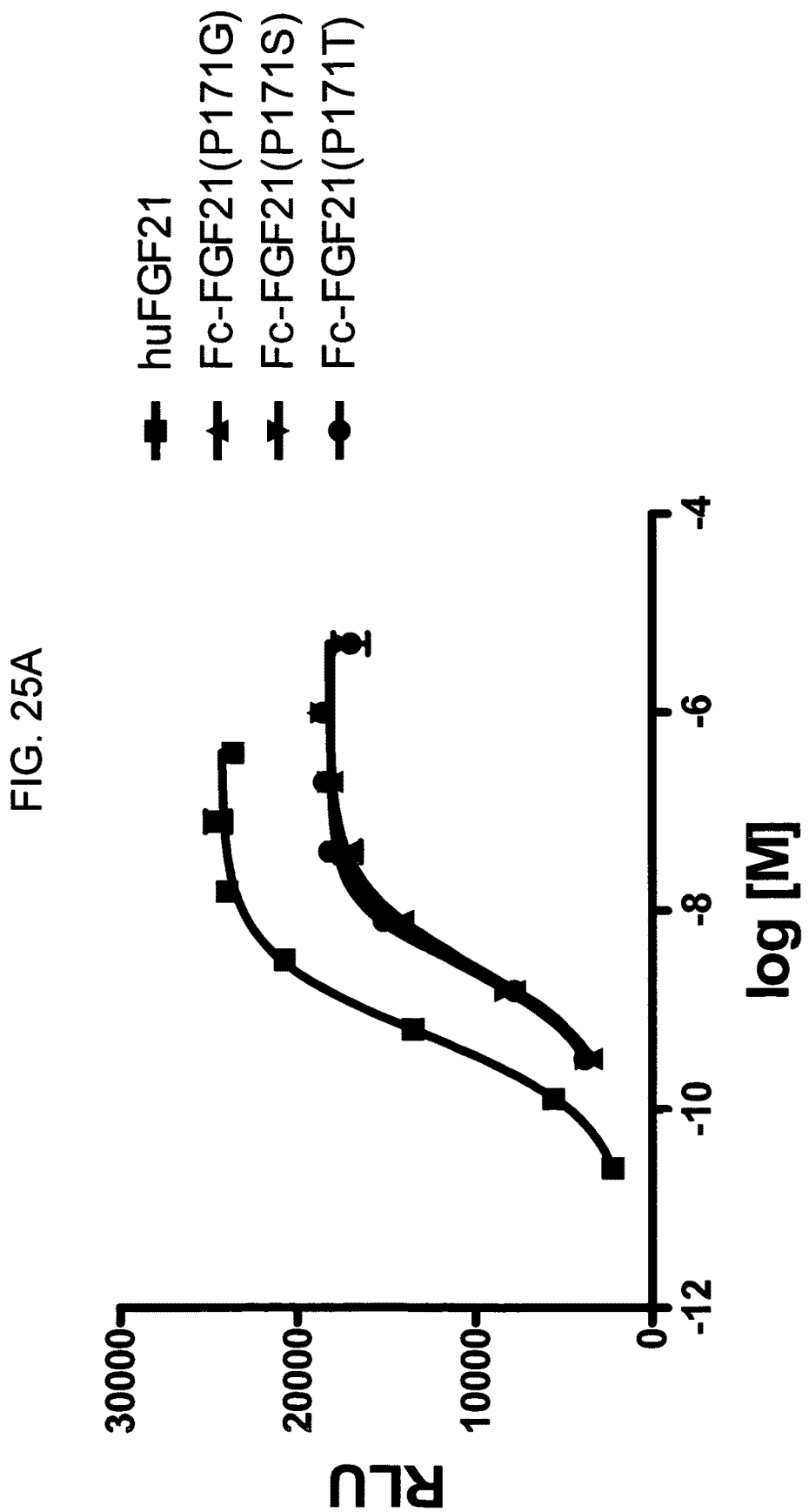
Figure 25B:
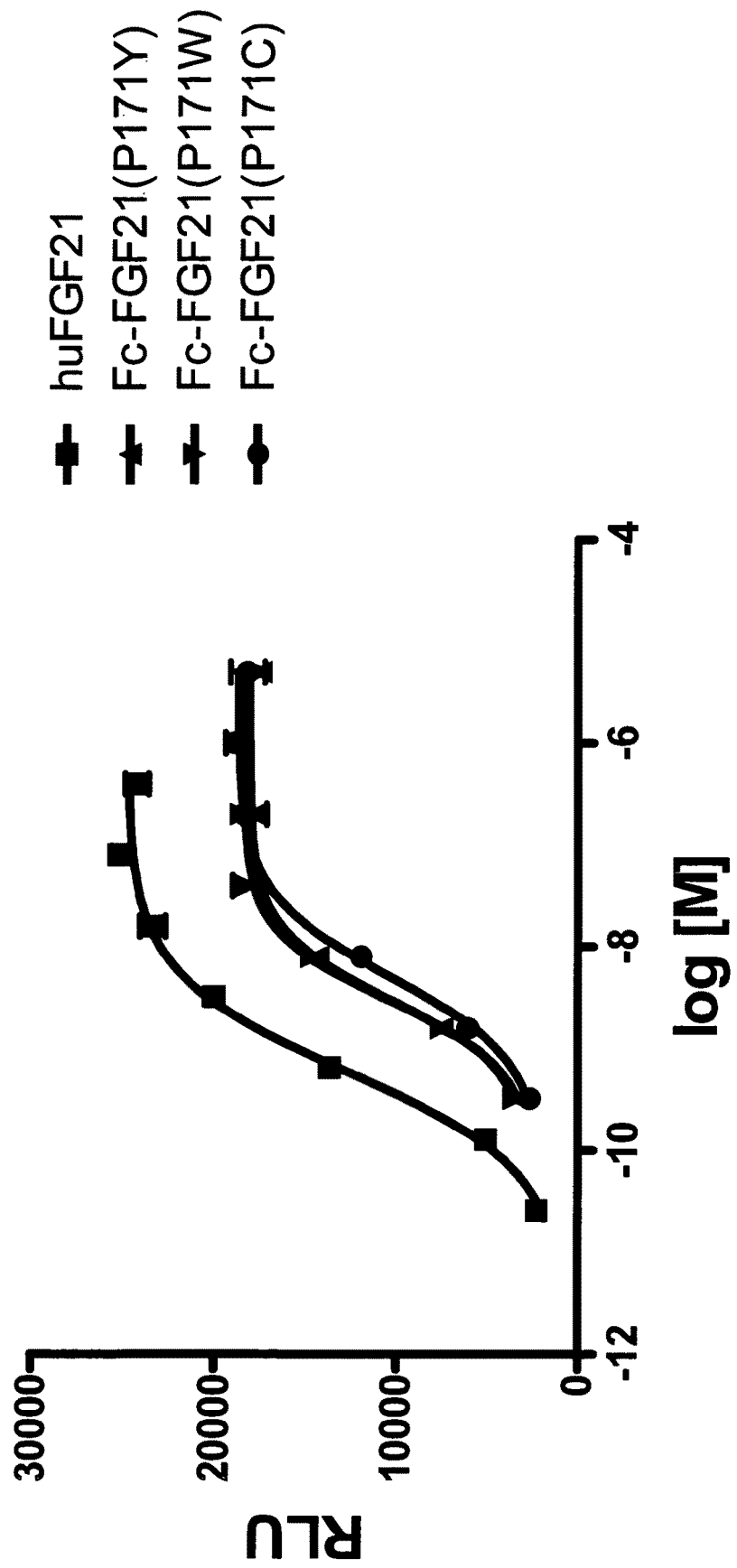

FIGS. 25A-25D show the results of an ELK-luciferase activity assay performed on the Fc-FGF21 mutants Fc-FGF21 P171G, Fc-FGF21 P171S, and Fc-FGF21 P171T (FIG. 25A); the Fc-FGF21 mutants Fc-FGF21 P171Y, Fc-FGF21 P171W, and Fc-FGF21 P171C (FIG. 25B); Fc(15) FGF21, Fc(15)FGF21 A45K/G170E, and FGF21 A45K (FIG. 25C); and Fc(15)FGF21, Fc(15)FGF21 P171E, and Fc(15)FGF21 A45K/G170E (FIG. 25D); each panel shows the results obtained for a human FGF21 control.

Figure 26A:
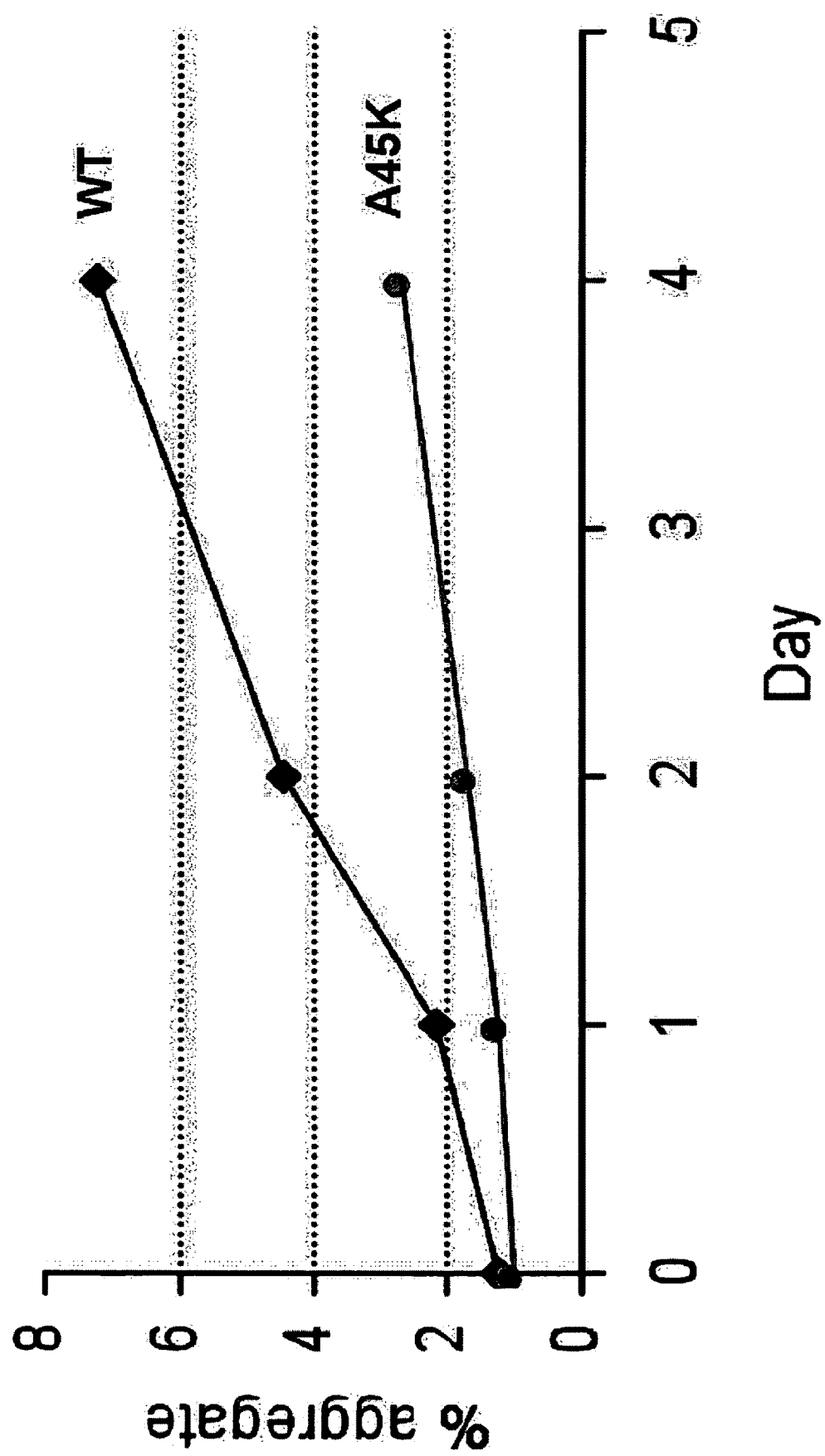
Figure 26B:
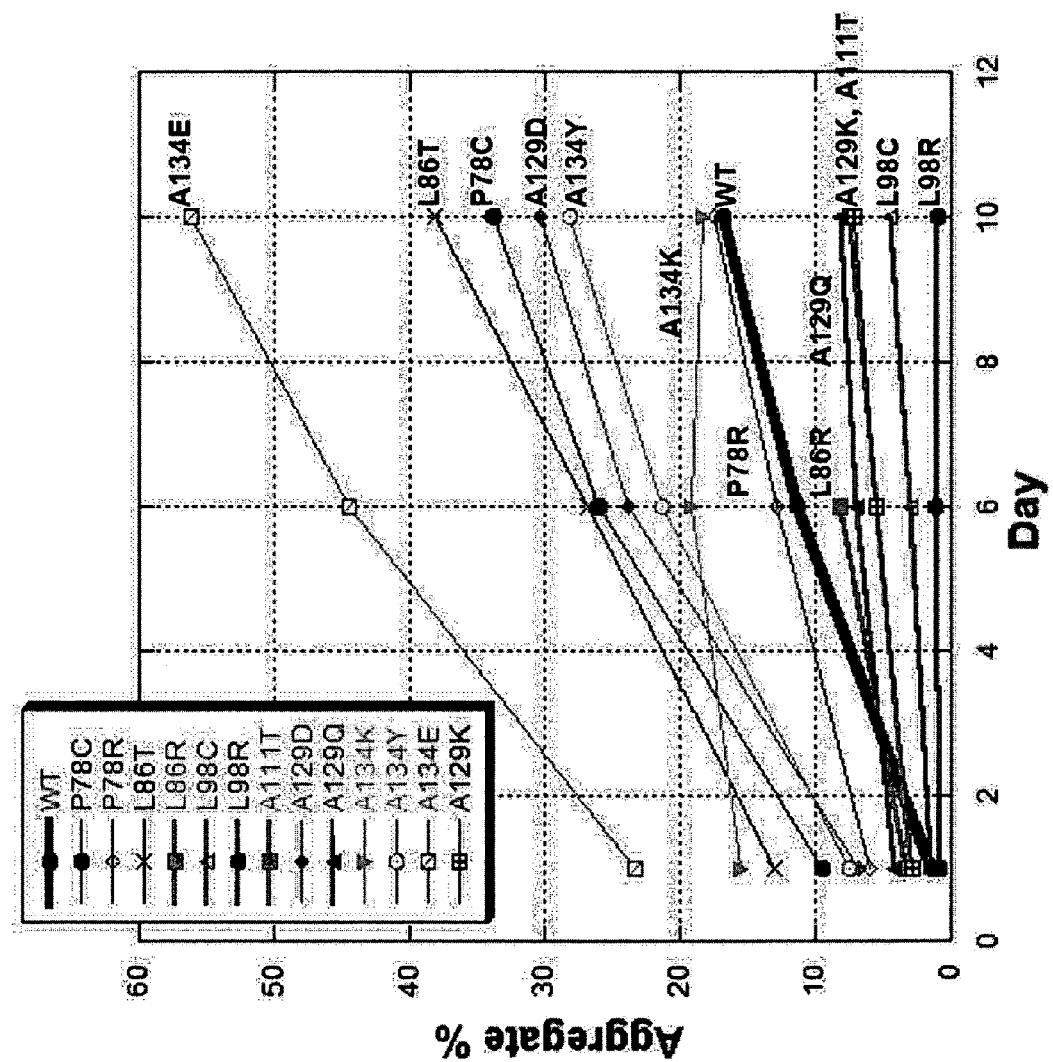

FIGS. 26A-B show the aggregation as a function of time for wild type mature FGF21 and various FGF21 mutants; FIG. 26A shows the change in percent aggregation for an FGF21 control (WT, solid diamonds) and FGF21 A45K (solid circles) following incubation of 65 mg/mL protein at 4° C. for 1, 2, and 4 days, while FIG. 26B shows the change in percent aggregation for an FGF21 control (WT) and FGF21 P78C, P78R, L86T, L86R, L98C, L98R, A111T, A129D, A129Q, A129K, A134K, A134Y, and A134E (all labeled on the plot) following incubation of 65 mg/mL protein at 4° C. for 1, 6, and 10 days.

Figure 27:
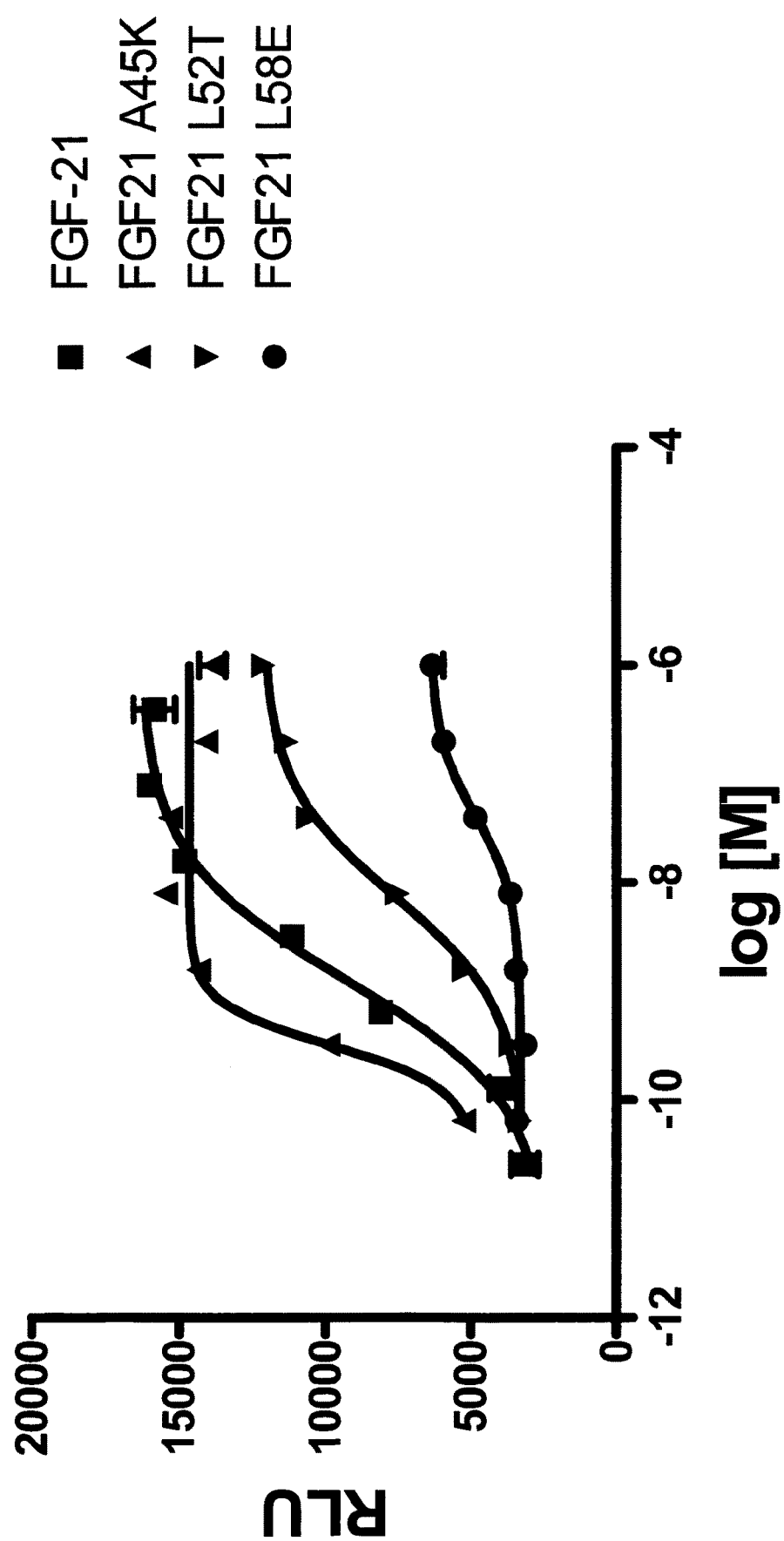

FIG. 27 shows the results of an ELK-luciferase activity assay performed on a human FGF21 control and the FGF21 mutants FGF21 A45K, FGF21 L52T, and FGF21 L58E.

Figure 28B:
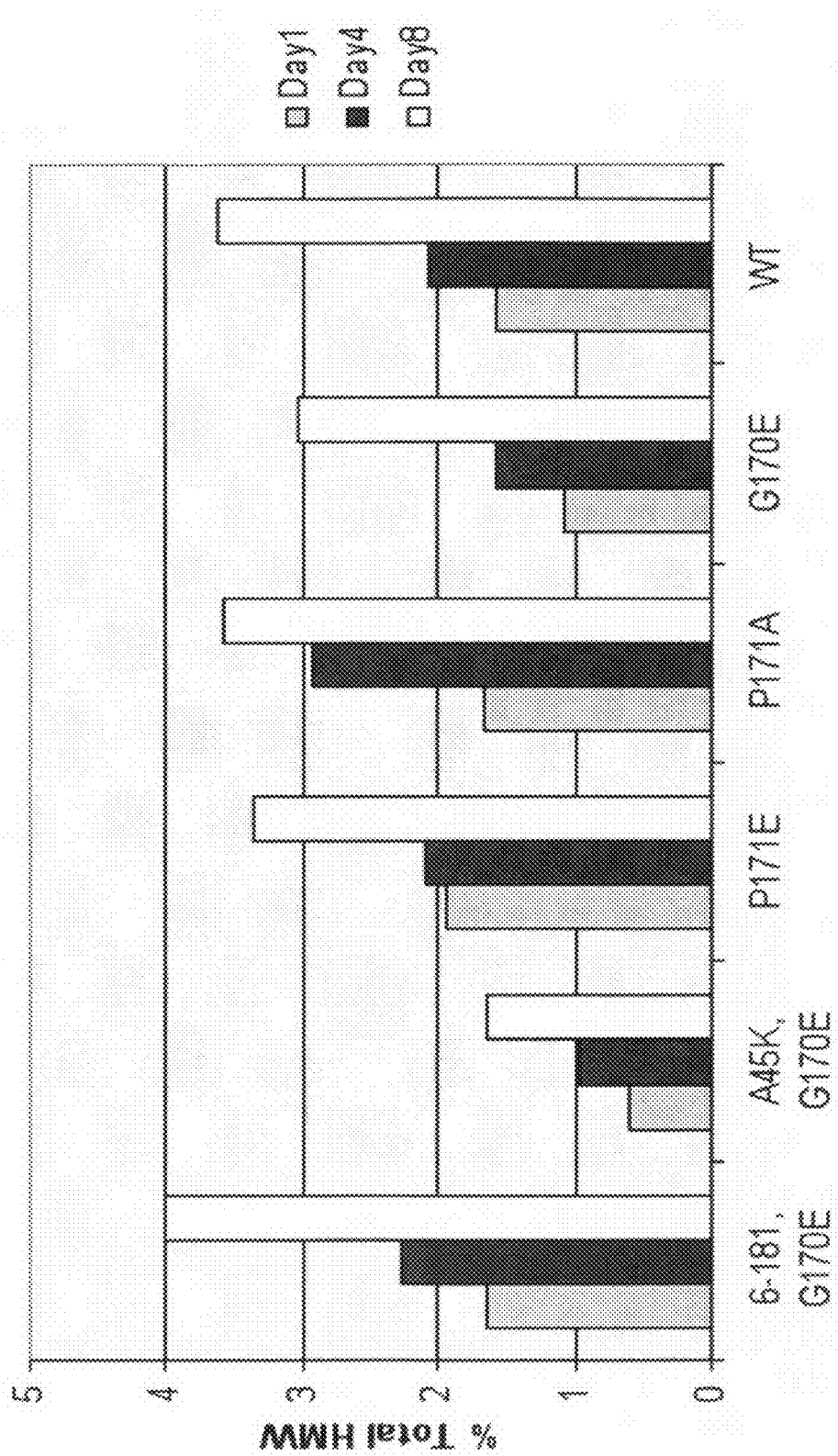

FIG. 28A is a plot show the change in aggregation levels for the Fc(15)FGF21 mutants Fc(15)FGF21 6-181/G170E (solid diamonds), Fc(15)FGF21 A45K/G170E (open squares), Fc(15)FGF21 P171E (solid triangles), Fc(15)FGF21 P171A (crosses), Fc(15)FGF21 G170E (open triangles), and an FGF21 control (solid circles) following incubation at 4° C. for 1, 4, and 8 days, and FIG. 28B is a bar graph also showing the results of the incubation.

Figure 29:
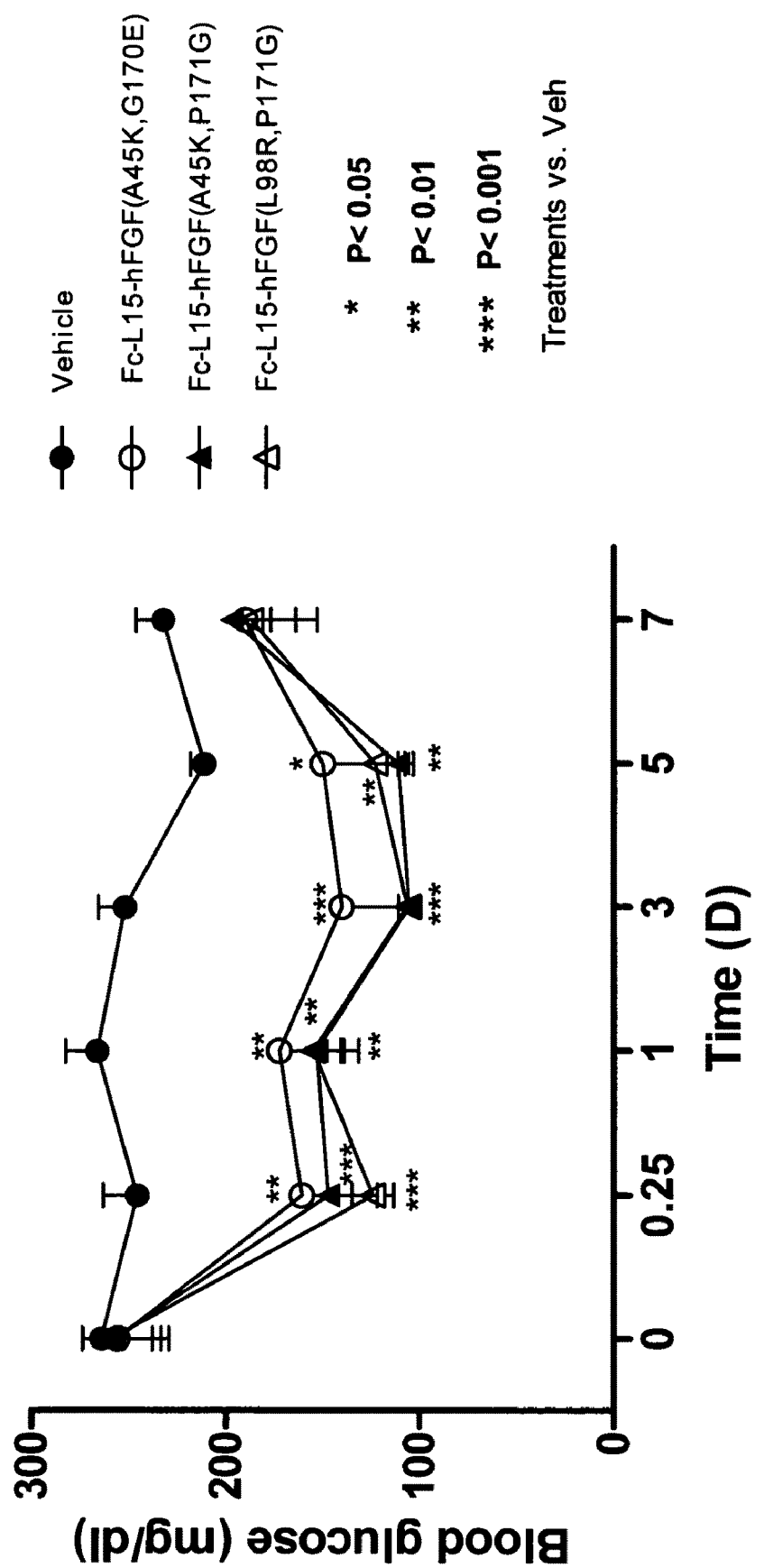

FIG. 29 shows the blood glucose levels measured in mice injected with PBS (vehicle) (solid circles) or the Fc(15) FGF21 mutants Fc(15)FGF21 A45K/G170E (open circles), Fc(15)FGF21 A45K/P171G (solid triangles), or Fc(15) FGF21 L98R/P171G (open triangles).

FIG. 30 is a plot showing the results of an ELK-luciferase activity assay performed on human FGF21 (solid circles, solid line), Fc(15)FGF21 (open circles, solid line) and Fc(15) FGF21 L98R/P171G (solid triangles, dotted line).

Figure 31A:
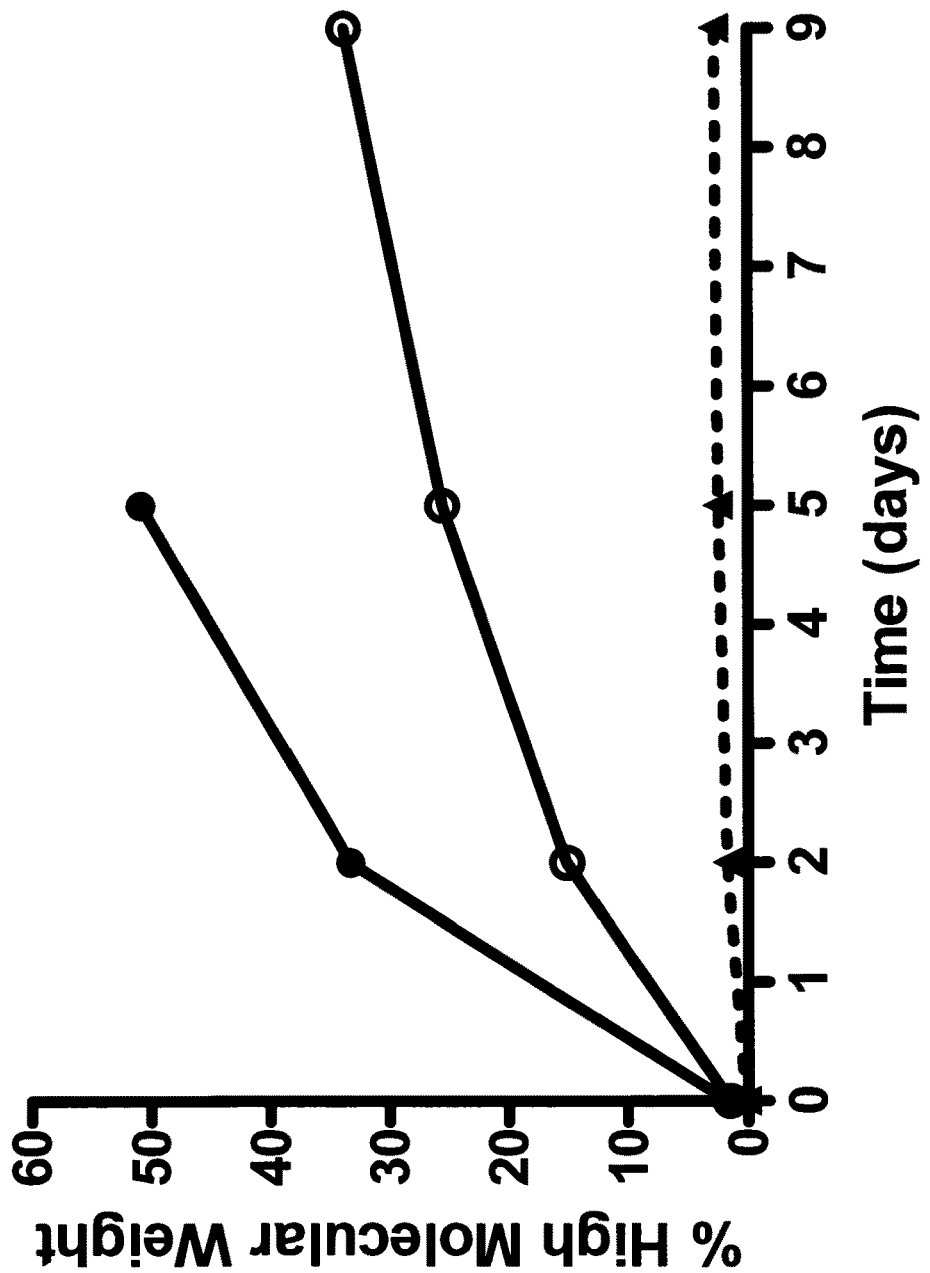
Figure 31B:
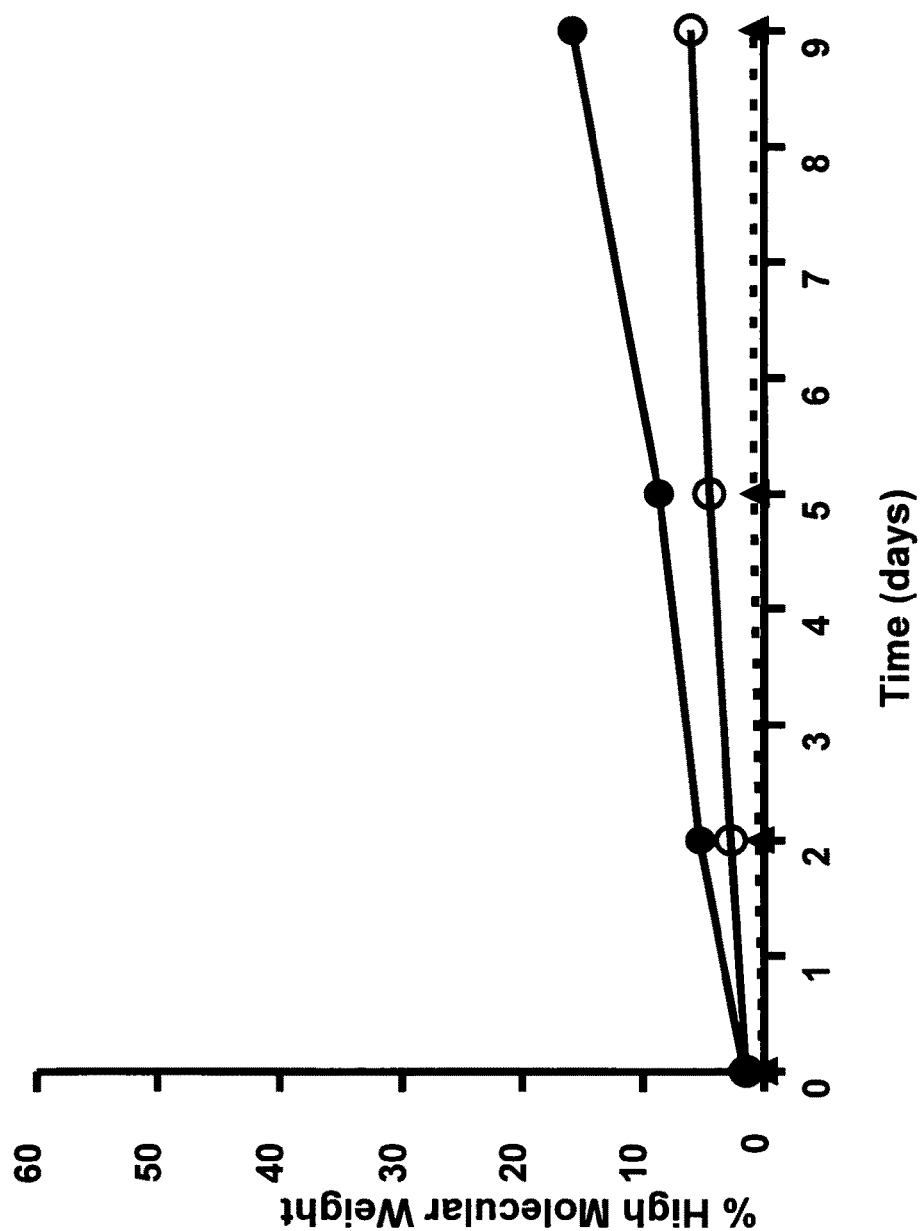

FIG. 31 is a plot showing the percent high molecular weight aggregates observed after nine days at room temperature (FIG. 31A) and at 4° C. (FIG. 31B) for FGF21 (solid circles, solid line), Fc(15)FGF21 (open circle, solid line) and Fc(15)FGF21 L98R/P171G (solid triangles, dotted line).

Figure 32:
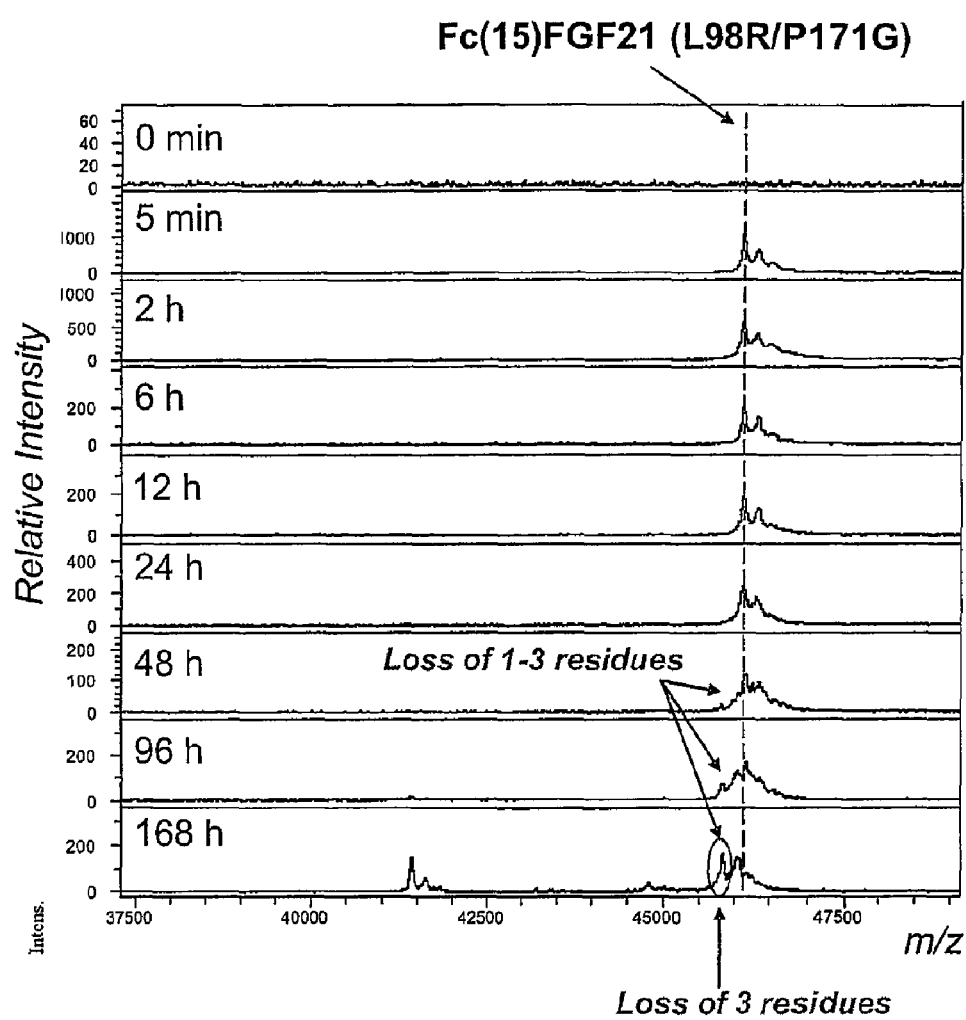

FIG. 32 is a series of MALDI mass spectrometry traces showing observed changes in Fc(15)FGF21 L98R/P171G at various points over a 168 hour time period.

Figure 33:
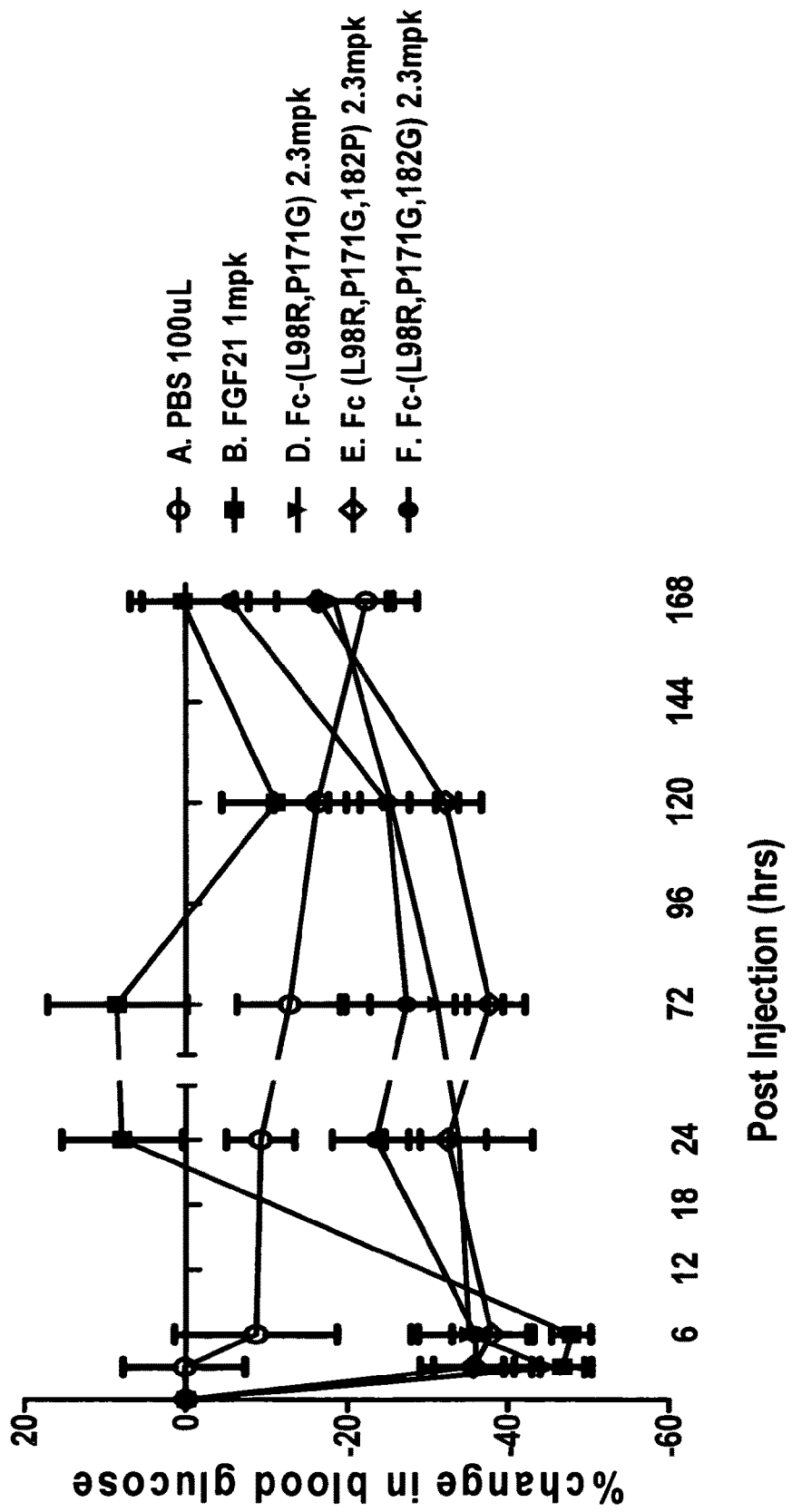

FIG. 33 is a plot showing the percent change in blood glucose levels in db/db mice for each of a PBS vehicle control (open circles), wild-type mature FGF21 (solid squares), and the FGF21 mutants L98R, P171G (inverted solid triangles); L98R, P171G, 182P (open diamonds), and L98R, P171G, 182G (solid circles).

Figure 34:
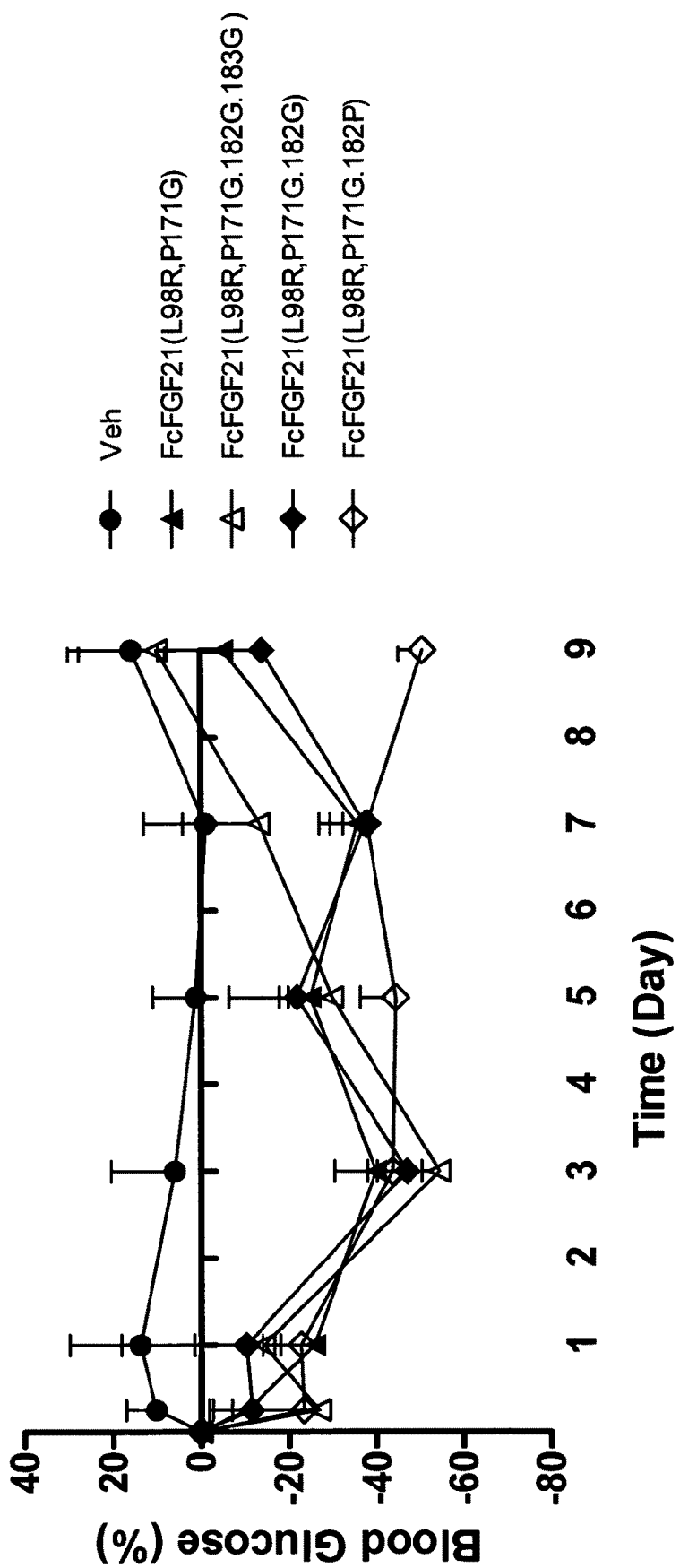

FIG. 34 is a plot showing the percent change in blood glucose levels in ob/ob mice for each of a PBS vehicle control (solid circles), and the FGF21 mutants L98R, P171G (solid triangles); L98R, P171G, 182G, 183G (open triangles), L98R, P171G, 182G (solid diamonds) and L98R, P171G, 182P (open diamonds).

Figure 35:
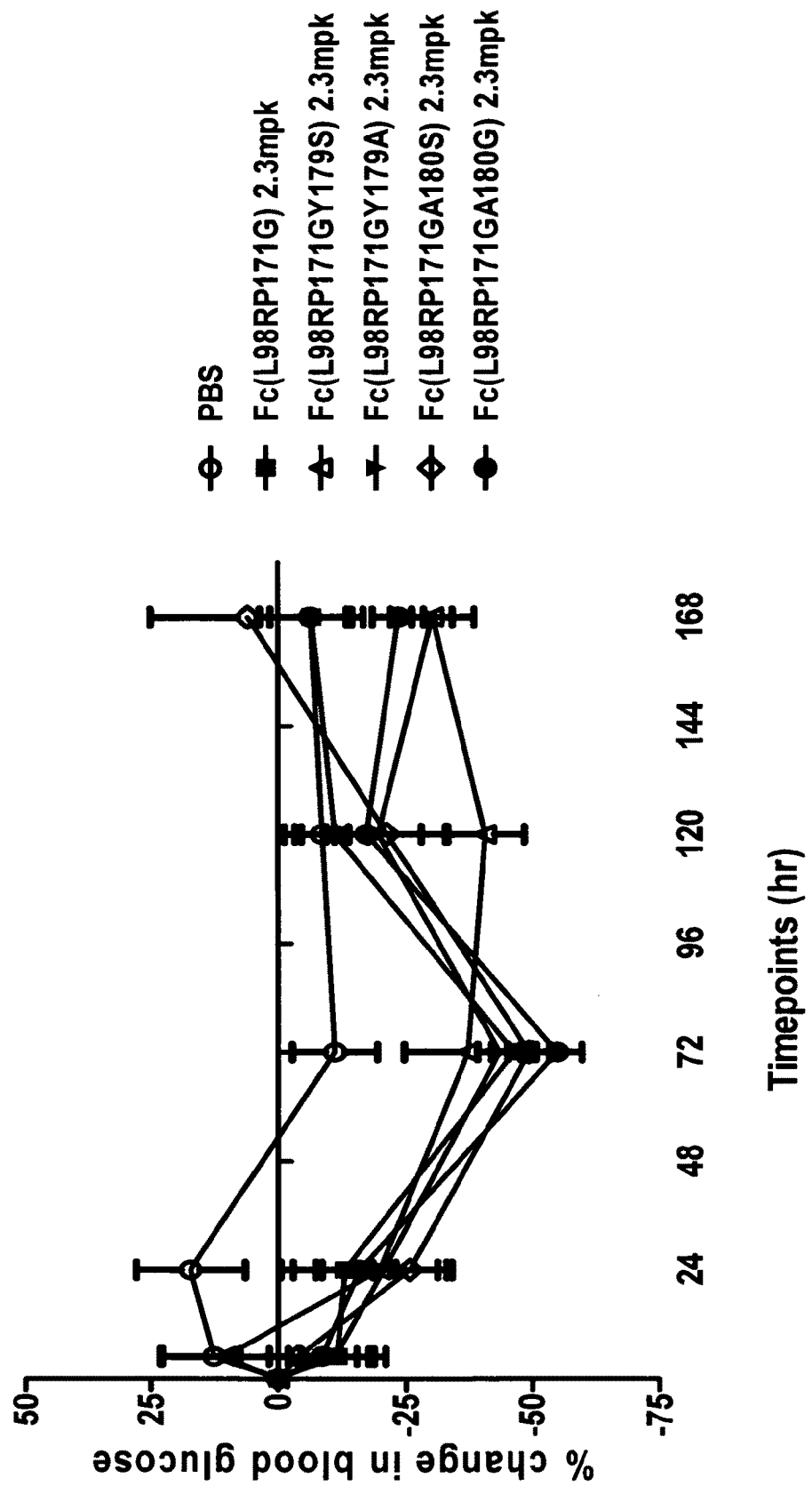

FIG. 35 is a plot showing the percent change in blood glucose levels in db/db mice for each of a PBS vehicle control (open circles), and the FGF21 mutants L98R, P171G (solid squares); L98R, P171G, Y179S (open triangles), L98R, P171G, Y179A (inverted solid triangles), L98R, P171G, 180S (open diamonds) and L98R, P171G, A180G (solid circles).

Figure 36:
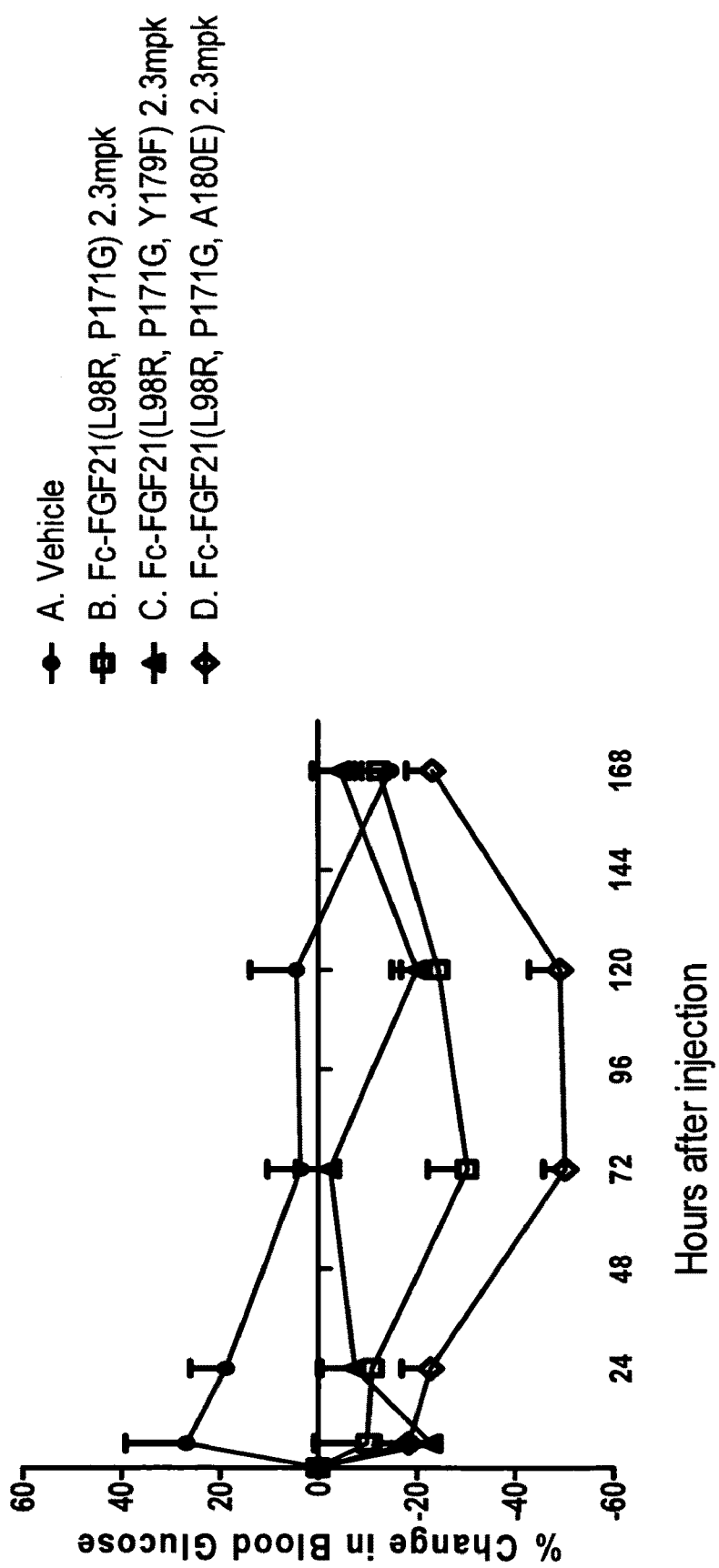

FIG. 36 is a plot showing the percent change in blood glucose levels db/db mice for each of a PBS vehicle control (solid circles), and the FGF21 mutants L98R, P171G (open squares); L98R, P171G, Y179F (solid triangles), and L98R, P171G, A180E (open diamonds).

Figure 37:
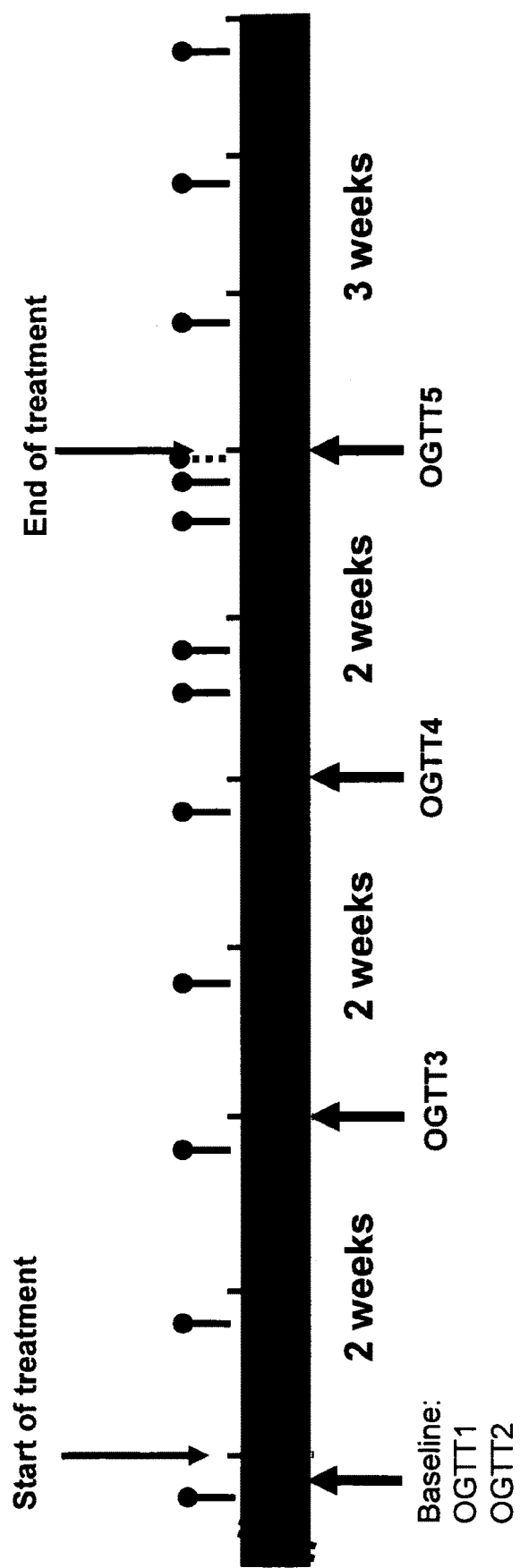

FIG. 37 is a diagram graphically depicting the study design for a six-week dose escalation study performed in Rhesus monkeys; in the figure shaded symbols indicate blood draws in the fasted state and stippled symbols indicated blood draws in the fed state.

Figure 38A:
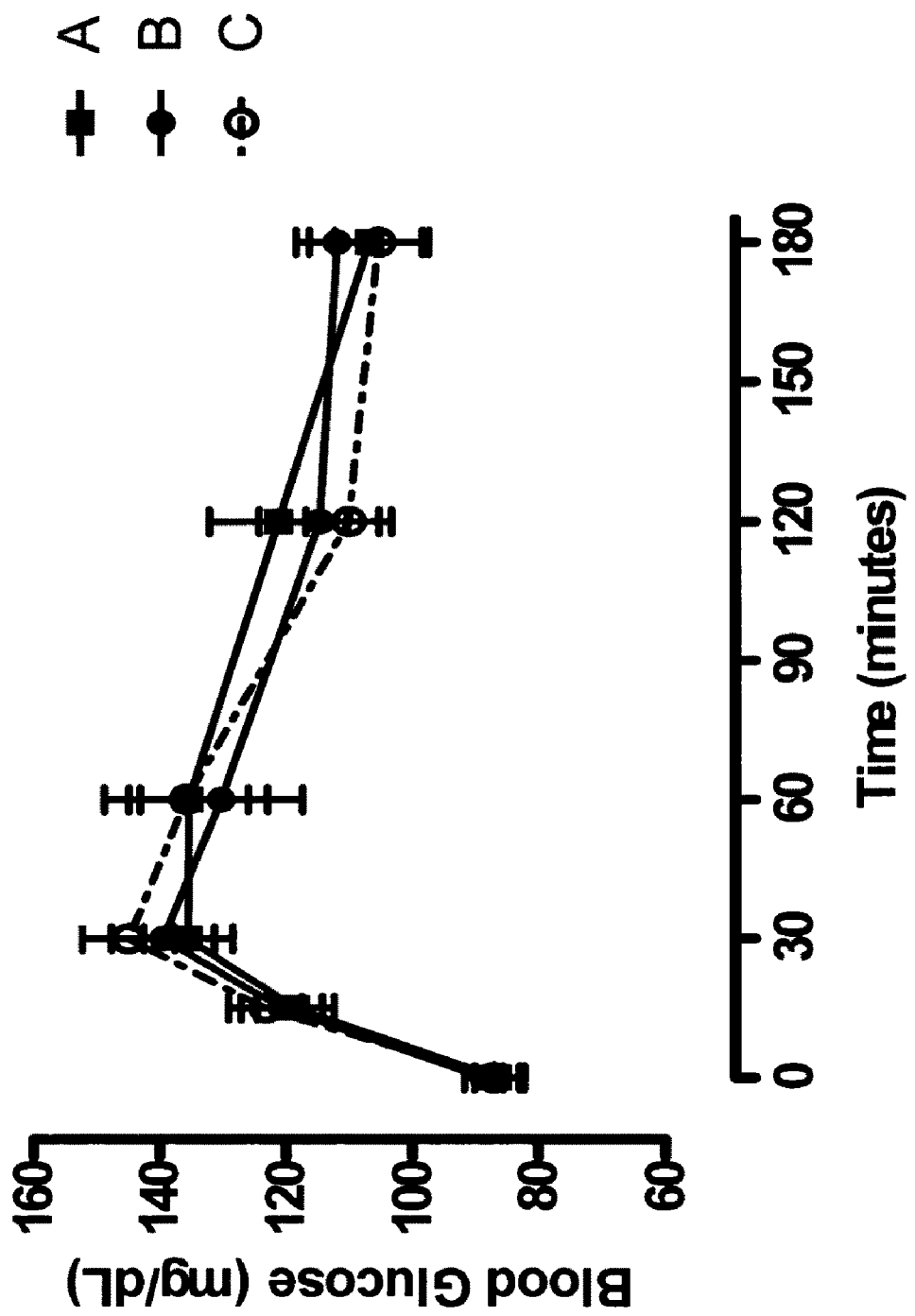
Figure 38B:
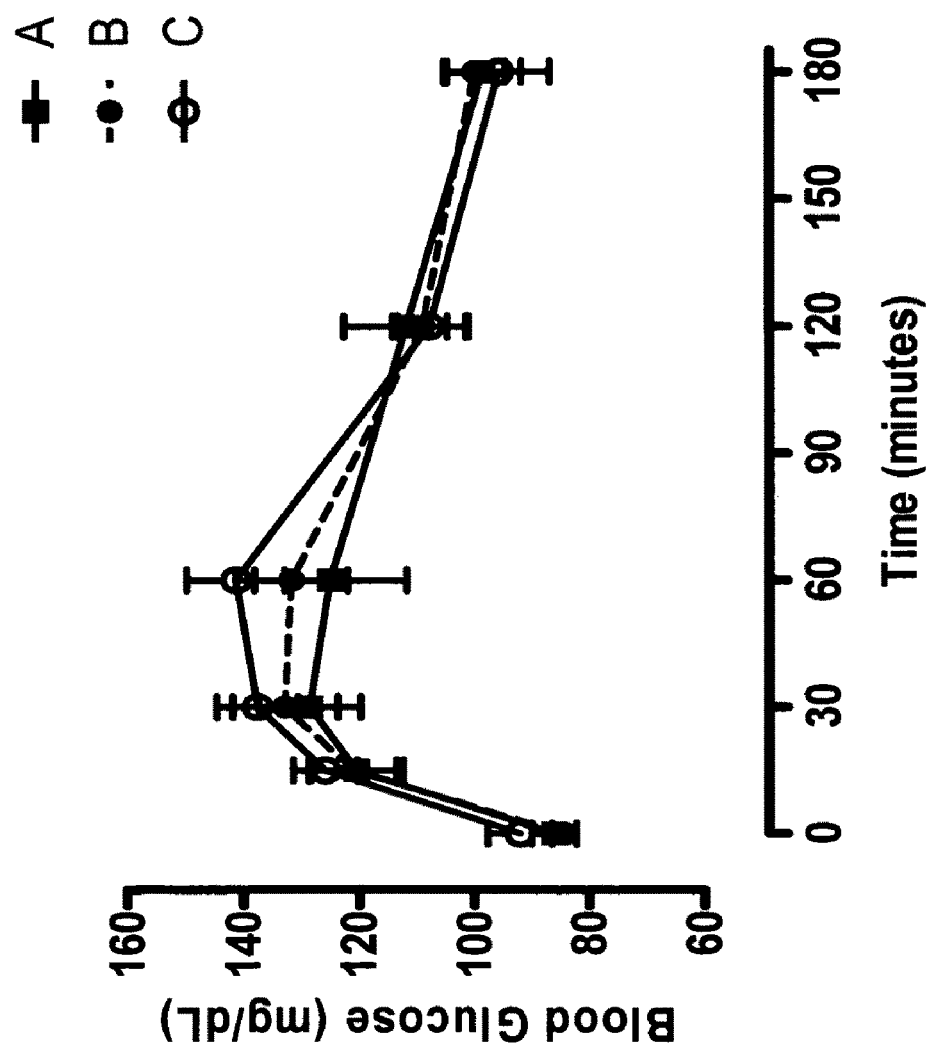
Figure 38C:
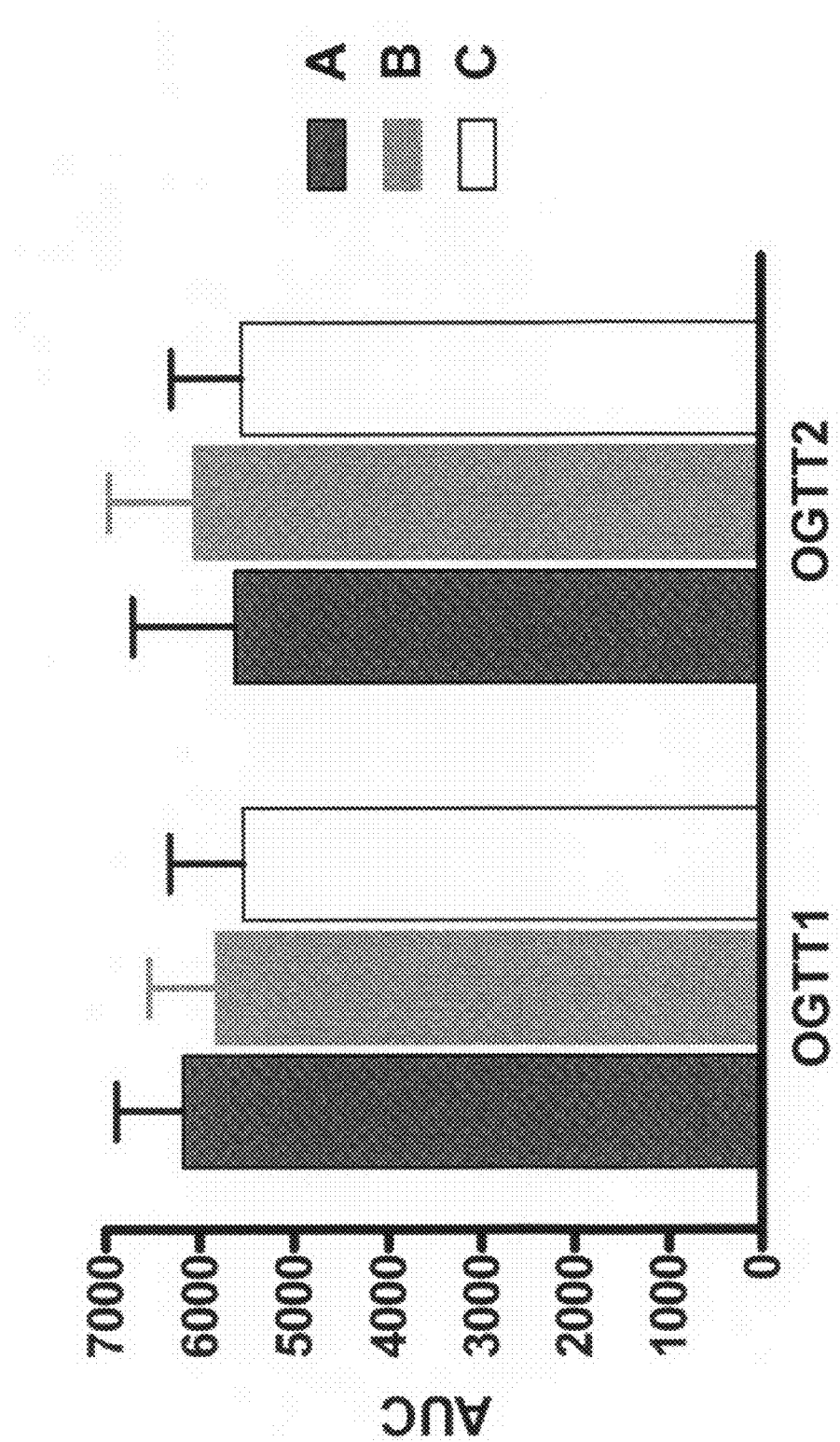
Figure 38D:
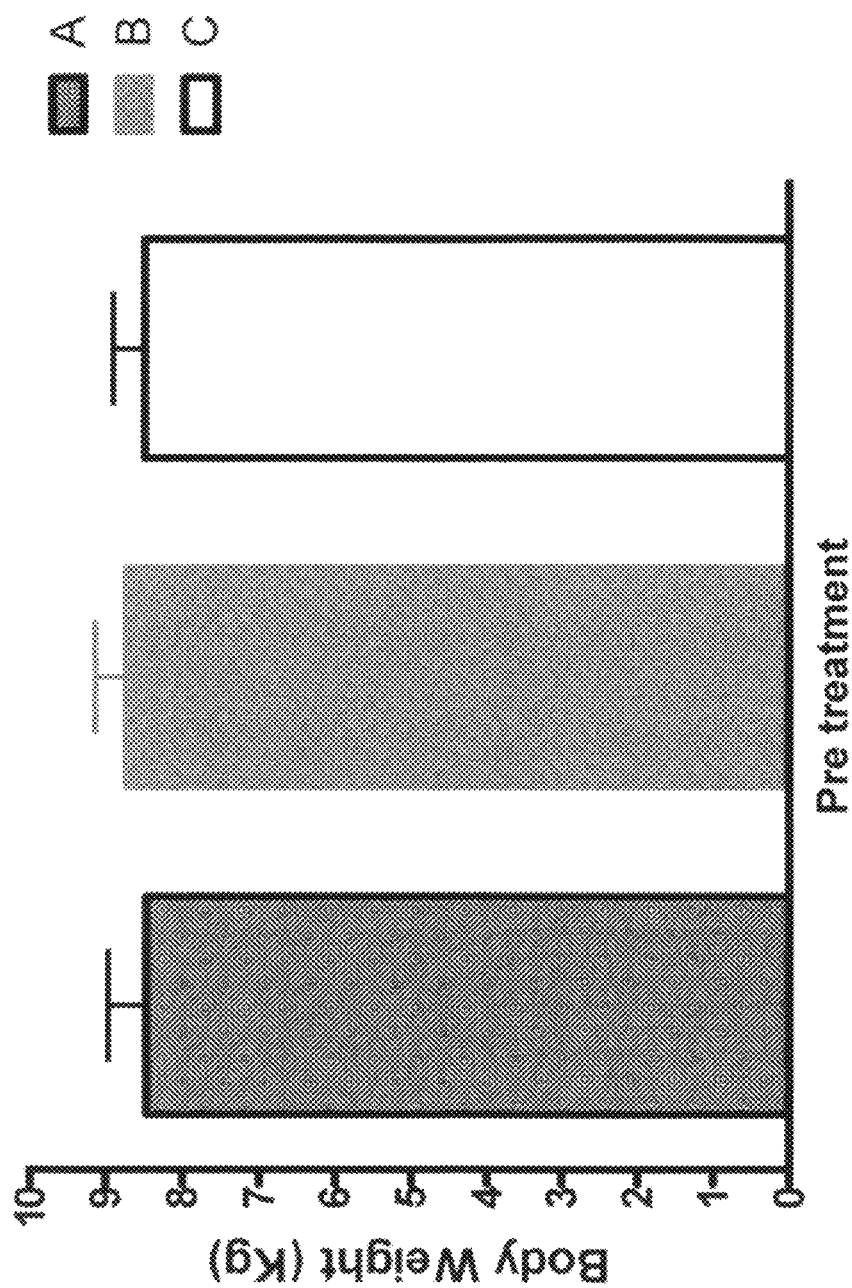

FIGS. 38A-D is a series of plots depicting how the rhesus monkeys were randomized on OGTT profiles, OGTT AUCs and body weight; FIG. 38A depicts baseline glucose levels in OGTT1, solid square corresponds to group A, solid circle, solid line corresponds to group B and open circle, dashed line corresponds to group C before compounds or vehicle were assigned to each group; FIG. 38B depicts baseline glucose levels in OGTT2, solid square corresponds to group A, solid circle, solid line corresponds to group B and open circle, solid line corresponds to group C before compounds or vehicle were assigned to each group; FIG. 38C shows baseline glucose levels for OGTTs 1 and 2 shown in terms of AUC, the stippled bar corresponds to group A, the shaded bar corresponds to group B and the open bar corresponds to group C; and FIG. 38D shows baseline body weight, the stippled bar corresponds to group A, the shaded bar corresponds to group B and the open bar corresponds to group C.

Figure 39:
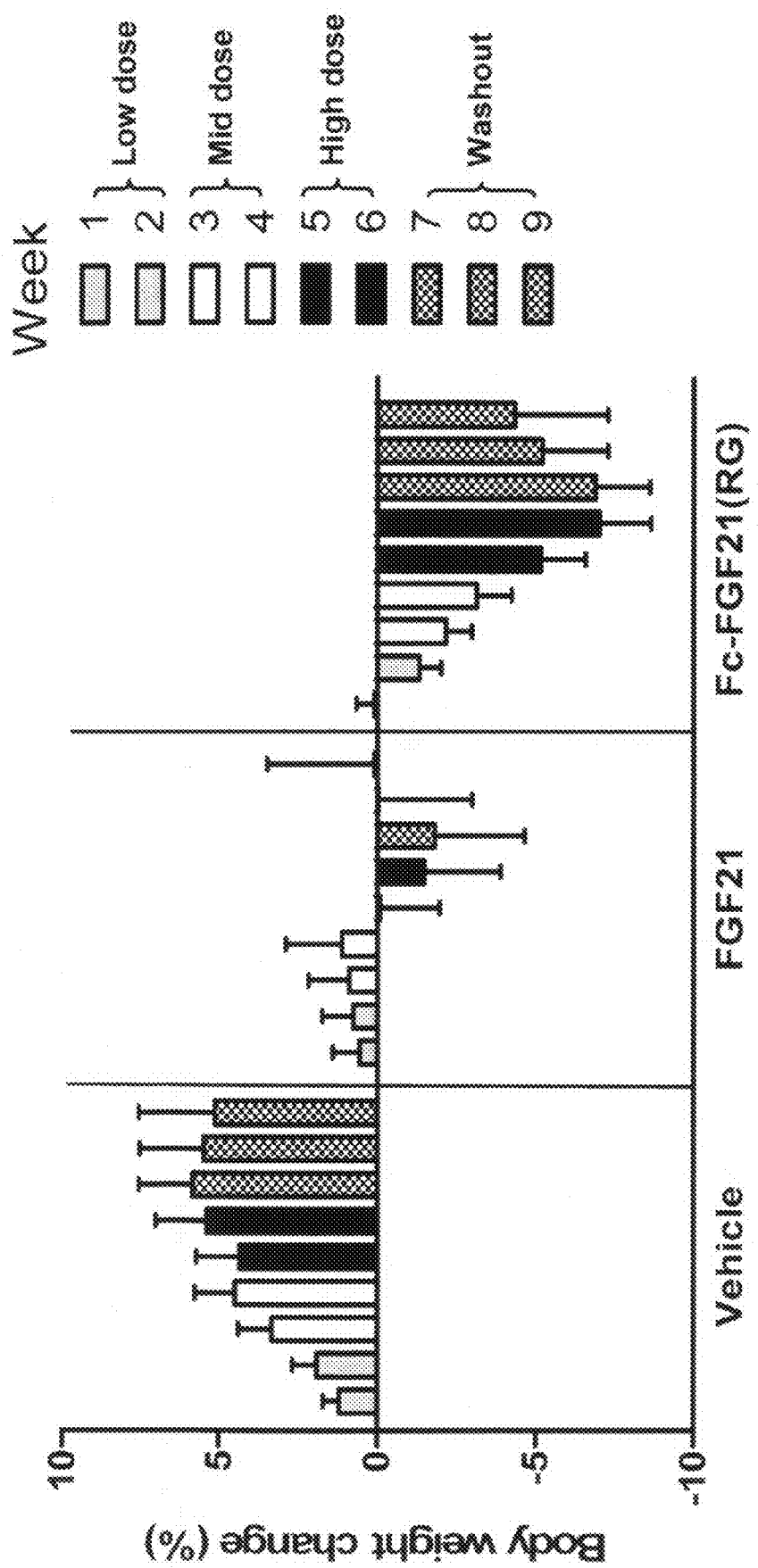

FIG. 39 is a plot showing the effects of vehicle, FGF21 and Fc-FGF21(RG) on body weight in Rhesus monkeys; shaded bars 1 and 2 correspond to weeks 1 and 2 at the low dose, open bars 3 and 4 correspond to weeks 3 and 4 at the mid dose, solid bars 5 and 6 correspond to weeks 5 and 6 at the high dose and stippled bars 7, 8 and 9 correspond to weeks 7-9 during the washout period.

Figure 40:
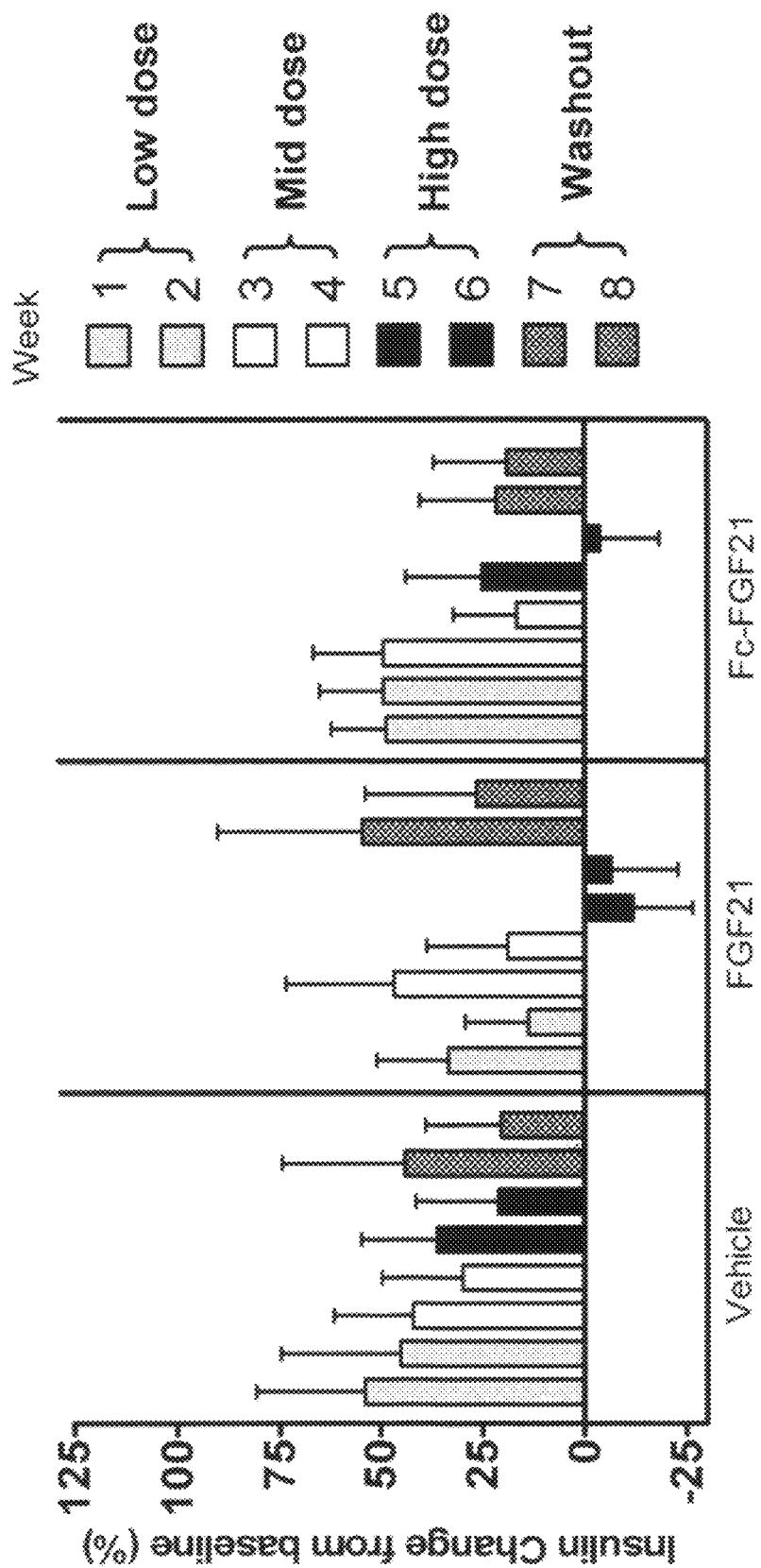

FIG. 40 is a plot showing the percent change in fasted insulin relative to baseline of vehicle, FGF21 and Fc-FGF21 (RG) on fasted insulin levels in Rhesus monkeys; shaded bars 1 and 2 correspond to weeks 1 and 2 at the low dose, open bars 3 and 4 correspond to weeks 3 and 4 at the mid dose, solid bars 5 and 6 correspond to 30 weeks 5 and 6 at the high dose and stippled bars 7 and 8 correspond to weeks 7 and 8 during the washout period.

Figure 41:
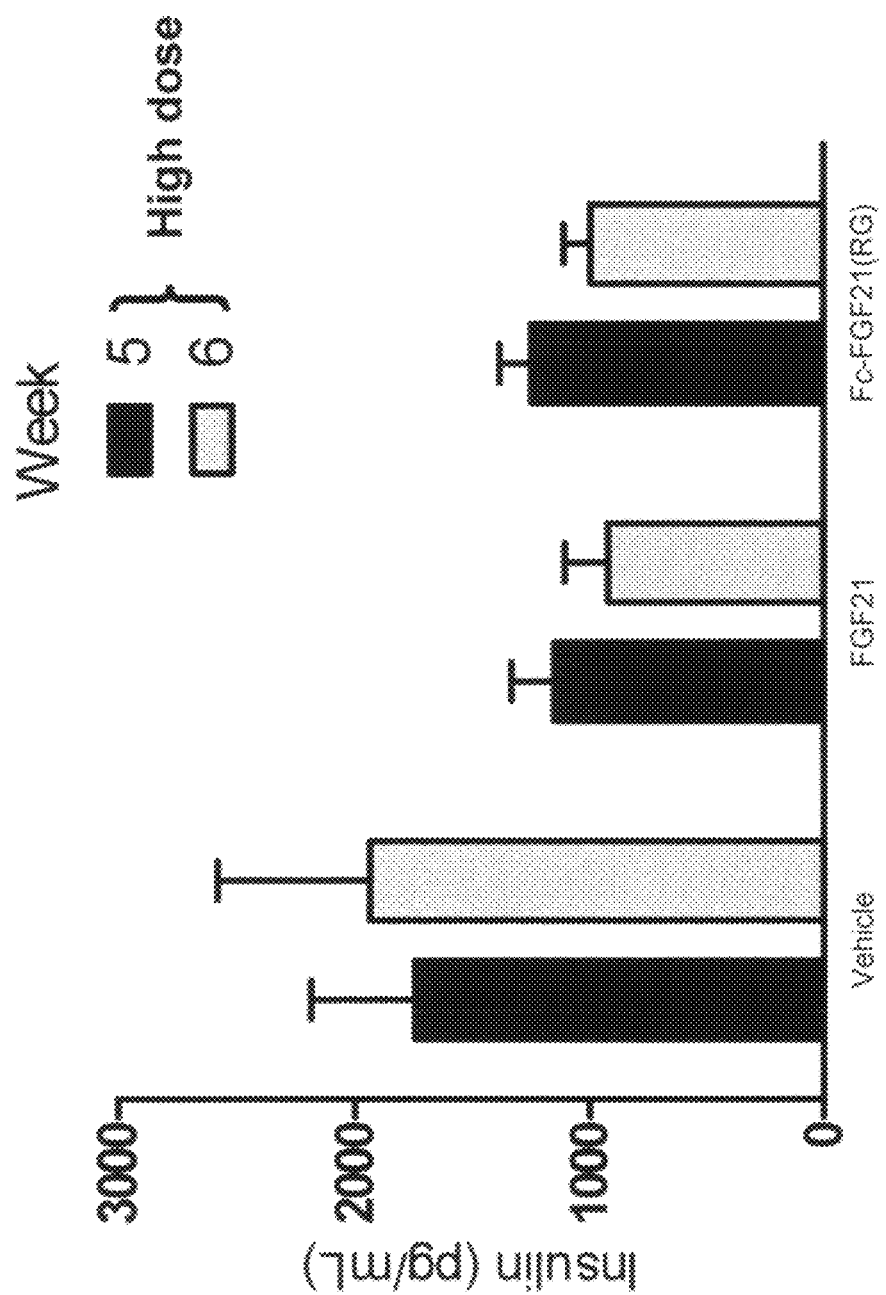

FIG. 41 is a plot showing the effects of vehicle, FGF21 and Fc-FGF21(RG), given at the high dose, on fed insulin levels of Rhesus monkeys acquired during weeks 5 and 6 of the study; solid bars correspond to week 5 and shaded bars correspond to week 6.

Figure 42:
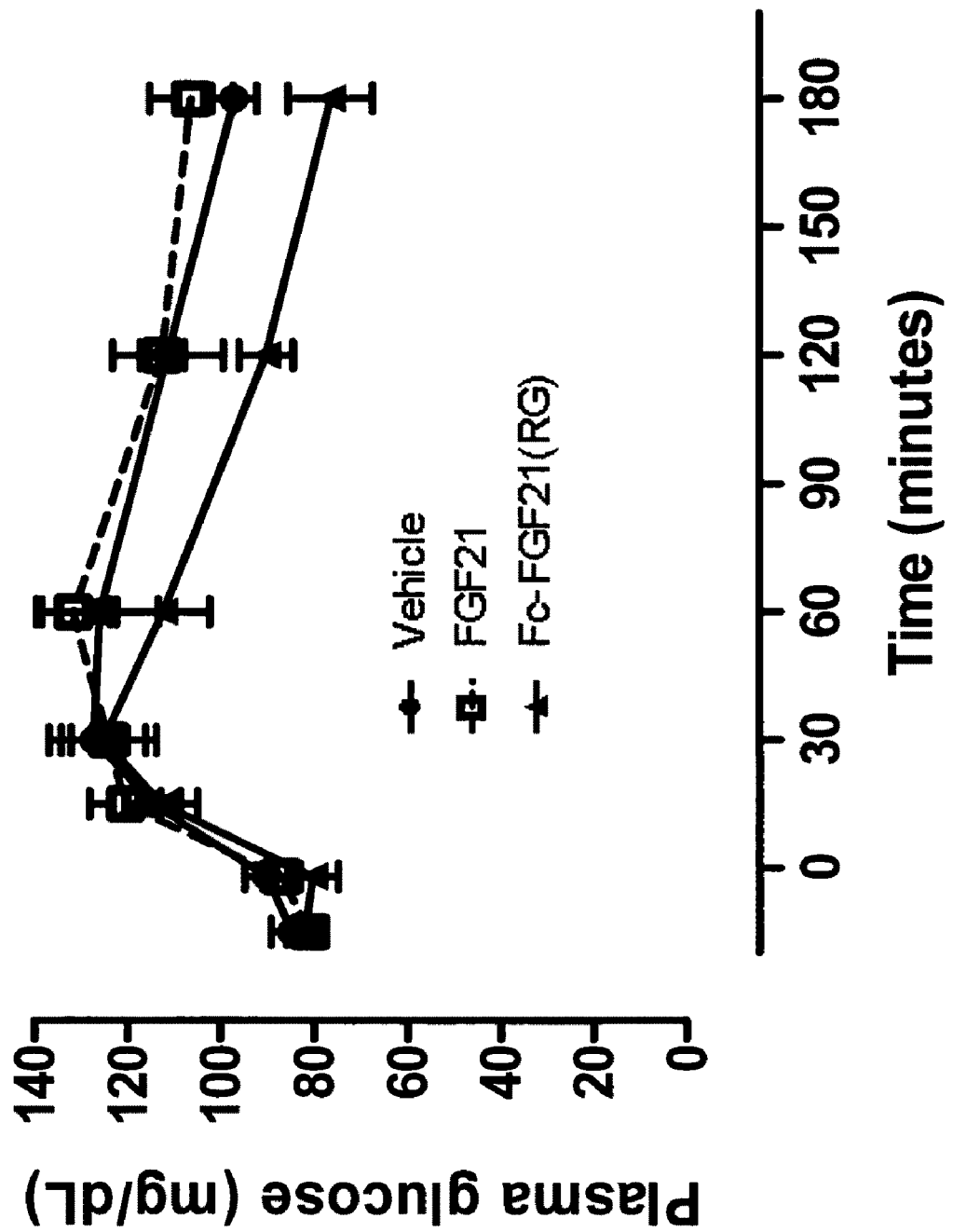

FIG. 42 is a plot showing the glucose profiles of OGTT5 performed at the end of the two week high-dose treatment with Fc-FGF21(RG); solid circle, solid line corresponds to vehicle, open square, dotted line corresponds to FGF21 and solid triangle, solid line corresponds to Fc-FGF21(RG).

Figure 43:
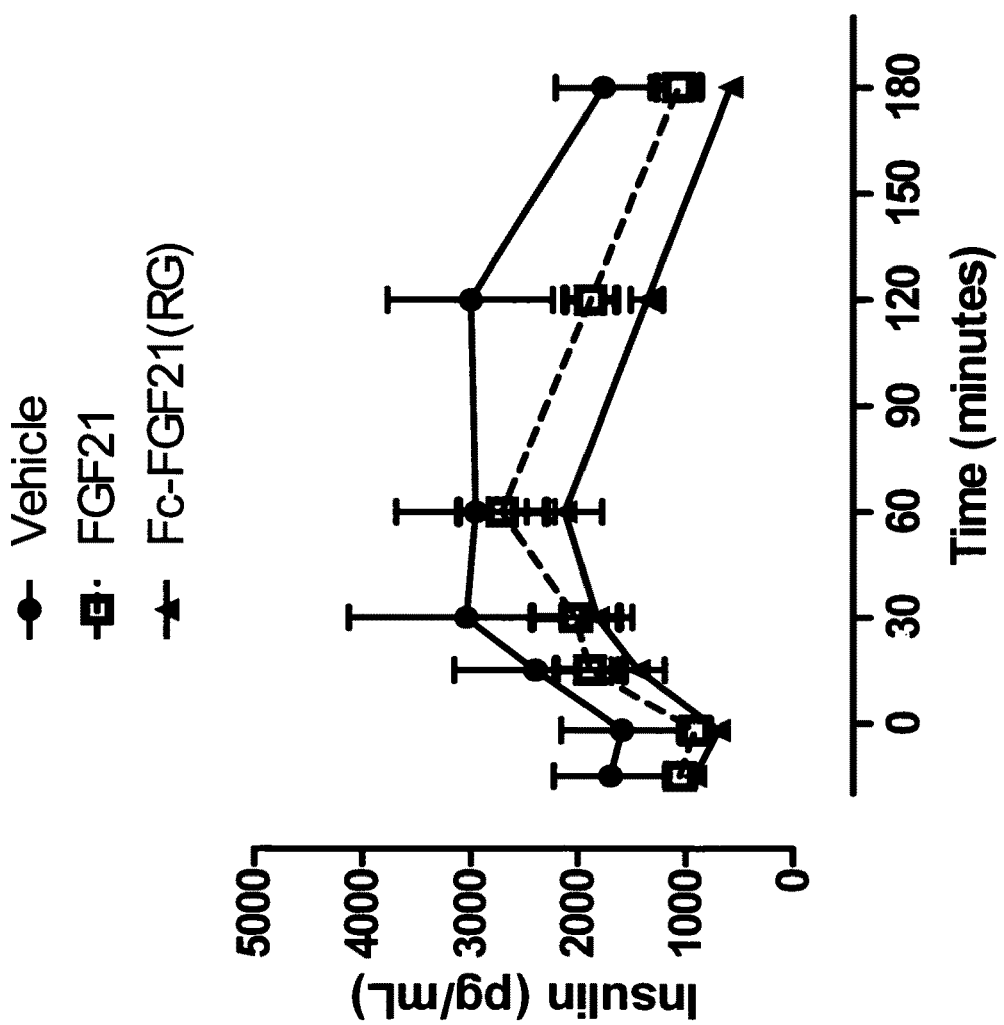

FIG. 43 is a plot showing the insulin profiles of OGTT5 performed at the end of the two week high-dose treatment with Fc-FGF21(RG); solid circle, solid line corresponds to vehicle, open square, dotted line corresponds to FGF21 and solid triangle, solid line corresponds to Fc-FGF21(RG).

Figure 44:
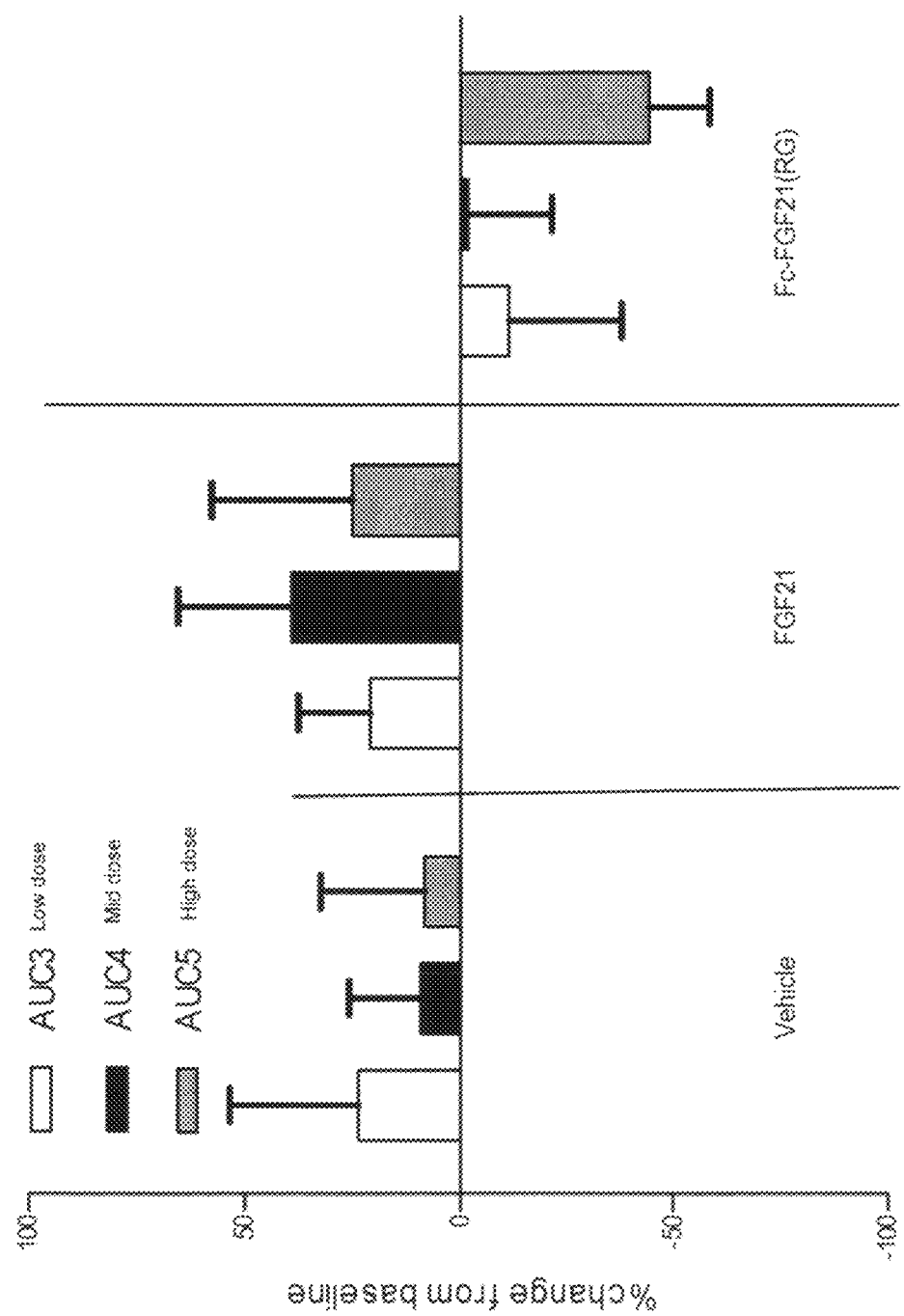

FIG. 44 is a plot showing the glucose OGTT AUC 1-3 determined at the end of each dose period (low, mid and high dose) of the Rhesus monkeys; open bars correspond to AUC3 calculated from glucose measurements during OGTT3, solid bars correspond to AUC4 calculated from glucose measurements during OGTT4 and shaded bars correspond to AUC5 calculated from glucose measurements during OGTT5.

Figure 45:
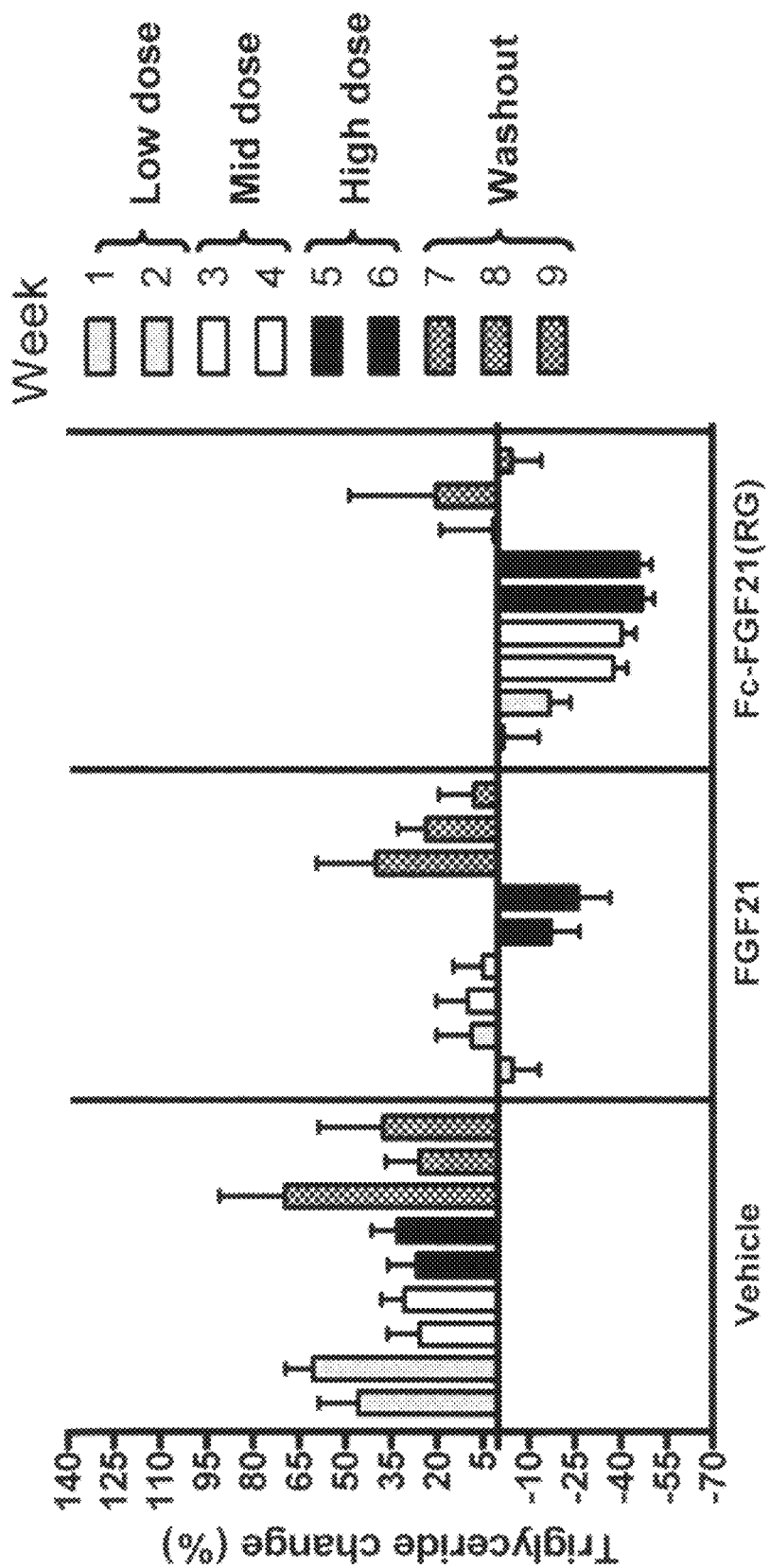

FIG. 45 is a graph showing the effects of vehicle, FGF21 and Fc-FGF21(RG) on percent change from baseline of the fasted plasma triglyceride levels from each group of Rhesus monkeys; shaded bars 1 and 2 correspond to weeks 1 and 2 at the low dose, open bars 3 and 4 correspond to weeks 3 and 4 at the mid dose, solid bars 5 and 6 correspond to weeks 5 and 6 at the high dose and stippled bars 7, 8 and 9 correspond to weeks 7-9 during the washout period.

Figure 46:
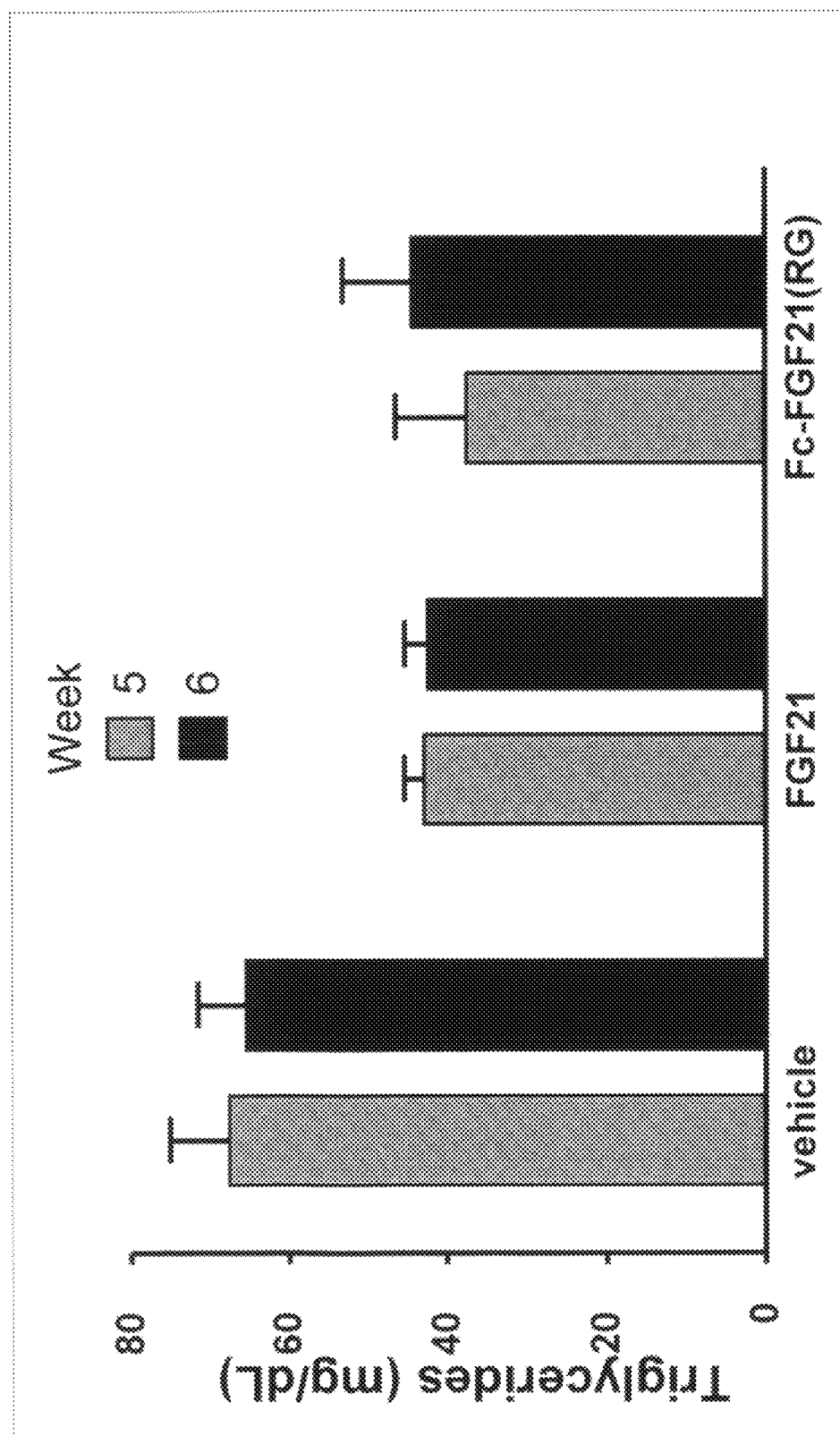

FIG. 46 is a graph showing fed plasma triglyceride levels from each group of the Rhesus monkeys; as measured during the fifth and sixth weeks of treatment with vehicle, FGF21 or Fc-FGF21(RG) at the high dose; shaded bars correspond to week 5 and solid bars correspond to week 6.

Figure 47:
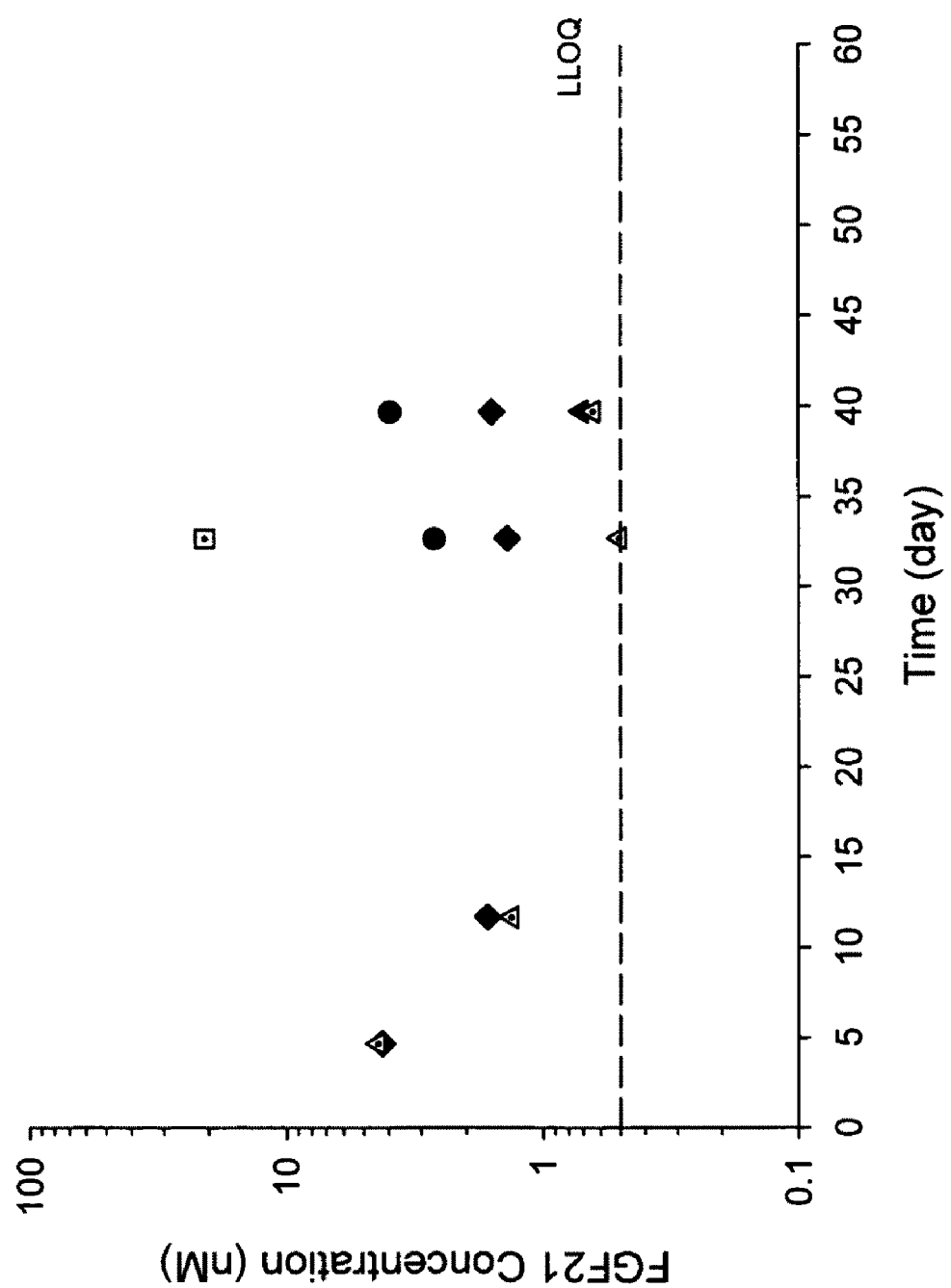

FIG. 47 is a plot showing individual monkey FGF21 levels measured at pre-dose, and 5, 12, 19, and 26 days, with samples acquired at approximately 21 hours after each injection.

Figure 48:
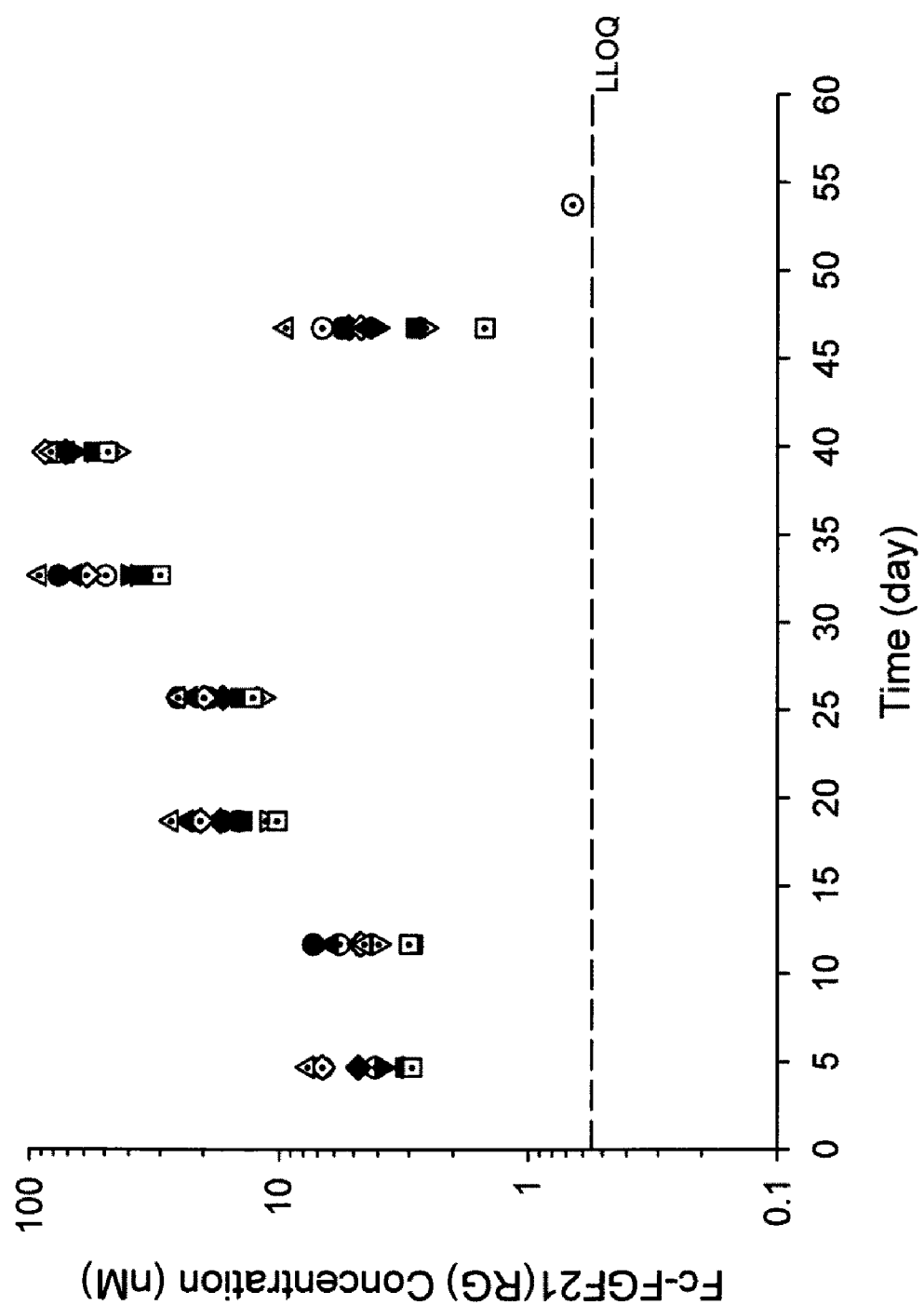

FIG. 48 is a plot showing individual monkey Fc-FGF21 (RG) levels measured at pre-dose, and 5, 12, 19, and 26 days, with samples acquired approximately 5 days after each injection.

Figure 49:
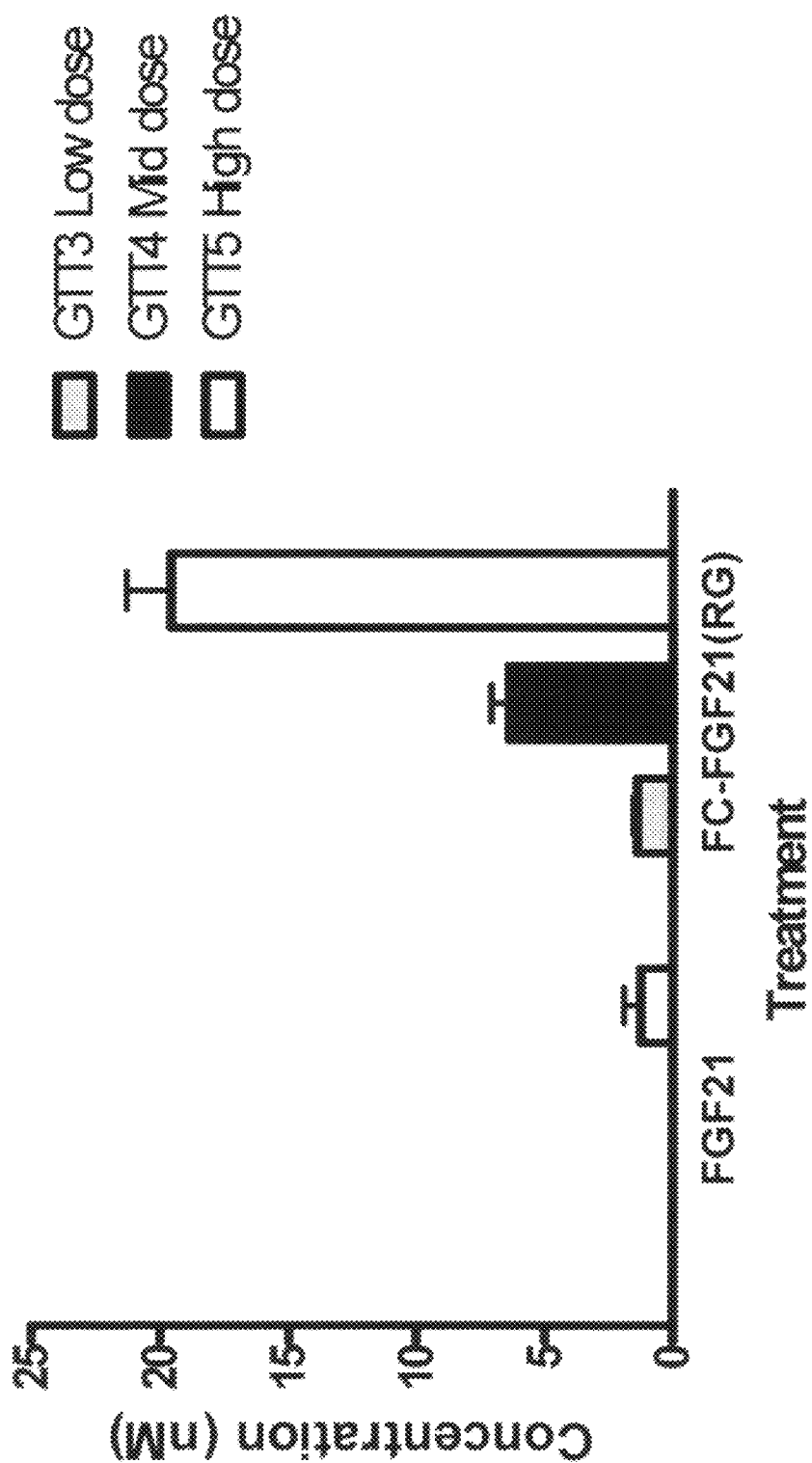

FIG. 49 is a plot showing mean concentrations of FGF21 and Fc-FGF21(RG) levels measured from the three OGTTs performed following each of the low, mid and high doses; shaded bars correspond to OGTT3 at the low dose, solid bars correspond to OGTT4 at the mid dose and open bars correspond to OGTT5 at the high dose.

DETAILED DESCRIPTION OF THE INVENTION

A human FGF21 protein having enhanced properties such as an increased half-life and/or decreased aggregation can be prepared using the methods disclosed herein and standard molecular biology methods. Optionally, the half-life can be further extended by fusing an antibody, or portion thereof, to the N-terminal or C-terminal end of the wild-type FGF21 sequence. It is also possible to further extend the half-life or decrease aggregation of the wild-type FGF21 protein by introducing amino acid substitutions into the protein. Such modified proteins are referred to herein as mutants, or FGF21 mutants, and form embodiments of the present invention.

Recombinant nucleic acid methods used herein, including in the Examples, are generally those set forth in Sambrook et al., *Molecular Cloning: A Laboratory Manual* (Cold Spring Harbor Laboratory Press, 1989) or *Current Protocols in Molecular Biology* (Ausubel et al., eds., Green Publishers Inc. and Wiley and Sons 1994), both of which are incorporated herein by reference for any purpose.

1. General Definitions

The term "isolated nucleic acid molecule" refers to a nucleic acid molecule of the invention that (1) has been separated from at least about 50 percent of proteins, lipids, carbohydrates, or other materials with which it is naturally found when total nucleic acid is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecules or other contaminants that are found in its natural environment that would interfere with its use in polypeptide production or its therapeutic, diagnostic, prophylactic or research use.

The term "vector" is used to refer to any molecule (e.g., nucleic acid, plasmid, or virus) used to transfer coding information to a host cell.

The term "expression vector" refers to a vector that is suitable for transformation of a host cell and contains nucleic acid sequences that direct and/or control the expression of inserted heterologous nucleic acid sequences. Expression includes, but is not limited to, processes such as transcription, translation, and RNA splicing, if introns are present.

The term "operably linked" is used herein to refer to an arrangement of flanking sequences wherein the flanking sequences so described are configured or assembled so as to perform their usual function. Thus, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "isolated polypeptide" refers to a polypeptide of the present invention that (1) has been separated from at least about 50 percent of polynucleotides, lipids, carbohydrates, or other materials with which it is naturally found when isolated from the source cell, (2) is not linked (by covalent or noncovalent interaction) to all or a portion of a polypeptide to which the "isolated polypeptide" is linked in nature, (3) is operably linked (by covalent or noncovalent interaction) to a polypeptide with which it is not linked in nature, or (4) does not occur in nature. Preferably, the isolated polypeptide is substantially free from any other contaminating polypeptides or other contaminants that are found in its natural environment that would interfere with its therapeutic, diagnostic, prophylactic or research use.

The term "naturally occurring" when used in connection with biological materials such as nucleic acid molecules, polypeptides, host cells, and the like, refers to materials which are found in nature and are not manipulated by man. Similarly, "non-naturally occurring" as used herein refers to a material that is not found in nature or that has been structurally modified or synthesized by man. When used in connection with nucleotides, the term "naturally occurring" refers to the bases adenine (A), cytosine (C), guanine (G), thymine (T), and uracil (U). When used in connection with amino acids, the term "naturally occurring" refers to the 20 amino acids alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y).

The term "FGF21 polypeptide" refers to a naturally-occurring wild-type polypeptide expressed in humans. For purposes of this disclosure, the term "FGF21 polypeptide" can be used interchangeably to refer to any full-length FGF21 polypeptide, e.g., SEQ ID NO:2, which consists of 209 amino acid residues and which is encoded by the nucleotide sequence of SEQ ID NO: 1; any mature form of the polypeptide, e.g., SEQ ID NO:4, which consists of 181 amino acid residues and which is encoded by the nucleotide sequence of SEQ ID NO: 3, and in which the 28 amino acid residues at the amino-terminal end of the full-length FGF21 polypeptide (i.e., which constitute the signal peptide) have been removed, and variants thereof.

The terms "FGF21 polypeptide mutant" and "FGF21 mutant" refer to an FGF21 polypeptide variant in which a naturally occurring FGF21 amino acid sequence has been modified. Such modifications include, but are not limited to, one or more amino acid substitutions, including substitutions with non-naturally occurring amino acid analogs, and truncations. Thus, FGF21 polypeptide mutants include, but are not limited to, site-directed FGF21 mutants, truncated FGF21 polypeptides, proteolysis-resistant FGF21 mutants, aggregation-reducing FGF21 mutants, FGF21 combination mutants, and FGF21 fusion proteins, as described herein. For the purpose of identifying the specific truncations and amino acid substitutions of the FGF21 mutants of the present invention, the numbering of the amino acid residues truncated or mutated corresponds to that of the mature 181-residue FGF21 polypeptide.

In other embodiments of the present invention, an FGF21 polypeptide mutant comprises an amino acid sequence that is at least about 85 percent identical to the amino acid sequence of SEQ ID NO: 4, but wherein specific residues conferring a desirable property to the FGF21 polypeptide mutant, e.g., proteolysis-resistance, increased half life or aggregation-reducing properties and combinations thereof, have not been further modified. In other words, with the exception of residues in the FGF21 mutant sequence that have been modified in order to confer proteolysis-resistance, aggregation-reducing, or other properties, about 15 percent of all other amino acid residues in the FGF21 mutant sequence can be modified. For example, in the FGF21 mutant Q173E, up to 15 percent of all amino acid residues other than the glutamic acid residue, which was substituted for glutamine at position 173, could be modified. In still other embodiments, an FGF21 polypeptide mutant comprises an amino acid sequence that is at least about 90 percent, or about 95, 96, 97, 98, or 99 percent identical to the amino acid sequence of SEQ ID NO: 4, but wherein the specific residues conferring the FGF21 polypeptide mutant's proteolysis-resistance or aggregation-reducing properties have not been further modified. Such FGF21 polypeptide mutants possess at least one activity of the wild-type FGF21 polypeptide.

The present invention also encompasses a nucleic acid molecule encoding an FGF21 polypeptide mutant comprising an amino acid sequence that is at least about 85 percent identical to the amino acid sequence of SEQ ID NO: 4, but wherein specific residues conferring a desirable property to the FGF21 polypeptide mutant, e.g., proteolysis-resistance, increased half life or aggregation-reducing properties and combinations thereof have not been further modified. In other words, with the exception of nucleotides that encode residues in the FGF21 mutant sequence that have been modified in order to confer proteolysis-resistance, aggregation-reducing, or other properties, about 15 percent of all other nucleotides in the FGF21 mutant sequence can be modified. For example, in the FGF21 mutant Q173E, up to 15 percent of all nucleotides other than the nucleotides encoding the glutamic acid residue, which was substituted for glutamine at position 173, could be modified. The present invention further encompasses a nucleic acid molecule encoding an FGF21 polypeptide mutant comprising an amino acid sequence that is at least about 90 percent, or about 95, 96, 97, 98, or 99 percent identical to the amino acid sequence of SEQ ID NO: 4, but wherein the specific residues conferring the FGF21 polypeptide mutant's proteolysis-resistance or aggregation-reducing properties have not been further modified. Such FGF21 mutants possess at least one activity of the wild-type FGF21 polypeptide.

The present invention also encompasses a nucleic acid molecule comprising a nucleotide sequence that is at least about 85 percent identical to the nucleotide sequence of SEQ ID NO: 3, but wherein the nucleotides encoding amino acid residues conferring the encoded FGF21 polypeptide mutant's proteolysis-resistance, aggregation-reducing or other properties have not been further modified. In other words, with the exception of residues in the FGF21 mutant sequence that have been modified in order to confer proteolysis-resistance, aggregation-reducing, or other properties, about 15 percent of all other amino acid residues in the FGF21 mutant sequence can be modified. For example, in the FGF21 mutant Q173E, up to 15 percent of all amino acid residues other than the glutamic acid residue, which was substituted for glutamine at position 173, could be modified. The present invention further encompasses a nucleic acid molecule comprising a nucleotide sequence that is at least about 90 percent, or about 95, 96, 97, 98, or 99 percent identical to the nucleotide sequence of SEQ ID NO: 3, but wherein the nucleotides encoding amino acid residues conferring the encoded FGF21 polypeptide mutant's proteolysis-resistance or aggregation-reducing properties have not been further modified. Such nucleic acid molecules encode FGF21 mutant polypeptides possessing at least one activity of the wild-type FGF21 polypeptide.

The term "biologically active FGF21 polypeptide mutant" refers to any FGF21 polypeptide mutant described herein that possesses an activity of the wild-type FGF21 polypeptide, such as the ability to lower blood glucose, insulin, triglyceride, or cholesterol; reduce body weight; and improve glucose tolerance, energy expenditure, or insulin sensitivity, regardless of the type or number of modifications that have been introduced into the FGF21 polypeptide mutant. FGF21 polypeptide mutants possessing a somewhat decreased level of FGF21 activity relative to the wild-type FGF21 polypeptide can nonetheless be considered to be biologically active FGF21 polypeptide mutants.

The terms "effective amount" and "therapeutically effective amount" each refer to the amount of an FGF21 polypeptide mutant used to support an observable level of one or more biological activities of the wild-type FGF21 polypeptide, such as the ability to lower blood glucose, insulin, triglyceride, or cholesterol levels; reduce body weight; or improve glucose tolerance, energy expenditure, or insulin sensitivity.

The term "pharmaceutically acceptable carrier" or "physiologically acceptable carrier" as used herein refers to one or more formulation materials suitable for accomplishing or enhancing the delivery of an FGF21 polypeptide mutant.

The term "antigen" refers to a molecule or a portion of a molecule that is capable of being bound by an antibody, and additionally that is capable of being used in an animal to produce antibodies that are capable of binding to an epitope of that antigen. An antigen may have one or more epitopes.

The term "native Fc" refers to molecule or sequence comprising the sequence of a non-antigen-binding fragment resulting from digestion of whole antibody or produced by other means, whether in monomeric or multimeric form, and can contain the hinge region. The original immunoglobulin source of the native Fc is preferably of human origin and can be any of the immunoglobulins, although IgG1 and IgG2 are preferred. Native Fc molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, and IgA2). One example of a native Fc is a disulfide-bonded dimer resulting from papain digestion of an IgG (see Ellison et al., 1982, *Nucleic Acids Res.* 10: 4071-9). The term "native Fc" as used herein is generic to the monomeric, dimeric, and multimeric forms. An example of an Fc polypeptide sequence is presented in SEQ ID NO:13.

The term "Fc variant" refers to a molecule or sequence that is modified from a native Fc but still comprises a binding site for the salvage receptor, FcRn (neonatal Fc receptor). International Publication Nos. WO 97/34631 and WO 96/32478 describe exemplary Fc variants, as well as interaction with the salvage receptor, and are hereby incorporated by reference. Thus, the term "Fc variant" can comprise a molecule or sequence that is humanized from a non-human native Fc. Furthermore, a native Fc comprises regions that can be removed because they provide structural features or biological activity that are not required for the fusion molecules of the FGF21 mutants of the present invention. Thus, the term "Fc variant" comprises a molecule or sequence that lacks one or more native Fc sites or residues, or in which one or more Fc sites or residues has be modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC). Fc variants are described in further detail hereinafter.

The term "Fc domain" encompasses native Fc and Fc variants and sequences as defined above. As with Fc variants and native Fc molecules, the term "Fc domain" includes molecules in monomeric or multimeric form, whether digested from whole antibody or produced by other means. In some embodiments of the present invention, an Fc domain can be fused to FGF21 or a FGF21 mutant (including a truncated form of FGF21 or a FGF21 mutant) via, for example, a covalent bond between the Fc domain and the FGF21 sequence. Such fusion proteins can form multimers via the association of the Fc domains and both these fusion proteins and their multimers are an aspect of the present invention.

2. Site-Specific FGF21 Mutants

The term "site-specific FGF21 mutant" or "substituted FGF21 mutant" refers to an FGF21 mutant polypeptide having an amino acid sequence that differs from the amino acid sequence of a naturally occurring FGF21 polypeptide sequence, e.g., SEQ ID NOs:2 and 4 and variants thereof. Site-specific FGF21 mutants can be generated by introducing amino acid substitutions, either conservative or non-conservative and using naturally or non-naturally occurring amino acids, at particular positions of the FGF21 polypeptide.

"Conservative amino acid substitution" can involve a substitution of a native amino acid residue (i.e., a residue found in a given position of the wild-type FGF21 polypeptide sequence) with a nonnative residue (i.e., a residue that is not found in a given position of the wild-type FGF21 polypeptide sequence) such that there is little or no effect on the polarity or charge of the amino acid residue at that position. Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties.

Naturally occurring residues can be divided into classes based on common side chain properties:
(1) hydrophobic: norleucine, Met, Ala, Val, Leu, Ile;
(2) neutral hydrophilic: Cys, Ser, Thr;
(3) acidic: Asp, Glu;
(4) basic: Asn, Gln, His, Lys, Arg;
(5) residues that influence chain orientation: Gly, Pro; and
(6) aromatic: Trp, Tyr, Phe.

Conservative substitutions can involve the exchange of a member of one of these classes for another member of the same class. Non-conservative substitutions can involve the exchange of a member of one of these classes for a member from another class.

Desired amino acid substitutions (whether conservative or non-conservative) can be determined by those skilled in the art at the time such substitutions are desired. An exemplary (but not limiting) list of amino acid substitutions is set forth in Table 1.

TABLE 1

Amino Acid Substitutions

| Original Residue | Exemplary Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala, Phe |
| Leu | Ile, Val, Met, Ala, Phe |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

3. Truncated FGF21 Polypeptides

One embodiment of the present invention is directed to truncated forms of the mature FGF21 polypeptide. This embodiment of the present invention arose from an effort to identify truncated FGF21 polypeptides that are capable of providing an activity that is similar, and in some instances superior, to untruncated forms of the mature FGF21 polypeptide.

As used herein, the term "truncated FGF21 polypeptide" refers to an FGF21 polypeptide in which amino acid residues have been removed from the amino-terminal (or N-terminal) end of the FGF21 polypeptide, amino acid residues have been removed from the carboxyl-terminal (or C-terminal) end of the FGF21 polypeptide, or amino acid residues have been removed from both the amino-terminal and carboxyl-terminal ends of the FGF21 polypeptide. The various truncations disclosed herein were prepared as described herein Examples 3 and 6.

The activity of N-terminally truncated FGF21 polypeptides and C-terminally truncated FGF21 polypeptides can be assayed using an in vitro ELK-luciferase assay as described in Example 4. Specific details of the in vitro assays that can be used to examine the activity of truncated FGF21 polypeptides can be found in Example 4.

The activity of the truncated FGF21 polypeptides of the present invention can also be assessed in an in vivo assay, such as ob/ob mice as shown in Examples 5 and 7. Generally, to assess the in vivo activity of a truncated FGF21 polypeptide, the truncated FGF21 polypeptide can be administered to a test animal intraperitoneally. After a desired incubation period (e.g., one hour or more), a blood sample can be drawn, and blood glucose levels can be measured. Specific details of the in vivo assays that can be used to examine the activity of truncated FGF21 polypeptides can be found in Examples 5 and 7.

a. N-Terminal Truncations

In some embodiments of the present invention, N-terminal truncations comprise 1, 2, 3, 4, 5, 6, 7, or 8 amino acid residues from the N-terminal end of the mature FGF21 polypeptide. As demonstrated in, for example, Example 5 and FIG. 3, truncated FGF21 polypeptides having N-terminal truncations of fewer than 9 amino acid residues retain the ability of the mature FGF21 polypeptide to lower blood glucose in an individual. Accordingly, in particular embodiments, the present invention encompasses truncated forms of the mature FGF21 polypeptide or FGF21 polypeptide mutants having N-terminal truncations of 1, 2, 3, 4, 5, 6, 7, or 8 amino acid residues.

b. C-Terminal Truncations

In some embodiments of the present invention, C-terminal truncations comprise 1, 2, 3, 4, 5, 6, 7, 8, 9, 10, 11, or 12 amino acid residues from the C-terminal end of the mature FGF21 polypeptide. As demonstrated in, for example, Example 4 and FIG. 1B, truncated FGF21 polypeptides having C-terminal truncations of fewer than 13 amino acid residues exhibited an efficacy of at least 50% of the efficacy of wild-type FGF21 in an in vitro ELK-luciferase assay, indicating that these FGF21 mutants retain the ability of the mature FGF21 polypeptide to lower blood glucose in an individual. Accordingly, in particular embodiments, the present invention encompasses truncated forms of the mature FGF21 polypeptide or FGF21 polypeptide mutants having C-terminal truncations of 1, 2, 3, 4, 5, 6, 7, 8, 9, 10, 11, or 12 amino acid residues.

c. N-Terminal and C-Terminal Truncations

In some embodiments of the present invention, truncated FGF21 polypeptides can have a combination of N-terminal and C-terminal truncations. Truncated FGF21 polypeptides having a combination of N-terminal and C-terminal truncations share the activity of corresponding truncated FGF21 polypeptides having either the N-terminal or C-terminal truncations alone. In other words, truncated FGF21 polypeptides having both N-terminal truncations of fewer than 9 amino acid residues and C-terminal truncations of fewer than 13 amino acid residues possess similar or greater blood glucose-lowering activity as truncated FGF21 polypeptides having N-terminal truncations of fewer than 9 amino acid residues or truncated FGF21 polypeptides having C-terminal truncations of fewer than 13 amino acid residues. Accordingly, in particular embodiments, the present invention encompasses truncated forms of the mature FGF21 polypeptide or FGF21 polypeptide mutants having both N-terminal truncations of 1, 2, 3, 4, 5, 6, 7, or 8 amino acid residues and C-terminal truncations of 1, 2, 3, 4, 5, 6, 7, 8, 9, 10, 11, or 12 amino acid residues.

As with all FGF21 mutants of the present invention, truncated FGF21 polypeptides can optionally comprise an amino-terminal methionine residue, which can be introduced by directed mutation or as a result of a bacterial expression process.

The truncated FGF21 polypeptides of the present invention can be prepared as described in Examples 3 and 6. Those of ordinary skill in the art, familiar with standard molecular biology techniques, can employ that knowledge, coupled with the instant disclosure, to make and use the truncated FGF21 polypeptides of the present invention. Standard techniques can be used for recombinant DNA, oligonucleotide synthesis, tissue culture, and transformation (e.g., electroporation, lipofection). See, e.g., Sambrook et al., *Molecular Cloning: A Laboratory Manual, supra*, which is incorporated herein by reference for any purpose. Enzymatic reactions and purification techniques can be performed according to manufacturer's specifications, as commonly accomplished in the art, or as described herein. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses; chemical analyses; pharmaceutical preparation, formulation, and delivery; and treatment of patients.

The truncated FGF21 polypeptides of the present invention can also be fused to another entity, which can impart additional properties to the truncated FGF21 polypeptide. In one embodiment of the present invention, a truncated FGF21 polypeptide can be fused to an Fc sequence. Such fusion can be accomplished using known molecular biological methods and/or the guidance provided herein. The benefits of such fusion polypeptides, as well as methods for making such fusion polypeptides, are discussed in more detail herein.

4. Proteolysis-Resistant FGF21 Mutants

As described in Example 8, mature FGF21 was found to be undergoing in vivo degradation, which was ultimately determined to arise from proteolytic attack. The in vivo degradation of mature FGF21 was found to lead to shorter effective half-life, which can adversely affect the therapeutic potential of a molecule. Accordingly, a directed study was performed to identify FGF21 mutants that exhibit a resistance to proteolysis. As a result of this investigation, the sites in the mature FGF21 polypeptide that were determined to be particularly susceptible to proteolysis include the peptide bond between the amino acid residues at positions 4-5, 20-21, 151-152, and 171-172.

A broad but focused and directed study was performed to identify particular substitutions that eliminate the observed proteolytic effect while not affecting the activity of the protein to an unacceptable degree. Tables 8 and 11 highlight some of the mutants that were prepared and tested. As described in, for example, Examples 13 and 14, not all FGF21 mutants exhibited an ideal profile; some mutants conferred proteolysis resistance but at the cost of compromised FGF21 activity. Other mutations retained FGF21 activity but did not confer proteolysis resistance. Several mutants, including, for example, FGF21 P171G, retained a similar level of activity as wild-type FGF21 while also exhibiting resistance to proteolytic degradation.

One selection criteria for identifying desirable proteolysis-resistant FGF21 mutants was that the activity of the FGF21 mutant be essentially the same as, or greater than, the activity of wild-type FGF21. Therefore, another embodiment of the present invention is directed to FGF21 mutants that are resistant to proteolysis and still retain activity that is essentially the same as, or greater than, wild-type FGF21. Although less desirable in some cases, FGF21 mutants that are resistant to proteolysis but exhibit somewhat decreased activity form another embodiment of the present invention. In some cases it can be desirable to maintain a degree of proteolysis, and consequently, FGF21 mutants that allow some degree of proteolysis to occur also form another embodiment of the present invention.

As with all FGF21 mutants of the present invention, the proteolysis-resistant FGF21 mutants of the present invention can be prepared as described herein. Those of ordinary skill in the art, for example, those familiar with standard molecular biology techniques, can employ that knowledge, coupled with the instant disclosure, to make and use the proteolysis-resistant FGF21 mutants of the present invention. Standard techniques can be used for recombinant DNA, oligonucleotide synthesis, tissue culture, and transformation (e.g., electroporation, lipofection). See, e.g., Sambrook et al., *Molecular Cloning: A Laboratory Manual, supra*, which is incorporated herein by reference for any purpose. Enzymatic reactions and purification techniques can be performed according to manufacturer's specifications, as commonly accomplished in the art, or as described herein. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses; chemical analyses; pharmaceutical preparation, formulation, and delivery; and treatment of patients.

The proteolysis-resistant FGF21 mutants of the present invention can be fused to another entity, which can impart additional properties to the proteolysis-resistant FGF21 mutant. In one embodiment of the present invention, a proteolysis-resistant FGF21 mutant can be fused to an IgG Fc sequence, e.g., SEQ ID NO:13. Such fusion can be accomplished using known molecular biological methods and/or the guidance provided herein. The benefits of such fusion polypeptides, as well as methods for making such fusion polypeptides, are known and are discussed in more detail herein.

5. Aggregation-Reducing FGF21 Mutants

As described in Example 15, one property of the wild-type FGF21 polypeptide is its propensity to aggregate. At concentrations over about 5 mg/mL, the aggregation rate is high at room temperature. As shown and described herein, the aggregation rate for the wild-type FGF21 polypeptide is both concentration and temperature dependent.

Aggregation can prove to be a challenge when working with wild-type FGF21 at these concentrations, such as in the context of a therapeutic formulation. Accordingly, a directed study was performed to identify FGF21 mutants that exhibit reduced FGF21 aggregation. The resulting FGF21 mutants were then tested for the propensity to aggregate at various concentrations.

A broad but focused and directed study was performed to identify particular substitutions that eliminate or reduce the observed aggregation effect of wild-type FGF21 while not affecting the activity of the protein to an unacceptable degree. The approach for identifying suitable aggregation-reducing mutants is described in Example 15. Table 16 highlights some of the mutants that were prepared and tested. As described in, for example, Example 17, not all FGF21 mutants exhibited an ideal profile. Some mutants, such as FGF21 L58E had compromised FGF21 activity and were not studied further. Other mutations, such as FGF21 A134E, retained FGF21 activity but did not confer reduced aggregation properties. Several mutants, such as FGF21 L98R, retained FGF21 activity and also exhibited reduced aggregation. One mutant, FGF21 A45K, surprisingly exhibited increased FGF21 activity while also exhibiting reduced aggregation properties.

One selection criteria for identifying desirable aggregation-reducing FGF21 mutants was that the activity of the FGF21 mutant be essentially similar to, or greater than, the activity of wild-type FGF21. Therefore, another embodiment of the present invention is directed to FGF21 mutants having reduced aggregation properties while still retaining an FGF21 activity that is similar to, or greater than, wild-type FGF21. Although less desirable in some cases, FGF21 mutants having reduced aggregation properties but exhibiting somewhat decreased FGF21 activity form another embodiment of the present invention. In some cases it may be desirable to maintain a degree of aggregation, and consequently, FGF21 mutants that allow some degree of aggregation to occur also form another embodiment of the present invention.

As with all FGF21 mutants of the present invention, the aggregation-reducing FGF21 mutants of the present invention can be prepared as described herein. Those of ordinary skill in the art, familiar with standard molecular biology techniques, can employ that knowledge, coupled with the instant disclosure, to make and use the aggregation-reducing FGF21 mutants of the present invention. Standard techniques can be used for recombinant DNA, oligonucleotide synthesis, tissue culture, and transformation (e.g., electroporation, lipofection). See, e.g., Sambrook et al., *Molecular Cloning: A Laboratory Manual, supra*, which is incorporated herein by reference for any purpose. Enzymatic reactions and purification techniques can be performed according to manufacturer's specifications, as commonly accomplished in the art, or as described herein. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses; chemical analyses; pharmaceutical preparation, formulation, and delivery; and treatment of patients.

The aggregation-reducing FGF21 mutants of the present invention can be fused to another entity, which can impart additional properties to the aggregation-reducing FGF21 mutant. In one embodiment of the present invention, an aggregation-reducing FGF21 mutant can be fused to an IgG Fc sequence, e.g., SEQ ID NO:13. Such fusion can be accomplished using known molecular biological methods and/or the guidance provided herein. The benefits of such fusion polypeptides, as well as methods for making such fusion polypeptides, are discussed in more detail herein.

6. FGF21 Combination Mutants

As described herein, the wild-type FGF21 sequence possesses several properties that can pose significant challenges when FGF21 is used as a therapeutic molecule. Among these challenges are the protein's susceptibility to degradation and its propensity for aggregation at high concentration. After an exhaustive effort to identify FGF21 polypeptides that overcome each of these challenges, a directed study was performed to determine whether the amino acid substitutions conferring proteolysis-resistance and those conferring aggregation-reducing properties could be combined in an additive or synergistic fashion in a single polypeptide sequence while maintaining activity levels that are equal to or greater than the activity of wild-type FGF21. This represented a significant challenge, as it is known in the art that the introduction of multiple mutations in a given polypeptide can sometimes adversely affect the expression, activity, and subsequent manufacture of the protein.

Surprisingly, as demonstrated in, for example, Examples 19 and 20, it was found that the desirable properties of several FGF21 mutants could indeed be combined in an additive or synergistic fashion to generate an FGF21 mutant having enhanced pharmaceutical properties. FGF21 mutants that are resistant to proteolysis, have a reduced rate of aggregation, and which still retain activity that is the same as, or greater than, wild-type FGF21, are disclosed herein.

One selection criteria for identifying desirable FGF21 combination mutants was that the activity of the FGF21 mutant be similar to, or greater than, the activity of wild-type FGF21. Therefore, another embodiment of the present invention is directed to FGF21 mutants that are proteolysis-resistant and have reduced aggregation properties while still retaining an FGF21 activity that is similar to, or greater than, wild-type FGF21. Although less desirable in some cases, FGF21 mutants that are proteolysis-resistant and have reduced aggregation properties but exhibit somewhat decreased FGF21 activity form another embodiment of the present invention. In some cases it may be desirable to maintain a degree of proteolysis and/or aggregation, and consequently, FGF21 mutants that allow some degree of proteolysis and/or aggregation also form another embodiment of the present invention.

As with all FGF21 mutants of the present invention, the FGF21 combination mutants of the present invention can be prepared as described herein. Those of ordinary skill in the art, familiar with standard molecular biology techniques, can employ that knowledge, coupled with the instant disclosure, to make and use the FGF21 combination mutants of the present invention. Standard techniques can be used for recombinant DNA, oligonucleotide synthesis, tissue culture, and transformation (e.g., electroporation, lipofection). See, e.g., Sambrook et al., *Molecular Cloning: A Laboratory Manual, supra*, which is incorporated herein by reference for any purpose. Enzymatic reactions and purification techniques can be performed according to manufacturer's specifications, as commonly accomplished in the art, or as described herein. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses; chemical analyses; pharmaceutical preparation, formulation, and delivery; and treatment of patients.

The FGF21 combination mutants of the present invention can be fused to another entity, which can impart additional properties to the FGF21 combination mutant. In one embodiment of the present invention, an FGF21 combination mutant can be fused to an IgG Fc sequence, e.g., SEQ ID NO:13. Such fusion can be accomplished using known molecular biological methods and/or the guidance provided herein. The benefits of such fusion polypeptides, as well as methods for making such fusion polypeptides, are discussed in more detail herein.

7. FGF21 Fusion Proteins

As used herein, the term "FGF21 fusion polypeptide" or "FGF21 fusion protein" refers to a fusion of one or more amino acid residues (such as a heterologous protein or peptide) at the N-terminus or C-terminus of any FGF21 polypeptide mutant described herein.

Heterologous peptides and polypeptides include, but are not limited to, an epitope to allow for the detection and/or isolation of an FGF21 polypeptide mutant; a transmembrane receptor protein or a portion thereof, such as an extracellular domain or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; a functional or non-functional antibody, or a heavy or light chain thereof; and a polypeptide which has an activity, such as a therapeutic activity, different from the FGF21 polypeptide mutants of the present invention. Also encompassed by the present invention are FGF21 mutants fused to human serum albumin (HSA).

FGF21 fusion proteins can be made by fusing heterologous sequences at either the N-terminus or at the C-terminus of an FGF21 polypeptide mutant. As described herein, a heterologous sequence can be an amino acid sequence or a non-amino acid-containing polymer. Heterologous sequences can be fused either directly to the FGF21 polypeptide mutant or via a linker or adapter molecule. A linker or adapter molecule can be one or more amino acid residues (or -mers), e.g., 1, 2, 3, 4, 5, 6, 7, 8, or 9 residues (or -mers), preferably from 10 to 50 amino acid residues (or -mers), e.g., 10, 11, 12, 13, 14, 15, 16, 17, 18, 19, 20, 25, 30, 35, 40, 45, or 50 residues (or -mers), and more preferably from 15 to 35 amino acid residues (or -mers). A linker or adapter molecule can also be designed with a cleavage site for a DNA restriction endonuclease or for a protease to allow for the separation of the fused moieties.

a. Fc Fusions

In one embodiment of the present invention, an FGF21 polypeptide mutant is fused to one or more domains of an Fc region of human IgG. Antibodies comprise two functionally independent parts, a variable domain known as "Fab," that binds an antigen, and a constant domain known as "Fc," that is involved in effector functions such as complement activation and attack by phagocytic cells. An Fc has a long serum half-life, whereas a Fab is short-lived (Capon et al., 1989, *Nature* 337: 525-31). When joined together with a therapeutic protein, an Fc domain can provide longer half-life or incorporate such functions as Fc receptor binding, protein A binding, complement fixation, and perhaps even placental transfer (Capon et al., 1989).

In vivo pharmacokinetic analysis indicated that human FGF21 has a short half-life of about 1 hour in mice due to rapid clearance and in vivo degradation. Therefore, to extend the half-life of FGF21 an Fc sequence was fused to the N- or C-terminal end of the FGF21 polypeptide. The fusion of an Fc region to wild type FGF21, in particularly Fc fused to the N-terminus of wild type FGF21, did not extend the half-life as expected, however, which led to an investigation of the proteolytic degradation of FGF21 in vivo and the identification of FGF21 mutants that were resistant to such degradation. Such mutants are described in, for example, Examples 8 and 11, and exhibit longer half-lives than wild-type FGF21. These and other FGF21 fusion proteins form embodiments of the present invention.

Throughout the disclosure, Fc-FGF21 refers to a fusion protein in which the Fc sequence is fused to the N-terminus of FGF21. Similarly, throughout the disclosure, FGF21-Fc refers to a fusion protein in which the Fc sequence is fused to the C-terminus of FGF21.

The resulting FGF21 fusion protein can be purified, for example, by the use of a Protein A affinity column. Peptides and proteins fused to an Fc region have been found to exhibit a substantially greater half-life in vivo than the unfused counterpart. Also, a fusion to an Fc region allows for dimerization/ multimerization of the fusion polypeptide. The Fc region can be a naturally occurring Fc region, or can be altered to improve certain qualities, such as therapeutic qualities, circulation time, or reduced aggregation.

Useful modifications of protein therapeutic agents by fusion with the "Fc" domain of an antibody are discussed in detail in International Publication No. WO 00/024782, which is hereby incorporated by reference in its entirety. This document discusses linkage to a "vehicle" such as polyethylene glycol (PEG), dextran, or an Fc region.

b. Fusion Protein Linkers

When forming the fusion proteins of the present invention, a linker can, but need not, be employed. When present, the linker's chemical structure may not critical, since it serves primarily as a spacer. The linker can be made up of amino acids linked together by peptide bonds. In some embodiments of the present invention, the linker is made up of from 1 to 20 amino acids linked by peptide bonds, wherein the amino acids are selected from the 20 naturally occurring amino acids. In various embodiments, the 1 to 20 amino acids are selected from the amino acids glycine, serine, alanine, proline, asparagine, glutamine, and lysine. In some embodiments, a linker is made up of a majority of amino acids that are sterically unhindered, such as glycine and alanine. In some embodiments, linkers are polyglycines (such as $(Gly)_4$ (SEQ ID NO:29) and $(Gly)_5$ (SEQ ID NO:30)), polyalanines, combinations of glycine and alanine (such as poly(Gly-Ala)), or combinations of glycine and serine (such as poly(Gly-Ser)). Other suitable linkers include: $(Gly)_5$-Ser-$(Gly)_3$-Ser-$(Gly)_4$-Ser (SEQ ID NO:23), $(Gly)_4$-Ser-(Gly)4-Ser-$(Gly)_4$-Ser (SEQ ID NO:31), $(Gly)_3$-Lys-$(Gly)_4$ (SEQ ID NO:32), $(Gly)_3$-Asn-Gly-Ser-$(Gly)_2$ (SEQ ID NO:33), $(Gly)_3$-Cys-$(Gly)_4$ (SEQ ID NO:34), and Gly-Pro-Asn-Gly-Gly (SEQ ID NO:35). While a linker of 15 amino acid residues has been found to work particularly well for FGF21 fusion proteins, the present invention contemplates linkers of any length or composition.

The linkers described herein are exemplary, and linkers that are much longer and which include other residues are contemplated by the present invention. Non-peptide linkers are also contemplated by the present invention. For example, alkyl linkers such as —NH—$(CH_2)_S$—C(O)—, wherein s=2 to 20, could be used. These alkyl linkers can further be substituted by any non-sterically hindering group, including, but not limited to, a lower alkyl (e.g., C1-C6), lower acyl, halogen (e.g., Cl, Br), CN, $NH_2$, or phenyl. An exemplary non-peptide linker is a polyethylene glycol linker, wherein the linker has a molecular weight of 100 to 5000 kD, for example, 100 to 500 kD.

8. Chemically-Modified FGF21 Mutants

Chemically modified forms of the FGF21 polypeptide mutants described herein, including the truncated forms of FGF21 described herein, can be prepared by one skilled in the art, given the disclosures described herein. Such chemically modified FGF21 mutants are altered such that the chemically modified FGF21 mutant is different from the unmodified FGF21 mutant, either in the type or location of the molecules naturally attached to the FGF21 mutant. Chemically modified FGF21 mutants can include molecules formed by the deletion of one or more naturally-attached chemical groups.

In one embodiment, FGF21 polypeptide mutants of the present invention can be modified by the covalent attachment of one or more polymers. For example, the polymer selected is typically water-soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable. Non-water soluble polymers conjugated to FGF21 polypeptide mutants of the present invention also form an aspect of the invention.

Exemplary polymers each can be of any molecular weight and can be branched or unbranched. The polymers each typically have an average molecular weight of between about 2 kDa to about 100 kDa (the term "about" indicating that in preparations of a water-soluble polymer, some molecules will weigh more and some less than the stated molecular weight). The average molecular weight of each polymer is preferably between about 5 kDa and about 50 kDa, more preferably between about 12 kDa and about 40 kDa, and most preferably between about 20 kDa and about 35 kDa.

Suitable water-soluble polymers or mixtures thereof include, but are not limited to, N-linked or O-linked carbohydrates, sugars, phosphates, polyethylene glycol (PEG) (including the forms of PEG that have been used to derivatize proteins, including mono-($C_1$-$C_{10}$), alkoxy-, or aryloxy-polyethylene glycol), monomethoxy-polyethylene glycol, dextran (such as low molecular weight dextran of, for example, about 6 kD), cellulose, or other carbohydrate based polymers, poly-(N-vinyl pyrrolidone) polyethylene glycol, propylene glycol homopolymers, polypropylene oxide/ethylene oxide co-polymers, polyoxyethylated polyols (e.g., glycerol), and polyvinyl alcohol. Also encompassed by the present invention are bifunctional crosslinking molecules that can be used to prepare covalently attached FGF21 polypeptide mutant multimers. Also encompassed by the present invention are FGF21 mutants covalently attached to polysialic acid.

In some embodiments of the present invention, an FGF21 mutant is covalently, or chemically, modified to include one or more water-soluble polymers, including, but not limited to, polyethylene glycol (PEG), polyoxyethylene glycol, or polypropylene glycol. See, e.g., U.S. Pat. Nos. 4,640,835; 4,496,689; 4,301,144; 4,670,417; 4,791,192; and 4,179,337. In some embodiments of the present invention, an FGF21 mutant comprises one or more polymers, including, but not limited to, monomethoxy-polyethylene glycol, dextran, cellulose, another carbohydrate-based polymer, poly-(N-vinyl pyrrolidone)-polyethylene glycol, propylene glycol homopolymers, a polypropylene oxide/ethylene oxide co-polymer, polyoxyethylated polyols (e.g., glycerol), polyvinyl alcohol, or mixtures of such polymers.

In some embodiments of the present invention, an FGF21 mutant is covalently-modified with PEG subunits. In some embodiments, one or more water-soluble polymers are bonded at one or more specific positions (for example, at the N-terminus) of the FGF21 mutant. In some embodiments, one or more water-soluble polymers are randomly attached to one or more side chains of an FGF21 mutant. In some embodiments, PEG is used to improve the therapeutic capacity of an FGF21 mutant. Certain such methods are discussed, for example, in U.S. Pat. No. 6,133,426, which is hereby incorporated by reference for any purpose.

In embodiments of the present invention wherein the polymer is PEG, the PEG group can be of any convenient molecular weight, and can be linear or branched. The average molecular weight of the PEG group will preferably range from about 2 kD to about 100 kDa, and more preferably from about 5 kDa to about 50 kDa, e.g., 10, 20, 30, 40, or 50 kDa. The PEG groups will generally be attached to the FGF21 mutant via acylation or reductive alkylation through a reactive group on the PEG moiety (e.g., an aldehyde, amino, thiol, or ester group) to a reactive group on the FGF21 mutant (e.g., an aldehyde, amino, or ester group).

The PEGylation of a polypeptide, including the FGF21 mutants of the present invention, can be specifically carried out using any of the PEGylation reactions known in the art. Such reactions are described, for example, in the following references: Francis et al., 1992, *Focus on Growth Factors* 3: 4-10; European Patent Nos. 0 154 316 and 0 401 384; and U.S. Pat. No. 4,179,337. For example, PEGylation can be carried out via an acylation reaction or an alkylation reaction with a reactive polyethylene glycol molecule (or an analogous reactive water-soluble polymer) as described herein. For the acylation reactions, a selected polymer should have a single reactive ester group. For reductive alkylation, a selected polymer should have a single reactive aldehyde group. A reactive aldehyde is, for example, polyethylene glycol propionaldehyde, which is water stable, or mono $C_1$-$C_{10}$ alkoxy or aryloxy derivatives thereof (see, e.g., U.S. Pat. No. 5,252,714).

In some embodiments of the present invention, a useful strategy for the attachment of the PEG group to a polypeptide involves combining, through the formation of a conjugate linkage in solution, a peptide and a PEG moiety, each bearing a special functionality that is mutually reactive toward the other. The peptides can be easily prepared with conventional solid phase synthesis. The peptides are "preactivated" with an appropriate functional group at a specific site. The precursors are purified and fully characterized prior to reacting with the PEG moiety. Ligation of the peptide with PEG usually takes place in aqueous phase and can be easily monitored by reverse phase analytical HPLC. The PEGylated peptides can be easily purified by preparative HPLC and characterized by analytical HPLC, amino acid analysis and laser desorption mass spectrometry.

Polysaccharide polymers are another type of water-soluble polymer that can be used for protein modification. Therefore, the FGF21 mutants of the present invention fused to a polysaccharide polymer form embodiments of the present invention. Dextrans are polysaccharide polymers comprised of individual subunits of glucose predominantly linked by alpha 1-6 linkages. The dextran itself is available in many molecular weight ranges, and is readily available in molecular weights from about 1 kD to about 70 kD. Dextran is a suitable water-soluble polymer for use as a vehicle by itself or in combination with another vehicle (e.g., Fc). See, e.g., International Publication No. WO 96/11953. The use of dextran conjugated to therapeutic or diagnostic immunoglobulins has been reported. See, e.g., European Patent Publication No. 0 315 456, which is hereby incorporated by reference. The present invention also encompasses the use of dextran of about 1 kD to about 20 kD.

In general, chemical modification can be performed under any suitable condition used to react a protein with an activated polymer molecule. Methods for preparing chemically modified polypeptides will generally comprise the steps of: (a) reacting the polypeptide with the activated polymer molecule (such as a reactive ester or aldehyde derivative of the polymer molecule) under conditions whereby a FGF21 polypeptide mutant becomes attached to one or more polymer molecules, and (b) obtaining the reaction products. The optimal reaction conditions will be determined based on known parameters and the desired result. For example, the larger the ratio of polymer molecules to protein, the greater the percentage of attached polymer molecule. In one embodiment of the present invention, chemically modified FGF21 mutants can have a single polymer molecule moiety at the amino-terminus (see, e.g., U.S. Pat. No. 5,234,784)

In another embodiment of the present invention, FGF21 polypeptide mutants can be chemically coupled to biotin. The biotin/FGF21 polypeptide mutants are then allowed to bind to avidin, resulting in tetravalent avidin/biotin/FGF21 polypeptide mutants. FGF21 polypeptide mutants can also be covalently coupled to dinitrophenol (DNP) or trinitrophenol (TNP) and the resulting conjugates precipitated with anti-DNP or anti-TNP-IgM to form decameric conjugates with a valency of 10.

Generally, conditions that can be alleviated or modulated by the administration of the present chemically modified FGF21 mutants include those described herein for FGF21 polypeptide mutants. However, the chemically modified FGF21 mutants disclosed herein can have additional activities, enhanced or reduced biological activity, or other characteristics, such as increased or decreased half-life, as compared to unmodified FGF21 mutants.

9. Therapeutic Compositions of FGF21 Mutants and Administration Thereof

Therapeutic compositions comprising FGF21 mutants are within the scope of the present invention, and are specifically contemplated in light of the identification of several mutant FGF21 sequences exhibiting enhanced properties. Such FGF21 mutant pharmaceutical compositions can comprise a therapeutically effective amount of an FGF21 polypeptide mutant in admixture with a pharmaceutically or physiologically acceptable formulation agent selected for suitability with the mode of administration.

Acceptable formulation materials preferably are nontoxic to recipients at the dosages and concentrations employed.

The pharmaceutical composition can contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants (see, e.g., *Remington's Pharmaceutical Sciences* (18th Ed., A. R. Gennaro, ed., Mack Publishing Company 1990), and subsequent editions of the same, incorporated herein by reference for any purpose).

The optimal pharmaceutical composition will be determined by a skilled artisan depending upon, for example, the intended route of administration, delivery format, and desired dosage (see, e.g., *Remington's Pharmaceutical Sciences, supra*). Such compositions can influence the physical state, stability, rate of in vivo release, and rate of in vivo clearance of the FGF21 polypeptide mutant.

The primary vehicle or carrier in a pharmaceutical composition can be either aqueous or non-aqueous in nature. For example, a suitable vehicle or carrier for injection can be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which can further include sorbitol or a suitable substitute. In one embodiment of the present invention, FGF21 polypeptide mutant compositions can be prepared for storage by mixing the selected composition having the desired degree of purity with optional formulation agents (*Remington's Pharmaceutical Sciences, supra*) in the form of a lyophilized cake or an aqueous solution. Further, the FGF21 polypeptide mutant product can be formulated as a lyophilizate using appropriate excipients such as sucrose.

The FGF21 polypeptide mutant pharmaceutical compositions can be selected for parenteral delivery. Alternatively, the compositions can be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this invention can be in the form of a pyrogen-free, parenterally acceptable, aqueous solution comprising the desired FGF21 polypeptide mutant in a pharmaceutically acceptable vehicle. A particularly suitable vehicle for parenteral injection is sterile distilled water in which an FGF21 polypeptide mutant is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which can then be delivered via a depot injection. Hyaluronic acid can also be used, and this can have the effect of promoting sustained duration in the circulation. Other suitable means for the introduction of the desired molecule include implantable drug delivery devices.

In one embodiment, a pharmaceutical composition can be formulated for inhalation. For example, an FGF21 polypeptide mutant can be formulated as a dry powder for inhalation. FGF21 polypeptide mutant inhalation solutions can also be formulated with a propellant for aerosol delivery. In yet another embodiment, solutions can be nebulized. Pulmonary administration is further described in International Publication No. WO 94/20069, which describes the pulmonary delivery of chemically modified proteins.

It is also contemplated that certain formulations can be administered orally. In one embodiment of the present invention, FGF21 polypeptide mutants that are administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of the FGF21 polypeptide mutant. Diluents, flavorings, low melting point waxes, vegetable oils, lubricants, suspending agents, tablet disintegrating agents, and binders can also be employed.

Another pharmaceutical composition can involve an effective quantity of FGF21 polypeptide mutants in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional FGF21 polypeptide mutant pharmaceutical compositions will be evident to those skilled in the art, including formulations involving FGF21 polypeptide mutants in sustained- or controlled-delivery formulations. Techniques for formulating a variety of other sustained- or controlled-delivery means, such as liposome carriers, bio-erodible microparticles or porous beads and depot injections, are also known to those skilled in the art (see, e.g., International Publication No. WO 93/15722, which describes the controlled release of porous polymeric microparticles for the delivery of pharmaceutical compositions, and Wischke & Schwendeman, 2008, *Int. J Pharm.* 364: 298-327, and Freiberg & Zhu, 2004, *Int. J Pharm.* 282: 1-18, which discuss microsphere/microparticle preparation and use).

Additional examples of sustained-release preparations include semipermeable polymer matrices in the form of shaped articles, e.g. films, or microcapsules. Sustained release matrices can include polyesters, hydrogels, polylactides (U.S. Pat. No. 3,773,919 and European Patent No. 0 058 481), copolymers of L-glutamic acid and gamma ethyl-L-glutamate (Sidman et al., 1983, *Biopolymers* 22: 547-56), poly(2-hydroxyethyl-methacrylate) (Langer et al., 1981, *J. Biomed. Mater. Res.* 15: 167-277 and Langer, 1982, *Chem. Tech.* 12: 98-105), ethylene vinyl acetate (Langer et al., supra) or poly-D(−)-3-hydroxybutyric acid (European Patent No. 0 133 988). Sustained-release compositions can also include liposomes, which can be prepared by any of several methods known in the art. See, e.g., Epstein et al., 1985, *Proc. Natl. Acad. Sci. U.S.A.* 82: 3688-92; and European Patent Nos. 0 036 676, 0 088 046, and 0 143 949.

The FGF21 polypeptide mutant pharmaceutical composition to be used for in vivo administration typically must be sterile. This can be accomplished by filtration through sterile filtration membranes. Where the composition is lyophilized, sterilization using this method can be conducted either prior to, or following, lyophilization and reconstitution. The composition for parenteral administration can be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) requiring reconstitution prior to administration.

In a specific embodiment, the present invention is directed to kits for producing a single-dose administration unit. The kits can each contain both a first container having a dried protein and a second container having an aqueous formulation. Also included within the scope of this invention are kits containing single and multi-chambered pre-filled syringes (e.g., liquid syringes and lyosyringes).

The effective amount of an FGF21 polypeptide mutant pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the FGF21 polypeptide mutant is being used, the route of administration, and the size (body weight, body surface, or organ size) and condition (the age and general health) of the patient. Accordingly, the clinician can titer the dosage and modify the route of administration to obtain the optimal therapeutic effect. A typical dosage can range from about 0.1 µg/kg to up to about 100 mg/kg or more, depending on the factors mentioned above. In other embodiments, the dosage can range from 0.1 µg/kg up to about 100 mg/kg; or 1 µg/kg up to about 100 mg/kg; or 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, up to about 100 mg/kg. In yet other embodiments, the dosage can be 50 µg/kg, 100 µg/kg, 150 µg/kg, 200 µg/kg, 250 µg/kg, 300 µg/kg, 350 µg/kg, 400 µg/kg, 450 µg/kg, 500 µg/kg, 550 µg/kg, 600 µg/kg, 650 µg/kg, 700 µg/kg, 750 µg/kg, 800 µg/kg, 850 µg/kg, 900 µg/kg, 950 µg/kg, 100 µg/kg, 200 µg/kg, 300 µg/kg, 400 µg/kg, 500 µg/kg, 600 µg/kg, 700 µg/kg, 800 µg/kg, 900 µg/kg, 1000 µg/kg, 2000 µg/kg, 3000 µg/kg, 4000 µg/kg, 5000 µg/kg, 6000 µg/kg, 7000 µg/kg, 8000 µg/kg, 9000 µg/kg or 10 mg/kg.

The frequency of dosing will depend upon the pharnacokinetic parameters of the FGF21 polypeptide mutant in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems (which may also be injected); or by implantation devices. Where desired, the compositions can be administered by bolus injection or continuously by infusion, or by implantation device.

Alternatively or additionally, the composition can be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

10. Therapeutic Uses of FGF21 Polypeptide Mutants

FGF21 polypeptide mutants can be used to treat, diagnose, ameliorate, or prevent a number of diseases, disorders, or conditions, including, but not limited to metabolic disorders. In one embodiment, the metabolic disorder to be treated is diabetes, e.g., type 2 diabetes. In another embodiment, the metabolic disorder is obesity. Other embodiments include metabolic conditions or disorders such as dyslipidimia; hypertension; hepatosteaotosis, such as non-alcoholic steatohepatitis (NASH); cardiovascular disease, such as atherosclerosis; and aging.

In application, a disorder or condition such as diabetes or obesity can be treated by administering an FGF21 polypeptide mutant as described herein to a patient in need thereof in the amount of a therapeutically effective dose. The administration can be performed as described herein, such as by IV injection, intraperitoneal injection, intramuscular injection, or orally in the form of a tablet or liquid formation. In most situations, a desired dosage can be determined by a clinician, as described herein, and can represent a therapeutically effective dose of the FGF21 mutant polypeptide. It will be apparent to those of skill in the art that a therapeutically effective dose of FGF21 mutant polypeptide will depend, inter alia, upon the administration schedule, the unit dose of antigen administered, whether the nucleic acid molecule or polypeptide is administered in combination with other therapeutic agents, the immune status and the health of the recipient. The term "therapeutically effective dose," as used herein, means that amount of FGF21 mutant polypeptide that elicits the biological or medicinal response in a tissue system, animal, or human being sought by a researcher, medical doctor, or other clinician, which includes alleviation of the symptoms of the disease or disorder being treated.

11. Antibodies

Antibodies and antibody fragments that specifically bind to the FGF21 mutant polypeptides of the present invention but do not specifically bind to wild-type FGF21 polypeptides are contemplated and are within the scope of the present invention. The antibodies can be polyclonal, including monospecific polyclonal; monoclonal (MAbs); recombinant; chimeric; humanized, such as complementarity-determining region (CDR)-grafted; human; single chain; and/or bispecific; as well as fragments; variants; or chemically modified molecules thereof. Antibody fragments include those portions of the antibody that specifically bind to an epitope on an FGF21 mutant polypeptide. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies directed toward an FGF21 mutant polypeptide generally are produced in animals (e.g., rabbits or mice) by means of multiple subcutaneous or intraperitoneal injections of the FGF21 mutant polypeptide and an adjuvant. It can be useful to conjugate an FGF21 mutant polypeptide to a carrier protein that is immunogenic in the species to be immunized, such as keyhole limpet hemocyanin, serum, albumin, bovine thyroglobulin, or soybean trypsin inhibitor. Also, aggregating agents such as alum are used to enhance the immune response. After immunization, the animals are bled and the serum is assayed for anti-FGF21 mutant antibody titer.

Monoclonal antibodies directed toward FGF21 mutant polypeptides can be produced using any method that provides for the production of antibody molecules by continuous cell lines in culture. Examples of suitable methods for preparing monoclonal antibodies include the hybridoma methods of Kohler et al., 1975, *Nature* 256: 495-97 and the human B-cell hybridoma method (Kozbor, 1984, *J. Immunol.* 133: 3001;

Brodeur et al., *Monoclonal Antibody Production Techniques and Applications* 51-63 (Marcel Dekker, Inc., 1987). Also provided by the invention are hybridoma cell lines that produce monoclonal antibodies reactive with FGF21 mutant polypeptides.

Monoclonal antibodies of the invention can be modified for use as therapeutics. In one embodiment, the monoclonal antibody is a "chimeric" antibody in which a portion of the heavy (H) and/or light (L) chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. Also included are fragments of such antibodies, so long as they exhibit the desired biological activity. See, e.g., U.S. Pat. No. 4,816,567; Morrison et al., 1985, *Proc. Natl. Acad. Sci U.S.A.* 81: 6851-55.

In another embodiment, a monoclonal antibody of the invention is a "humanized" antibody. Methods for humanizing non-human antibodies are well known in the art. See, e.g., U.S. Pat. Nos. 5,585,089 and 5,693,762. Generally, a humanized antibody has one or more amino acid residues introduced into it from a source that is non-human. Humanization can be performed, for example, using methods described in the art (see, e.g., Jones et al., 1986, *Nature* 321: 522-25; Riechmann et al., 1998, *Nature* 332: 323-27; Verhoeyen et al., 1988, *Science* 239: 1534-36), by substituting at least a portion of a rodent complementarity-determining region for the corresponding regions of a human antibody.

Also encompassed by the invention are human antibodies that bind the FGF21 mutant polypeptides of the present invention. Using transgenic animals (e.g., mice) that are capable of producing a repertoire of human antibodies in the absence of endogenous immunoglobulin production such antibodies are produced by immunization with an FGF21 mutant antigen (i.e., having at least 6 contiguous amino acids), optionally conjugated to a carrier. See, e.g., Jakobovits et al., 1993, *Proc. Natl. Acad. Sci. U.S.A.* 90: 2551-55; Jakobovits et al., 1993, *Nature* 362: 255-58; Bruggermann et al., 1993, *Year in Immuno.* 7: 33. In one method, such transgenic animals are produced by incapacitating the endogenous loci encoding the heavy and light immunoglobulin chains therein, and inserting loci encoding human heavy and light chain proteins into the genome thereof. Partially modified animals, i.e., animals having less than the full complement of modifications, are then cross-bred to obtain an animal having all of the desired immune system modifications. When administered an immunogen, these transgenic animals produce antibodies with human (rather than, e.g., murine) amino acid sequences, including variable regions that are immunospecific for these antigens. See, e.g., International Publication Nos. WO 96/33735 and WO 94/02602. Additional methods are described in U.S. Pat. No. 5,545,807, International Publication Nos. WO 91/10741 and WO 90/04036, and in European Patent No. 0 546 073. Human antibodies can also be produced by the expression of recombinant DNA in host cells or by expression in hybridoma cells as described herein.

In an alternative embodiment, human antibodies can also be produced from phage-display libraries (see, e.g., Hoogenboom et al., 1991, *J. Mol. Biol.* 227: 381; Marks et al., 1991, *J. Mol. Biol.* 222: 581). These processes mimic immune selection through the display of antibody repertoires on the surface of filamentous bacteriophage, and subsequent selection of phage by their binding to an antigen of choice. One such technique is described in International Publication No. WO 99/10494, which describes the isolation of high affinity and functional agonistic antibodies for MPL- and msk-receptors using such an approach.

Chimeric, CDR grafted, and humanized antibodies are typically produced by recombinant methods. Nucleic acids encoding the antibodies are introduced into host cells and expressed using materials and procedures described herein. In one embodiment, the antibodies are produced in mammalian host cells, such as CHO cells. Monoclonal (e.g., human) antibodies can be produced by the expression of recombinant DNA in host cells or by expression in hybridoma cells as described herein.

The anti-FGF21 mutant antibodies of the invention can be employed in any known assay method, such as competitive binding assays, direct and indirect sandwich assays, and immunoprecipitation assays (see, e.g., Sola, *Monoclonal Antibodies: A Manual of Techniques* 147-158 (CRC Press, Inc., 1987), incorporated herein by reference in its entirety) for the detection and quantitation of FGF21 mutant polypeptides. The antibodies will bind FGF21 mutant polypeptides with an affinity that is appropriate for the assay method being employed.

For diagnostic applications, in certain embodiments, anti-FGF21 mutant antibodies can be labeled with a detectable moiety. The detectable moiety can be any one that is capable of producing, either directly or indirectly, a detectable signal. For example, the detectable moiety can be a radioisotope, such as $^{3}$H, $^{14}$C, $^{32}$P, $^{35}$S, $^{125}$I, $^{99}$Tc, $^{111}$In, or $^{67}$Ga; a fluorescent or chemiluminescent compound, such as fluorescein isothiocyanate, rhodamine, or luciferin; or an enzyme, such as alkaline phosphatase, β-galactosidase, or horseradish peroxidase (Bayer et al., 1990, *Meth. Enz.* 184: 138-63).

Competitive binding assays rely on the ability of a labeled standard (e.g., an FGF21 mutant polypeptide, or an immunologically reactive portion thereof) to compete with the test sample analyte (e.g., an FGF21 mutant polypeptide) for binding with a limited amount of anti-FGF21 mutant antibody. The amount of an FGF21 mutant polypeptide in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies can conveniently be separated from the standard and analyte that remain unbound.

Sandwich assays typically involve the use of two antibodies, each capable of binding to a different immunogenic portion, or epitope, of the protein to be detected and/or quantitated. In a sandwich assay, the test sample analyte is typically bound by a first antibody that is immobilized on a solid support, and thereafter a second antibody binds to the analyte, thus forming an insoluble three-part complex. See, e.g., U.S. Pat. No. 4,376,110. The second antibody can itself be labeled with a detectable moiety (direct sandwich assays) or can be measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme.

The anti-FGF21 mutant antibodies of the present invention are also useful for in vivo imaging. An antibody labeled with a detectable moiety can be administered to an animal, preferably into the bloodstream, and the presence and location of the labeled antibody in the host assayed. The antibody can be labeled with any moiety that is detectable in an animal, whether by nuclear magnetic resonance, radiology, or other detection means known in the art.

The FGF21 mutant antibodies of the invention can be used as therapeutics. These therapeutic agents are generally agonists or antagonists, in that they either enhance or reduce, respectively, at least one of the biological activities of an FGF21 mutant polypeptide. In one embodiment, antagonist antibodies of the invention are antibodies or binding fragments thereof which are capable of specifically binding to an FGF21 mutant polypeptide and which are capable of inhibiting or eliminating the functional activity of an FGF21 mutant polypeptide in vivo or in vitro. In some embodiments, the antagonist antibody will inhibit the functional activity of an FGF21 mutant polypeptide by at least about 50%, and preferably by at least about 80%. In another embodiment, the anti-FGF21 mutant antibody is capable of interfering with the interaction between an FGF21 mutant polypeptide and an FGF receptor thereby inhibiting or eliminating FGF21 mutant polypeptide activity in vitro or in vivo. Agonist and antagonist anti-FGF21 mutant antibodies are identified by screening assays that are well known in the art.

The invention also relates to a kit comprising FGF21 mutant antibodies and other reagents useful for detecting FGF21 mutant polypeptide levels in biological samples. Such reagents can include a detectable label, blocking serum, positive and negative control samples, and detection reagents.

EXAMPLES

The Examples that follow are illustrative of specific embodiments of the invention, and various uses thereof. They are set forth for explanatory purposes only, and should not be construed as limiting the scope of the invention in any way.

Example 1

Preparation of FGF21 Expression Constructs

A nucleic acid sequence encoding the mature FGF21 polypeptide was obtained by polymerase chain reaction (PCR) amplification using primers having nucleotide sequences corresponding to the 5' and 3' ends of the mature FGF21 sequence. Table 2 lists the primers that were used to amplify the mature FGF21 sequence.

TABLE 2

| PCR Primers for Preparing FGF21 Construct | | |
|---|---|---|
| Primer | Sequence | SEQ ID NO: |
| Sense | 5'-AGGAGGAATAACATATGCATCCAATTCCAGATTCTTCTCC-3' | 5 |
| Antisense | 5'-TAGTGAGCTCGAATTCTTAGGAAGCGTAGCTGG-3' | 6 |

The primers used to prepare the FGF21 expression construct incorporated restriction endonuclease sites for directional cloning of the sequence into a suitable expression vector (e.g., pET30 (Novagen/EMD Biosciences; San Diego, Calif.) or pAMG33 (Amgen; Thousand Oaks, Calif.)). The expression vector pAMG33 contains a low-copy number R-100 origin of replication, a modified lac promoter, and a kanamycin-resistance gene. The expression vector pET30 contains a pBR322-derived origin of replication, an inducible T7 promoter, and a kanamycin-resistance gene. While expression from pAMG33 was found to be higher, pET30 was found to be a more reliable cloning vector. Thus, the majority of the constructs described in the instant application were first generated in pET30 and then screened for efficacy. Selected sequences were then transferred to pAMG33 for further amplification.

The FGF21 sequence was amplified in a reaction mixture containing 40.65 µL dH$_2$O, 5 µL PfuUltra II Reaction Buffer (10×), 1.25 µL dNTP Mix (40 mM-4×10 mM), 0.1 µL Template (100 ng/mL), 1 µL Primer1 (10 µM), 1 µL Primer2 (10 µM), and 1 µL PfuUltra II fusion HS DNA Polymerase (Stratagene; La Jolla, Calif.). Amplification reactions were performed by heating for 2 minutes at 95° C.; followed by ten cycles at 95° C. for 20 seconds, 60° C. for 20 seconds (with an additional 1° C. subtracted per cycle), and 72° C. for 15 seconds/kilobase of desired product; followed by 20 cycles at 94° C. for 20 seconds, 55° C. for 20 seconds, and 72° C. for 15 seconds/kilobase of desired product; followed by 72° C. for 3 minutes. Amplification products were digested with the restriction endonucleases NdeI, DpnI, and EcoRI; ligated into a suitable vector; and then transformed into competent cells.

Example 2

Purification of FGF21 Proteins from Bacteria

In the Examples that follow, various FGF21 proteins, including the wild-type FGF21 polypeptide, truncated FGF21 polypeptides, FGF21 mutants, and FGF21 fusion proteins, were expressed in a bacterial expression system. After expression, which is described below, the FGF21 proteins were purified as described in this Example, unless otherwise indicated.

To purify the wild-type FGF21 polypeptide, truncated FGF21 polypeptides, and FGF21 mutants from bacterial inclusion bodies, double-washed inclusion bodies (DWIBs) were solubilized in a solubilization buffer containing guanidine hydrochloride and DTT in Tris buffer at pH 8.5 and then mixed for one hour at room temperature, and the solubilization mixture was added to a refold buffer containing urea, arginine, cysteine, and cystamine hydrochloride at pH 9.5 and then mixed for 24 hours at 5° C. (see, e.g., Clarke, 1998, *Curr. Opin. Biotechnol.* 9: 157-63; Mannall et al., 2007, *Biotechnol. Bioeng.* 97: 1523-34; Rudolph et al., 1997, "Folding proteins," Protein Function: A Practical Approach (Creighton, ed., New York, IRL Press) 57-99; and Ishibashi et al., 2005, *Protein Expr. Purif.* 42: 1-6).

Following solubilization and refolding, the mixture was filtered through a 0.45 micron filter. The refold pool was then concentrated approximately 10-fold with a 10 kD molecular weight cut-off Pall Omega cassette at a transmembrane pressure (TMP) of 20 psi, and dialfiltered with 3 column volumes of 20 mM Tris, pH 8.0 at a TMP of 20 psi.

The clarified sample was then subjected to anion exchange (AEX) 5 chromatography using a Q Sepharose HP resin. A linear salt gradient of 0 to 250 mM NaCl in 20 mM Tris was run at pH 8.0 at 5° C. Peak fractions were analyzed by SDS-PAGE and pooled.

The AEX eluate pool was then subjected to hydrophobic interaction chromatography (HIC) using a Phenyl Sepharose HP resin. Protein was eluted using a decreasing linear gradient of 0.7 M to 0 M ammonium sulfate at pH 8.0 and ambient temperature. Peak fractions were analyzed by SDS-PAGE (Laemmli, 1970, *Nature* 227: 680-85) and pooled.

The HIC pool was concentrated with a 10 kD molecular weight cut-off Pall Omega 0.2 $m^2$ cassette to 7 mg/mL at a TMP of 20 psi. The concentrate was dialfiltered with 5 column volumes of 10 mM $KPO_4$, 5% sorbitol, pH 8.0 at a TMP of 20 psi, and the recovered concentrate was diluted to 5 mg/mL. Finally, the solution was filtered through a Pall mini-Kleenpac 0.2 µM Posidyne membrane.

To purify FGF21 fusion proteins and FGF21 fusion mutant proteins from bacterial inclusion bodies, double-washed inclusion bodies (DWIBs) were solubilized in a solubilization buffer containing guanidine hydrochloride and DTT in Tris buffer at pH 8.5 and then mixed for one hour at room temperature, and the solubilization mixture was added to a refold buffer containing urea, arginine, cysteine, and cystamine hydrochloride at pH 9.5 and then mixed for 24 hours at 5° C. (see, e.g., Clarke, 1998, *Curr. Opin. Biotechnol.* 9: 157-63; Mannall et al., 2007, *Biotechnol. Bioeng* 97: 1523-34; Rudolph et al., 1997, "Folding proteins," Protein Function: A Practical Approach (Creighton, ed., New York, IRL Press) 57-99; and Ishibashi et al., 2005, *Protein Expr. Purif* 42: 1-6).

Following solubilization and refolding, the mixture was dialyzed against 5 volumes of 20 mM Tris, pH 8.0 using 10 kD dialysis tubing. The pH of the dialyzed refold was adjusted to 5.0 with 50% acetic acid, and then clarified by centrifugation for 30 minutes at 4K.

The clarified sample was then subjected to anion exchange (AEX) chromatography using a Q Sepharose HP resin. A linear salt gradient of 0 to 250 mM NaCl in 20 mM Tris was run at pH 8.0 at 5° C. Peak fractions were analyzed by SDS-PAGE (Laemmli, 1970, *Nature* 227: 680-85) and pooled.

The AEX eluate pool was then subjected to hydrophobic interaction chromatography (HIC) using a Phenyl Sepharose HP resin. Protein was eluted using a decreasing linear gradient of 0.6 M to 0 M ammonium sulfate at pH 8.0 at ambient temperature. Peak fractions were analyzed by SDS-PAGE and pooled.

Following the HIC step, the pool was then dialyzed 60 volumes of 10 mM Tris, 2.2% sucrose, 3.3% sorbitol, pH 8.5. The dialyzed pool was concentrated to 5 mg/mL using a jumbosep. Finally, the solution was filtered through a Pall mini-Kleenpac 0.2 µM Posidyne membrane.

Example 3

Preparation and Expression of Truncated FGF21 Proteins

Constructs encoding the truncated FGF21 proteins listed in Table 3 were prepared by PCR amplification of the wild-type FGF21 expression vector as described below (the construction of the wild-type FGF21 expression vector is described in Example 1).

TABLE 3

FGF21 Truncations

| Amino Acid Residues | Number of Residues Truncated* |
|---|---|
| C-terminus Truncations | |
| 1-180 | 1 |
| 1-179 | 2 |
| 1-178 | 3 |
| 1-177 | 4 |
| 1-176 | 5 |
| 1-175 | 6 |
| 1-174 | 7 |
| 1-173 | 8 |
| 1-172 | 9 |
| 1-171 | 10 |
| 1-169 | 12 |
| 1-168 | 13 |
| 1-167 | 14 |
| 1-166 | 15 |
| 1-165 | 16 |
| 1-164 | 17 |
| 1-160 | 21 |
| 1-156 | 25 |
| 1-152 | 29 |
| 1-149 | 32 |
| 1-113 | 68 |
| N-terminus Truncations | |
| 2-181 | 1 |
| 3-181 | 2 |
| 4-181 | 3 |
| 5-181 | 4 |
| 6-181 | 5 |
| 7-181 | 6 |
| 8-181 | 7 |
| 9-181 | 8 |
| C- and N-terminus Truncations | |
| 5-174 | 11 |
| 7-172 | 17 |
| 9-169 | 20 |
| 9-149 | 40 |
| 15-169 | 26 |
| 15-149 | 46 |
| 15-113 | 82 |

*relative to mature FGF21 polypeptide

Truncated FGF21 protein constructs were prepared using primers having sequences that are homologous to regions upstream and downstream of a codon (or codons) to be deleted (resulting in the truncation). The primers used in such amplification reactions also provided approximately 15 nucleotides of overlapping sequence to allow for recircularization of the amplified product, namely the entire vector now having the desired mutant.

An exemplary truncated FGF21 construct, encoding an FGF21 protein lacking the histidine residue at position 1 of the mature FGF21 sequence (i.e., the 2-181 truncation mutant), was prepared using the primers shown in Table 4.

TABLE 4

PCR Primers for Preparing Exemplary Truncation FGF21 Mutant

| Primer | Sequence | SEQ ID NO: |
|---|---|---|
| Sense | 5'-GGAGATATACATATGCCAATTCCAGATTCTTCTCCATTATT-3' | 7 |
| Antisense | 5'-CATATGTATATCTCCTTCTTAAAGTTAAACAAAA-3' | 8 |

The primers shown in Table 4 allow for the deletion of the histidine residue as shown below, wherein the upper sequence (SEQ ID NO: 10) is a portion of a mature FGF21 polypeptide comprising a N-terminal methionine, the second sequence is the sense primer (SEQ ID NO: 7), the third and fourth sequences (SEQ ID NOs: 11 and 12) are portions of an FGF21 expression construct, and the fifth sequence is the antisense primer (SEQ ID NO: 9):

```
                              MetHisProIleProAspSerSerProLeu
        5'-GGAGATATACATATG---CCAATTCCAGATTCTTCTCCATTATT

TTTTGTTTAACTTTAAGAAGGAGATATACATATGCATCCAATTCCAGATTCTTCTCCATTATT

AAAACAAATTGAAATTCTTCCTCTATATGTATACGTAGGTTAAGGTCTAAGAAGAGGTAATAA

AAAACAAATTGAAATTCTTCCTCTATATGTATAC-5'
```

Truncated FGF21 protein constructs were prepared using essentially the PCR conditions described in Example 1. Amplification products were digested with the restriction endonuclease DpnI, and then transformed into competent cells. The resulting clones were sequenced to confirm the absence of polymerase-generated errors.

Truncated FGF21 proteins were expressed by transforming competent BL21 (DE3) or BL21 Star (Invitrogen; Carlsbad, Calif.) cells with the construct encoding a particular truncated FGF21 protein. Transformants were grown overnight with limited aeration in TB media supplemented with 40 µg/mL kanamycin, were aerated the next morning, and after a short recovery period, were induced in 0.4 mM IPTG. FGF21 mutants were harvested by centrifugation 18-20 hours after induction.

Example 4

In Vitro Activity of Truncated FGF21 Proteins

Experiments were performed to identify truncated FGF21 proteins that retain wild-type FGF21 activity in an ELK-luciferase in vitro assay. Table 5 summarizes the results obtained for FGF21 proteins having truncations at the N-terminus, the C-terminus, or at both the N-terminus and C-terminus. ELK-luciferase assays were performed using a recombinant human 293T kidney cell system, in which the 293T cells overexpress beta-klotho and luciferase reporter constructs. These constructs also contain sequences encoding GAL4-ELK1 and 5xUAS-Luc, a luciferase reporter driven by a promoter containing five tandem copies of the Gal4 binding site. Beta-klotho is a co-receptor that is required by FGF21 for activation of its FGF receptors and induction of intracellular signal transduction, which in turn leads to Erk and ELK phosphorylation. Luciferase activity is regulated by the level of phosphorylated Erk/ELK1, and is used to indirectly monitor and quantify FGF21 activity.

Figure 1A:
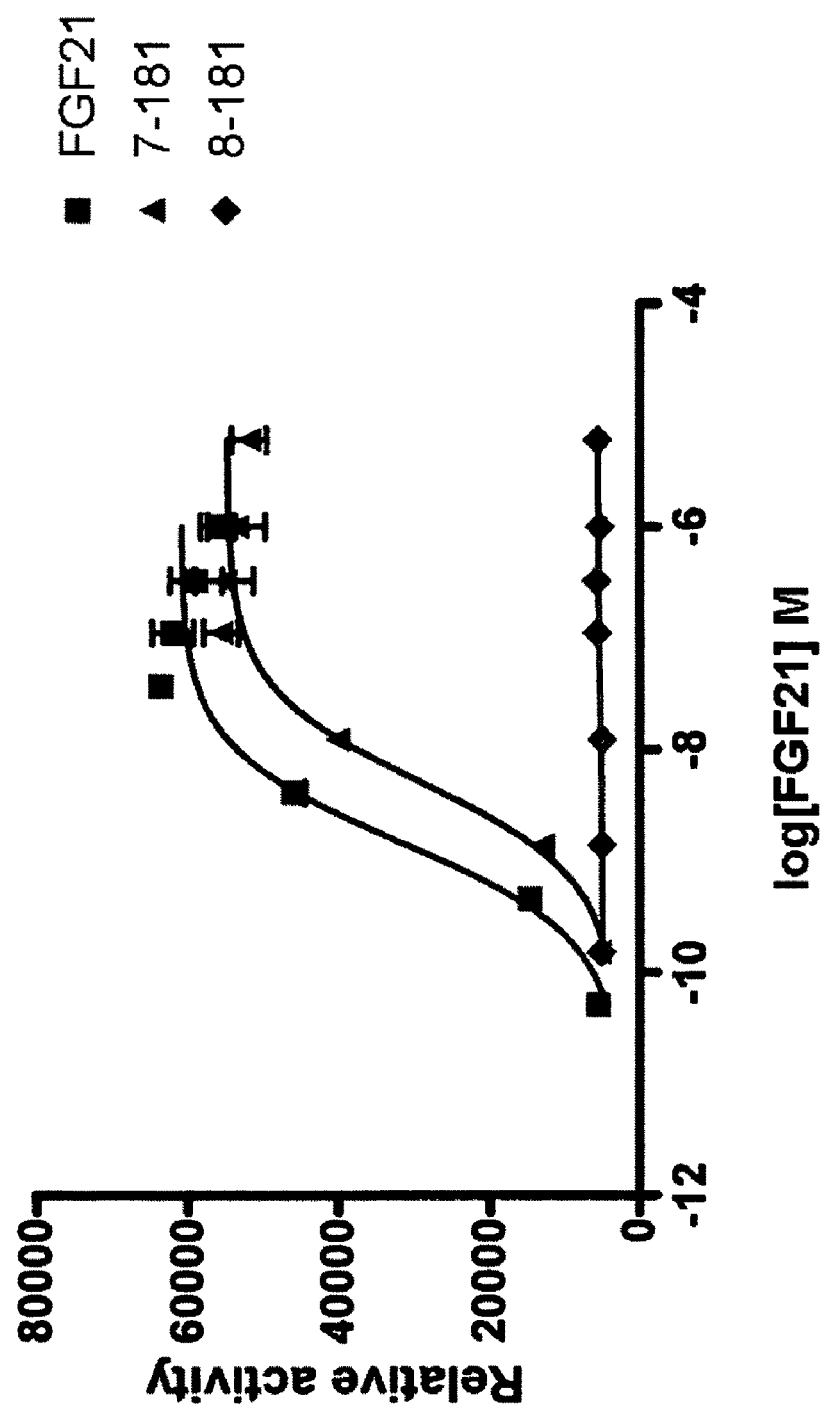
FIGS. 1A-1B show the results of an ELK-luciferase activity assay performed on the FGF21 truncation mutants 7-181 and 8-181 (FIG. 1A) and the FGF21 truncation mutants 1-172, 1-171, 1-169, and 1-164 (FIG. 1B); each panel shows the results obtained for a human FGF21 control.
Figure 1B:
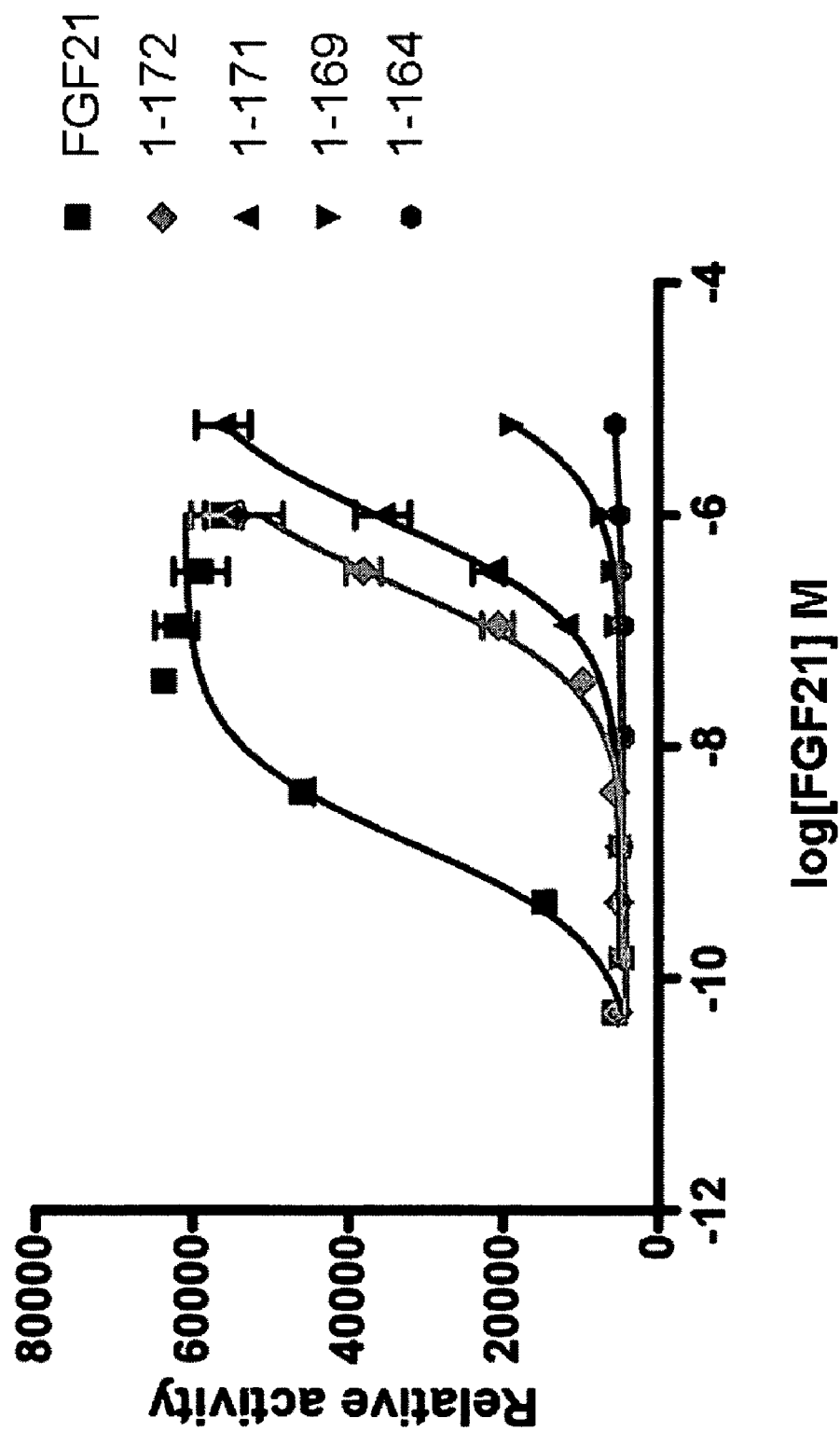
Figure 2:
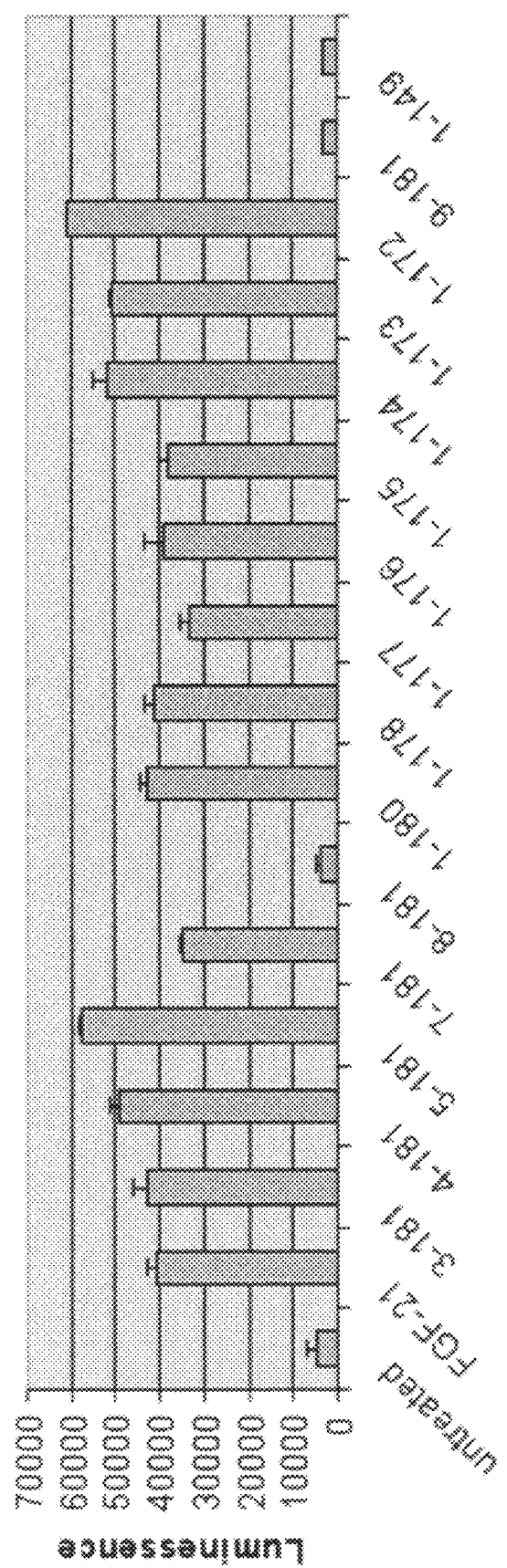
FIG. 2 shows the results of an ELK-luciferase activity assay performed on a human FGF21 control and the FGF21 truncation mutants 3-181, 4-181, 5-181, 7-181, 8-181, 1-180, 1-178, 1-177, 1-176, 1-175, 1-174, 1-173, 1-172, 9-181, and 1-149.

ELK-luciferase assays were performed by culturing the 293T cells in the presence of different concentrations of wild-type FGF21 or FGF21 mutant polypeptide for 6 hours, and then assaying the cell lysates for luciferase activity. FIGS. 1A-1B show the results of an ELK-luciferase activity assay performed on the FGF21 truncation mutants 7-181 and 8-181 (FIG. 1A) and the FGF21 truncation mutants 1-172, 1-171, 1-169, and 1-164 (FIG. 1B). The luminescence obtained in ELK-luciferase assays for each of the FGF21 truncation mutants 3-181, 4-181, 5-181, 7-181, 8-181, 1-180, 1-178, 1-177, 1-176, 1-175, 1-174, 1-173, 1-172, 9-181, and 1-149 is shown in FIG. 2.

FGF21 mutant polypeptides were compared with a wild-type FGF21 standard and mutants showing an efficacy of at least 50% of the efficacy of wild-type FGF21 were considered as having not lost FGF21 activity and were assigned a "+" in Table 5.

TABLE 5

Truncated FGF21 Proteins: in vitro Assay

| Amino Acid Residues | Efficacy | Activity (+/−) |
|---|---|---|
| C-terminus Truncations | | |
| 1-180 | 93.2% | + |
| 1-178 | 95.0% | + |
| 1-177 | 112.0% | + |
| 1-176 | 104.8% | + |
| 1-174 | 104.6% | + |
| 1-173 | 96.1% | + |
| 1-172 | 97.5% | + |
| 1-171 | 113.0% | + |
| 1-169 | 84.9% | + |
| 1-167 | 20% | − |
| 1-166 | 20% | − |
| 1-165 | 10% | − |
| N-terminus Truncations | | |
| 2-181 | 112.5% | + |
| 3-181 | 130.3% | + |
| 4-181 | 117.0% | + |
| 5-181 | 119.6% | + |
| 7-181 | 74.2% | + |
| 8-181 | 24.9% | − |
| 9-181 | 12.5% | − |

Collectively, the results presented in Table 5 indicate that C-terminal deletions of 14 or more amino acid residues (i.e., a C-terminally truncated FGF21 protein consisting of amino acid residues 1-167 and shorter proteins) eliminate the activity of FGF21. In addition, Table 5 indicates that N-terminal deletions of 7 or more amino acid residues (i.e., an N-terminally truncated FGF21 protein consisting of amino acid residues 8-181 and shorter proteins) eliminate the activity of FGF21. Not surprisingly, truncated FGF21 proteins possessing both an N-terminal truncation of 8 to 14 residues and a C-terminal truncation of 12 or 32 residues were found to lack activity in ELK-luciferase assays.

Consistent with the data presented in Table 5, truncated FGF21 polypeptides having N-terminal truncations of fewer than 7 amino acid residues constitute embodiments of the present invention. Similarly, truncated FGF21 polypeptides having C-terminal truncations of fewer than 13 amino acid residues constitute embodiments of the present invention.

Example 5

In Vivo Activity of Truncated FGF21 Proteins

FGF21 possesses a number of biological activities, including the ability to lower blood glucose, insulin, triglyceride, or cholesterol levels; reduce body weight; or improve glucose tolerance, energy expenditure, or insulin sensitivity. Truncated FGF21 polypeptides were further analyzed for in vivo FGF21 activity, by introducing the truncated FGF21 polypeptides into insulin resistant ob/ob mice, and measuring the ability of a particular truncated FGF21 polypeptide to lower blood glucose. The truncated FGF21 polypeptide to be tested was injected intraperitoneally into an 8 week old ob/ob mouse (Jackson Laboratory), and blood samples were obtained at various time points following a single injection, e.g., 0, 6, 24, 72, 120, and 168 hours after injection. Blood glucose levels were measured with a OneTouch Glucometer (LifeScan, Inc. Milpitas, Calif.), and the results expressed as a percent change of blood glucose relative to the baseline level of blood glucose (i.e., at time 0).

Figure 3:
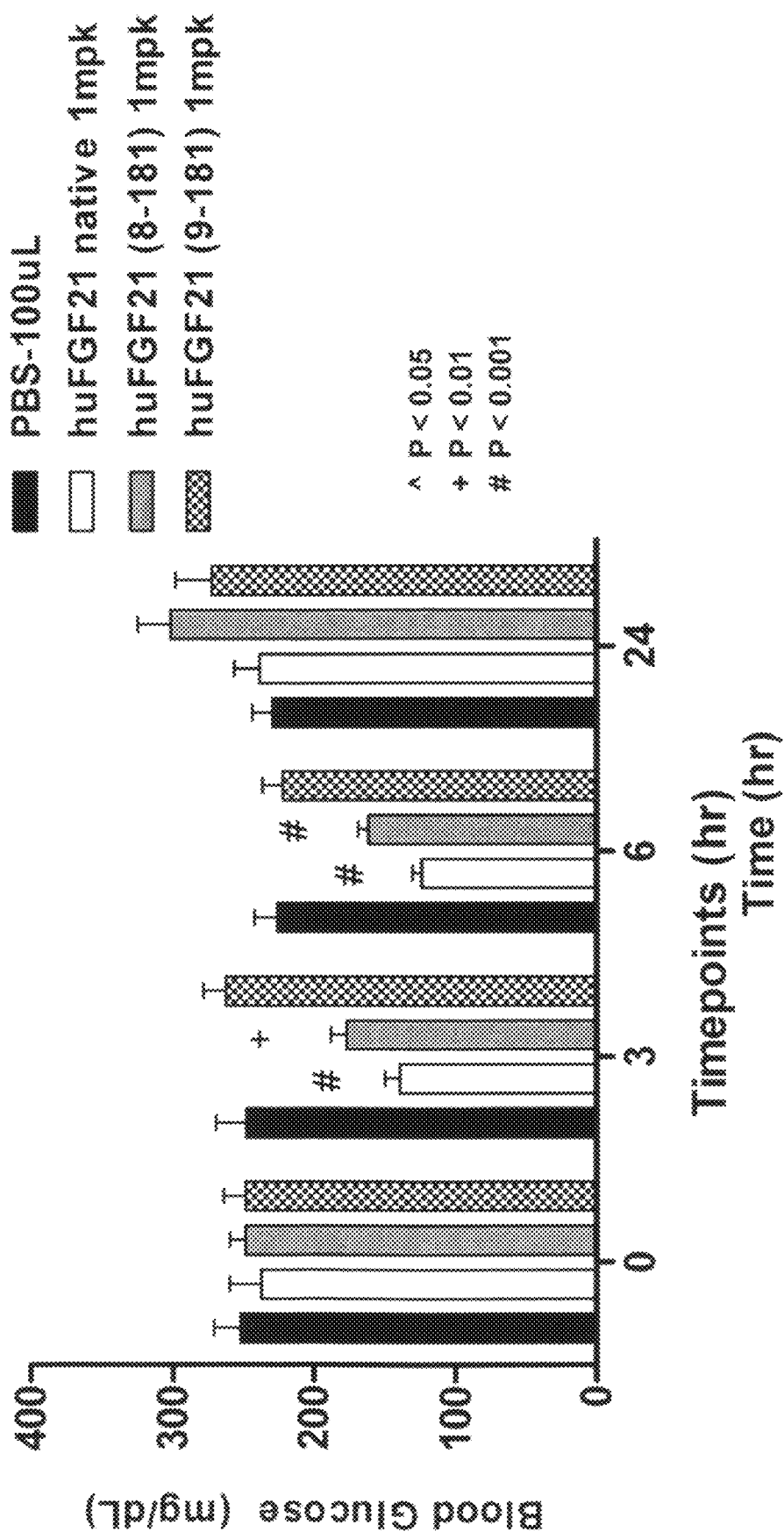
FIG. 3 shows the blood glucose levels measured in mice injected with PBS (solid bar), human FGF21 control (open bar), or the FGF21 truncation mutants 8-181 (gray bar) and 9-181 (stippled bar).

The results of one experiment are provided in FIG. 3, which shows the amount of blood glucose detected in mice injected with the FGF21 truncation mutants 8-181 and 9-181. This experiment demonstrated that truncated FGF21 fusion proteins comprising amino acid residues 8-181 exhibit blood glucose lowering activity in vivo however the activity is slightly less than the activity of wild-type FGF21 at 3 and 6 hours after injection, but that truncated FGF21 fusion proteins comprising amino acid residues 9-181 do not exhibit such activity. Thus, the in vivo analysis of truncated FGF21 polypeptides indicated that the deletion of up to 7 amino acids from the N-terminus of mature FGF21 does not abolish the molecule's biological activity (in contrast with the in vitro analysis, which suggested that the deletion of 7 amino acids from the N-terminus of mature FGF21 would abolish activity).

The differing results obtained with particular N-terminally truncated FGF21 polypeptides (e.g., FGF21 8-181) in in vitro and in vivo assays can be explained by the interaction of FGF21 with beta-klotho and FGF receptor in effecting signal transduction. In particular, FGF21 activates a dual receptor complex comprising the co-receptor beta-klotho and FGF receptor (FGFR), which initiates a signaling cascade involving tyrosine kinase. The N-terminus of FGF21 has been shown involved in binding and activation of FGFR while the C-terminus of FGF21 is required for beta-klotho interaction (Yie et al., 2009 *FEBS Lett.* 583:19-24). The ELK-luciferase in vitro assay is performed in 293 kidney cells in which the co-receptor beta-klotho is overexpressed and FGFR is expressed at normal levels. The amount of FGFR is low in relative to that of beta-klotho and the ratio of beta-klotho to FGFR in 293 cells is therefore non-physiological, which may affect receptor complex formation and ultimately ligand binding and activation of FGFR. The 293 in vitro system appears to be more vulnerable to N-terminally truncated FGF21 polypeptides and therefore may have produced loss of activity results for a few of the N-terminally truncated mutants tested, such as FGF21 8-181. Thus, in determining whether a particular N-terminally truncated FGF21 mutant retained wild-type FGF21 activity, the activity of that FGF21 mutant in the in vivo assay was considered to be dispositive. Accordingly, truncated FGF21 polypeptides having N-terminal truncations of fewer than 8 amino acid residues are encompassed by the invention.

Example 6

Preparation and Expression of Truncated FGF21 Fusion Proteins

Because the half-life of a protein can be increased by fusing the protein to an Fc sequence, fusion proteins comprising truncated FGF21 polypeptides were prepared and analyzed. The truncated FGF21 fusion proteins listed in Table 6 were prepared from amplified FGF21 sequences by SOEing (gene splicing by overlap extension) PCR. FGF21 fusion proteins were prepared such that the Fc portion of the human immunoglobulin IgG1 gene (SEQ ID NO: 13) was fused to either the N-terminus or the C-terminus of the FGF21 protein.

TABLE 6

Truncated FGF21 Fusion Proteins

| Amino Acid Residues | Fc Position | Linker |
|---|---|---|
| C-terminus Truncations | | |
| 1-178 | —NH$_2$ | 15 |
| 1-175 | —NH$_2$ | 14 |
| 1-175 | —COOH | 15 |
| 1-171 | —NH$_2$ | 15 |
| 1-171 | —COOH | 15 |
| 1-170 | —COOH | 15 |
| N-terminus Truncations | | |
| 5-181 | —NH$_2$ | 15 |
| 5-181 | —COOH | 15 |
| 7-181 | —NH$_2$ | 15 |
| 7-181 | —COOH | 15 |
| C- and N-terminus Truncations | | |
| 5-175 | —NH$_2$ | 15 |
| 5-175 | —COOH | 15 |
| 5-171 | —NH$_2$ | 15 |
| 5-171 | —COOH | 15 |
| 6-170 | —COOH | 15 |
| 7-178 | —COOH | 35 |
| 7-175 | —NH$_2$ | 15 |
| 7-175 | —COOH | 15 |
| 7-174 | —COOH | 35 |
| 7-172 | —COOH | 35 |
| 7-171 | —NH$_2$ | 15 |
| 7-171 | —COOH | 35 |
| 7-171 | —COOH | 15 |

In particular, FGF21 fusion protein constructs (including those encoding truncated FGF21 fusion proteins) were prepared in a series of three amplification reactions using essentially the reaction conditions described in Example 1. In the first reaction, a pair of primers was designed to produce a sequence containing an NdeI cloning site, Fc region, and linker sequence. In the second reaction, a pair of primers was designed to produce a sequence containing an overlapping portion of the linker, a portion of the FGF21 coding sequence, and an EcoRI cloning site. Finally, in the third reaction, a pair of primers was designed for the purpose of linking the products of the first two reactions. An exemplary set of primers for the construction of Fc-FGF21 1-181 is listed in Table 7.

TABLE 7

PCR Primers for Preparing Exemplary FGF21 Fusion Protein Construct

| Primer | Sequence | SEQ ID NO: |
|---|---|---|
| Reaction 1 | | |
| Sense | 5'-AGGAGGAATAACATATGGACAAAACTCACACATG-3' | 14 |
| Antisense | 5'-GGATCCACCACCACCGCTACCAC-3' | 15 |
| Reaction 2 | | |
| Sense | 5'-GGTGGTGGTGGATCCCATCCAATTCCAGATTCTTCTCCA-3' | 16 |
| Antisense | 5'-TAGTGAGCTCGAATTCTTAGGAAGCGTAGCTGG-3' | 17 |
| Reaction 3 | | |
| Sense | 5'-AGGAGGAATAACATATGGACAAAACTCACACATG-3' | 14 |
| Antisense | 5'-TAGTGAGCTCGAATTCTTAGGAAGCGTAGCTGG-3' | 17 |

The product of the final reaction was digested with the restriction endonucleases NdeI and EcoRI, ligated into the pET30 vector, and then transformed into competent cells. The resulting clones were sequenced to confirm the absence of polymerase-generated errors.

Example 7

In Vivo Activity of Truncated FGF21 Fusion Proteins

Fusion proteins comprising a truncated FGF21 sequence fused to an Fc sequence were generated and assayed for in vivo activity. Truncated FGF21 fusion proteins were prepared by fusing an IgG1 Fc molecule to either the N-terminal or C-terminal end of a truncated FGF21 protein to form a single contiguous sequence. To distinguish between N-terminal and C-terminal fusions, FGF21 fusion proteins in which the Fc molecule was fused to the N-terminal end of the FGF21 protein are designated as Fc-FGF21, and fusion proteins in which the Fc molecule was fused to the C-terminal end of the FGF21 protein are designated as FGF21-Fc.

FGF21 possesses a number of biological activities, including the ability to lower blood glucose, insulin, triglyceride, or cholesterol levels; reduce body weight; or improve glucose tolerance, energy expenditure, or insulin sensitivity. To assess in vivo FGF21 activity, FGF21 polypeptides, FGF21 mutant polypeptides, and FGF21 fusion polypeptides were introduced into insulin resistant ob/ob mice, and the ability of a particular FGF21 protein to lower blood glucose levels was measured. The FGF21 polypeptide, FGF21 mutant polypeptide, or FGF21 fusion polypeptide to be tested was injected intraperitoneally into 8 week old ob/ob mice (Jackson Laboratory), and blood 25 samples were obtained at various time points following a single injection, e.g., 0, 6, 24, 72, 120, and 168 hours after injection. Blood glucose levels were measured with a OneTouch Glucometer (LifeScan, Inc. Milpitas, Calif.), and the results expressed as a percent change of blood glucose relative to the baseline level of blood glucose (i.e., at time 0).

Figure 4:
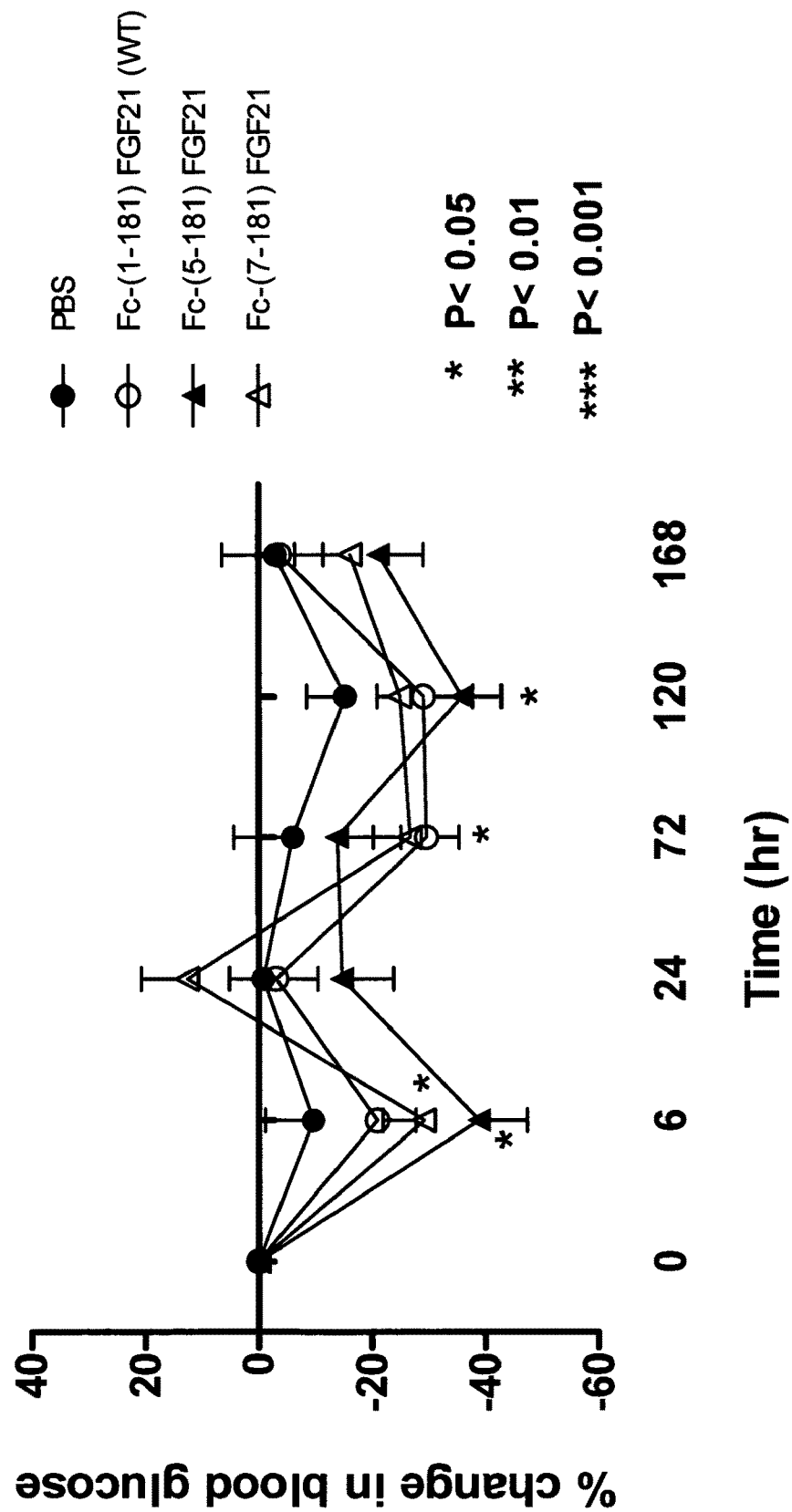
FIG. 4 shows the percent change in blood glucose levels measured in mice injected with PBS (solid circles), an Fc-FGF21 control (WT) (open circles), or truncated Fc-FGF21 fusion proteins comprising amino acid residues 5-181 (solid triangles) or 7-181 (open triangles).

The results of one experiment are provided in FIG. 4, which shows the percent change in blood glucose levels observed in mice injected with a PBS control, a wild-type Fc-FGF21 control comprising amino acid residues 1-181, or truncated Fc-FGF21 fusion proteins comprising amino acid residues 5-181 or 7-181. This experiment demonstrated that truncated Fc-FGF21 fusion proteins comprising amino acid residues 5-181 or 7-181 exhibit blood glucose lowering activity that is similar to the activity of wild-type Fc-FGF21 at 6 hours after injection. Thus, the in vivo analysis of truncated FGF21 polypeptides indicated that the deletion of up to 6 amino acids from the N-terminus of mature FGF21 does not affect the molecule's biological activity. In vivo analysis also indicated, however, that the ability of truncated FGF21 polypeptides to lower blood glucose was reduced and that blood glucose levels returned to baseline at 24 hours after injection (similar results were obtained with wild-type FGF21). The short in vivo activity was found to be a result of the proteolytic degradation of FGF21, as described in Example 8.

Figure 5:
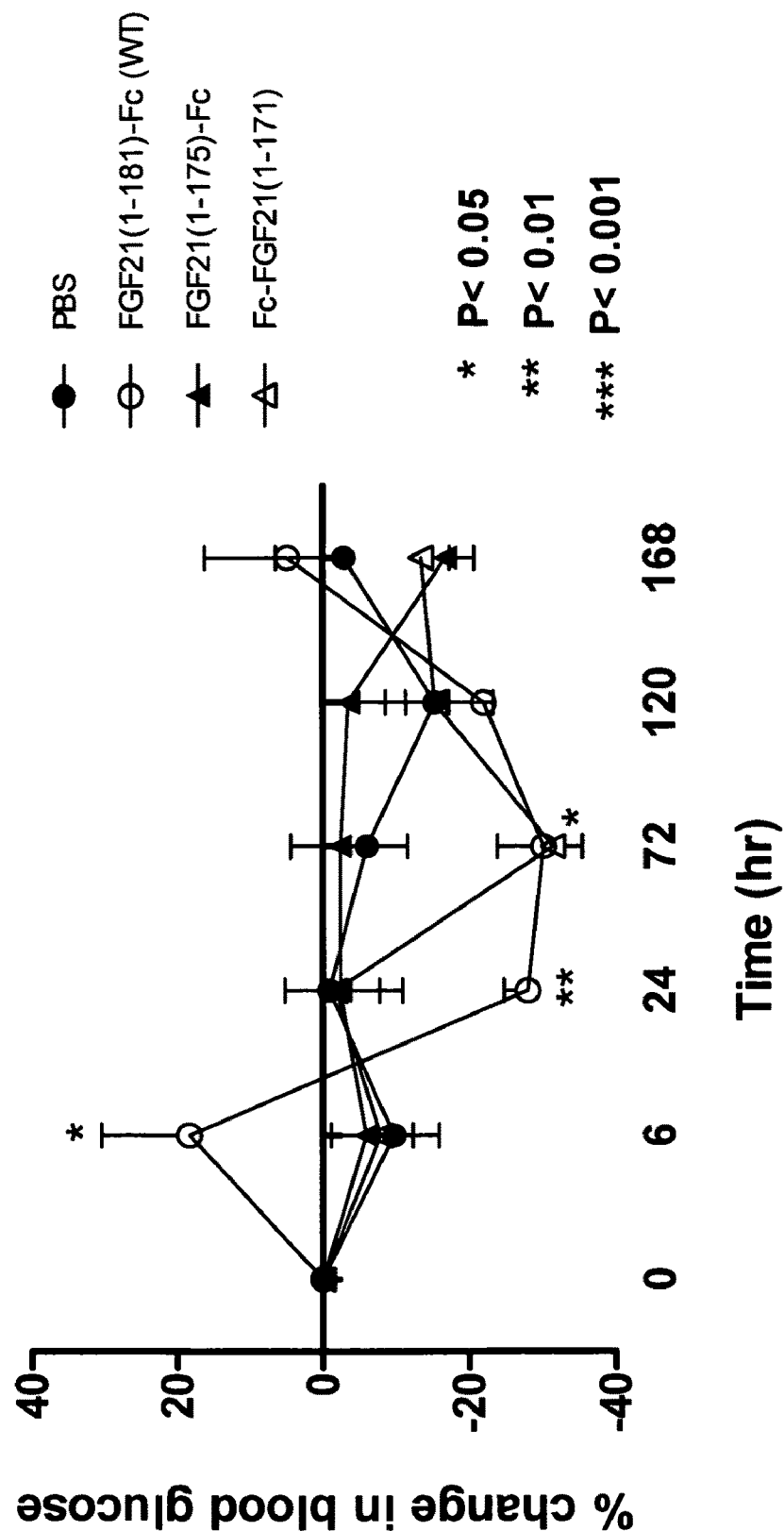
FIG. 5 shows the percent change in blood glucose levels measured in mice injected with PBS (solid circles), an FGF21-Fc control (WT) (open circles), a truncated FGF21-Fc fusion protein comprising residues 1-175 (solid triangles), or a truncated Fc-FGF21 protein comprising amino acid residues 1-171 (open triangles).
Figure 7A:
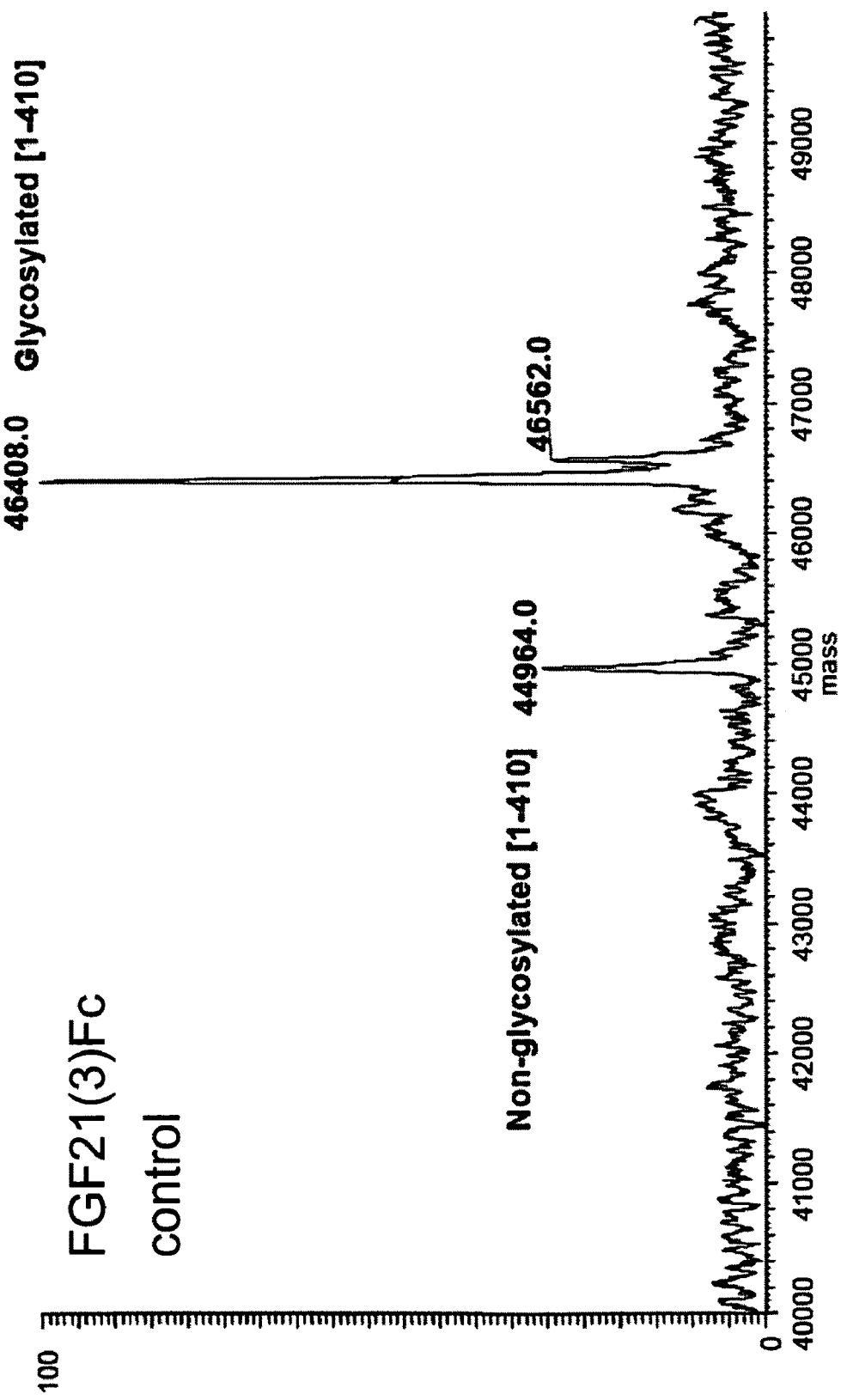
Figure 8D:
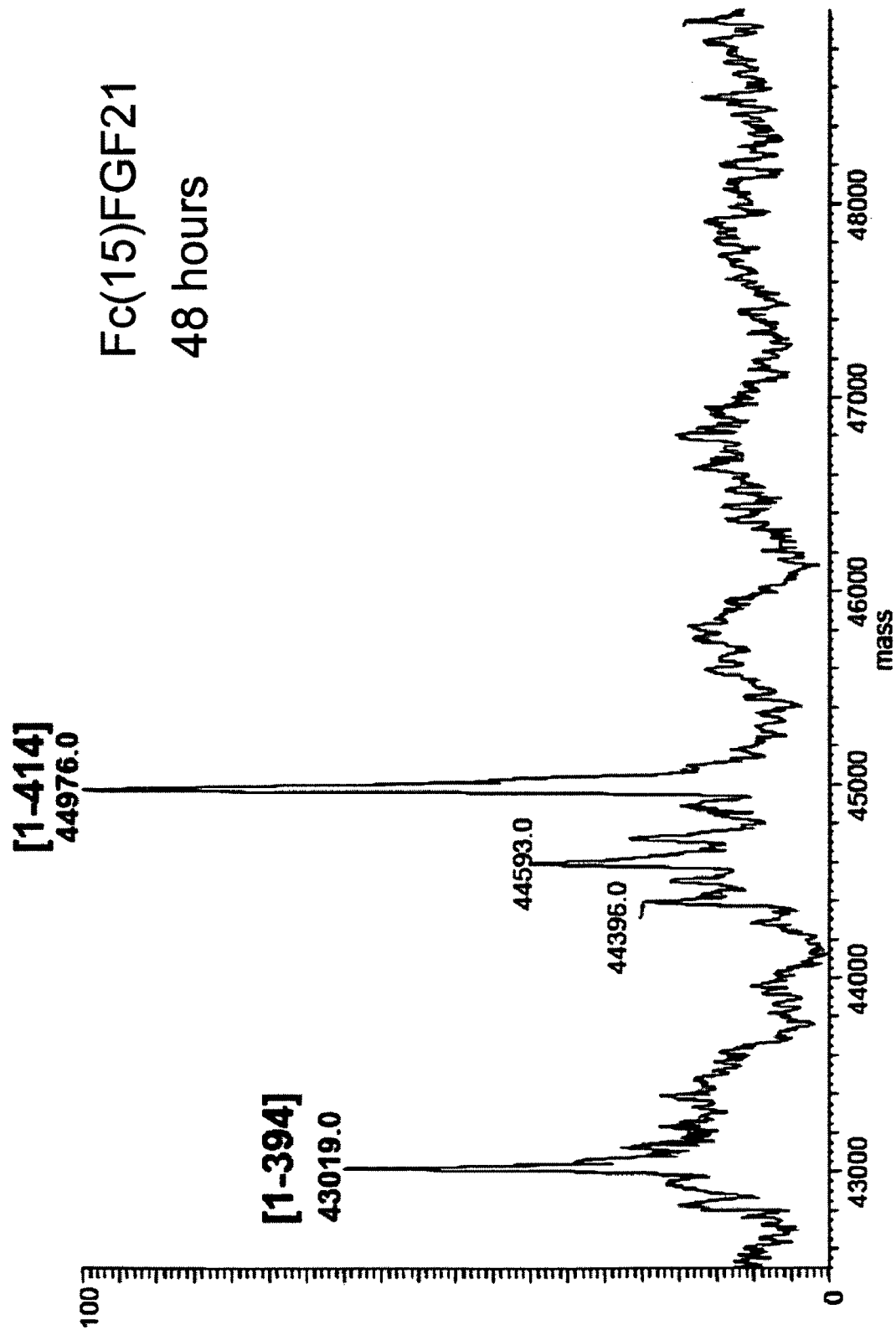
Figure 9C:
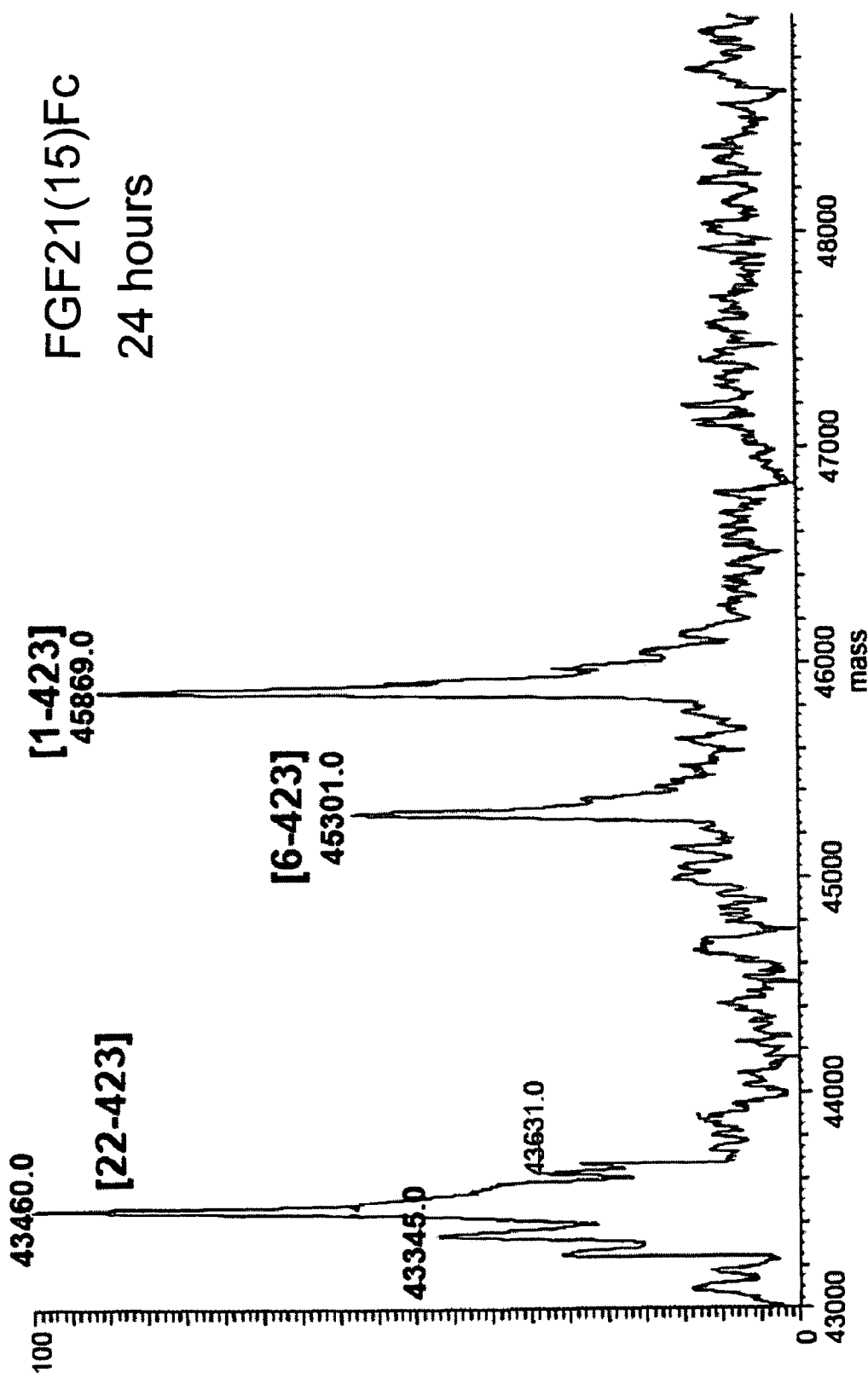
Figure 9D:
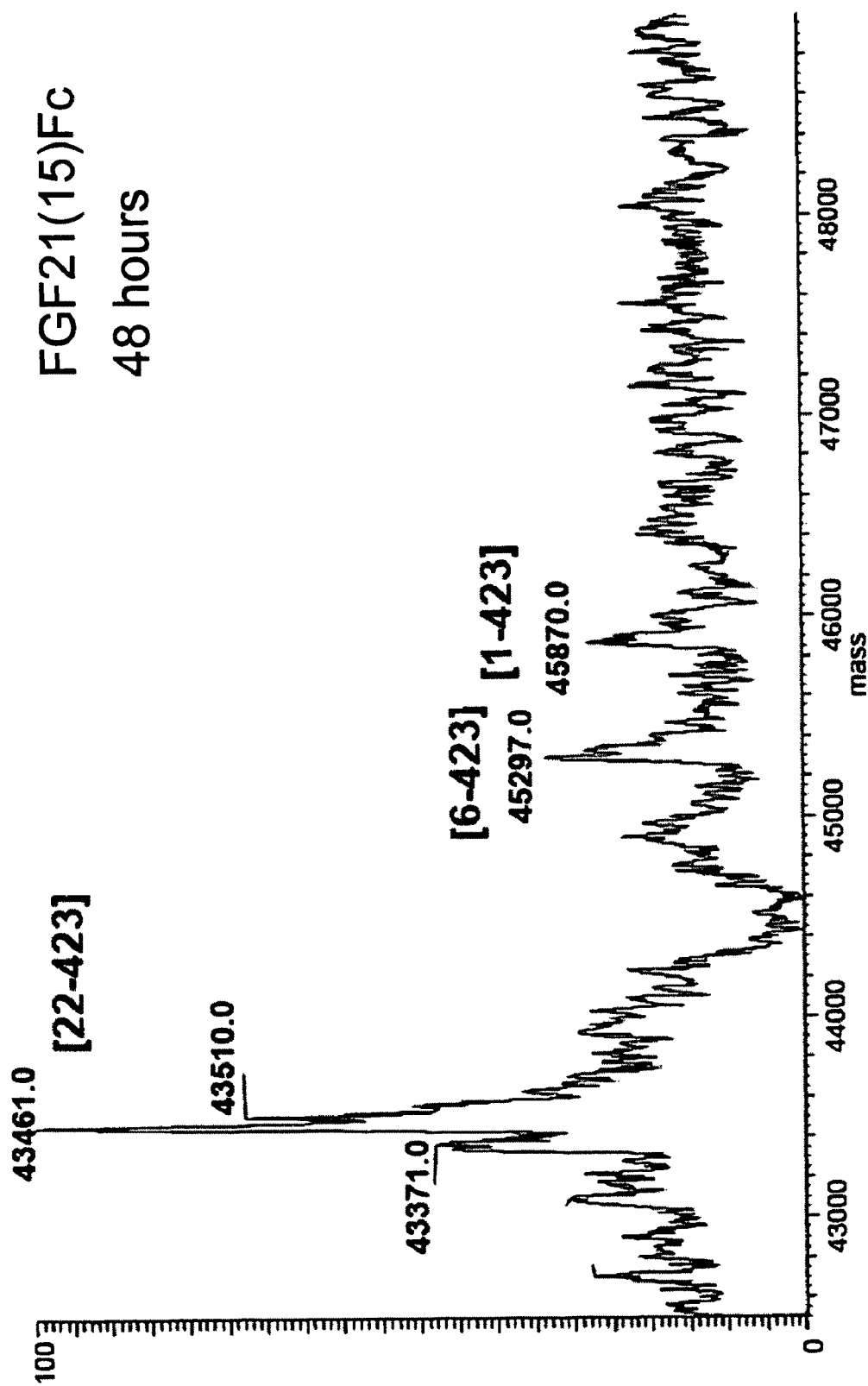

The results of another experiment are provided in FIG. 5, which shows the percent change in blood glucose levels observed in mice injected with a PBS control, a wild-type FGF21-Fc control comprising amino acid residues 1-181, a truncated FGF21-Fc fusion protein comprising residues 1-175, or a truncated Fc-FGF21 protein comprising amino acid residues 1-171. This experiment demonstrates that the wild-type FGF21-Fc comprising amino acid residues 1-181 has a sustained glucose-lowering activity resulting in a reduction of blood glucose levels of approximately 30% over the time period of 24 hours to 120 hours following injection. The truncated Fc-FGF21 protein comprising amino acid residues 1-171 exhibits delayed blood glucose lowering activity evident only at 72 hours after injection. However, the activity observed is the same as the activity of wild-type FGF21-Fc. The truncated FGF21-Fc fusion protein comprising residues 1-175 is not active in vivo in lowering blood glucose.

Collectively, the truncation experiments described herein demonstrate that truncated FGF21 fusion proteins having an N-terminal truncation exhibit blood glucose lowering activity that is similar to that of the wild-type FGF21 fusion protein, and further, that truncated FGF21 fusion proteins in which the Fc molecule has been fused to the N-terminal end of the truncated FGF21 protein exhibit more activity than fusion proteins in which the Fc molecule has been fused to the C-terminal end of the truncated FGF21 protein.

Example 8

Observed in Vivo Degradation of FGF21

FGF21 degradation was first observed with FGF21 Fc fusion protein constructs as described in Example 7. In vivo pharmacokinetic analysis indicated that human FGF21 has a short half-life of about 1 hour in mice due to rapid clearance and in vivo degradation. Therefore, to extend the half-life of FGF21 an Fc sequence was fused to the N- or C-terminal end of the FGF21 polypeptide. However, the fusion of an Fc region did not completely resolve the half-life issue since fusion proteins in which an Fc sequence was fused to the N- or C-terminal end of the FGF21 polypeptide (and in particular Fc-FGF21 fusions, i.e., in which the Fc sequence is fused to the N-terminus of mature FGF21), did not exhibit the expected in vivo efficacy, and instead were found to maintain blood glucose lowering activity for no more than 24 hours in ob/ob mice. As described in FIG. 4, Fc-FGF21 fusion proteins reduced blood glucose levels by about 30-40% at 6 hours after injection, while the blood glucose levels returned to baseline levels at 24 hours.

The proteolytic degradation of wild-type FGF21 was subsequently investigated, and the rapid loss of in vivo activity with Fc-FGF21 fusion proteins was found to be the result of in vivo degradation of FGF21. Proteolytic degradation leads to decreased biological activity of the molecule in vivo and thus a shorter effective half-life, and such degradation adversely impacts the therapeutic use of that molecule. Accordingly, the observed degradation of FGF21 Fc fusion proteins led to the investigation of the proteolytic degradation of FGF21 in vivo and to identify FGF21 mutants that were resistant to such degradation.

To determine the sites of degradation, LC-MS analysis and Edman sequencing was performed on wild-type human FGF21 and FGF21 Fc fusion proteins obtained at various time points after injection into male C57B6 mice. The Edman sequencing helped confirm whether the N-terminal or C-terminal end of the protein was undergoing degradation. When an Fc sequence was fused to the N-terminus of human FGF21, degradation was found to occur at the peptide bond between amino acid residues 151 and 152 and between amino acid residues 171 and 172 of the human FGF21 portion of the fusion molecule (the residue numbering above is based on the mature FGF21 sequence and does not include the Fc portion of the fusion protein). The degradation at 171-172 was found to occur first, and was followed by degradation at 151-152. Degradation at 171-172 appears to be the rate-limiting step and plays a role in the half-life of the molecule. When an Fc sequence was fused to the C-terminus of FGF21, degradation was found to occur at the peptide bond between amino acid residues 4 and 5 and between amino acid residues 20 and 21. As a result of these experiments, it was determined that the Fc sequence appears to protect the portion of the FGF21 sequence that is adjacent to the Fc sequence from degradation. An analysis of the in vivo degradation of wild-type FGF21 and Fc-FGF21 fusion proteins was further conducted in cynomolgus monkeys. These studies confirmed that the cleavage site of FGF21 at amino acid residues 171-172 is the major site of degradation in monkeys and that this site of degradation is conserved between murine and primate.

Example 9

Identification of FGF21 Proteolysis-Resistant Mutants

Suitable FGF21 mutants were identified by experimentally determining the positions of the wild-type FGF21 sequence that are sites of major proteolytic activity, and specific amino acid substitutions were introduced at these sites. Amino acid substitutions were based on FGF21 sequence conservation with other species (as described in Example 8) and biochemical conservation with other amino acid residues. A list of amino acid substitutions that were or can be introduced into the wild-type FGF21 protein is provided in Table 8, although Table 8 is only exemplary and other substitutions can be made. The numbers of the positions given in Table 8 correspond to the residue position in the mature FGF21 protein, which consists of 181 amino acid residues.

TABLE 8

FGF21 Residues Mutated

| Amino Acid Position | Native Residue | Mutations |
|---|---|---|
| 19 | Arg | Gln, Ile, Lys |
| 20 | Tyr | His, Leu, Phe |
| 21 | Leu | Ile, Phe, Tyr, Val |
| 22 | Tyr | Ile, Phe, Val |
| 150 | Pro | Ala, Arg |
| 151 | Gly | Ala, Val |
| 152 | Ile | His, Leu, Phe, Val |
| 170 | Gly | Ala, Asn, Asp, Cys, Gln, Glu, Pro, Ser |
| 171 | Pro | Ala, Arg, Asn, Asp, Cys, Glu, Gln, Gly, His, Lys, Ser, Thr, Trp, Tyr |
| 172 | Ser | Leu, Thr |
| 173 | Gln | Arg, Glu |

Example 10

In Vivo Analysis of Fc-FGF21 and FGF21-Fc Degradation

The stability of FGF21 Fc fusion proteins in vivo was determined by injecting mice with a fusion protein, drawing blood from the mice at various time points, and analyzing the serum by liquid chromatography-mass spectrometry (LC-MS). In particular, mice were intraperitoneally injected with 10 mg/kg of Fc(5)FGF21 (expressed in E. coli and purified as described in Example 2) or FGF21(3)Fc (expressed in mammalian cells and purified according to standard procedures). Blood was drawn from the mice at 6, 24, and 48 hours after injection (Table 9) and collected into EDTA tubes pretreated with protease inhibitor cocktails (Roche Diagnostics). Plasma was separated by centrifuging the samples at 12,000 g for 10 minutes. FGF21 proteins were affinity purified from blood using an anti-human-Fc agarose resin.

TABLE 9

FGF21 Samples

| Sample | Protein Administered | Blood Withdrawn |
|---|---|---|
| D6 | Fc-FGF21 | 6 hours |
| D24 | Fc-FGF21 | 24 hours |
| D48 | Fc-FGF21 | 48 hours |
| E6 | FGF21-Fc | 6 hours |
| E24 | FGF21-Fc | 24 hours |
| E48 | FGF21-Fc | 48 hours |

Prior to analyzing the affinity purified samples by LC-MS, Fc-FGF21 and FGF21-Fc protein standards were analyzed as a reference. Protein standards were either reduced with tris [2-carboxyethyl]phosphine (TCEP) or not reduced. Reduced and non-reduced standards were analyzed by LC-MS using an ACE cyano 0.3 mm×30 cm column with the column effluent spraying into an LCQ Classic ion-trap mass spectrometer. Since the deconvoluted spectra of the reduced samples were cleaner, the affinity purified samples were reduced prior to LC-MS analysis.

The observed masses for the reduced Fc(5)FGF21 standard and samples D6, D24, and D48 are shown in FIGS. 6A-6D. The observed masses for the reduced FGF21(3)Fc standard and samples E6, E24, and E48 are shown in FIGS. 7A-7D. Some of the standard and sample eluates were subjected to Edman sequencing in order to confirm the N-terminus of the proteins and the fragments as determined by LC-MS. Results of the LC-MS analysis of the standards and samples are provided in Table 10.

TABLE 10

Results of LC-MS Analysis and Predicted Fragments

| FGF21 Sample | Major Observed Masses | Fragment | Intact N-terminus? |
|---|---|---|---|
| Fc(5)FGF21 standard | 45,339 Da | 1-414 | Yes |
| D6 | 45,338 Da | 1-414 | Yes |
|  | 44,317 Da | 1-404 |  |
| D24 | 44,321 Da | 1-404 | Yes |
| D48 | 44,327 Da | 1-404 | Yes |
|  | 42,356 Da | ? |  |
| FGF21(3)Fc standard | 46,408 Da (glycosylated, G0F) | 1-410 | Yes |
|  | 44,964 Da (non-glycosylated) | 1-410 |  |
| E6 | 45,963 Da (glycosylated, G0F) | 5-410 | No |
|  | 44,516 Da (non-glycoylated) | 5-410 |  |
| E24 | 45,963 Da (glycosylated, G0F) | 5-410 | No |
|  | 44,526 Da (non-glycosylated) | 5-410 |  |
|  | 44,130 Da (glycosylated, G0F) | 21-410 |  |
| E48 | 45,984 Da | 5-410? | No |
|  | 44,130 Da | 21-410 |  |
|  | 44,022 Da | ? |  |

As indicated in Table 10, all of the affinity purified samples showed some degree of degradation after only 6 hours of circulation. After 24 hours of circulation, the major product of Fc-FGF21 was a fragment consisting of amino acid residues 1-404, which was seen in both the D and E samples. In the E samples, however, the major product of FGF21-Fc was a fragment consisting of amino acid residues 5-410. For both of the fusion proteins tested, the FGF21 portion of the fusion protein was more susceptible to degradation than the Fc portion of the protein.

Example 11

Preparation and Expression of Proteolysis-Resistant FGF21 Mutants and Fusion Proteins Constructs encoding the FGF21 mutants listed in Table 11 were prepared by PCR amplification of the wild-type FGF21 expression vector as described below (the construction of the wild-type FGF21 expression vector is described in Example 1). The goal of these experiments was to generate FGF21 mutants that are resistant to proteolysis and exhibit longer half-lives.

TABLE 11

Proteolysis-Resistant FGF21 Mutants

| Mutation(s) | Fc | Linker |
|---|---|---|
| R19I |  |  |
| R19I | —COOH | 15 |
| R19K |  |  |
| R19K | —COOH | 15 |
| R19Q |  |  |
| R19Q | —COOH | 15 |
| R19K, Y20H |  |  |
| R19K, Y20H | —COOH | 15 |
| R19K, L21I |  |  |
| R19K, L21I | —COOH | 15 |
| R19K, Y20H, L21I |  |  |
| R19K, Y20H, L21I | —COOH | 15 |
| Y20F |  |  |
| Y20F | —COOH | 15 |
| Y20H |  |  |
| Y20H | —COOH | 15 |
| Y20L |  |  |
| Y20L | —COOH | 15 |
| Y20H, L21I |  |  |
| Y20H, L21I | —COOH | 15 |
| L21I |  |  |
| L21I | —COOH | 15 |
| L21F |  |  |
| L21F | —COOH | 15 |
| L21V |  |  |
| L21V | —COOH | 15 |
| L21Y |  |  |
| L21Y | —COOH | 15 |
| Y22F |  |  |
| Y22F | —COOH | 15 |
| Y22I |  |  |
| Y22I | —COOH | 15 |
| Y22V |  |  |
| Y22V | —COOH | 15 |
| P150A |  |  |
| P150A | —NH$_2$ | 15 |
| P150R | —NH$_2$ | 15 |
| P150A, G151A |  |  |
| P150A, G151A | —NH$_2$ | 15 |
| P150A, I152V |  |  |
| P150A, I152V | —NH$_2$ | 15 |
| P150A, G151A, I152V |  |  |
| P150A, G151A, I152V | —NH$_2$ | 15 |
| G151A |  |  |
| G151A | —NH$_2$ | 15 |
| G151V |  |  |
| G151V | —NH$_2$ | 15 |
| G151A, I152V |  |  |
| G151A, I152V | —NH$_2$ | 15 |
| I152F |  |  |
| I152F | —NH$_2$ | 15 |
| I152H |  |  |
| I152H | —NH$_2$ | 15 |
| I152L |  |  |
| I152L | —NH$_2$ | 15 |
| I152V |  |  |
| G170A |  |  |
| G170A | —NH$_2$ | 15 |
| G170C |  |  |
| G170C | —NH$_2$ | 15 |
| G170D |  |  |
| G170D | —NH$_2$ | 15 |
| G170E |  |  |
| G170E | —NH$_2$ | 15 |
| G170N |  |  |
| G170N | —NH$_2$ | 15 |
| G170P |  |  |
| G170P | —NH$_2$ | 15 |
| G170Q |  |  |
| G170Q | —NH$_2$ | 15 |
| G170S |  |  |
| G170S | —NH$_2$ | 15 |
| G170E, P171A |  |  |
| G170E, P171A | —NH$_2$ | 15 |
| G170E, S172L |  |  |
| G170E, S172L | —NH$_2$ | 15 |
| G170E, P171A, S172L |  |  |
| G170E, P171A, S172L | —NH$_2$ | 15 |

TABLE 11-continued

Proteolysis-Resistant FGF21 Mutants

| Mutation(s) | Fc | Linker |
|---|---|---|
| P171A | | |
| P171A | —NH₂ | 15 |
| P171C | —NH₂ | 15 |
| P171D | —NH₂ | 15 |
| P171E | —NH₂ | 15 |
| P171G | —NH₂ | 15 |
| P171H | —NH₂ | 15 |
| P171K | —NH₂ | 15 |
| P171N | —NH₂ | 15 |
| P171Q | —NH₂ | 15 |
| P171S | —NH₂ | 15 |
| P171T | —NH₂ | 15 |
| P171W | —NH₂ | 15 |
| P171Y | —NH₂ | 15 |
| P171A, S172L | | |
| P171A, S172L | —NH₂ | 15 |
| S172L | —NH₂ | 15 |
| S172T | | |
| S172T | —NH₂ | 15 |
| Q173E | | |
| Q173E | —NH₂ | 15 |
| Q173R | | |
| Q173R | —NH₂ | 15 |

FGF21 mutant constructs were prepared using primers having sequences that are homologous to regions upstream and downstream of a codon (or codons) to be mutated. The primers used in such amplification reactions also provided approximately 15 nucleotides of overlapping sequence to allow for recircularization of the amplified product, namely the entire vector now having the desired mutant.

An exemplary FGF21 mutant construct, encoding an FGF21 mutant having a glutamic acid residue at position 170 instead of the native glycine residue (i.e., the G170E mutant) was prepared using the primers shown in Table 12.

TABLE 12

PCR Primers for Preparing Exemplary FGF21 Mutant

| Primer | Sequence | SEQ ID NO: |
|---|---|---|
| Sense | 5'-ATGGTGGAACCTTCCCAGGGCCGAAGC-3' | 18 |
| Antisense | 5'-GGAAGGTTCCACCATGCTCAGAGGGTCCGA-3' | 19 |

The primers shown in Table 12 allow for the substitution of the glycine residue with a glutamic acid residue as shown below, wherein the upper sequence is the sense primer (SEQ ID NO: 18), the second and third sequences (SEQ ID NOs: 20 and 22) are portions of an FGF21 expression construct, and the fourth sequence is the antisense primer (SEQ ID NO: 21):

```
               5'-ATGGTGGAACCTTCCCAGGGCCGAAGC
CTCCTCGGACCCTCTGAGCATGGTGGGACCTTCCCAGGGCCGAAGCCCCA
GAGGAGCCTGGGAGACTCGTACCACCCTGGAAGGGTCCCGGCTTCGGGT
   AGCCTGGGAGACTCGTACCACCTTGGAAGG-5'
```

FGF21 mutant constructs were prepared using essentially the PCR conditions described in Example 1. Amplification products were digested with the restriction endonuclease DpnI, and then transformed into competent cells. The resulting clones were sequenced to confirm the absence of poly-merase-generated errors. Fc-FGF21 and FGF21-Fc fusion proteins were generated as described herein, e.g., in Example 6.

FGF21 mutants were expressed by transforming competent BL21 (DE3) or BL21 Star (Invitrogen; Carlsbad, Calif.) cells with the construct encoding a particular mutant. Transformants were grown overnight with limited aeration in TB media supplemented with 40 µg/mL kanamycin, were aerated the next morning, and after a short recovery period, were induced in 0.4 mM IPTG. FGF21 mutant polypeptides were harvested by centrifugation 18-20 hours after induction.

FGF21 mutants were also analyzed for predicted immunogenicity. Immune responses against proteins are enhanced by antigen processing and presentation in the major histocompatibility complex (MHC) class II binding site. This interaction is required for T cell help in maturation of antibodies that recognize the protein. Since the binding sites of MHC class II molecules have been characterized, it is possible to predict whether proteins have specific sequences that can bind to a series of common human alleles. Computer algorithms have been created based on literature references and MHC class II crystal structures to determine whether linear amino acid peptide sequences have the potential to break immune tolerance. The TEPITOPE computer program was used to determine if point mutations in particular FGF21 mutants would increase antigen specific T cells in a majority of humans. Based on an analysis of the linear protein sequence of each FGF21 mutant, none of the mutants was predicted to enhance immunogenicity.

Example 12

Impact of Linker Sequence on FGF21 Degradation

To determine whether the presence of a longer amino acid linker between the Fc sequence and the FGF21 sequence affects FGF21 degradation, mice were injected with FGF21 fusion proteins in which the Fc region was separated from the FGF21 sequence by a 15 amino acid linker having the sequence GGGGGSGGGSGGGS (SEQ ID NO: 23), blood was withdrawn from the mice at various time points, and the serum was analyzed by LC-MS. In particular, mice were injected with Fc(15)FGF21 or FGF21(15)Fc. (obtained from E. coli) at 23 mg/kg, blood was drawn at 6, 24, and 48 hours, and drawn blood was affinity purified using an anti-human-Fc agarose resin.

Prior to analyzing the purified samples by LC-MS, Fc(15) FGF21 and FGF21(15)Fc protein standards were analyzed as a reference. Protein standards were either reduced with TCEP or not reduced. Both reduced and non-reduced standards were analyzed by LC-MS using an ACE cyano 0.3 mm×30 cm column with the column effluent spraying into an LCQ Classic ion-trap mass spectrometer. Since the deconvoluted spectra of the reduced samples were cleaner, the affinity purified samples were reduced prior to LC-MS analysis.

The observed masses for the reduced Fc(15)FGF21 standard and corresponding affinity purified samples withdrawn at various time points are shown in FIGS. 8A-8D. The observed masses for the reduced FGF21(15)Fc standard and corresponding affinity purified samples withdrawn at various time points are shown in FIGS. 9A-9D. Some of the standard and sample eluates were subjected to Edman sequencing in order to confirm the N-terminus of the proteins and assist in predicting the identity of the fragments observed by LC-MS. Results of the LC-MS analysis of the standards and samples and an indication of predicted fragments are provided in Table 13.

TABLE 13

Results of LC-MS Analysis and Predicted Fragments

| FGF21 Sample | Major Observed Masses | Percent of Total | Fragment | Intact N-terminus? |
|---|---|---|---|---|
| Fc(15)FGF21 standard | 46,002 Da | 100% | 1-424 | Yes |
| Fc(15)FGF21 6 hours | 46,000 Da | 65% | 1-424 | Yes |
| | 44,978 Da | 35% | 1-414 | |
| Fc(15)FGF21 24 hours | 44,978 Da | 85% | 1-414 | Yes |
| | 43,022 Da | 15% | 1-394 | |
| Fc(15)FGF21 48 hours | 44,976 Da | 60% | 1-414 | Yes |
| | 43,019 Da | 40% | 1-394 | |
| FGF21(15)Fc standard | 45,999 Da | 100% | 1-424 | Yes |
| FGF21(15)Fc 6 hours | 45,870 Da | 100% | 1-423 | Yes |
| FGF21(15)Fc 24 hours | 45,869 Da | 40% | 1-423 | Some |
| | 45,301 Da | 35% | 6-423 | |
| | 43,460 Da | 25% | 22-423 | |
| FGF21(15)Fc 48 hours | 45,870 Da | 15% | 1-423 | Some |
| | 45,297 Da | 20% | 6-423 | |
| | 43,461 Da | 65% | 22-423 | |

As indicated in Table 13, all of the affinity purified samples showed some degree of degradation after only 6 hours of circulation. After 24 hours of circulation, the major products of Fc(15)FGF21 were fragments consisting of amino acid residues 1-414 (85% of sample) and 1-394 (15% of sample), and the major products of FGF21(15)Fc were fragments consisting of amino acid residues 1-423 (40% of sample), 6-423 (35% of sample), and 22-423 (25% of sample). Identified cleavage points for the Fc(15)FGF21 and FGF21(15)Fc proteins are shown in FIGS. 10A and 10B, respectively.

Example 13

In Vivo Activity of Proteolysis-Resistant Fc(15)FGF21 Mutants at 1-7 Days After Injection As described herein, proteolytic cleavage of FGF21 Fc fusion proteins depends upon the orientation of the Fc sequence, with the Fc end of the fusion protein being more stable than the FGF21 end of the fusion protein (i.e., the N-terminal portion of Fc-FGF21 fusion proteins and the C-terminal portion of FGF21-Fc fusion proteins were found to be more stable). For example, cleavage was identified at positions 5 and 21 of FGF21-Fc and positions 151 and 171 of Fc-FGF21.

As a result of these observations, an investigation was performed to identify proteolysis-resistant FGF21 mutants. LC-MS analysis of Fc-FGF21 demonstrates that in vivo proteolytic degradation first occurs between amino acid residues 171-172, followed by degradation between amino acid residues 151-152. By blocking proteolytic degradation at position 171, the cleavage at position 151 can be prevented, effectively extending the half-life of the molecule. However, proteolysis-resistant mutants in which cleavage is prevented at position 151 can still possess residues at position 171 that are susceptible to protease attack, thereby resulting in a molecule missing the last 10 amino acids, which are known to be involved in the binding of the co-receptor beta-klotho, which is a determinant of ligand receptor affinity and in vitro and in vivo potency. Therefore, the mutagenesis of amino acid residues surrounding position 171 in mature FGF21 appear to be more critical for improving the in vivo stability, potency, and efficacy of the molecule.

Figure 11:
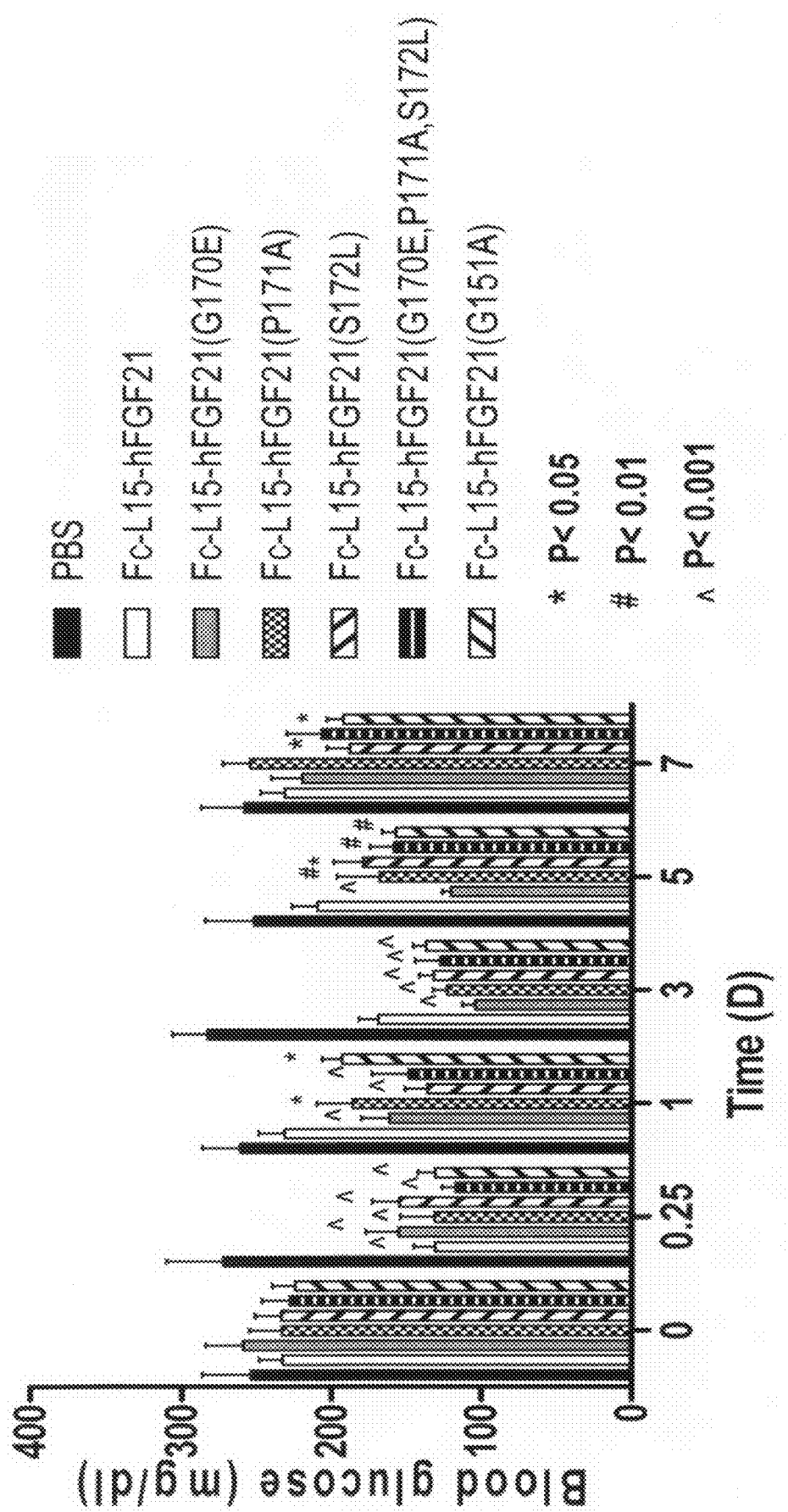
FIG. 11 shows the blood glucose levels measured in mice injected with PBS (solid bar), Fc(15)FGF21 (open bar), or the Fc(15)FGF21 mutants Fc(15)FGF21 G170E (gray bar), Fc(15)FGF21 P171A (stippled bar), Fc(15)FGF21 S172L (open diagonally crosshatched bar), Fc(15)FGF21 G170E/P171A/S172L (solid horizontally crosshatched bar), or Fc(15)FGF21 G151A (open diagonally crosshatched bar).
Figure 12:
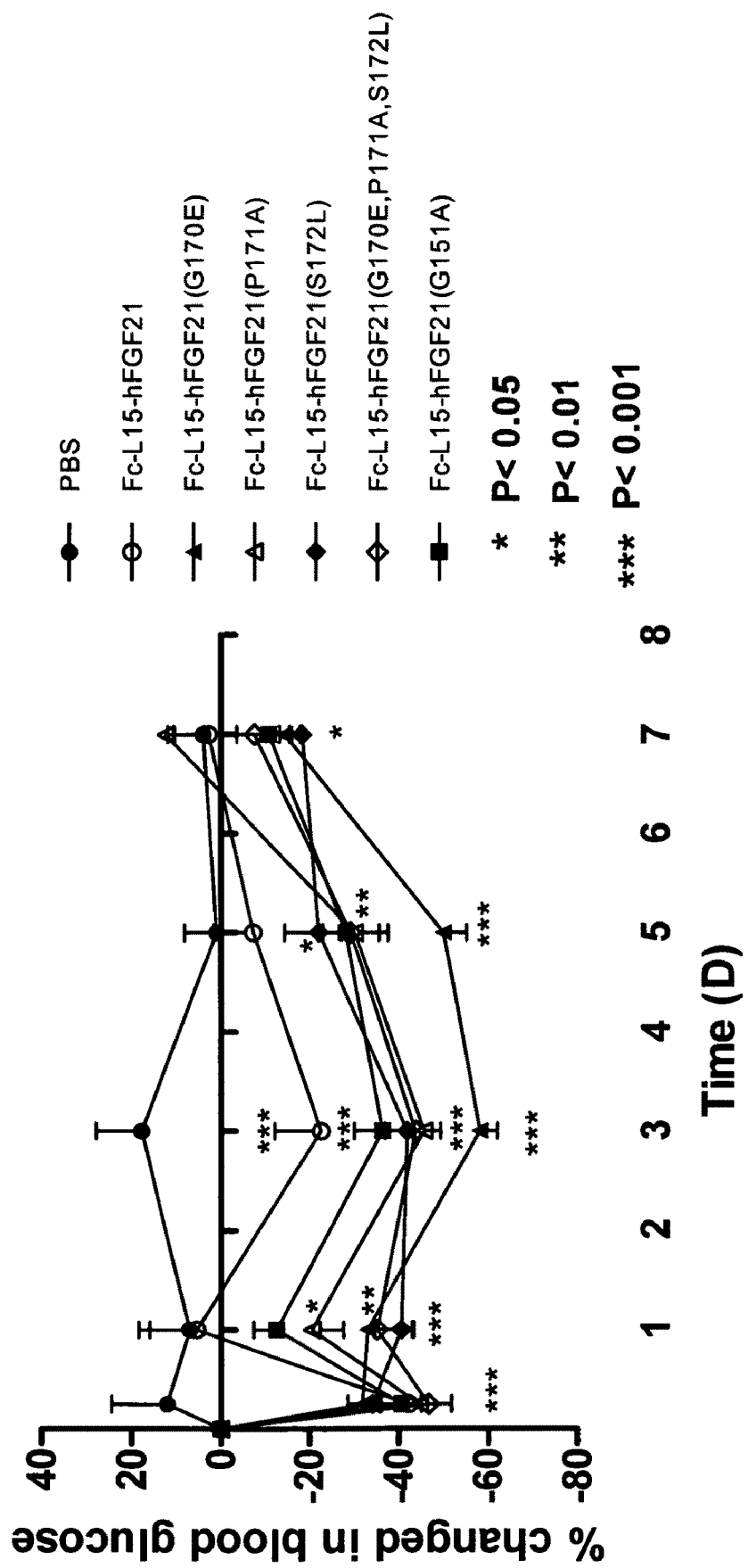
FIG. 12 shows the percent change in blood glucose levels measured in mice injected with PBS (solid circles), Fc(15) FGF21 (open circles), or the Fc(15)FGF21 mutants Fc(15) FGF21 G170E (solid triangles), Fc(15)FGF21 P171A (open triangles), Fc(15)FGF21 S172L (solid diamonds), Fc(15) FGF21 G170E/P171A/S172L (open diamonds), or Fc(15) FGF21 G151A (solid squares).

The in vivo activity of particular proteolysis-resistant Fc(15)FGF21 mutants was assayed by intraperitoneally injecting ob/ob mice with an FGF21 mutant, drawing blood samples from injected mice at 0, 0.25, 1, 3, 5, and 7 days after injection, and then measuring blood glucose levels in the samples. The results of one experiment are provided in FIG. 11, which shows the blood glucose levels measured in mice injected with a PBS control, an Fc(15)FGF21 control, or the Fc(15)FGF21 mutants Fc(15)FGF21 G170E, Fc(15)FGF21 P171A, Fc(15)FGF21 S172L, Fc(15)FGF21 G170E/P171A/S172L, or Fc(15)FGF21 G151A. FIG. 12 shows the percent change in blood glucose levels as determined in this experiment. This experiment demonstrates that the Fc(15)FGF21 G170E, Fc(15)FGF21 P171A, Fc(15)FGF21 S172L, and Fc(15)FGF21 G170E/P171A/S172L mutants exhibit sustained blood glucose lowering activity for up to 5 days, which is superior to the activity of wild-type Fc-FGF21 The Fc(15) FGF21 G151A mutant only partially improved the duration of blood glucose lowering activity as compared with wild-type Fc-FGF21 fusion protein. Surprisingly, although the Fc(15)-FGF21 S172L mutant is not a proteolysis-resistant mutant, and therefore has similar degradation profile as the wild-type Fc(15)-FGF21 polypeptide, this mutant was found to exhibit improved in vivo efficacy as compared with the wild-type Fc(15)-FGF21 polypeptide.

Figure 13:
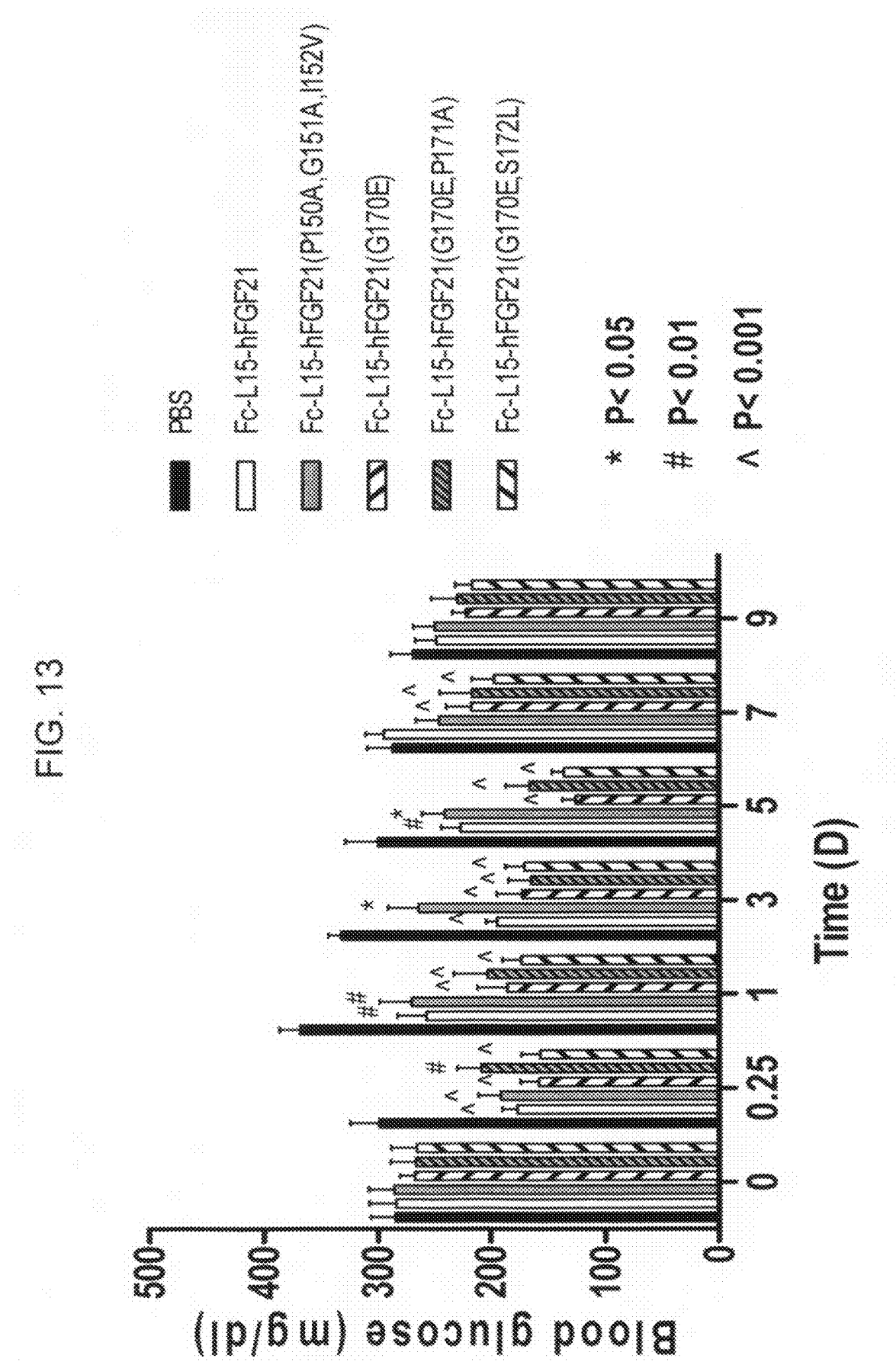
FIG. 13 shows the blood glucose levels measured in mice injected with PBS (solid bar), Fc(15)FGF21 (open bar), or the Fc(15)FGF21 mutants Fc(15)FGF21 P150A/G151A/I152V (gray bar), Fc(15)FGF21 G170E (open diagonally crosshatched bar), Fc(15)FGF21 G170E/P171A (gray diagonally crosshatched bar), or Fc(15)FGF21 G170E/S172L (open diagonally crosshatched bar).
Figure 14:
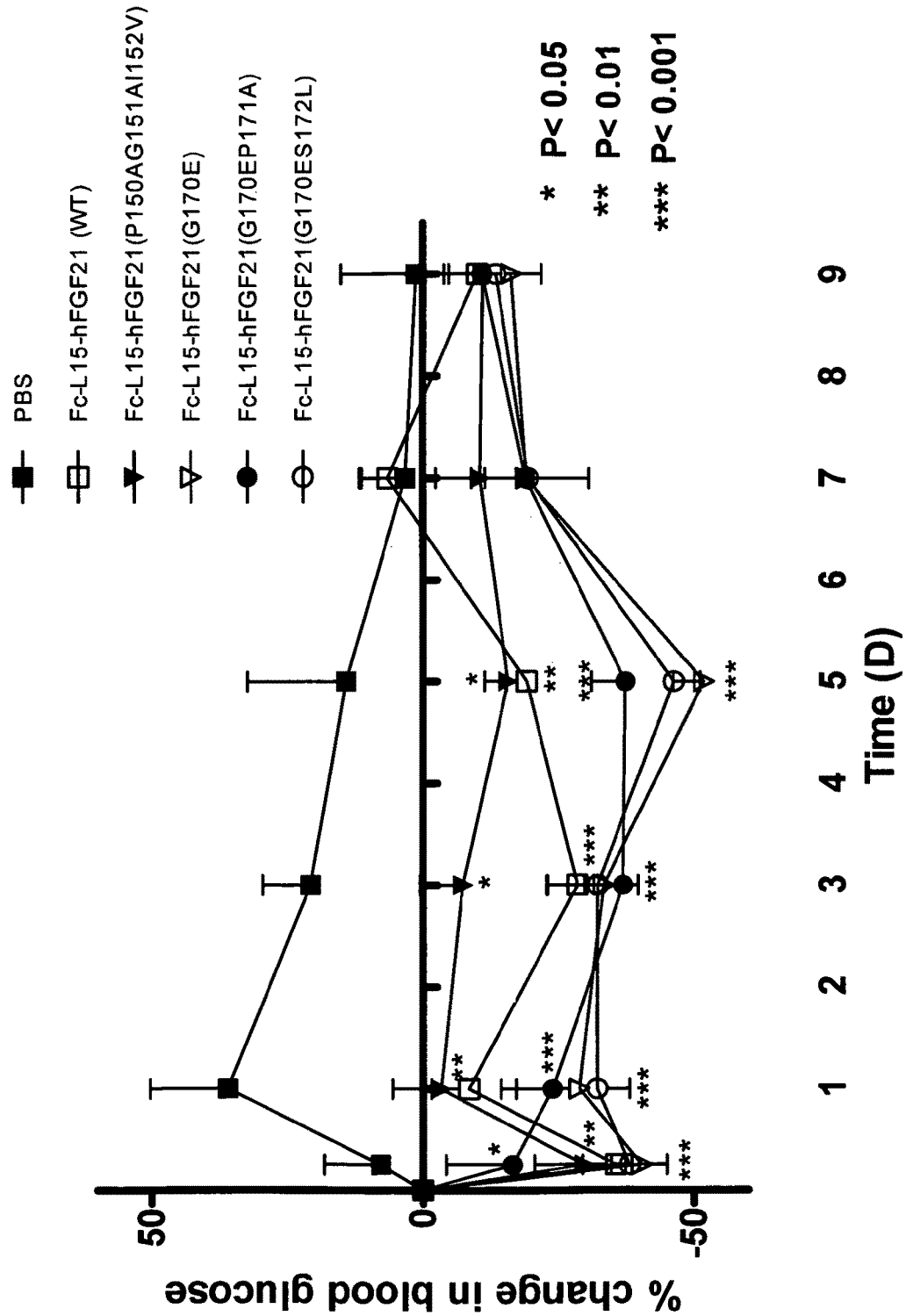
FIG. 14 shows the percent change in blood glucose levels measured in mice injected with PBS (solid squares), Fc(15) FGF21 (open squares), or the Fc(15)FGF21 mutants Fc(15) FGF21 P150A/G151A/I152V (solid inverted triangles), Fc(15)FGF21 G170E (open inverted triangles), Fc(15) FGF21 G170E/P171A (solid circles), or Fc(15)FGF21 G170E/S172L (open circles).

The results of another experiment are provided in FIG. 13, which shows the blood glucose levels measured in mice injected with a PBS control, an Fc(15)FGF21 control, or the Fc(15)FGF21 mutants Fc(15)FGF21 P150A/G151A/I152V, Fc(15)FGF21 G170E, Fc(15)FGF21 G170E/P171A, or Fc(15)FGF21 G170E/S172L. FIG. 14 shows the percent change in blood glucose levels as determined in this experiment. As in the experiment described above, the wild-type Fc-FGF21 fusion protein and the Fc(15)FGF21 P150A/G151A/I152V mutant do not exhibit sustained blood glucose lowering activity, possibly because the degradation at 171 site could still occur, and blood glucose levels in animals injected with these proteins returned to baseline at 24 hours after injection. However, the Fc(15)FGF21 G170E, Fc(15)FGF21 G170E/P171A, or Fc(15)FGF21 G170E/S172L exhibit maximal blood glucose lowering activity up to 5 days after injection, which is superior to the wild-type Fc-FGF21 fusion protein and the Fc(15)FGF21 P150A/G151A/I152V mutant.

Figure 15:
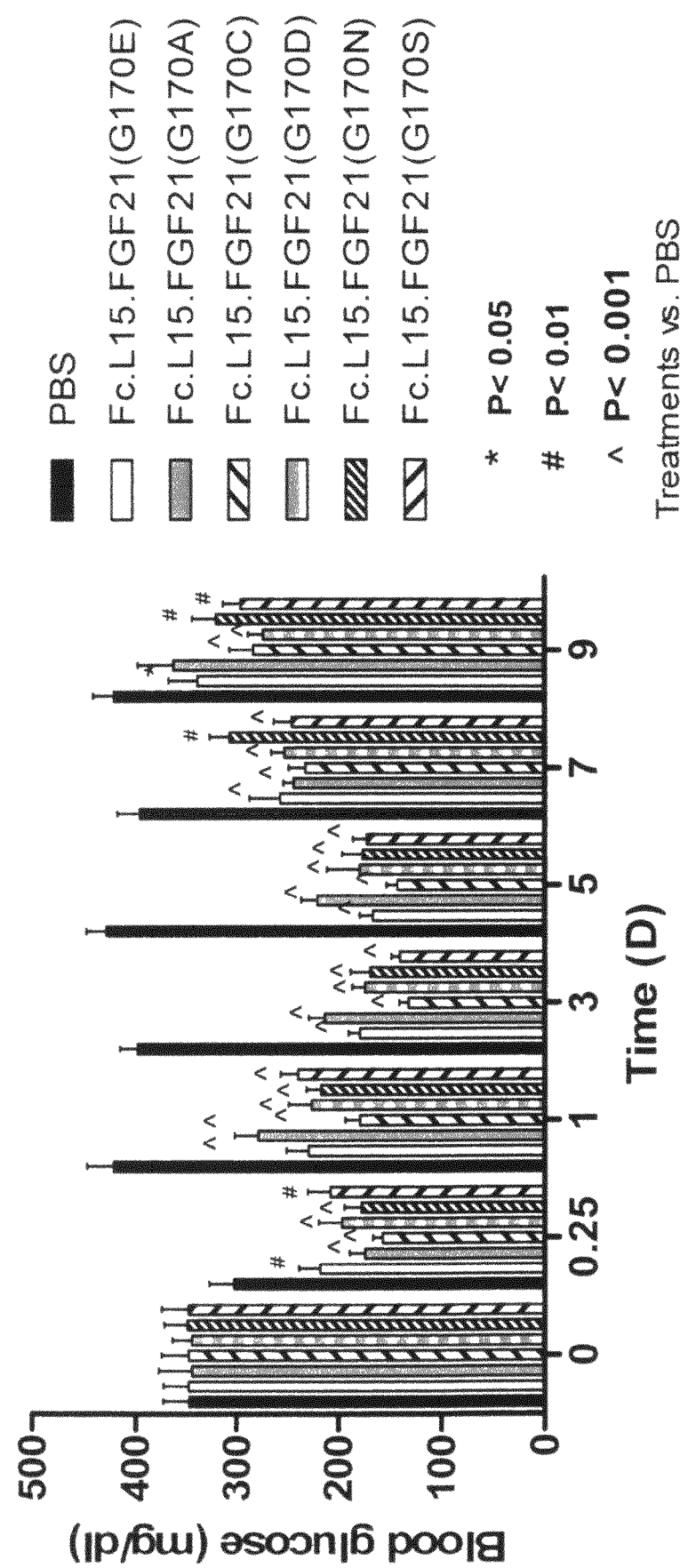
FIG. 15 shows the blood glucose levels measured in mice injected with PBS (solid bar) or the Fc(15)FGF21 mutants Fc(15)FGF21 G170E (open bar), Fc(15)FGF21 G170A (gray bar), Fc(15)FGF21 G170C (open crosshatched bar), Fc(15) FGF21 G170D (gray and white bar), Fc(15)FGF21 G170N (solid crosshatched bar), or Fc(15)FGF21 G170S (open crosshatched bar).
Figure 16:
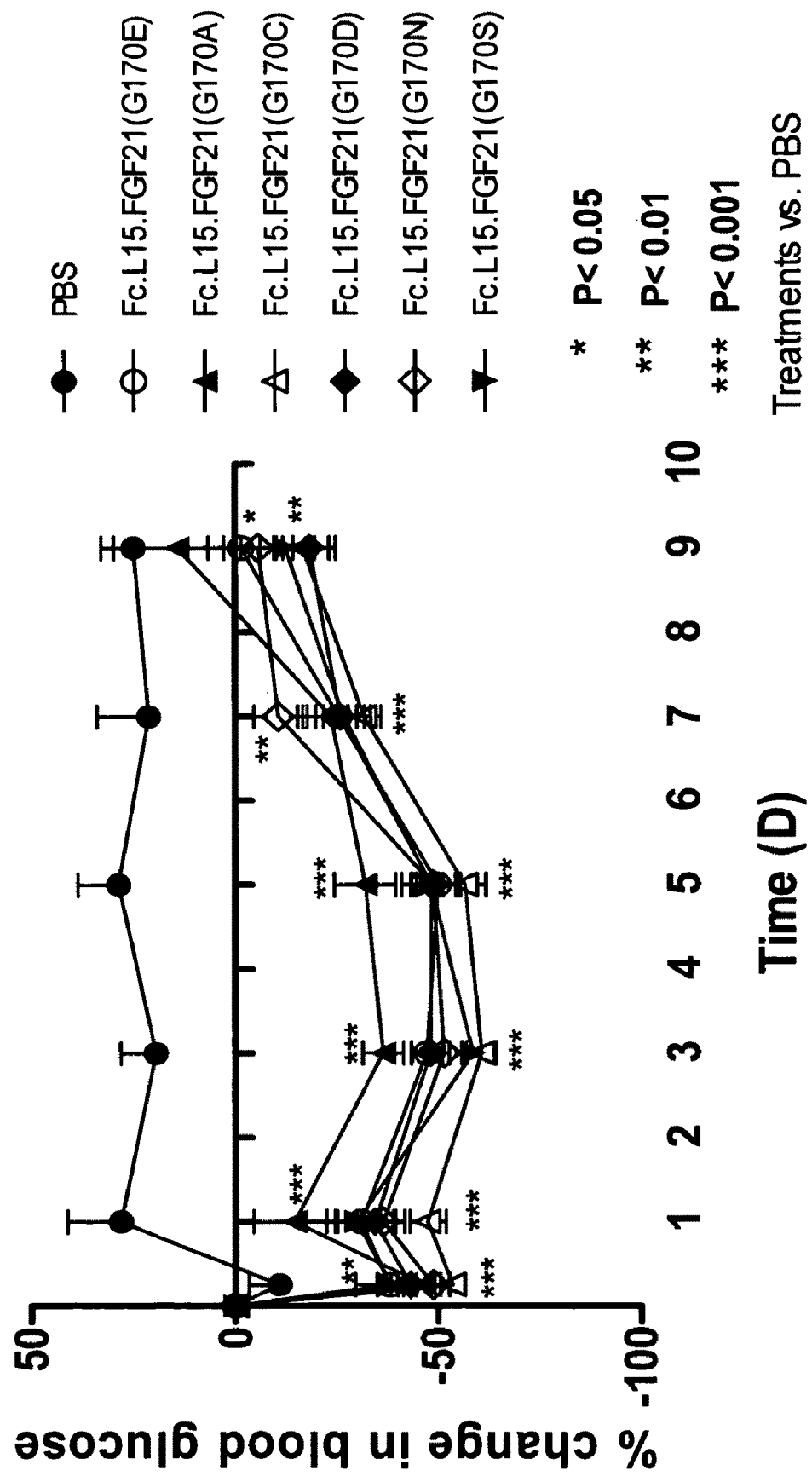
FIG. 16 shows the percent change in blood glucose levels measured in mice injected with PBS (solid circles) or the Fc(15)FGF21 mutants Fc(15)FGF21 G170E (open circles), Fc(15)FGF21 G170A (solid triangles), Fc(15)FGF21 G170C (open triangles), Fc(15)FGF21 G170D (solid diamonds), Fc(15)FGF21 G170N (open diamonds), or Fc(15)FGF21 G170S (inverted solid triangles).

The results of another experiment are provided in FIG. 15, which shows the blood glucose levels measured in mice injected with a PBS control or the Fc(15)FGF21 mutants Fc(15)FGF21 G170E, Fc(15)FGF21 G170A, Fc(15)FGF21 G170C, Fc(15)FGF21 G170D, Fc(15)FGF21 G170N, or Fc(15)FGF21 G170S. FIG. 16 shows the percent change in blood glucose levels as determined in this experiment. All of the FGF21 mutants tested in this experiment exhibited sustained blood glucose lowering activity for up to 5 days after injection.

Figure 17:
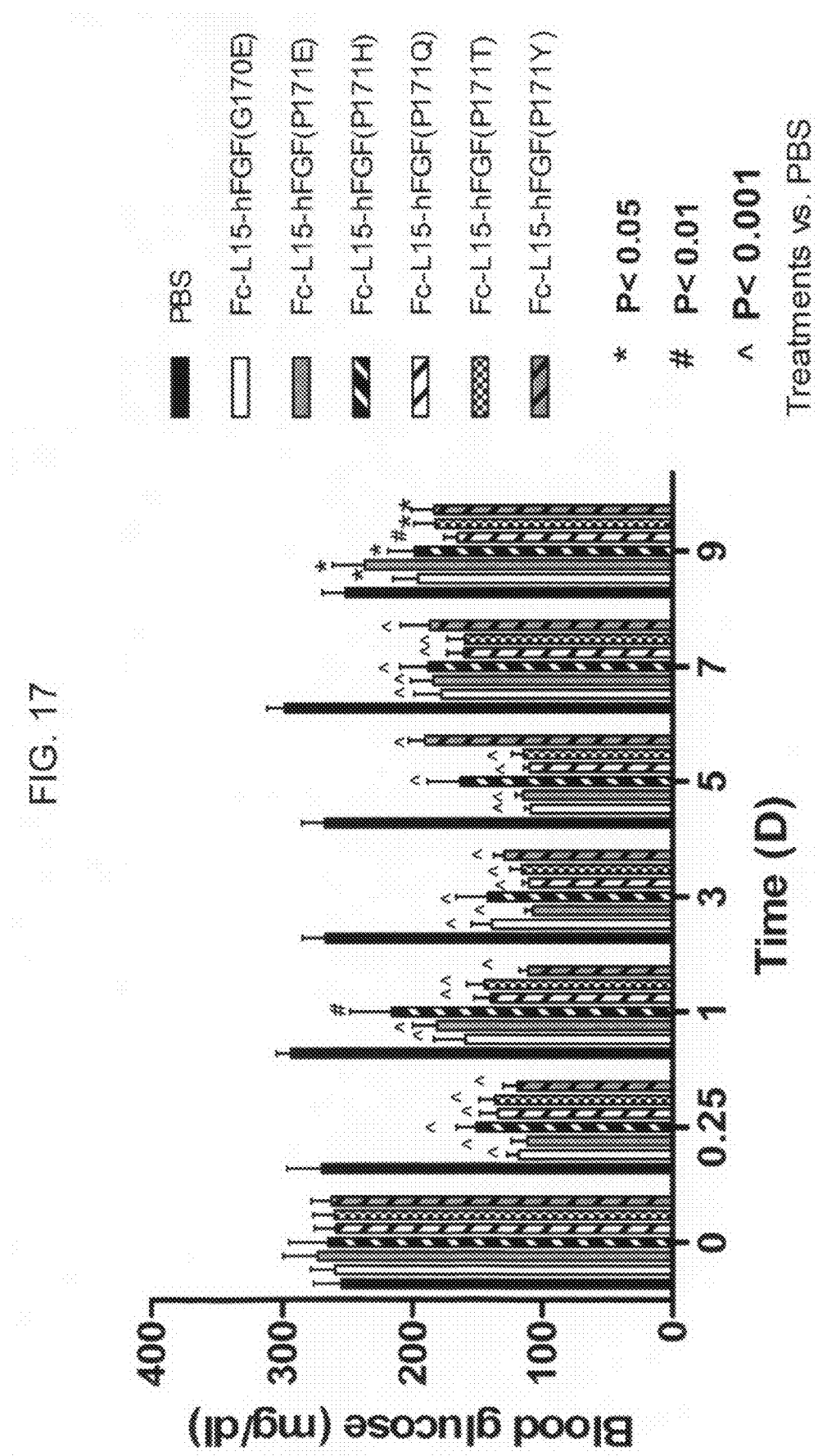
FIG. 17 shows the blood glucose levels measured in mice injected with PBS (solid bar) or the Fc(15)FGF21 mutants Fc(15)FGF21 G170E (open bar), Fc(15)FGF21 P171E (gray bar), Fc(15)FGF21 P171H (solid crosshatched bar), Fc(15) FGF21 P171Q (open crosshatched bar), Fc(15)FGF21 P171T (stippled bar), or Fc(15)FGF21 P171Y (gray crosshatched bar).
Figure 18:
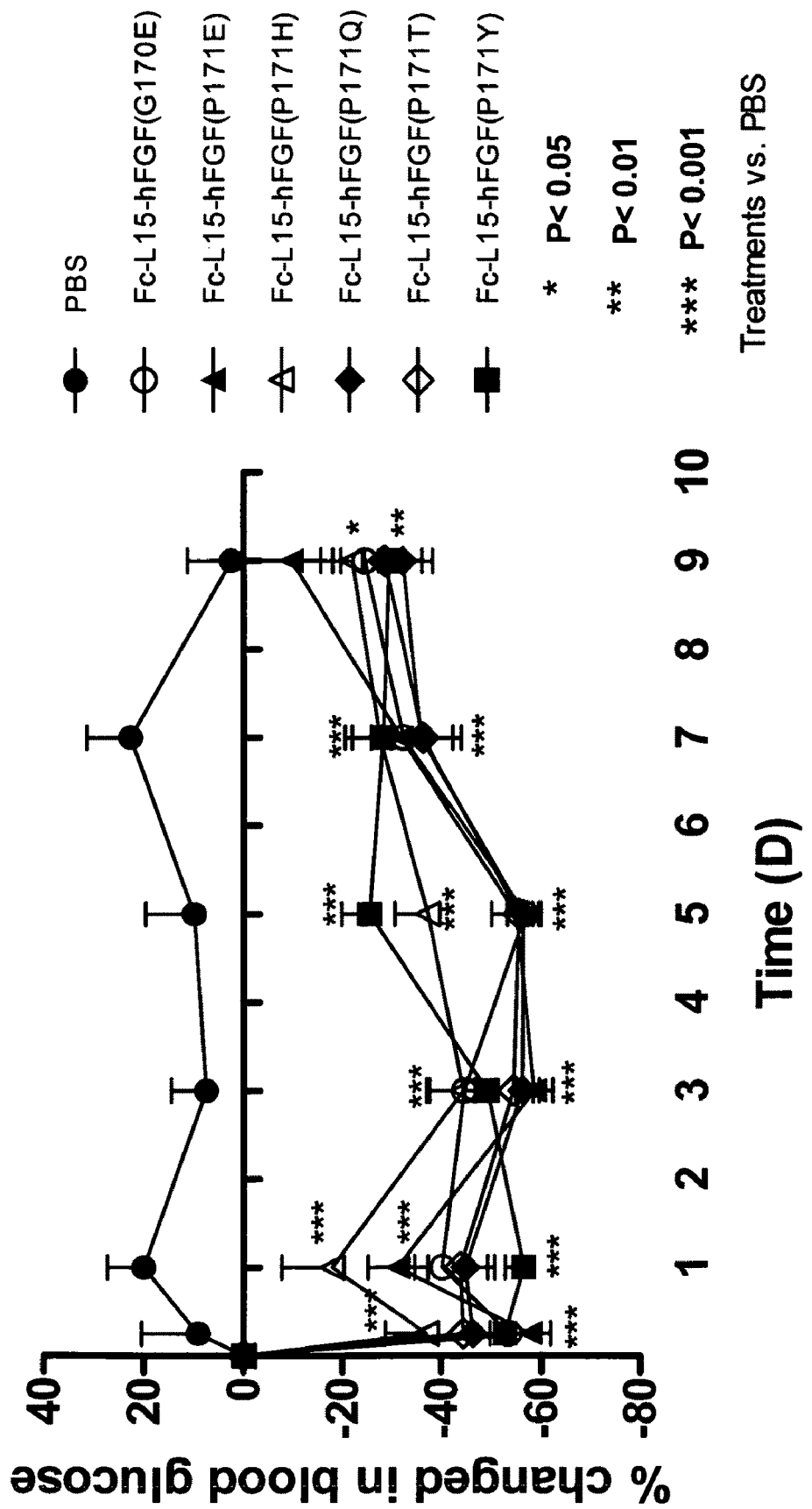
FIG. 18 shows the percent change in blood glucose levels measured in mice injected with PBS (solid circles) or the Fc(15)FGF21 mutants Fc(15)FGF21 G170E (open circles), Fc(15)FGF21 P171E (solid triangles), Fc(15)FGF21 P171H (open triangles), Fc(15)FGF21 P171Q (solid diamonds), Fc(15)FGF21 P171T (open diamonds), or Fc(15)FGF21 P171Y (solid squares).
Figure 19A:
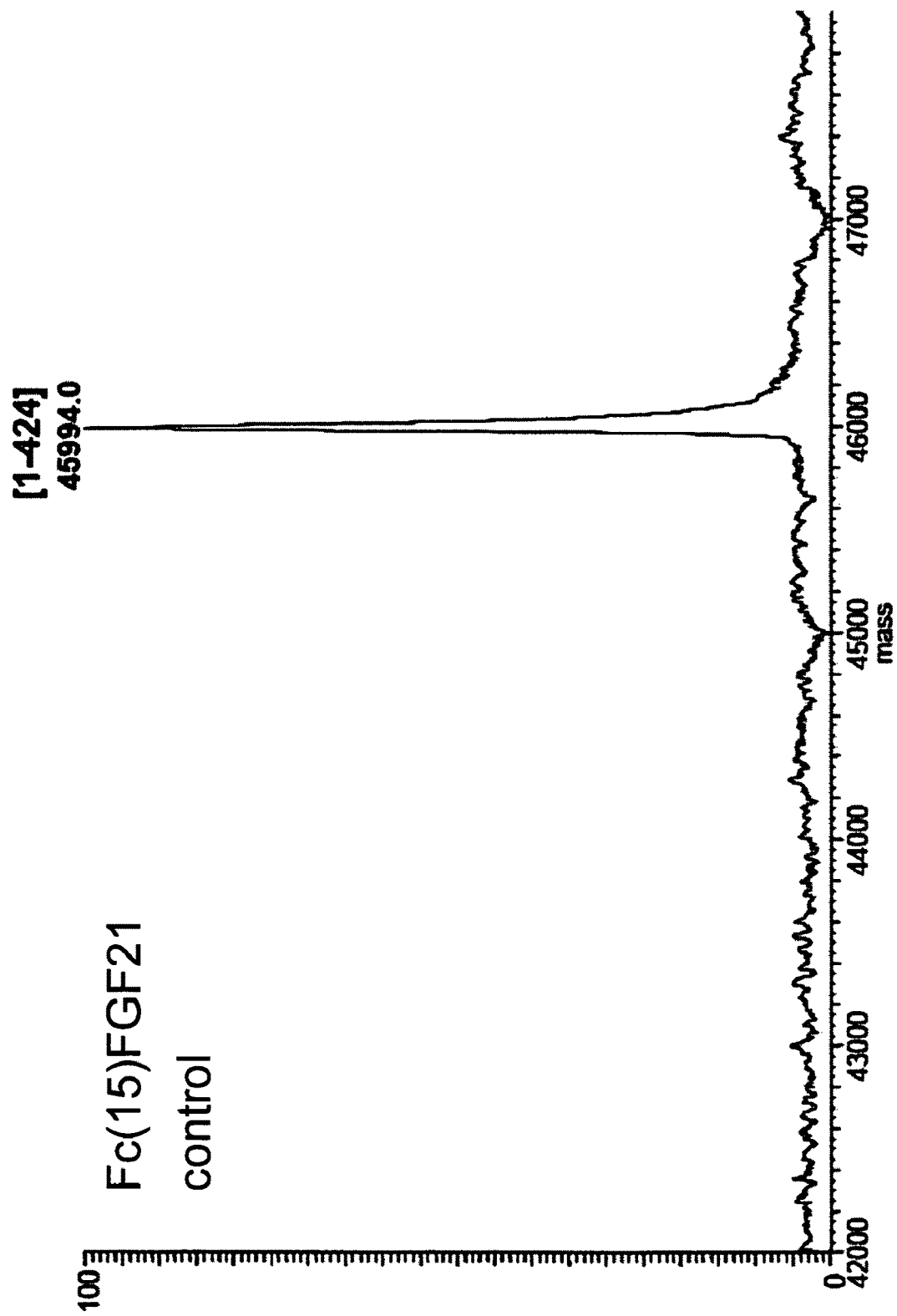
Figure 20B:
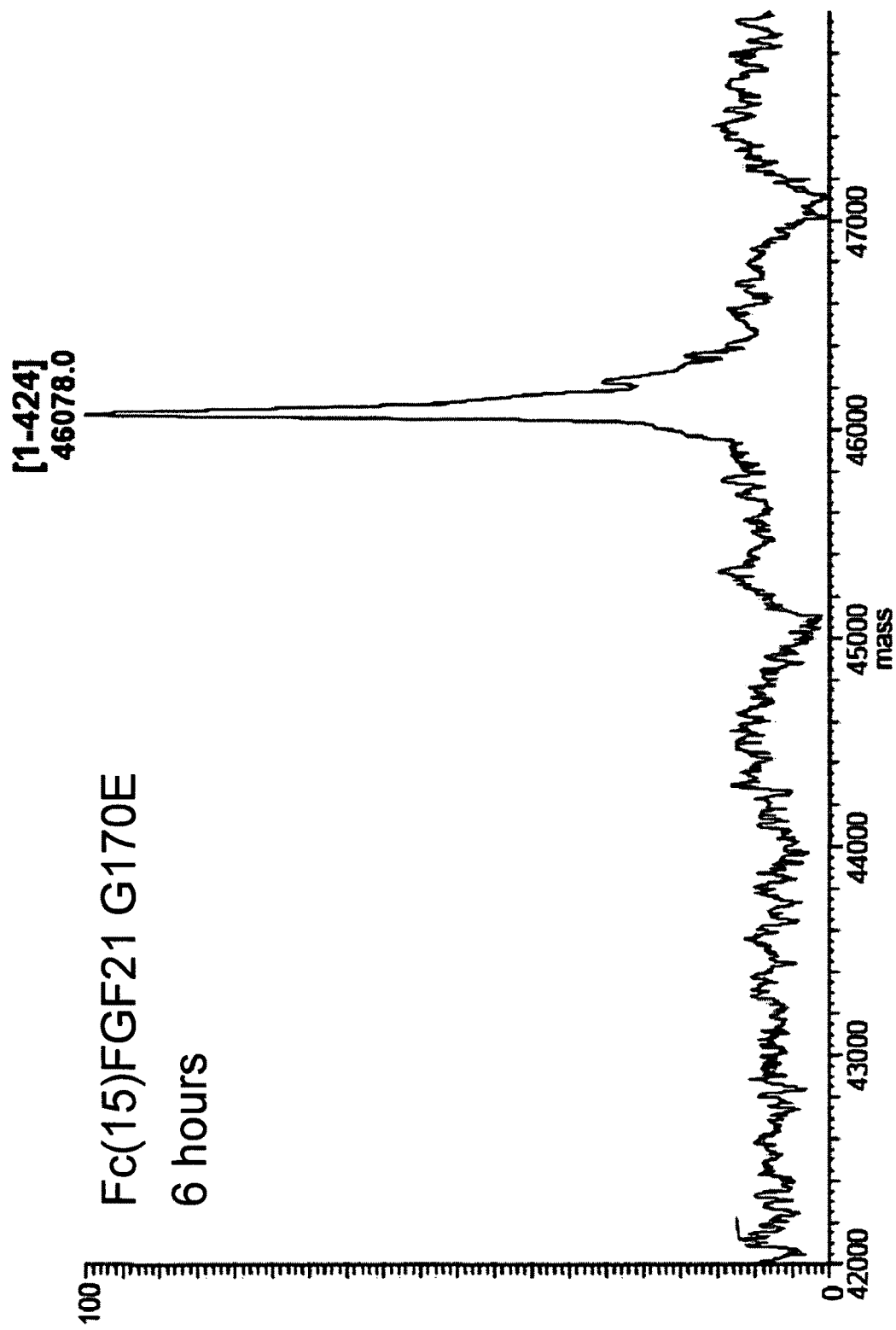
Figure 20C:
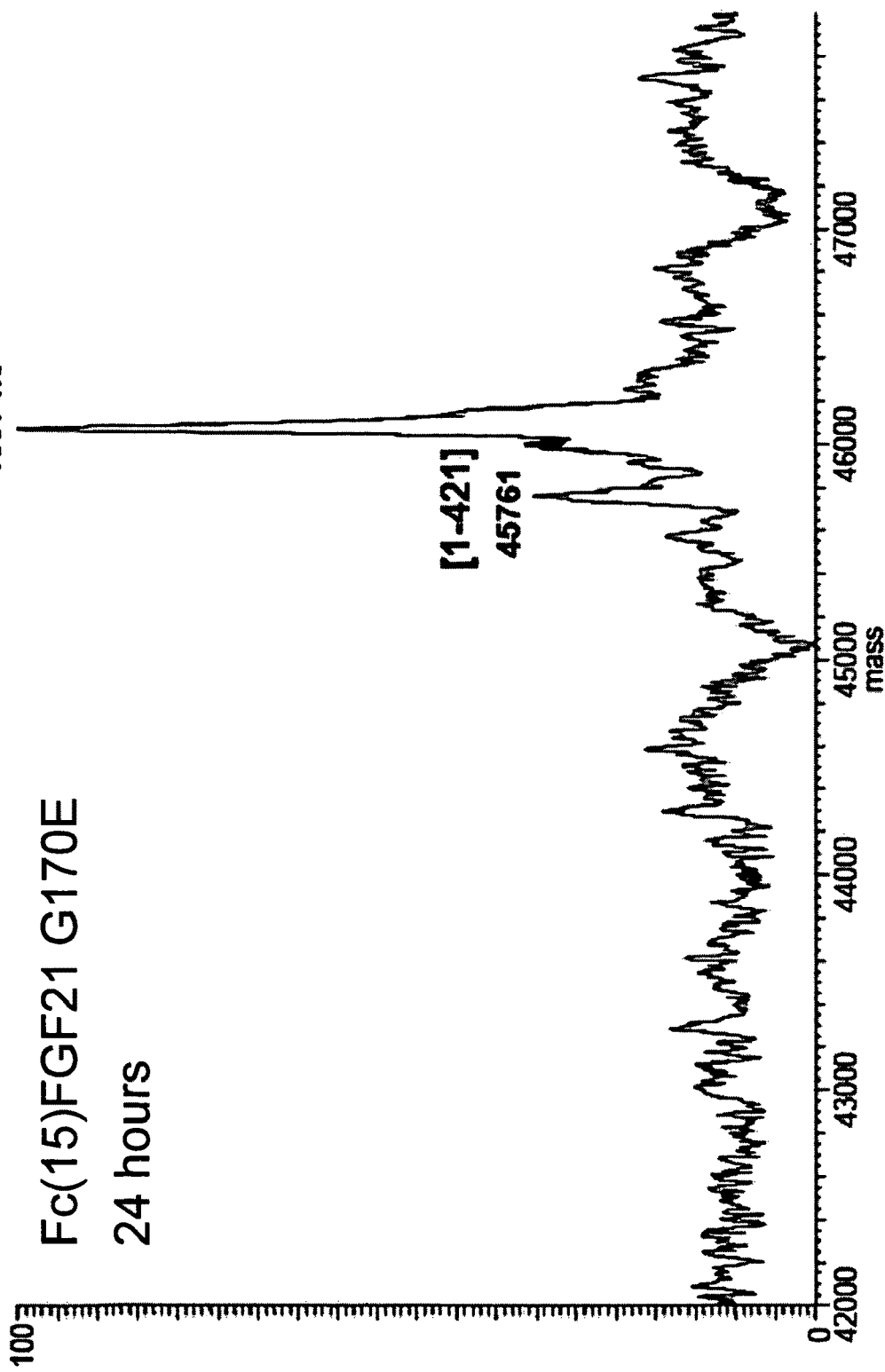
Figure 21A:
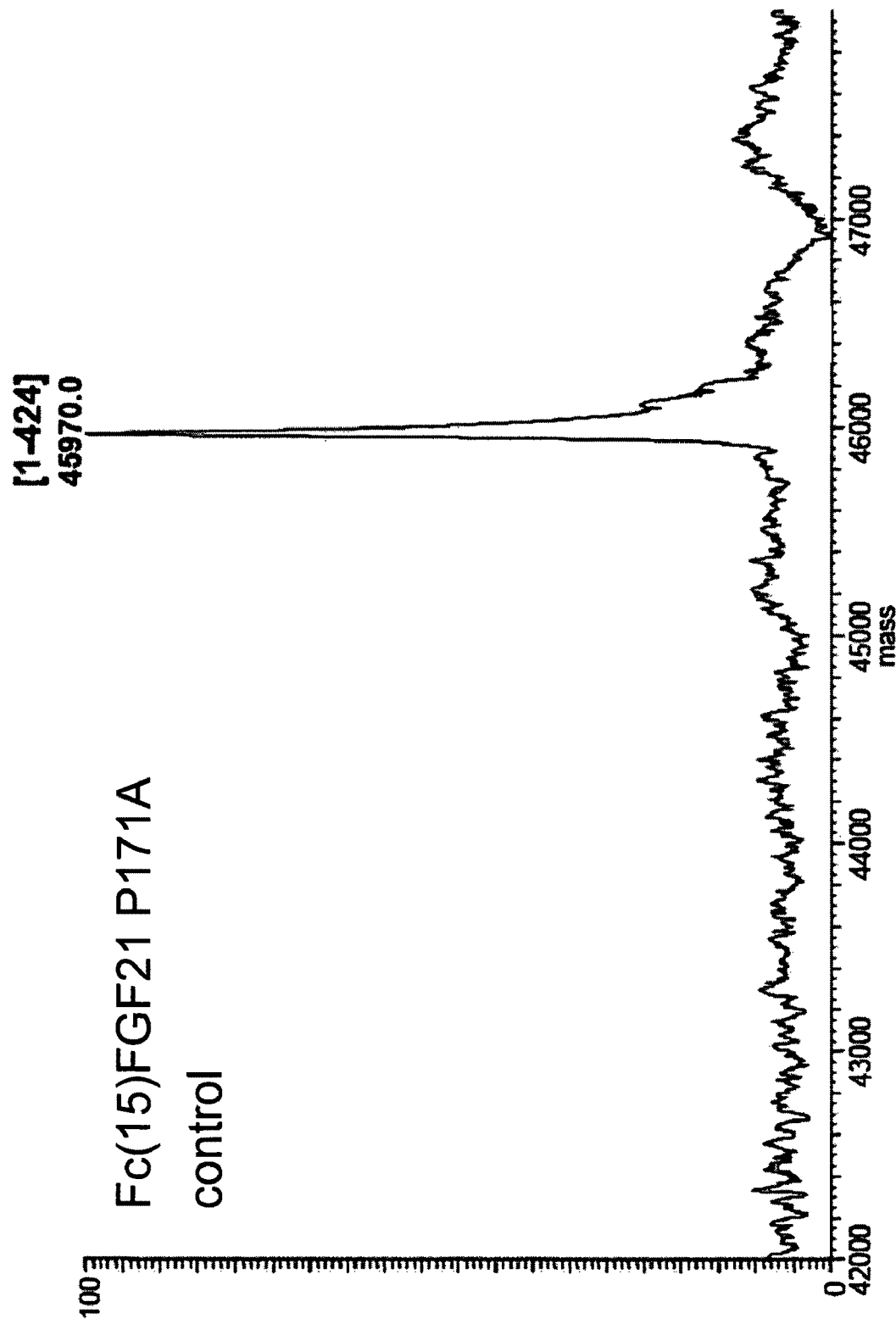

The results of another experiment are provided in FIG. 17, which shows the blood glucose levels measured in mice injected with PBS or the Fc(15)FGF21 mutants Fc(15)FGF21 G170E, Fc(15)FGF21 P171E, Fc(15)FGF21 P171H, Fc(15) FGF21 P171Q, Fc(15)FGF21 P171T, or Fc(15)FGF21 P171Y. FIG. 18 shows the percent change in blood glucose levels as determined in this experiment. All of the FGF21 mutants tested in this experiment exhibited improved blood glucose lowering activity when compared with wild-type Fc-FGF21.

Example 14

In Vivo Degradation of Proteolysis-Resistant Fc(15)FGF21 Mutants at 6 to 120 Hours after Injection The in vivo stability of selected FGF21 mutants was analyzed by injecting mice with an FGF21 mutant, drawing blood from the mice at various time points, and analyzing the serum by LC-MS. In particular, mice were injected with either the Fc(15)FGF21 G170E, Fc(15)FGF21 P171A, or Fc(15)FGF21 S172L mutants (obtained from *E. coli* as described in Example 2), each of which were diluted in approximately 180 μL of 10 mM HCl prior to injection, and blood was drawn at 6, 24, 48, 72, and 120 hours. FGF21 proteins were affinity purified from the drawn blood using an anti-human-Fc agarose resin column. Samples were eluted from the column using 10 mM HCl. All of the FGF21 constructs comprise an Fc region and 15 amino acid linker at the amino-terminal end of the FGF21 protein. Mice were also injected with a wild-type FGF21 control.

Prior to analyzing the affinity purified samples by LC-MS, unprocessed wild-type FGF21 and unprocessed FGF21 mutants were analyzed as a reference. All standards and time point samples were reduced with TCEP, and then analyzed by LC-MS using an ACE cyano 0.3 mm×30 cm column with the column effluent spraying into an LCQ Classic ion-trap mass spectrometer. Affinity purified samples were diluted with ammonium acetate, reduced with TCEP, and then analyzed by LC-MS as described above.

The observed masses for wild-type Fc(15)FGF21 at 0, 6, 24, and 48 hours after injection are shown in FIGS. 19A-19D, respectively. The observed masses for Fc(15)FGF21 G170E at 0, 6, 24, and 48 hours after injection are shown in FIGS. 20A-20D, respectively. The observed masses for Fc(15) FGF21 P171A at 0, 6, 24, and 48 hours after injection are shown in FIGS. 21A-21D, respectively. The observed masses for Fc(15)FGF21 S172L at 0, 6, 24, and 48 hours after injection are shown in FIGS. 22A-22D, respectively.

All of the samples drawn at 72 and 120 hours were found to contain a high molecular weight (>200 kDa by non-reducing SDS-PAGE) component of fibrinogen that is much more abundant than the remaining Fc(15)FGF21 fusion protein. Results of the LC-MS analysis of the other standards and samples are provided in Table 14.

TABLE 14

Results of LC-MS Analysis and Predicted Fragments

| FGF21 Sample | Major Observed Masses | Percent of Total | Fragment | Edman |
|---|---|---|---|---|
| Fc(15)FGF21 WT standard | 45,994 Da | 100% | 1-424 | — |
| Fc(15)FGF21 WT 6 hours | 46,001 Da | 80% | 1-424 | No |
|  | 44,987 Da | 20% | 1-414 |  |
| Fc(15)FGF21 WT 24 hours | 44,979 Da | ~100% | 1-414 | No |
| Fc(15)FGF21 WT 48 hours | 44,980 Da | ~100% | 1-414 | — |
| Fc(15)FGF21 G170E standard | 46,068 Da | 100% | 1-424 | — |
| Fc(15)FGF21 G170E 6 hours | 46,078 Da | 100% | 1-424 | No |
| Fc(15)FGF21 G170E 24 hours | 46,074 Da | 80% | 1-424 | No |
|  | 45,761 Da | 20% | 1-421 |  |
| Fc(15)FGF21 G170E 48 hours | 46,072 Da | ~60% | 1-424 | No |
|  | 45,760 Da | ~40% | 1-421 |  |
| Fc(15)FGF21 P171A standard | 45,970 Da | 100% | 1-424 | — |
| Fc(15)FGF21 P171A 6 hours | 45,980 Da | 100% | 1-424 | No |
| Fc(15)FGF21 P171A 24 hours | 45,973 Da | ~70% | 1-424 | No |
|  | 45,657 Da | ~30% | 1-421 |  |
| Fc(15)FGF21 P171A 48 hours | 45,992 Da | ~50% | 1-424 | No |
|  | 45,673 Da | ~50% | 1-421 |  |
| Fc(15)FGF21 S172L standard | 46,022 Da | 100% | 1-424 | — |
| Fc(15)FGF21 S172L 6 hours | 46,027 Da | 100% | 1-424 | No |
| Fc(15)FGF21 S172L 24 hours | 44,984 Da | 100% | 1-414 | No |
| Fc(15)FGF21 S172L 48 hours | 44,985 Da | 100% | 1-414 | No |

As indicated in Table 14, the degradation of wild-type Fc(15)FGF21 and the S172L mutant look similar, in that after 24 hours of circulation, the major product of the fusion protein was a fragment consisting of amino acid residues 1-414. The degradation products of the Fc(15)FGF21 G170E and Fc(15)FGF21 P171A mutants also look similar in that the samples drawn after 24 hours of circulation contain 70-80% intact protein (amino acids 1-424) and 20-30% of a fragment consisting of amino acid residues 1-421. Even after 48 hours, the Fc(15)FGF21 G170E and Fc(15)FGF21 P171A mutants still retain intact protein while showing an increase in the amount of the fragment consisting of amino acid residues 1-421. As observed in prior analyses of Fc-FGF21 constructs, degradation of the FGF21 portion of the fusion protein was detected and the Fc portion was found to remain stable. The cleavage sites identified for wild-type, Fc(15)FGF21 G170E, Fc(15)FGF21 P171A, and Fc(15)FGF21 S172L are shown in FIGS. 23A-23D, respectively.

Example 15

Identification of Aggregation-Reducing FGF21 Mutants

One property of wild-type FGF21 is its propensity to aggregate. Aggregation-reducing FGF21 mutants were identified on the basis of two hypotheses. The first hypothesis is that, with respect to FGF21, aggregation (or dimerization) is triggered by hydrophobic interactions and van der Waals interactions between FGF21 molecules caused by hydrophobic residues that are exposed to hydrophilic water-based solvent environment. The second hypothesis is that these exposed hydrophobic residues can be substituted to create aggregation-reducing point-mutation variants without compromising FGF21 activity.

A systematic rational protein engineering approach was used to identify exposed hydrophobic residues in FGF21. As there were no known X-ray or NMR structures of FGF21 that could be used to identify exposed hydrophobic residues, a high resolution (1.3 Å) X-ray crystal structure of FGF19 (1PWA) obtained from the Protein Databank (PDB) was used to create a 3D homology model of FGF21 using MOE (Molecular Operating Environment; Chemical Computing Group; Montreal, Quebec, Canada) modeling software. FGF19 was chosen as a template, since among the proteins deposited in the PDB, FGF19 is the most closely related protein to FGF21 in terms of the amino acid sequence homology.

Solvent accessibility was calculated by the following method using MOE. A first measure of surface area (SA1) is defined as the area of the residue's accessible surface in Å$^2$. While a particular amino acid residue appears in a protein's primary sequence multiple times, each occurrence of the residue can have a different surface area due to differences in, inter alia, the residue's proximity to the protein surface, the orientation of the residue's side-chain, and the spatial position of adjacent amino acid residues. Therefore, a second measure of surface area (SA2) is made wherein the residue of interest is extracted from the protein structure along with that residue's neighboring, or adjacent, residues. These spatially adjacent residues are mutated in silico to glycines to remove their side-chains, and then the SA2 for the residue of interest is calculated, giving a measure of the total possible surface area for that residue in its particular conformation. A ratio of SA1 to SA2 (SA1/SA2) can then give a measure of the percentage of the possible surface area for that residue that is actually exposed.

Several hydrophobic residues that are highly exposed to the solvent were selected for further analysis, and in silico point mutations were made to these residues to replace the selected residue with the other naturally occurring amino acid residues. The changes in protein thermal stability resulting from different substitutions were calculated using the FGF21 model and the interactive web-based program CUPSAT (Cologne University Protein Stability Analysis Tools) according to instructions provided at the CUPSAT website. See Parthiban et al., 2006, *Nucleic Acids Res.* 34: W239-42; Parthiban et al., 2007, *BMC Struct. Biol.* 7:54. Significantly destabilizing or hydrophobic mutations were excluded in the design of aggregation-reducing point-mutation variants. Stabilizing (or, in rare cases, slightly destabilizing) substitutions that introduce improved hydrophilic and/or ionic characteristics were considered as candidates for aggregation-reducing FGF21 mutants.

A summary of the data generated through this rational protein engineering approach is provided in Table 15, which also lists exemplary FGF21 mutants expected to have reduced protein aggregation and improved stability.

TABLE 15

Calculated Effect of FGF21 Mutants on Stability

| Residue # | WT Residue | Mutation | Stabilization (Kcal/mol) |
|---|---|---|---|
| 26 | A | K | 1.25 |
|  |  | E | 1.54 |
|  |  | R | 2.016 |
| 45 | A | T | 0.66 |
|  |  | Q | 0.71 |
|  |  | K | 1.8 |
|  |  | E | 2.34 |
|  |  | R | 1.59 |
| 52 | L | T | −0.33 |
| 58 | L | G | 0.16 |
|  |  | S | −0.15 |
|  |  | C | 1.0 |
|  |  | E | 0.08 |
| 60 | P | A | 1.3 |
|  |  | K | 1.51 |
|  |  | E | 0.66 |
|  |  | R | 1.31 |
| 78 | P | A | 0.14 |
|  |  | C | 2.48 |
|  |  | R | 0.08 |
|  |  | H | 0.13 |
| 86 | L | T | 0.18 |
|  |  | C | 4.1 |
| 88 | F | A | 2.52 |
|  |  | S | 3.08 |
|  |  | K | 2.88 |
|  |  | E | 1.48 |
| 98 | L | T | 0.49 |
|  |  | Q | 0.17 |
|  |  | K | −0.19 |
|  |  | C | 3.08 |
|  |  | E | 0.84 |

TABLE 15-continued

Calculated Effect of FGF21 Mutants on Stability

| Residue # | WT Residue | Mutation | Stabilization (Kcal/mol) |
|---|---|---|---|
|  |  | R | 3.4 |
| 99 | L | C | 7.34 |
|  |  | E | 2.0 |
|  |  | D | 1.01 |
|  |  | R | 1.61 |
| 111 | A | T | 0.47 |
|  |  | K | −0.12 |
| 129 | A | Q | 3.93 |
|  |  | K | 1.02 |
|  |  | N | 3.76 |
|  |  | E | 3.01 |
|  |  | D | 3.76 |
|  |  | R | 1.68 |
|  |  | H | 2.9 |
| 134 | A | K | 5.37 |
|  |  | Y | 4.32 |
|  |  | E | 5.13 |
|  |  | R | 6.18 |
|  |  | H | 2.86 |

Example 16

Preparation and Expression of Aggregation-Reducing FGF21 Mutants and Fusion Proteins Constructs encoding the FGF21 mutants listed in Table 16 were prepared by PCR amplification of the wild-type FGF21 expression vector as described in Example 11 (the construction of the wild-type FGF21 expression vector is described in Example 1). Fusion proteins were generated as described herein, e.g., in Example 6.

TABLE 16

Aggregation-reducing FGF21 Mutants

| Mutation(s) | Fc | Linker |
|---|---|---|
| A26E |  |  |
| A26K |  |  |
| A26R |  |  |
| A45E |  |  |
| A45K |  |  |
| A45K | —NH$_2$ | 15 |
| A45R | —NH$_2$ | 15 |
| A45Q | —NH$_2$ | 15 |
| A45T | —NH$_2$ | 15 |
| A45K, L98R | —NH$_2$ | 15 |
| L52T |  |  |
| L58C |  |  |
| L58E |  |  |
| L58G |  |  |
| L58S |  |  |
| P60A |  |  |
| P60E |  |  |
| P60K |  |  |
| P60R |  |  |
| P78A |  |  |
| P78C |  |  |
| P78H |  |  |
| P78R |  |  |
| L86C |  |  |
| L86T |  |  |
| F88A |  |  |
| F88E |  |  |
| F88K |  |  |
| F88R |  |  |
| F88S |  |  |

TABLE 16-continued

Aggregation-reducing FGF21 Mutants

| Mutation(s) | Fc | Linker |
|---|---|---|
| L98C | | |
| L98E | —NH₂ | 15 |
| L98K | —NH₂ | 15 |
| L98Q | —NH₂ | 15 |
| L98R | | |
| L98R | —NH₂ | 15 |
| L99C | | |
| L99D | | |
| L99E | | |
| L99R | | |
| A111K | —NH₂ | 15 |
| A111T | | |
| A129D | | |
| A129E | —NH₂ | 15 |
| A129H | —NH₂ | 15 |
| A129K | | |
| A129N | —NH₂ | 15 |
| A129R | —NH₂ | 15 |
| A129Q | | |
| A134E | | |
| A134H | —NH₂ | 15 |
| A134K | | |
| A134Y | | |

The aggregation of various FGF21 proteins, including wild-type FGF21, truncated FGF21 polypeptides, FGF21 mutants, and FGF21 fusion proteins was assayed by Size Exclusion Chromatography (SEC). Samples to be analyzed were incubated at 4° C., room temperature, or 37° C. for various time points, and then subjected to SEC analysis. Experiments were performed on a Beckman HPLC system equipped with a SEC column. For wild-type FGF21, a TOSOHAAS TSK-Gel G2000 SEC column was used with 2×PBS containing 2% isopropyl alcohol as the mobile phase. For FGF21 Fc fusion proteins and FGF21 mutant polypeptides, a TOSOHAAS TSK-Gel G3000 SEC column was used with 2×PBS as the mobile phase.

Example 17

In Vitro Activity of Aggregation-Reducing FGF21 Mutants

Experiments were performed to identify aggregation-reducing mutants that retain wild-type FGF21 activity in an ELK-luciferase in vitro assay. ELK-luciferase assays were performed as described in Example 4. FIGS. 24A-24C show the results of an ELK-luciferase activity assay performed on the FGF21 mutants FGF21 L99R, FGF21 L99D, and FGF21 A111T (FIG. 24A); the FGF21 mutants FGF21 A129D, FGF21 A129Q, and FGF21 A134K (FIG. 24B); and the FGF21 mutants FGF21 A134Y, FGF21 A134E, and FGF21 A129K (FIG. 24C). The results of these experiments demonstrate that some of the aggregation-reducing mutations did not adversely impact FGF21 activity as assayed in ELK-luciferase assays.

Example 18

Preparation and Expression of Fc(15)FGF21 Combination Mutants Showing Longer Half-Life and Lower Levels of Aggregation A number of FGF21 combination mutants, containing mutations shown to reduce aggregation as well as to increase half-life by disrupting proteolytic degradation, were prepared and conjugated to IgG1 Fc molecules. These FGF21 mutants were prepared essentially as described in Example 11.

Example 19

In Vitro Studies of Fc(15)FGF21 Mutants Showing Longer Half-Life and Lower Levels of Aggregation Experiments were performed to identify FGF21 combination mutants that retain wild-type FGF21 activity in an ELK-luciferase in vitro assay. ELK-luciferase assays were performed as described in Example 4.

Figure 25D:
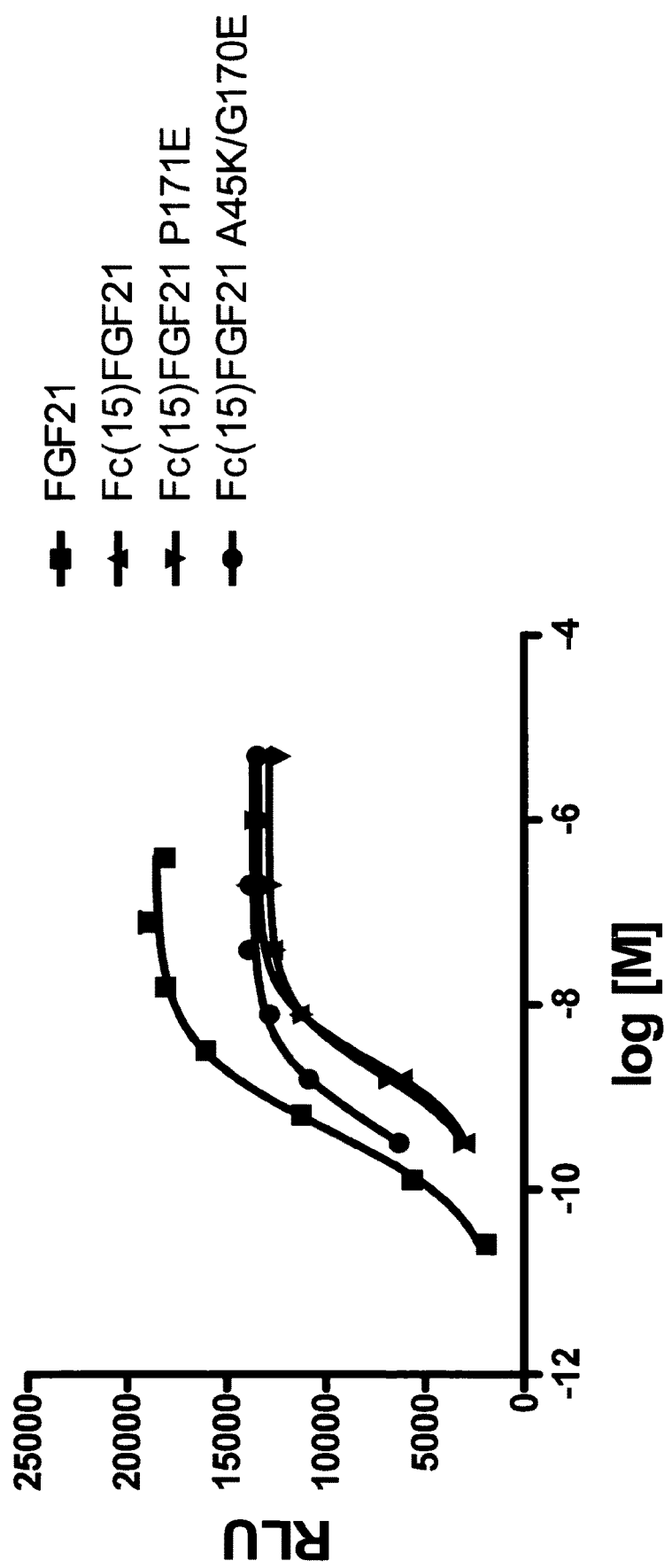

FIGS. 25A-25D show the results of an ELK-luciferase activity assay performed on the Fc-FGF21 mutants Fc-FGF21 P171G, Fc-FGF21 P171S, and Fc-FGF21 P171T (FIG. 25A); the Fc-FGF21 mutants Fc-FGF21 P171Y, Fc-FGF21 P171W, and Fc-FGF21 P171C (FIG. 25B); Fc(15) FGF21, Fc(15)FGF21 A45K/G170E, and FGF21 A45K (FIG. 25C); and Fc(15)FGF21, Fc(15)FGF21 P171E, and Fc(15)FGF21 A45K/G170E (FIG. 25D). The results of these experiments demonstrate that mutations aimed at improving stability, or both stability and solubility, did not compromise the in vitro activity as compared with wild-type Fc-FGF21. Interestingly, the FGF21 A45K mutant showed improved potency relative to wild-type Fc-FGF21.

FIG. 26A shows the change in percent aggregation for an FGF21 control (WT) and FGF21 A45K following incubation of 65 mg/mL protein at 4° C. for 1, 2, and 4 days. The data indicated that the A45K mutation leads to a decrease in aggregation of the protein, compared to the wild-type protein.

FIG. 26B shows the change in percent aggregation for an FGF21 control (WT) and FGF21 P78C, P78R, L86T, L86R, L98C, L98R, A111T, A129D, A129Q, A129K, A134K, A134Y, and A134E following incubation of 65 mg/mL protein at 4° C. for 1, 6, and 10 days. The data indicated that the L86R, L98C, L98R, A111T, A129Q, and A129K lead to a decrease in aggregation of the protein, compared to the wild-type protein.

FIG. 27 shows the results of an ELK-luciferase activity assay performed on a human FGF21 control and the FGF21 mutants FGF21 A45K, FGF21 L52T, and FGF21 L58E. This experiment demonstrates that the FGF21 A45K mutant retains the full efficacy of wild-type FGF21 and exhibits a potency that is even greater than wild-type FGF21. However, the FGF21 L52T, and FGF21 L58E mutants show reduced potency and efficacy as compared with wild-type FGF21.

FIGS. 28A-28B show the change in aggregation levels for the Fc(15)FGF21 mutants Fc(15)FGF21 6-181/G170E, Fc(15)FGF21 A45K/G170E, Fc(15)FGF21 P171E Fc(15) FGF21 P171A, Fc(15)FGF21 G170E, and an FGF21 control following incubation at 4° C. for 1, 4, and 8 days. This experiment demonstrates that over the 8 day period, the Fc(15)FGF21 A45K/G170E mutant showed less aggregation than did the Fc(15)FGF21 G170E or Fc(15)FGF21 P171E mutants, but all three mutants showed less aggregation than did the Fc(15)FGF21 control. Table 17 shows the percent aggregation obtained for an Fc-FGF21 control and the Fc-FGF21 A45K/G170E mutant following incubation at 4° C. or room temperature for 0, 2, 3, 4, or 7 days.

TABLE 17

Percent Aggregation for Fc-FGF21 and Fc-FGF21 Mutant

| Sample | | Day 0 | Day 2 | Day 3 | Day 4 | Day 7 |
|---|---|---|---|---|---|---|
| Fc(15)FGF21 WT | 4° C. | 1.12 | 1.71 | 1.89 | 2.14 | 2.32 |
| 32 mg/mL | RT | 1.12 | 6.09 | 7.94 | 9.57 | 12.59 |

TABLE 17-continued

Percent Aggregation for Fc-FGF21 and Fc-FGF21 Mutant

| Sample | | Day 0 | Day 2 | Day 3 | Day 4 | Day 7 |
|---|---|---|---|---|---|---|
| Fc(15)FGF21 A45K/G170E | 4° C. | 0.45 | 0.77 | 0.88 | 1.03 | 1.24 |
| 33 mg/mL | RT | 0.45 | 3.86 | 5.22 | 6.62 | 8.60 |

Example 20

Preparation and Expression of Fc-FGF21 Fusion Combination Mutants

As described above, the stability and solubility of FGF21 can be modulated through the introduction of specific truncations and amino acid substitutions. In addition, FGF21 stability can be further enhanced by fusing such modified FGF21 proteins with the Fc portion of the human immunoglobulin IgG1 gene. Moreover, by introducing combinations of the above modifications, FGF21 molecules having both enhanced stability and solubility can be generated. Nucleic acid sequences encoding the FGF21 combination mutants listed in Table 18 were prepared using the techniques described above.

TABLE 18

FGF21 Combination Mutants

| Amino Acid Residues | Proteolysis Mutation | Aggregation Mutation | Fc | Linker |
|---|---|---|---|---|
| 1-181 | G170E | A45K | —NH$_2$ | 15 |
| 1-181 | G170E | L98R | —NH$_2$ | 15 |
| 1-181 | G170E | A45K, L98R | —NH$_2$ | 15 |
| 1-181 | P171G | A45K | —NH$_2$ | 15 |
| 1-181 | P171S | A45K | —NH$_2$ | 15 |
| 1-181 | P171G | L98R | —NH$_2$ | 15 |
| 1-181 | P171S | L98R | —NH$_2$ | 15 |
| 1-181 | P171G | A45K, L98R | —NH$_2$ | 15 |
| 1-178 | G170E | | —NH$_2$ | 15 |
| 6-181 | G170E | | —NH$_2$ | 15 |
| 6-181 | G170E | A45K | —NH$_2$ | 15 |
| 6-181 | G170E | L98R | —NH$_2$ | 15 |
| 6-181 | P171G | | —NH$_2$ | 15 |
| 6-181 | P171G | L98R | —NH$_2$ | 15 |
| 7-181 | G170E | | —NH$_2$ | 15 |

FIG. 29 shows the blood glucose levels measured in mice injected with the Fc(15)FGF21 combination mutants Fc(15)FGF21 A45K/G170E, Fc(15)FGF21 A45K/P171G, or Fc(15)FGF21 L98R/P171G.

In another experiment the FGF21 mutant Fc(15)FGF21 L98R/P171G was studied side-by-side with wild-type mature FGF21 and Fc-FGF21. In one experiment, a recombinant 293T cell line was cultured in the presence of different concentrations of FGF21, Fc-FGF21, or Fc(15)FGF21 L98R/P171G for 6 hours. Cell lysates were then assayed for luciferase activity. As shown in FIG. 30, Fc(15)FGF21 L98R/P171G had similar activity to Fc-FGF21, indicating that the introduction of the two point mutations didn't alter the molecule's in vitro activity.

In yet another experiment, the stability of the Fc(15)FGF21 L98R/P171G at 65 mg/mL was evaluated for nine days at two different temperatures, namely room temperature and 4° C., side-by-side with FGF21 and Fc-FGF21. After the incubation period cell lysates were then analyzed with SEC-HPLC to determine an aggregation versus time profile at various temperatures. The data shown in FIGS. 31A and 31B indicate that the rate of aggregation formation was significantly reduced in the Fc(15)FGF21 L98R/P171G at room temperature (solid triangles, dotted line in FIG. 31A) and at 4° C. (solid triangles, dotted line in FIG. 31B).

Example 21

Proteolysis-Resistant FGF21 Mutants Comprising C-Terminal Mutations

The in vivo stability of combination mutants was also studied. Specifically, the in vivo stability of Fc(15)FGF21 L98R/P171G was compared with the stability of Fc(15)FGF21 in murine and cynomolgus models. The results were found to be similar in both species. In the cynomolgus study, Fc(15)FGF21 L98R/P171G and Fc(15)FGF21 were injected IV at 23.5 mg/kg and aliquots of serum and plasma were collected at time points out to 840 hours post dose. Time points out to 168 hours were analyzed. Time point samples were affinity-purified using anti-Fc reagents, then analyzed using MALDI mass spectrometry. The results correlated well between the two analyses.

Analyzing data generated using immunoaffinity-MALDI, clipping at the P171 site was seen to be eliminated in the Fc(15)FGF21 L98R/P171G molecule as a result of the mutation of P171 to P171G. However, a minor and slow degradation resulting in a loss of up to 3 C-terminal residues was observed for Fc(15)FGF21 L98R/P171G (FIG. 32). The minor cleavages at the three C-terminal residues were also observed with other FGF21 mutants after the more susceptible cleavage site between amino acid residues 171 and 172 was blocked as shown in FIGS. 20 and 21. The 3 C-terminal residue cleavage may represent the cessation of cleavage from the C-terminal end of the molecule by a carboxypeptidase in a sequential, residue-by-residue fashion or a specific protease attack at amino acid residues 178 and 179 with non-specific clipping at amino acid residues 179-180 and 180-181. The loss of 2-3 amino acids at the C-terminus could cause reduced beta-klotho binding and ultimately decreased potency and in vivo activity of the molecule See, e.g., Yie et al., 2009, *FEBS Lett.* 583:19-24. To address the apparent carboxypeptidase degradation of the C-terminus, the impact of adding an amino acid residue "cap" to various FGF21 mutant polypeptides were studied. A variety of constructs, including those presented in Table 19, were made and assayed using the techniques described herein. Table 19 summarizes the results of the in vitro ELK luciferase assay.

Suitable amino acid caps can be between 1 and 15 amino acids in length, for example 1, 2, 3, 4, 5, 10 or 15 amino acids in length. Any number and type of amino acid(s) can be employed as a cap, for example, a single proline residue, and single glycine residue, two glycine residues, five glycine residues, as well as other combinations. Additional examples of caps are provided in the instant Example and in Table 19.

Additionally, to address the apparent protease attack at amino acid residues 178 and 179, mutation of amino acid residues at positions 179, 180 and 181 was studied. Again, a variety of constructs, including those presented in Table 19, were made and assayed using the techniques described herein. The impact of combinations of cap and mutations at these sites was also explored. Table 19 summarizes exemplary constructs that were made and studied in the in vitro ELK-luciferase assay, which was performed as described herein. Consistent with the terminology used herein, hFc means a human Fc sequence (i.e., SEQ ID NO:13), L15 refers to a linker having 15 residues (i.e., SEQ ID NO:23)

TABLE 19

Efficacy and EC50 Values for FGF21 Polypeptides Comprising C-terminal Modifications

| Constructs | Efficacy | EC50 (nM) |
|---|---|---|
| huFGF21 | 0.4 | 100.0% |
| hFc.L15.hFGF21(L98R, P171G) | 2.5 | 76.1% |
| hFc.L15.hFGF21(L98R, P171G, Y179F) | 2.6 | 78.3% |
| hFc.L15.hFGF21(L98R, P171G, 1-180) | | |
| hFc.L15.hFGF21(L98R, P171G, 1-179) | 7.8 | 77.4% |
| hFc.L15.hFGF21(L98R, P171G, A180E) | 1.9 | 79.6% |
| hFc.L15.hFGF21(L98R, P171G, S181K) | 130 | 87.9% |
| GSGSGSGSGS.hFGF21.L15.hFc | | |
| MKEDD.hFGF21.L15.hFc | 834 | 83.1% |
| hFc.L15.hFGF21(L98R, P171G, S181P, P182) | 272 | 69.9% |
| hFc.L15.hFGF21(L98R, P171G, A180G) | 3.25 | 76.9% |
| hFc.L15.hFGF21(L98R, P171G, S181G) | 3.43 | 77.3% |
| hFc.L15.hFGF21(L98R, P171G, L182) | | |
| hFGF21(L98R, P171G, G182) | | |
| hFc.L15.hFGF21(L98R, P171G, Y179P) | 428 | 44.4% |
| hFc.L15.hFGF21(L98R, P171G, Y179G) | 61 | 82.6% |
| hFc.L15.hFGF21(L98R, P171G, Y179S) | 25.3 | 74.8% |
| hFc.L15.hFGF21(L98R, P171G, Y179A) | 43.2 | 79.6% |
| hFc.L15.hFGF21(L98R, P171G, S181T) | 3.07 | 77.6% |
| hFc.L15.hFGF21(L98R, P171G, S181A) | 2.66 | 73.5% |
| hFc.L15.hFGF21(L98R, P171G, S181L) | 3.46 | 72.6% |
| hFc.L15.hFGF21(L98R, P171G, S181P) | 33.8 | 79.5% |
| hFc.L15.hFGF21(L98R, P171G, A180P) | 617 | 77.1% |
| hFc.L15.hFGF21(L98R, P171G, A180S) | 2.18 | 84.7% |
| hFGF21(L98R, P171G, GGGGG182-6) | | |
| hFc.L15.hFGF21(L98R, P171G, P182) | 6.1 | 85.9% |
| hFc.L15.hFGF21(L98R, P171G, G182) | 6.5 | 71.1% |
| hFc.L15.hFGF21(1-178, L98R, P171G) | 167 | 63.9% |
| hFc.L15.hFGF21(L98R, P171G, GG182-3) | 1941 | 84.2% |
| hFc.L15.hFGF21(L98R, P171G, GGGGG182-6) | 4307 | 99.7% |

FIG. 33 shows the percent change in blood glucose levels observed in diabetic db/db mice (C57B6 background) injected with a PBS control, wild type native FGF21, Fc(15) FGF21 (L98R, P171G) and two capped molecules to which either a proline or glycine residue was added at the C-terminal end, i.e. Fc(15)FGF21 (L98R, P171G, 182P) and Fc(15) FGF21 (L98R, P171G, 182G). In the instant Example, when a residue was added to the C-terminus of a wild-type or mutant FGF21 polypeptide, the residue is referred to by its position in the resultant protein. Thus, "182G" indicates that a glycine residue was added to the C-terminus of the mature 181 residue wild-type or mutant protein. FIG. 33 shows that native FGF21 lowered blood glucose levels for 6 hours while all three Fc(15)FGF21 mutants studied showed sustained blood glucose-lowering activity for at least 120 hours. Fc(15) FGF21 (L98R, P171G, 182P), molecule comprising the addition of a proline residue at the C-terminus of the FGF21 component of the fusion molecule, appeared most potent and resulted in lowest blood glucose levels compared with Fc(15) FGF21 (L98R, P171G) and Fc(15)FGF21 (L98R, P171G, 182 G).

In a subsequent experiment, the in vivo activity of (L98R, P171G, 182G) and Fc(15)FGF21 (L98R, P171G, 182P) was studied and compared to the in vivo activity of a capped molecule comprising a two glycine addition at the C-terminus, namely Fc(15)FGF21 (L98R, P171G, 182G 183G). FIG. 34 shows the results of that experiment. FIG. 34 shows the percent change in blood glucose levels observed in ob/ob mice injected with PBS control, Fc(15)FGF21 (L98R, P171G), Fc(15)FGF21 (L98R, P171G, 182G 183G), Fc(15) FGF21 (L98R, P171G, 182G) and Fc(15)FGF21 (L98R, P171G, 182P).

As shown in FIG. 34, all of the molecules studied showed sustained glucose-lowering activity compared with the PBS control. This experiment confirmed the previous results (FIG. 33) that Fc(15)FGF21 (L98R, P171G, 182P) with a proline addition at the C-terminus showed slightly enhanced glucose-lowering efficacy compared with the molecule without a proline cap, e.g. Fc(15)FGF21 (L98R, P171G). However, the addition of two glycine residues at the C-terminus, e.g. Fc(15) FGF21 (L98R, P171G, 182G 183G), appeared to reduce the molecule's in vivo potency and shortened the duration of in vivo glucose-lowering effect.

FIG. 35 shows the percent change in blood glucose levels observed in diabetic db/db mice (C57B6 background) injected with PBS control or the FGF21 mutant polypeptides Fc(15)FGF21 (L98R, P171G), Fc(15)FGF21 (L98R, P171Q, Y179S), Fc(15)FGF21 (L98R, P171G, Y179A), Fc(15) FGF21 (L98R, P171G, A180S), and Fc(15)FGF21 (L98R, P171G, A180G). All mutants showed similar glucose-lowering activity with similar duration of action.

FIG. 36 shows the percent change in blood glucose levels observed in diabetic db/db mice (C57B6 background) injected with vehicle control, Fc(15)FGF21 (L98R, P171G), Fc-FGF21 (L98R, P171G, Y179F), and Fc(15)FGF21 (L98R, P171G, A180E). Compared with Fc(15)FGF21 (L98R, P171G), Fc(15)FGF21 (L98R, P171G, Y179F) was less efficacious in lowering blood glucose. However, Fc(15) FGF21 (L98R, P171G, A180E), in which alanine at amino acid position of 180 was mutated to glutamic acid, was more efficacious than Fc(15)FGF21 (L98R, P171G) and caused additional 20% reduction of blood glucose levels compared with Fc(15)FGF21 (L98R, P171G). These data suggest that A180E mutation may have reduced the C-terminal degradation in vivo and thereby improved in vivo potency and efficacy of the molecule.

Example 22

Rhesus Monkey Study

An Fc-Linker-FGF21 construct was generated using methodology described herein. The construct comprised an IgG1 Fc sequence (SEQ ID NO:13) fused at the C-terminus to a (Gly)$_5$-Ser-(Gly)$_3$-Ser-(Gly)$_4$-Ser linker sequence (SEQ ID NO:23) which was then fused at the C-terminus to the N terminus of a mature FGF21 sequence (SEQ ID NO:4), into which two mutations, L98R and P171G, had been introduced. This construct was then expressed and purified as described herein, and was isolated as a dimeric form of the protein, each monomer of which was linked via intermolecular disulfide bonds between the Fc region of each monomer. This molecule is referred to in the instant Example as "Fc-FGF21(RG)" and has the amino acid sequence of SEQ ID NO:38 and is encoded by SEQ ID NO:37. In this Example, FGF21 refers to the mature form of FGF21, namely SEQ ID NO:4.

22.1 Study Design

The Fc-FGF21(RG) construct was administered chronically and subcutaneously ("SC") into non-diabetic male Rhesus monkeys with a BMI>35. Two other groups of monkeys (n=10 per group) were treated with either mature FGF21 (i.e., SEQ ID NO:4) or a vehicle control.

Animals were acclimated for 42 days prior to administration of any test compound and were then divided into groups of 10 and administered multiple SC injections of test compounds or control article in a blinded fashion, as depicted graphically in FIG. 37. In brief, each animal was injected once a day with compound or vehicle. FGF21 was administered daily, whereas Fc-FGF21(RG) was administered weekly. Fc-FGF21(RG) and FGF21 doses were escalated every 2 weeks, as shown in FIG. 37. Body weight and food intake were monitored throughout the study. The CRO was blinded to the treatment.

Two oral glucose tolerance tests (OGTTs) were performed prior to the start of the treatment. OGTT1 was used to sort the animals into three equivalent groups having a similar distribution of animals based on area under the curve (AUC) and body weight. The results of the second OGTT (OGTT2) was used to confirm the sorting of the first OGTT (OGTT1). Monkeys with OGTT profiles that were inconsistent from one test (OGTT1) to the next (OGTT2) were excluded. The results of OGTTs 1 and 2 are shown in FIGS. 38A and 38B, with AUC measurements shown in FIG. 38C. Baseline body weight is shown in FIG. 38D and Table 20.

OGTTs 3, 4, and 5 were performed every 2 weeks at the end of each dose treatment of low, mid and high doses. Blood samples were collected from fasted animals weekly and were used to measure glucose, insulin, triglyceride levels, as well as the levels of test compound. Blood samples were also collected weekly during the 3-week washout period.

Baseline OGTT1 and OGTT2 showed an expected glucose profile as seen in normal animals, with a maximum plasma glucose obtained at 30 minutes, and demonstrated stable AUCs for the 3 different groups.

Fasting baselines values for plasma chemistry are shown in Table 20. Plasma chemistry measurements were performed on blood samples collected prior to the start of the treatment.

TABLE 20

Baseline Values for Body Weight, Fasting Plasma Glucose, Insulin, and Triglyceride Levels of the Three Groups of *Rhesus* Monkeys

|  | Vehicle | FGF21 | Fc-FG21 (RG) |
|---|---|---|---|
| N | 10 | 10 | 10 |
| Body weight (kg) | 8.5 ± 0.5 | 8.7 ± 0.4 | 8.5 ± 0.4 |
| Plasma glucose (mg/dL) | 91.9 ± 4.8 | 94.8 ± 5.3 | 82.2 ± 3.7 |
| Insulin (pg/mL) | 942.6 ± 121.4 | 976.1 ± 107.7 | 1023.4 ± 205.1 |
| Triglycerides (mg/dL) | 44.4 ± 4.8 | 58.6 ± 5.2 | 71.7 ± 9.8 |

Three different dose levels were selected, the low dose was 0.1 and 0.3 mg/kg, the mid dose was 0.3 and 1 mg/kg and the high dose was 1 and 5 mg/kg for FGF21 and Fc-FGF21(RG), respectively. Dose levels were chosen based on the observed dose-response in mice, with a dosing regimen based on the anticipated frequency of injection in humans. Equimolar doses of FGF21 were used for the low and mid doses, and the Fc-FGF21(RG) high dose was raised to 5 mg/kg (i.e., instead of 3 mg/kg, which would have been equimolar to the 1 mg/kg FGF21 dose).

22.2 Effect of Test Compounds on Body Weight

In this experiment, in order to measure effect of the test compounds on body weight measured weekly, the percent body weight change from baseline was calculated weekly in the three different groups of Rhesus monkeys. Body weight was also measured during the three week of wash out period. Baseline body weight values for each group are included in Table 20.

Body weight was followed throughout the study, both pre- and post-administration of test compounds. Body weight percent change from baseline of the vehicle animals increased with time, whereas body weight of animals treated with Fc-FGF21(RG) and FGF21 decreased in a dose-dependent fashion over the course of the 6 week treatment period, as shown in FIG. 39. As observed previously in rodents (Xu et al., *Diabetes* 58(1):250-9 (2009)), treatment with FGF21 statistically significantly decreased body weight. Fc-FGF21 (RG) had a greater exposure than did FGF21 (FIG. 48 and FIG. 47, respectively), offering a possible explanation for the observation that Fc-FGF21(RG) showed a more pronounced body weight decrease than FGF21.

22.3. Effect of Test Compounds on Insulin Levels

Insulin levels were measured in blood samples that had been collected after an overnight fast or after an afternoon meal.

Fasting plasma insulin levels were measured in Rhesus monkeys every week in animals treated with either vehicle, FGF21 or Fc-FGF21(RG) and during the 3-week washout period. Fasted blood samples were drawn approximately five days after the last Fc-FGF21(RG) injection and approximately 21 hours after the last FGF21 injection.

Fed plasma insulin levels were measured in Rhesus monkeys during the fifth and sixth week of treatment with either vehicle or FGF21 during the high dose treatment. Fed blood samples were drawn approximately three days after Fc-FGF21(RG) injection and approximately 2 hours after last FGF21 injection. FIG. 40 shows the effect of vehicle, FGF21 and Fc-FGF21(RG) on fasted insulin levels over the full nine week study, while FIG. 41 depicts fed insulin levels determined from samples taken during weeks 5 and 6.

Summarily, at the two highest doses, both FGF21 and Fc-FGF21(RG) statistically significantly decreased fasted and fed plasma insulin levels. The observation that insulin levels of animals treated with FGF21 and Fc-FGF21(RG) were decreased without observing increased glucose levels is indicative of increased insulin sensitivity.

22.4 Effect of Test Compounds on OGTT (Glucose and Insulin)

Three OGTTs (OGTTs 3, 4 and 5) were performed after treatment was initiated. OGTT5 glucose and insulin level profiles were measured in animals treated for 6 weeks with vehicle, FGF21 or Fc-FGF21(RG), corresponding to the last two weeks of the high dose escalation regimen. OGTT5 was conducted approximately 7 days after the last Fc-FGF21(RG) injection, and approximately 21 hours after the last FGF21 injection. The OGTT5 glucose and insulin profiles are shown in FIG. 42 and FIG. 43, respectively. Animals treated with Fc-FGF21(RG) showed an improved glucose clearance compared to vehicle-treated animals only at the highest dose and at the last time point measured, as shown in FIG. 42. At the end of the last dose, Fc-FGF21(RG) showed the strongest improvement in glucose clearance. FGF21 showed no improvement in glucose clearance. Fc-FGF21(RG) had a greater exposure than did FGF21 (FIG. 48 and FIG. 47, respectively), offering a possible explanation for the observation that Fc-FGF21(RG) showed a more pronounced effect in glucose clearance than FGF21. Insulin levels during OGTT5 were statistically significantly lowered at the last time point measured in animals treated with Fc-FGF21(RG) compared to animals treated with vehicle.

Glucose AUC percent change from baseline was calculated for the three OGTT (OGTTs 3, 4 and 5) performed at the end of each of the low, mid and high doses in the three groups different groups of Rhesus monkeys as shown in FIG. 44. OGTT5 was conducted approximately seven days after the last Fc-FGF21(RG) injection and 21 hours after last FGF21 injection and showed that Fc-FGF21(RG) statistically significantly reduced AUC5. Baseline OGTT values for each group are shown on FIG. 38C.

Fasted plasma glucose levels were measured on days when no OGTTs were performed. There were no meaningful statistical differences observed in fasted plasma glucose levels measured among the three groups of animals.

22.5 Effect of Test Compounds on Triglyceride Levels

Percent change of fasting plasma triglyceride levels was calculated in Rhesus monkeys every week in animals treated with either vehicle, FGF21 or Fc-FGF21(RG) and during the 3-week washout period. Fasted blood samples were drawn approximately five days after last Fc-FGF21(RG) injection and approximately 21 hours after last FGF21 injection. Triglyceride levels were measured every week after the treatment was initiated and percent changes from baseline are shown in FIG. 45, fasting baseline values are shown in Table 20.

As depicted in FIG. 45, animals treated with either Fc-FGF21(RG) or FGF21 showed a dose-dependent decrease in triglyceride levels, with Fc-FGF21(RG) having the greatest lowering effect compared to FGF21.

FIG. 46 shows the plasma triglyceride levels in samples acquire from Rhesus monkeys in a fed state, during the fifth and sixth week of treatment with vehicle or Fc-FGF21(RG) or FGF21. Fed blood samples were drawn approximately 3 days after Fc-FGF21(RG) injection and approximately 2 hours after last FGF21 injection. Fed plasma triglyceride levels of animals treated with FGF21 and Fc-FGF21(RG) were statistically significantly reduced, compared to the triglyceride levels of animals treated with vehicle (FIG. 46).

22.6 Concentration of Test Compounds

The exposure of the tested compounds administered at approximately equivalent molar dose levels was assessed throughout the study period. The concentration of Fc-FGF21 (RG) was measured at pre-dose, and approximately 5 days after the last injection. FGF21 levels were measured at pre-dose, and at 5, 12, 19, and 26 days. Blood samples were drawn at approximately 21 hours after the last injection.

The individual concentration of the tested compounds in each monkeys are shown in FIGS. 47 and 48. As shown in FIG. 47, the majority of the animals in the FGF21-treated group had concentrations below the quantitation limit. FIG. 48 shows that animals in the Fc-FGF21(RG)-treated group had detectable levels of Fc-FGF21(RG) during each dosing phase (two weekly doses at the same dose strength). The average concentration from each dosing phase increased approximately dose-proportionally from 0.3 to 5 mg/kg for Fc-FGF21(RG). There is minimal accumulation as demonstrated by the steady concentrations after the first and second weekly dose within each dose escalation phase for both compounds. During the treatment-free phase (washout period) Fc-FGF21(RG) levels were detectable up to approximately day 47 (12 days post last dose) and were below lower limit of quantification (LLOQ) afterwards.

Exposure of the test compounds was also monitored during each OGTT. FGF21 was not detectable during OGTTs 3 and 4, following low- and mid-dose FGF21 treatment. However, measurable levels were observed during OGTT5, following high-dose treatment. A dose proportional increase in Fc-FGF21(RG) levels was observed across the third to fifth OGTT with escalating dose levels, as shown in FIG. 49.

Compound levels data confirm that the animals were exposed to the expected amount of each compound, namely FGF21 and Fc-FGF21(RG), in a dose escalation manner. A large variability was observed in the amount of FGF21 measured, which was an expected result considering the sampling was performed approximately 21 hours post the last dose and the half life of FGF21 is approximately 1 hour.

22.7 Conclusions

FGF21 decreased fasted and fed plasma triglyceride and insulin levels and decreased body weight at the highest doses. Fc-FGF21(RG) improved OGTT and decreased insulin levels at the highest dose, and dose dependently decreased fasted and fed plasma triglyceride levels as well as body weight. Both FGF21 and Fc-FGF21(RG) decreased a number of metabolic parameters in the non diabetic Rhesus monkeys. Insulin and triglyceride level decreases were identical between FGF21 and Fc-FGF21(RG) when circulating compound levels were in a similar range, in the fed condition. Due to its improved properties, Fc-FGF21(RG) was superior to FGF21 in most of the parameters measured and could be administered once-a-week to observe efficacy on metabolic parameters.

While the present invention has been described in terms of various embodiments, it is understood that variations and modifications will occur to those skilled in the art. Therefore, it is intended that the appended claims cover all such equivalent variations that come within the scope of the invention as claimed. In addition, the section headings used herein are for organizational purposes only and are not to be construed as limiting the subject matter described.

All references cited in this application are expressly incorporated by reference herein.

What is claimed is:

1. An isolated polypeptide comprising the amino acid sequence of SEQ ID NO:4, wherein the polypeptide comprises (a) an arginine residue at position 98 of SEQ ID NO:4; and (b) a glycine residue at position 171 of SEQ ID NO:4.

2. A fusion polypeptide comprising the polypeptide of claim 1 linked to a heterologous polypeptide.

3. The fusion polypeptide of claim 2, wherein the heterologous polypeptide is an Fc polypeptide.

4. The fusion polypeptide of claim 3, wherein the Fc polypeptide comprises the amino acid sequence of SEQ ID NO:13.

5. The fusion polypeptide of claim 4, wherein the polypeptide is joined to the Fc polypeptide by a linker.

6. The fusion polypeptide of claim 5 wherein the linker is GGGGGSGGGSGGGS (SEQ ID NO:23).

7. The fusion polypeptide of claim 6, wherein the fusion polypeptide comprises the amino acid sequence of SEQ ID NO:38.

8. A multimer comprising two or more copies of the fusion polypeptide of claim 7.

9. A pharmaceutical composition comprising the fusion polypeptide of claim 7 and a pharmaceutically acceptable formulation agent.

10. The fusion polypeptide of claim 5 wherein the linker is GGGGSGGGGSGGGGS (SEQ ID NO:31).

11. The fusion polypeptide of claim 10, wherein the fusion polypeptide comprises the amino acid sequence of SEQ ID NO:36.

12. A multimer comprising two or more copies of the fusion polypeptide of claim 11.

13. A pharmaceutical composition comprising the fusion polypeptide of claim 11 and a pharmaceutically acceptable formulation agent.

14. The isolated polypeptide of claim 1, further comprising a mutation at position 180.

15. A fusion polypeptide encoded by nucleotides 1-1272 of SEQ ID NO:37.

* * * * *

UNITED STATES PATENT AND TRADEMARK OFFICE
CERTIFICATE OF CORRECTION

| | | |
|---|---|---|
| PATENT NO. | : 8,034,770 B2 | Page 1 of 1 |
| APPLICATION NO. | : 12/455610 | |
| DATED | : October 11, 2011 | |
| INVENTOR(S) | : Edward John Belouski | |

It is certified that error appears in the above-identified patent and that said Letters Patent is hereby corrected as shown below:

Column 8, Line 50 should read:

--...5 and 6 correspond to ~~30~~ weeks 5 and 6 at the high dose...--

Column 27, Line 35:

--...pharnacokinetic should read pharmacokinetic...--

Column 39, Line 59 should read:

--...ratory), and blood ~~25~~ samples were obtained at various time...--

Column 43, Line 29:

--...glycoylated should read glycosylated...--

Column 57, Line 54 should read:

--...In a subsequent experiment, the in vivo activity of Fc(15)FGF21 (L98R,...--

Column 58, Line 12:

--...P171Q, should read P171G...--

Signed and Sealed this
Twenty-fifth Day of September, 2012

David J. Kappos
*Director of the United States Patent and Trademark Office*

SEQUENCE LISTING

<160> NUMBER OF SEQ ID NOS: 42

<210> SEQ ID NO 1
<211> LENGTH: 630
<212> TYPE: DNA
<213> ORGANISM: Homo sapiens

<400> SEQUENCE: 1

| | | | | | |
|---|---|---|---|---|---|
| atggactcgg | acgagaccgg | gttcgagcac | tcaggactgt | gggtttctgt | gctggctggt | 60 |
| cttctgctgg | gagcctgcca | ggcacacccc | atccctgact | ccagtcctct | cctgcaattc | 120 |
| gggggccaag | tccggcagcg | gtacctctac | acagatgatg | cccagcagac | agaagcccac | 180 |

```
ctggagatca gggaggatgg gacggtgggg ggcgctgctg accagagccc cgaaagtctc    240
ctgcagctga aagccttgaa gccgggagtt attcaaatct tgggagtcaa gacatccagg    300
ttcctgtgcc agcggccaga tggggccctg tatggatcgc tccactttga ccctgaggcc    360
tgcagcttcc gggagctgct tcttgaggac ggatacaatg tttaccagtc cgaagcccac    420
ggcctcccgc tgcacctgcc agggaacaag tccccacacc gggaccctgc accccgagga    480
ccagctcgct tcctgccact accaggcctg ccccccgcac ccccggagcc acccggaatc    540
ctggcccccc agcccccccga tgtgggctcc tcggaccctc tgagcatggt gggaccttcc    600
cagggccgaa gccccagcta cgcttcctga                                     630
```

<210> SEQ ID NO 2
<211> LENGTH: 209
<212> TYPE: PRT
<213> ORGANISM: Homo sapiens

<400> SEQUENCE: 2

```
Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser
```

<210> SEQ ID NO 3
<211> LENGTH: 546
<212> TYPE: DNA
<213> ORGANISM: Homo sapiens

<400> SEQUENCE: 3

```
cacccccatcc ctgactccag tcctctcctg caattcgggg gccaagtccg gcagcggtac     60
ctctacacag atgatgccca gcagacagaa gcccacctgg agatcaggga ggatgggacg    120
gtggggggcg ctgctgacca gagccccgaa agtctcctgc agctgaaagc cttgaagccg    180
```

```
ggagttattc aaatcttggg agtcaagaca tccaggttcc tgtgccagcg gccagatggg    240
gccctgtatg gatcgctcca ctttgaccct gaggcctgca gcttccggga gctgcttctt    300
gaggacggat acaatgttta ccagtccgaa gccacggcc tcccgctgca cctgccaggg    360
aacaagtccc cacaccggga ccctgcaccc cgaggaccag ctcgcttcct gccactacca    420
ggcctgcccc ccgcaccccc ggagccaccc ggaatcctgg ccccccagcc cccgatgtg     480 ggctcctcgg accctctgag catggtggga ccttcccagg gccgaagccc cagctacgct    540
tcctga                                                               546
```

```
<210> SEQ ID NO 4
<211> LENGTH: 181
<212> TYPE: PRT
<213> ORGANISM: Homo sapiens

<400> SEQUENCE: 4

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 5
<211> LENGTH: 40
<212> TYPE: DNA
<213> ORGANISM: Artificial Sequence
<220> FEATURE:
<223> OTHER INFORMATION: PCR primer

<400> SEQUENCE: 5
aggaggaata acatatgcat ccaattccag attcttctcc                          40

<210> SEQ ID NO 6
<211> LENGTH: 33
<212> TYPE: DNA
<213> ORGANISM: Artificial Sequence
<220> FEATURE:
<223> OTHER INFORMATION: PCR primer

<400> SEQUENCE: 6
```

```
tagtgagctc gaattcttag gaagcgtagc tgg                                    33
```

<210> SEQ ID NO 7
<211> LENGTH: 41
<212> TYPE: DNA
<213> ORGANISM: Artificial Sequence
<220> FEATURE:
<223> OTHER INFORMATION: PCR primer

<400> SEQUENCE: 7

```
ggagatatac atatgccaat tccagattct tctccattat t                           41
```

<210> SEQ ID NO 8
<211> LENGTH: 34
<212> TYPE: DNA
<213> ORGANISM: Artificial Sequence
<220> FEATURE:
<223> OTHER INFORMATION: PCR primer

<400> SEQUENCE: 8

```
catatgtata tctccttctt aaagttaaac aaaa                                   34
```

<210> SEQ ID NO 9
<211> LENGTH: 34
<212> TYPE: DNA
<213> ORGANISM: Artificial
<220> FEATURE:
<223> OTHER INFORMATION: PCR primer

<400> SEQUENCE: 9

```
aaaacaaatt gaaattcttc ctctatatgt atac                                   34
```

<210> SEQ ID NO 10
<211> LENGTH: 10
<212> TYPE: PRT
<213> ORGANISM: Artificial Sequence
<220> FEATURE:
<223> OTHER INFORMATION: portion of a mature human FGF21 polypeptide

<400> SEQUENCE: 10

```
Met His Pro Ile Pro Asp Ser Ser Pro Leu
 1               5                  10
```

<210> SEQ ID NO 11
<211> LENGTH: 63
<212> TYPE: DNA
<213> ORGANISM: Artificial Sequence
<220> FEATURE:
<223> OTHER INFORMATION: sense strand from a portion of an FGF21
      expression construct

<400> SEQUENCE: 11

```
ttttgtttaa ctttaagaag gagatataca tatgcatcca attccagatt cttctccatt       60
att                                                                    63
```

<210> SEQ ID NO 12
<211> LENGTH: 63
<212> TYPE: DNA
<213> ORGANISM: Artificial
<220> FEATURE:
<223> OTHER INFORMATION: antisense strand from a portion of an FGF21
      expression construct

<400> SEQUENCE: 12

```
aaaacaaatt gaaattcttc ctctatatgt atacgtaggt taaggtctaa gaagaggtaa       60
taa                                                                    63
```

```
<210> SEQ ID NO 13
<211> LENGTH: 227
<212> TYPE: PRT
<213> ORGANISM: Homo sapiens

<400> SEQUENCE: 13

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 14
<211> LENGTH: 34
<212> TYPE: DNA
<213> ORGANISM: Artificial Sequence
<220> FEATURE:
<223> OTHER INFORMATION: PCR primer

<400> SEQUENCE: 14
aggaggaata acatatggac aaaactcaca catg                               34

<210> SEQ ID NO 15
<211> LENGTH: 23
<212> TYPE: DNA
<213> ORGANISM: Artificial Sequence
<220> FEATURE:
<223> OTHER INFORMATION: PCR primer

<400> SEQUENCE: 15
ggatccacca ccaccgctac cac                                           23

<210> SEQ ID NO 16
```

```
<211> LENGTH: 39
<212> TYPE: DNA
<213> ORGANISM: Artificial Sequence
<220> FEATURE:
<223> OTHER INFORMATION: PCR primer

<400> SEQUENCE: 16
ggtggtggtg gatcccatcc aattccagat tcttctcca                           39

<210> SEQ ID NO 17
<211> LENGTH: 33
<212> TYPE: DNA
<213> ORGANISM: Artificial Sequence
<220> FEATURE:
<223> OTHER INFORMATION: PCR primer

<400> SEQUENCE: 17
tagtgagctc gaattcttag gaagcgtagc tgg                                 33

<210> SEQ ID NO 18
<211> LENGTH: 27
<212> TYPE: DNA
<213> ORGANISM: Artificial Sequence
<220> FEATURE:
<223> OTHER INFORMATION: PCR primer

<400> SEQUENCE: 18
atggtggaac ctcccaggg ccgaagc                                         27

<210> SEQ ID NO 19
<211> LENGTH: 30
<212> TYPE: DNA
<213> ORGANISM: Artificial Sequence
<220> FEATURE:
<223> OTHER INFORMATION: PCR primer

<400> SEQUENCE: 19
ggaaggttcc accatgctca gagggtccga                                     30

<210> SEQ ID NO 20
<211> LENGTH: 50
<212> TYPE: DNA
<213> ORGANISM: Artificial Sequence
<220> FEATURE:
<223> OTHER INFORMATION: sense strand from a portion of an FGF21
      expression construct

<400> SEQUENCE: 20
ctcctcggac cctctgagca tggtgggacc ttcccagggc cgaagcccca               50

<210> SEQ ID NO 21
<211> LENGTH: 30
<212> TYPE: DNA
<213> ORGANISM: Artificial
<220> FEATURE:
<223> OTHER INFORMATION: PCR primer

<400> SEQUENCE: 21
agcctgggag actcgtacca ccttggaagg                                     30

<210> SEQ ID NO 22
<211> LENGTH: 50
<212> TYPE: DNA
<213> ORGANISM: artificial
<220> FEATURE:
<223> OTHER INFORMATION: antisense strand from a portion of an FGF21
      expression construct
```

```
<400> SEQUENCE: 22
gaggagcctg ggagactcgt accaccctgg aagggtcccg gcttcggggt          50

<210> SEQ ID NO 23
<211> LENGTH: 15
<212> TYPE: PRT
<213> ORGANISM: Artificial Sequence
<220> FEATURE:
<223> OTHER INFORMATION: linker sequence

<400> SEQUENCE: 23

Gly Gly Gly Gly Gly Ser Gly Gly Gly Ser Gly Gly Gly Gly Ser
1               5                   10                  15

<210> SEQ ID NO 24
<211> LENGTH: 424
<212> TYPE: PRT
<213> ORGANISM: Artificial
<220> FEATURE:
<223> OTHER INFORMATION: Fc-(G4S)3-FGF21

<400> SEQUENCE: 24
```

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
        50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Gly Gly Gly Gly Ser Gly Gly Gly Ser Gly Gly Gly
225                 230                 235                 240

Gly Gly Ser His Pro Ile Pro Asp Ser Ser Pro Leu Leu Gln Phe Gly
                245                 250                 255

Gly Gln Val Arg Gln Arg Tyr Leu Tyr Thr Asp Asp Ala Gln Gln Thr
            260                 265                 270

Glu Ala His Leu Glu Ile Arg Glu Asp Gly Thr Val Gly Gly Ala Ala
        275                 280                 285

```
Asp Gln Ser Pro Glu Ser Leu Leu Gln Leu Lys Ala Leu Lys Pro Gly
        290                 295                 300

Val Ile Gln Ile Leu Gly Val Lys Thr Ser Arg Phe Leu Cys Gln Arg
305                 310                 315                 320

Pro Asp Gly Ala Leu Tyr Gly Ser Leu His Phe Asp Pro Glu Ala Cys
                325                 330                 335

Ser Phe Arg Glu Leu Leu Leu Glu Asp Gly Tyr Asn Val Tyr Gln Ser
            340                 345                 350

Glu Ala His Gly Leu Pro Leu His Leu Pro Gly Asn Lys Ser Pro His
        355                 360                 365

Arg Asp Pro Ala Pro Arg Gly Pro Ala Arg Phe Leu Pro Leu Pro Gly
370                 375                 380

Leu Pro Pro Ala Pro Pro Glu Pro Pro Gly Ile Leu Ala Pro Gln Pro
385                 390                 395                 400

Pro Asp Val Gly Ser Ser Asp Pro Leu Ser Met Val Gly Pro Ser Gln
                405                 410                 415

Gly Arg Ser Pro Ser Tyr Ala Ser
                420

<210> SEQ ID NO 25
<211> LENGTH: 424
<212> TYPE: PRT
<213> ORGANISM: Artificial
<220> FEATURE:
<223> OTHER INFORMATION: FGF21(15)-Fc

<400> SEQUENCE: 25

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
        50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser Gly Gly Gly Gly Ser Gly Gly Gly Gly Ser
            180                 185                 190

Gly Gly Gly Gly Ser Asp Lys Thr His Thr Cys Pro Pro Cys Pro Ala
        195                 200                 205

Pro Glu Leu Leu Gly Gly Pro Ser Val Phe Leu Phe Pro Pro Lys Pro
210                 215                 220
```

```
Lys Asp Thr Leu Met Ile Ser Arg Thr Pro Glu Val Thr Cys Val Val
225                 230                 235                 240

Val Asp Val Ser His Glu Asp Pro Glu Val Lys Phe Asn Trp Tyr Val
            245                 250                 255

Asp Gly Val Glu Val His Asn Ala Lys Thr Lys Pro Arg Glu Glu Gln
        260                 265                 270

Tyr Asn Ser Thr Tyr Arg Val Val Ser Val Leu Thr Val Leu His Gln
    275                 280                 285

Asp Trp Leu Asn Gly Lys Glu Tyr Lys Cys Lys Val Ser Asn Lys Ala
290                 295                 300

Leu Pro Ala Pro Ile Glu Lys Thr Ile Ser Lys Ala Lys Gly Gln Pro
305                 310                 315                 320

Arg Glu Pro Gln Val Tyr Thr Leu Pro Pro Ser Arg Asp Glu Leu Thr
            325                 330                 335

Lys Asn Gln Val Ser Leu Thr Cys Leu Val Lys Gly Phe Tyr Pro Ser
        340                 345                 350

Asp Ile Ala Val Glu Trp Glu Ser Asn Gly Gln Pro Glu Asn Asn Tyr
    355                 360                 365

Lys Thr Thr Pro Pro Val Leu Asp Ser Asp Gly Ser Phe Phe Leu Tyr
370                 375                 380

Ser Lys Leu Thr Val Asp Lys Ser Arg Trp Gln Gln Gly Asn Val Phe
385                 390                 395                 400

Ser Cys Ser Val Met His Glu Ala Leu His Asn His Tyr Thr Gln Lys
            405                 410                 415

Ser Leu Ser Leu Ser Pro Gly Lys
            420

<210> SEQ ID NO 26
<211> LENGTH: 424
<212> TYPE: PRT
<213> ORGANISM: Artificial
<220> FEATURE:
<223> OTHER INFORMATION: Fc-(G4S)3-FGF21 G170E

<400> SEQUENCE: 26

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
```

Pro Val Leu Asp Ser Asp Gly Ser Phe Phe Leu Tyr Ser Lys Leu Thr
        165                 170                 175
Val Asp Lys Ser Arg Trp Gln Gln Gly Asn Val Phe Ser Cys Ser Val
        180                 185                 190
Met His Glu Ala Leu His Asn His Tyr Thr Gln Lys Ser Leu Ser Leu
        195                 200                 205
Ser Pro Gly Lys Gly Gly Gly Gly Ser Gly Gly Gly Gly Ser Gly Gly
225             210                 215                 220
Gly Gly Ser His Pro Ile Pro Asp Ser Ser Pro Leu Leu Gln Phe Gly
                245                 250                 255
Gly Gln Val Arg Gln Arg Tyr Leu Tyr Thr Asp Asp Ala Gln Gln Thr
        260                 265                 270
Glu Ala His Leu Glu Ile Arg Glu Asp Gly Thr Val Gly Gly Ala Ala
        275                 280                 285
Asp Gln Ser Pro Glu Ser Leu Leu Gln Leu Lys Ala Leu Lys Pro Gly
        290                 295                 300
Val Ile Gln Ile Leu Gly Val Lys Thr Ser Arg Phe Leu Cys Gln Arg
305             310                 315                 320
Pro Asp Gly Ala Leu Tyr Gly Ser Leu His Phe Asp Pro Glu Ala Cys
                325                 330                 335
Ser Phe Arg Glu Leu Leu Leu Glu Asp Gly Tyr Asn Val Tyr Gln Ser
        340                 345                 350
Glu Ala His Gly Leu Pro Leu His Leu Pro Gly Asn Lys Ser Pro His
        355                 360                 365
Arg Asp Pro Ala Pro Arg Gly Pro Ala Arg Phe Leu Pro Leu Pro Gly
        370                 375                 380
Leu Pro Pro Ala Pro Pro Glu Pro Pro Gly Ile Leu Ala Pro Gln Pro
385             390                 395                 400
Pro Asp Val Gly Ser Ser Asp Pro Leu Ser Met Val Glu Pro Ser Gln
                405                 410                 415
Gly Arg Ser Pro Ser Tyr Ala Ser
                420

<210> SEQ ID NO 27
<211> LENGTH: 424
<212> TYPE: PRT
<213> ORGANISM: Artificial
<220> FEATURE:
<223> OTHER INFORMATION: Fc-(G4S)3-FGF21 P171A

<400> SEQUENCE: 27

Met Asp Lys Thr His Thr Cys Pro Pro Cys Pro Ala Pro Glu Leu Leu
1               5                   10                  15
Gly Gly Pro Ser Val Phe Leu Phe Pro Pro Lys Pro Lys Asp Thr Leu
            20                  25                  30
Met Ile Ser Arg Thr Pro Glu Val Thr Cys Val Val Val Asp Val Ser
        35                  40                  45
His Glu Asp Pro Glu Val Lys Phe Asn Trp Tyr Val Asp Gly Val Glu
    50                  55                  60
Val His Asn Ala Lys Thr Lys Pro Arg Glu Glu Gln Tyr Asn Ser Thr
65                  70                  75                  80
Tyr Arg Val Val Ser Val Leu Thr Val Leu His Gln Asp Trp Leu Asn
                85                  90                  95
Gly Lys Glu Tyr Lys Cys Lys Val Ser Asn Lys Ala Leu Pro Ala Pro
            100                 105                 110

```
Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
210                 215                 220

Ser Pro Gly Lys Gly Gly Gly Ser Gly Gly Gly Ser Gly Gly
225                 230                 235                 240

Gly Gly Ser His Pro Ile Pro Asp Ser Ser Pro Leu Leu Gln Phe Gly
                245                 250                 255

Gly Gln Val Arg Gln Arg Tyr Leu Tyr Thr Asp Asp Ala Gln Gln Thr
            260                 265                 270

Glu Ala His Leu Glu Ile Arg Glu Asp Gly Thr Val Gly Gly Ala Ala
        275                 280                 285

Asp Gln Ser Pro Glu Ser Leu Leu Gln Leu Lys Ala Leu Lys Pro Gly
290                 295                 300

Val Ile Gln Ile Leu Gly Val Lys Thr Ser Arg Phe Leu Cys Gln Arg
305                 310                 315                 320

Pro Asp Gly Ala Leu Tyr Gly Ser Leu His Phe Asp Pro Glu Ala Cys
                325                 330                 335

Ser Phe Arg Glu Leu Leu Leu Glu Asp Gly Tyr Asn Val Tyr Gln Ser
            340                 345                 350

Glu Ala His Gly Leu Pro Leu His Leu Pro Gly Asn Lys Ser Pro His
        355                 360                 365

Arg Asp Pro Ala Pro Arg Gly Pro Ala Arg Phe Leu Pro Leu Pro Gly
            370                 375                 380

Leu Pro Pro Ala Pro Pro Glu Pro Pro Gly Ile Leu Ala Pro Gln Pro
385                 390                 395                 400

Pro Asp Val Gly Ser Ser Asp Pro Leu Ser Met Val Gly Ala Ser Gln
                405                 410                 415

Gly Arg Ser Pro Ser Tyr Ala Ser
                420

<210> SEQ ID NO 28
<211> LENGTH: 424
<212> TYPE: PRT
<213> ORGANISM: Artificial
<220> FEATURE:
<223> OTHER INFORMATION: Fc-(G4S)3-FGF21 S172L

<400> SEQUENCE: 28

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45
```

His Glu Asp Pro Glu Val Lys Phe Asn Trp Tyr Val Asp Gly Val Glu
 50                  55                  60

Val His Asn Ala Lys Thr Lys Pro Arg Glu Glu Gln Tyr Asn Ser Thr
 65                  70                  75                  80

Tyr Arg Val Val Ser Val Leu Thr Val Leu His Gln Asp Trp Leu Asn
                 85                  90                  95

Gly Lys Glu Tyr Lys Cys Lys Val Ser Asn Lys Ala Leu Pro Ala Pro
                100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
210                 215                 220

Ser Pro Gly Lys Gly Gly Gly Gly Ser Gly Gly Gly Gly Ser Gly Gly
225                 230                 235                 240

Gly Gly Ser His Pro Ile Pro Asp Ser Ser Pro Leu Leu Gln Phe Gly
                245                 250                 255

Gly Gln Val Arg Gln Arg Tyr Leu Tyr Thr Asp Asp Ala Gln Gln Thr
            260                 265                 270

Glu Ala His Leu Glu Ile Arg Glu Asp Gly Thr Val Gly Gly Ala Ala
        275                 280                 285

Asp Gln Ser Pro Glu Ser Leu Leu Gln Leu Lys Ala Leu Lys Pro Gly
    290                 295                 300

Val Ile Gln Ile Leu Gly Val Lys Thr Ser Arg Phe Leu Cys Gln Arg
305                 310                 315                 320

Pro Asp Gly Ala Leu Tyr Gly Ser Leu His Phe Asp Pro Glu Ala Cys
                325                 330                 335

Ser Phe Arg Glu Leu Leu Leu Glu Asp Gly Tyr Asn Val Tyr Gln Ser
            340                 345                 350

Glu Ala His Gly Leu Pro Leu His Leu Pro Gly Asn Lys Ser Pro His
        355                 360                 365

Arg Asp Pro Ala Pro Arg Gly Pro Ala Arg Phe Leu Pro Leu Pro Gly
    370                 375                 380

Leu Pro Pro Ala Pro Pro Glu Pro Pro Gly Ile Leu Ala Pro Gln Pro
385                 390                 395                 400

Pro Asp Val Gly Ser Ser Asp Pro Leu Ser Met Val Gly Pro Leu Gln
                405                 410                 415

Gly Arg Ser Pro Ser Tyr Ala Ser
            420

<210> SEQ ID NO 29
<211> LENGTH: 4
<212> TYPE: PRT
<213> ORGANISM: Artificial
<220> FEATURE:
<223> OTHER INFORMATION: linker

```
<400> SEQUENCE: 29

Gly Gly Gly Gly
1

<210> SEQ ID NO 30
<211> LENGTH: 5
<212> TYPE: PRT
<213> ORGANISM: Artificial
<220> FEATURE:
<223> OTHER INFORMATION: linker

<400> SEQUENCE: 30

Gly Gly Gly Gly Gly
1               5

<210> SEQ ID NO 31
<211> LENGTH: 15
<212> TYPE: PRT
<213> ORGANISM: Artificial
<220> FEATURE:
<223> OTHER INFORMATION: linker

<400> SEQUENCE: 31

Gly Gly Gly Gly Ser Gly Gly Gly Gly Ser Gly Gly Gly Gly Ser
1               5                   10                  15

<210> SEQ ID NO 32
<211> LENGTH: 8
<212> TYPE: PRT
<213> ORGANISM: Artificial
<220> FEATURE:
<223> OTHER INFORMATION: linker

<400> SEQUENCE: 32

Gly Gly Gly Lys Gly Gly Gly Gly
1               5

<210> SEQ ID NO 33
<211> LENGTH: 8
<212> TYPE: PRT
<213> ORGANISM: Artificial
<220> FEATURE:
<223> OTHER INFORMATION: linker

<400> SEQUENCE: 33

Gly Gly Gly Asn Gly Ser Gly Gly
1               5

<210> SEQ ID NO 34
<211> LENGTH: 8
<212> TYPE: PRT
<213> ORGANISM: Artificial
<220> FEATURE:
<223> OTHER INFORMATION: linker

<400> SEQUENCE: 34

Gly Gly Gly Cys Gly Gly Gly Gly
1               5

<210> SEQ ID NO 35
<211> LENGTH: 5
<212> TYPE: PRT
<213> ORGANISM: Artificial
<220> FEATURE:
<223> OTHER INFORMATION: linker

<400> SEQUENCE: 35
```

-continued

Gly Pro Asn Gly Gly
1               5

<210> SEQ ID NO 36
<211> LENGTH: 424
<212> TYPE: PRT
<213> ORGANISM: Artificial
<220> FEATURE:
<223> OTHER INFORMATION: Fc-(G4S)3-FGF21 L98R, P171G

<400> SEQUENCE: 36

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
        50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
210                 215                 220

Ser Pro Gly Lys Gly Gly Gly Ser Gly Gly Gly Ser Gly Gly
225                 230                 235                 240

Gly Gly Ser His Pro Ile Pro Asp Ser Ser Pro Leu Leu Gln Phe Gly
                245                 250                 255

Gly Gln Val Arg Gln Arg Tyr Leu Tyr Thr Asp Asp Ala Gln Gln Thr
            260                 265                 270

Glu Ala His Leu Glu Ile Arg Glu Asp Gly Thr Val Gly Gly Ala Ala
        275                 280                 285

Asp Gln Ser Pro Glu Ser Leu Leu Gln Leu Lys Ala Leu Lys Pro Gly
290                 295                 300

Val Ile Gln Ile Leu Gly Val Lys Thr Ser Arg Phe Leu Cys Gln Arg
305                 310                 315                 320

Pro Asp Gly Ala Leu Tyr Gly Ser Leu His Phe Asp Pro Glu Ala Cys
                325                 330                 335

Ser Phe Arg Glu Arg Leu Leu Glu Asp Gly Tyr Asn Val Tyr Gln Ser
            340                 345                 350

Glu Ala His Gly Leu Pro Leu His Leu Pro Gly Asn Lys Ser Pro His

-continued

```
                         355                     360                     365
Arg Asp Pro Ala Pro Arg Gly Pro Ala Arg Phe Leu Pro Leu Pro Gly
            370                     375                     380

Leu Pro Pro Ala Pro Pro Glu Pro Pro Gly Ile Leu Ala Pro Gln Pro
385                     390                     395                     400

Pro Asp Val Gly Ser Ser Asp Pro Leu Ser Met Val Gly Gly Ser Gln
                405                     410                     415

Gly Arg Ser Pro Ser Tyr Ala Ser
            420

<210> SEQ ID NO 37
<211> LENGTH: 1274
<212> TYPE: DNA
<213> ORGANISM: Artificial
<220> FEATURE:
<223> OTHER INFORMATION: Fc(15)FGF21 L98R, P171G
<220> FEATURE:
<221> NAME/KEY: CDS
<222> LOCATION: (1)..(1272)

<400> SEQUENCE: 37 atg gac aaa act cac aca tgt cca cct tgt cca gct ccg gaa ctc ctg      48
Met Asp Lys Thr His Thr Cys Pro Pro Cys Pro Ala Pro Glu Leu Leu
1               5                   10                  15 ggg gga ccg tca gtc ttc ctc ttc ccc cca aaa ccc aag gac acc ctc      96
Gly Gly Pro Ser Val Phe Leu Phe Pro Pro Lys Pro Lys Asp Thr Leu
            20                  25                  30 atg atc tcc cgt acc cct gag gtc aca tgc gtg gtg gtg gac gtg agc     144
Met Ile Ser Arg Thr Pro Glu Val Thr Cys Val Val Val Asp Val Ser
        35                  40                  45 cac gaa gac cct gag gtc aag ttc aac tgg tac gtg gac ggc gtg gag     192
His Glu Asp Pro Glu Val Lys Phe Asn Trp Tyr Val Asp Gly Val Glu
    50                  55                  60 gtg cat aat gcc aag aca aag ccg cgt gag gag cag tac aac agc acg     240
Val His Asn Ala Lys Thr Lys Pro Arg Glu Glu Gln Tyr Asn Ser Thr
65                  70                  75                  80 tac cgt gtg gtc agc gtc ctc acc gtc ctg cac cag gac tgg ctg aat     288
Tyr Arg Val Val Ser Val Leu Thr Val Leu His Gln Asp Trp Leu Asn
                85                  90                  95 ggc aag gag tac aag tgc aag gtc tcc aac aaa gcc ctc cca gcc ccc     336
Gly Lys Glu Tyr Lys Cys Lys Val Ser Asn Lys Ala Leu Pro Ala Pro
            100                 105                 110 atc gag aaa acc atc tcc aaa gcc aaa ggg cag ccc cga gaa cca cag     384
Ile Glu Lys Thr Ile Ser Lys Ala Lys Gly Gln Pro Arg Glu Pro Gln
        115                 120                 125 gtg tac acc ctg ccc cca tcc cgt gat gag ctg acc aag aac cag gtc     432
Val Tyr Thr Leu Pro Pro Ser Arg Asp Glu Leu Thr Lys Asn Gln Val
    130                 135                 140 agc ctg acc tgc ctg gtc aaa ggc ttc tat ccc agc gac atc gcc gtg     480
Ser Leu Thr Cys Leu Val Lys Gly Phe Tyr Pro Ser Asp Ile Ala Val
145                 150                 155                 160 gag tgg gag agc aat ggg cag ccg gag aac aac tac aag acc acg cct     528
Glu Trp Glu Ser Asn Gly Gln Pro Glu Asn Asn Tyr Lys Thr Thr Pro
                165                 170                 175 ccc gtg ctg gac tcc gac ggc tcc ttc ttc ctc tac agc aag ctc acc     576
Pro Val Leu Asp Ser Asp Gly Ser Phe Phe Leu Tyr Ser Lys Leu Thr
            180                 185                 190 gtg gac aag agc cgt tgg cag cag ggg aac gtc ttc tca tgc tcc gtg     624
Val Asp Lys Ser Arg Trp Gln Gln Gly Asn Val Phe Ser Cys Ser Val
        195                 200                 205 atg cat gag gct ctg cac aac cac tac acg cag aag agc ctc tcc ctg     672
```

```
Met His Glu Ala Leu His Asn His Tyr Thr Gln Lys Ser Leu Ser Leu
    210                 215                 220 tct ccg ggt aaa ggt gga ggt ggt ggt tct ggt ggt ggt agc ggt ggt      720
Ser Pro Gly Lys Gly Gly Gly Gly Gly Ser Gly Gly Gly Ser Gly Gly
225                 230                 235                 240 ggt gga tcc cat cca att cca gat tct tct cca tta tta caa ttc ggg      768
Gly Gly Ser His Pro Ile Pro Asp Ser Ser Pro Leu Leu Gln Phe Gly
                245                 250                 255 ggc caa gtc cgg cag cgg tac ctc tac aca gat gat gcc cag cag aca      816
Gly Gln Val Arg Gln Arg Tyr Leu Tyr Thr Asp Asp Ala Gln Gln Thr
            260                 265                 270 gaa gcc cac ctg gag atc agg gag gat ggg acg gtg ggg ggc gct gct      864
Glu Ala His Leu Glu Ile Arg Glu Asp Gly Thr Val Gly Gly Ala Ala
        275                 280                 285 gac cag agc ccc gaa agt ctc ctg cag ctg aaa gcc ttg aag ccg gga      912
Asp Gln Ser Pro Glu Ser Leu Leu Gln Leu Lys Ala Leu Lys Pro Gly
    290                 295                 300 gtt att caa atc ttg gga gtc aag aca tcc agg ttc ctg tgc cag cgg      960
Val Ile Gln Ile Leu Gly Val Lys Thr Ser Arg Phe Leu Cys Gln Arg
305                 310                 315                 320 cca gat ggg gcc ctg tat gga tcg ctc cac ttt gac cct gag gcc tgc     1008
Pro Asp Gly Ala Leu Tyr Gly Ser Leu His Phe Asp Pro Glu Ala Cys
                325                 330                 335 agc ttc cgg gag cgt ctt ctt gag gac gga tac aat gtt tac cag tcc     1056
Ser Phe Arg Glu Arg Leu Leu Glu Asp Gly Tyr Asn Val Tyr Gln Ser
            340                 345                 350 gaa gcc cac ggc ctc ccg ctg cac ctg cca ggg aac aag tcc cca cac     1104
Glu Ala His Gly Leu Pro Leu His Leu Pro Gly Asn Lys Ser Pro His
        355                 360                 365 cgg gac cct gca ccc cga gga cca gct cgc ttc ctg cca cta cca ggc     1152
Arg Asp Pro Ala Pro Arg Gly Pro Ala Arg Phe Leu Pro Leu Pro Gly
    370                 375                 380 ctg ccc ccc gca ccc ccg gag cca ccc gga atc ctg gcc ccc cag ccc     1200
Leu Pro Pro Ala Pro Pro Glu Pro Pro Gly Ile Leu Ala Pro Gln Pro
385                 390                 395                 400 ccc gat gtg ggc tcc tcg gac cct ctg agc atg gtg gga ggt tcc cag     1248
Pro Asp Val Gly Ser Ser Asp Pro Leu Ser Met Val Gly Gly Ser Gln
                405                 410                 415 ggc cga agc ccc agc tac gct tcc ta                                   1274
Gly Arg Ser Pro Ser Tyr Ala Ser
            420

<210> SEQ ID NO 38
<211> LENGTH: 424
<212> TYPE: PRT
<213> ORGANISM: Artificial
<220> FEATURE:
<223> OTHER INFORMATION: Synthetic Construct

<400> SEQUENCE: 38

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
        50                  55                  60

Val His Asn Ala Lys Thr Lys Pro Arg Glu Glu Gln Tyr Asn Ser Thr
65                  70                  75                  80
```

```
Tyr Arg Val Val Ser Val Leu Thr Val Leu His Gln Asp Trp Leu Asn
            85                  90                  95

Gly Lys Glu Tyr Lys Cys Lys Val Ser Asn Lys Ala Leu Pro Ala Pro
        100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Gly Gly Gly Gly Ser Gly Gly Gly Ser Gly Gly Gly
225                 230                 235                 240

Gly Gly Ser His Pro Ile Pro Asp Ser Ser Pro Leu Leu Gln Phe Gly
                245                 250                 255

Gly Gln Val Arg Gln Arg Tyr Leu Tyr Thr Asp Asp Ala Gln Gln Thr
            260                 265                 270

Glu Ala His Leu Glu Ile Arg Glu Asp Gly Thr Val Gly Gly Ala Ala
        275                 280                 285

Asp Gln Ser Pro Glu Ser Leu Leu Gln Leu Lys Ala Leu Lys Pro Gly
    290                 295                 300

Val Ile Gln Ile Leu Gly Val Lys Thr Ser Arg Phe Leu Cys Gln Arg
305                 310                 315                 320

Pro Asp Gly Ala Leu Tyr Gly Ser Leu His Phe Asp Pro Glu Ala Cys
                325                 330                 335

Ser Phe Arg Glu Arg Leu Leu Glu Asp Gly Tyr Asn Val Tyr Gln Ser
            340                 345                 350

Glu Ala His Gly Leu Pro Leu His Leu Pro Gly Asn Lys Ser Pro His
        355                 360                 365

Arg Asp Pro Ala Pro Arg Gly Pro Ala Arg Phe Leu Pro Leu Pro Gly
    370                 375                 380

Leu Pro Pro Ala Pro Pro Glu Pro Pro Gly Ile Leu Ala Pro Gln Pro
385                 390                 395                 400

Pro Asp Val Gly Ser Ser Asp Pro Leu Ser Met Val Gly Gly Ser Gln
                405                 410                 415

Gly Arg Ser Pro Ser Tyr Ala Ser
            420

<210> SEQ ID NO 39
<211> LENGTH: 424
<212> TYPE: PRT
<213> ORGANISM: Artificial
<220> FEATURE:
<223> OTHER INFORMATION: Fc(15)FGF21

<400> SEQUENCE: 39

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
```

```
                    20                  25                  30
Met Ile Ser Arg Thr Pro Glu Val Thr Cys Val Val Asp Val Ser
                35                  40                  45
His Glu Asp Pro Glu Val Lys Phe Asn Trp Tyr Val Asp Val Glu
 50                  55                  60
Val His Asn Ala Lys Thr Lys Pro Arg Glu Glu Gln Tyr Asn Ser Thr
 65                  70                  75                  80
Tyr Arg Val Val Ser Val Leu Thr Val Leu His Gln Asp Trp Leu Asn
                85                  90                  95
Gly Lys Glu Tyr Lys Cys Lys Val Ser Asn Lys Ala Leu Pro Ala Pro
                100                 105                 110
Ile Glu Lys Thr Ile Ser Lys Ala Lys Gly Gln Pro Arg Glu Pro Gln
                115                 120                 125
Val Tyr Thr Leu Pro Pro Ser Arg Asp Glu Leu Thr Lys Asn Gln Val
                130                 135                 140
Ser Leu Thr Cys Leu Val Lys Gly Phe Tyr Pro Ser Asp Ile Ala Val
145                 150                 155                 160
Glu Trp Glu Ser Asn Gly Gln Pro Glu Asn Asn Tyr Lys Thr Thr Pro
                165                 170                 175
Pro Val Leu Asp Ser Asp Gly Ser Phe Phe Leu Tyr Ser Lys Leu Thr
                180                 185                 190
Val Asp Lys Ser Arg Trp Gln Gln Gly Asn Val Phe Ser Cys Ser Val
                195                 200                 205
Met His Glu Ala Leu His Asn His Tyr Thr Gln Lys Ser Leu Ser Leu
                210                 215                 220
Ser Pro Gly Lys Gly Gly Gly Ser Gly Gly Ser Gly Gly
225                 230                 235                 240
Gly Gly Ser His Pro Ile Pro Asp Ser Ser Pro Leu Leu Gln Phe Gly
                245                 250                 255
Gly Gln Val Arg Gln Arg Tyr Leu Tyr Thr Asp Asp Ala Gln Gln Thr
                260                 265                 270
Glu Ala His Leu Glu Ile Arg Glu Asp Gly Thr Val Gly Gly Ala Ala
                275                 280                 285
Asp Gln Ser Pro Glu Ser Leu Leu Gln Leu Lys Ala Leu Lys Pro Gly
                290                 295                 300
Val Ile Gln Ile Leu Gly Val Lys Thr Ser Arg Phe Leu Cys Gln Arg
305                 310                 315                 320
Pro Asp Gly Ala Leu Tyr Gly Ser Leu His Phe Asp Pro Glu Ala Cys
                325                 330                 335
Ser Phe Arg Glu Leu Leu Leu Glu Asp Gly Tyr Asn Val Tyr Gln Ser
                340                 345                 350
Glu Ala His Gly Leu Pro Leu His Leu Pro Gly Asn Lys Ser Pro His
                355                 360                 365
Arg Asp Pro Ala Pro Arg Gly Pro Ala Arg Phe Leu Pro Leu Pro Gly
                370                 375                 380
Leu Pro Pro Ala Pro Pro Glu Pro Pro Gly Ile Leu Ala Pro Gln Pro
385                 390                 395                 400
Pro Asp Val Gly Ser Ser Asp Pro Leu Ser Met Val Gly Pro Ser Gln
                405                 410                 415
Gly Arg Ser Pro Ser Tyr Ala Ser
                420

<210> SEQ ID NO 40
<211> LENGTH: 424
```

```
<212> TYPE: PRT
<213> ORGANISM: Artificial
<220> FEATURE:
<223> OTHER INFORMATION: Fc(15)FGF21 G170E

<400> SEQUENCE: 40

Met Asp Lys Thr His Thr Cys Pro Pro Cys Pro Ala Pro Glu Leu Leu
 1               5                  10                  15

Gly Gly Pro Ser Val Phe Leu Phe Pro Pro Lys Pro Lys Asp Thr Leu
             20                  25                  30

Met Ile Ser Arg Thr Pro Glu Val Thr Cys Val Val Val Asp Val Ser
         35                  40                  45

His Glu Asp Pro Glu Val Lys Phe Asn Trp Tyr Val Asp Gly Val Glu
     50                  55                  60

Val His Asn Ala Lys Thr Lys Pro Arg Glu Glu Gln Tyr Asn Ser Thr
 65                  70                  75                  80

Tyr Arg Val Val Ser Val Leu Thr Val Leu His Gln Asp Trp Leu Asn
                 85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Gly Gly Gly Gly Ser Gly Gly Ser Gly Gly
225                 230                 235                 240

Gly Gly Ser His Pro Ile Pro Asp Ser Ser Pro Leu Leu Gln Phe Gly
                245                 250                 255

Gly Gln Val Arg Gln Arg Tyr Leu Tyr Thr Asp Asp Ala Gln Gln Thr
            260                 265                 270

Glu Ala His Leu Glu Ile Arg Glu Asp Gly Thr Val Gly Gly Ala Ala
        275                 280                 285

Asp Gln Ser Pro Glu Ser Leu Leu Gln Leu Lys Ala Leu Lys Pro Gly
    290                 295                 300

Val Ile Gln Ile Leu Gly Val Lys Thr Ser Arg Phe Leu Cys Gln Arg
305                 310                 315                 320

Pro Asp Gly Ala Leu Tyr Gly Ser Leu His Phe Asp Pro Glu Ala Cys
                325                 330                 335

Ser Phe Arg Glu Leu Leu Leu Glu Asp Gly Tyr Asn Val Tyr Gln Ser
            340                 345                 350

Glu Ala His Gly Leu Pro Leu His Leu Pro Gly Asn Lys Ser Pro His
        355                 360                 365

Arg Asp Pro Ala Pro Arg Gly Pro Ala Arg Phe Leu Pro Leu Pro Gly
    370                 375                 380

Leu Pro Pro Ala Pro Pro Glu Pro Pro Gly Ile Leu Ala Pro Gln Pro
```

```
                385                 390                 395                 400
Pro Asp Val Gly Ser Ser Asp Pro Leu Ser Met Val Glu Pro Ser Gln
                405                 410                 415

Gly Arg Ser Pro Ser Tyr Ala Ser
                420

<210> SEQ ID NO 41
<211> LENGTH: 424
<212> TYPE: PRT
<213> ORGANISM: Artificial
<220> FEATURE:
<223> OTHER INFORMATION: Fc(15)FGF21 P171A

<400> SEQUENCE: 41

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
                100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
                180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
210                 215                 220

Ser Pro Gly Lys Gly Gly Gly Gly Ser Gly Gly Gly Ser Gly Gly
225                 230                 235                 240

Gly Gly Ser His Pro Ile Pro Asp Ser Ser Pro Leu Leu Gln Phe Gly
                245                 250                 255

Gly Gln Val Arg Gln Arg Tyr Leu Tyr Thr Asp Asp Ala Gln Gln Thr
            260                 265                 270

Glu Ala His Leu Glu Ile Arg Glu Asp Gly Thr Val Gly Gly Ala Ala
        275                 280                 285

Asp Gln Ser Pro Glu Ser Leu Leu Gln Leu Lys Ala Leu Lys Pro Gly
    290                 295                 300

Val Ile Gln Ile Leu Gly Val Lys Thr Ser Arg Phe Leu Cys Gln Arg
305                 310                 315                 320

Pro Asp Gly Ala Leu Tyr Gly Ser Leu His Phe Asp Pro Glu Ala Cys
                325                 330                 335
```

-continued

```
Ser Phe Arg Glu Leu Leu Leu Glu Asp Gly Tyr Asn Val Tyr Gln Ser
            340                 345                 350

Glu Ala His Gly Leu Pro Leu His Leu Pro Gly Asn Lys Ser Pro His
            355                 360                 365

Arg Asp Pro Ala Pro Arg Gly Pro Ala Arg Phe Leu Pro Leu Pro Gly
            370                 375                 380

Leu Pro Pro Ala Pro Pro Glu Pro Pro Gly Ile Leu Ala Pro Gln Pro
385                 390                 395                 400

Pro Asp Val Gly Ser Ser Asp Pro Leu Ser Met Val Gly Ala Ser Gln
                405                 410                 415

Gly Arg Ser Pro Ser Tyr Ala Ser
            420

<210> SEQ ID NO 42
<211> LENGTH: 424
<212> TYPE: PRT
<213> ORGANISM: Artificial
<220> FEATURE:
<223> OTHER INFORMATION: Fc(15)FGF21 S172L

<400> SEQUENCE: 42

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
    210                 215                 220

Ser Pro Gly Lys Gly Gly Gly Gly Ser Gly Gly Gly Ser Gly Gly
225                 230                 235                 240

Gly Gly Ser His Pro Ile Pro Asp Ser Ser Pro Leu Leu Gln Phe Gly
                245                 250                 255

Gly Gln Val Arg Gln Arg Tyr Leu Tyr Thr Asp Asp Ala Gln Gln Thr
            260                 265                 270
```

-continued

```
Glu Ala His Leu Glu Ile Arg Glu Asp Gly Thr Val Gly Gly Ala Ala
        275                 280                 285

Asp Gln Ser Pro Glu Ser Leu Leu Gln Leu Lys Ala Leu Lys Pro Gly
        290                 295                 300

Val Ile Gln Ile Leu Gly Val Lys Thr Ser Arg Phe Leu Cys Gln Arg
305                 310                 315                 320

Pro Asp Gly Ala Leu Tyr Gly Ser Leu His Phe Asp Pro Glu Ala Cys
                325                 330                 335

Ser Phe Arg Glu Leu Leu Leu Glu Asp Gly Tyr Asn Val Tyr Gln Ser
                340                 345                 350

Glu Ala His Gly Leu Pro Leu His Leu Pro Gly Asn Lys Ser Pro His
        355                 360                 365

Arg Asp Pro Ala Pro Arg Gly Pro Ala Arg Phe Leu Pro Leu Pro Gly
        370                 375                 380

Leu Pro Pro Ala Pro Pro Glu Pro Pro Gly Ile Leu Ala Pro Gln Pro
385                 390                 395                 400

Pro Asp Val Gly Ser Ser Asp Pro Leu Ser Met Val Gly Pro Leu Gln
                405                 410                 415

Gly Arg Ser Pro Ser Tyr Ala Ser
                420
```